United States Patent
McKnight et al.

(10) Patent No.: US 9,902,713 B2
(45) Date of Patent: Feb. 27, 2018

(54) NEUROPROTECTIVE COMPOUNDS AND USE THEREOF

(71) Applicants: BOARD OF REGENTS OF THE UNIVERSITY OF TEXAS SYSTEM, Austin, TX (US); UNIVERSITY OF IOWA RESEARCH FOUNDATION, Iowa City, IA (US)

(72) Inventors: Steven L. McKnight, Dallas, TX (US); Joseph M. Ready, Carrollton, TX (US); Andrew A. Pieper, Iowa City, IA (US)

(73) Assignees: Board of Regents of the University of Texas System, Austin, TX (US); University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 15/035,909

(22) PCT Filed: Nov. 11, 2014

(86) PCT No.: PCT/US2014/065054
§ 371 (c)(1),
(2) Date: May 11, 2016

(87) PCT Pub. No.: WO2015/070234
PCT Pub. Date: May 14, 2015

(65) Prior Publication Data
US 2016/0272619 A1    Sep. 22, 2016

Related U.S. Application Data

(60) Provisional application No. 61/902,680, filed on Nov. 11, 2013, provisional application No. 61/912,625, (Continued)

(51) Int. Cl.
*C07D 209/88*    (2006.01)
*C07D 401/12*    (2006.01)

(52) U.S. Cl.
CPC ......... *C07D 401/12* (2013.01); *C07D 209/88* (2013.01)

(58) Field of Classification Search
CPC .......................... C07D 401/12; C07D 209/88
(Continued)

(56) References Cited

U.S. PATENT DOCUMENTS 3,409,628 A    11/1968    Berger et al.
3,518,250 A    6/1970    Schumaker
(Continued)

FOREIGN PATENT DOCUMENTS

CN    101139347 A    3/2008
CN    101429198 A    5/2009
(Continued)

OTHER PUBLICATIONS

Dutca; Invest Ophthalmol Vis Sci 2014, 55, 8330-8341. (Year: 2014).*
(Continued)

*Primary Examiner* — Daniel R Carcanague
(74) *Attorney, Agent, or Firm* — Greenberg Traurig, LLP; David J. Dykeman; Fang Xie

(57) ABSTRACT

Provided herein are compositions and methods for reducing one or both of axonal degeneration and neuronal cell death associated with a disease or traumatic brain injury. An aminopropyl carbazole agent with potent neuroprotective properties is described. Specifically, (−)-(S)-N-(3-(3,6-dibromo-9H-carbazol-9-yl)-2-fluoropropyl)-6-methoxypyridin-2-amine, is proposed as a new pharmacological agent for protecting patients against axonal degeneration and chronic consequences of TBI.

6 Claims, 39 Drawing Sheets

Related U.S. Application Data filed on Dec. 6, 2013, provisional application No. 62/002,961, filed on May 26, 2014.

(58) Field of Classification Search
USPC .................................................. 546/268.1
See application file for complete search history.

(56) References Cited

U.S. PATENT DOCUMENTS

| | | |
|---|---|---|
| 4,495,281 A | 1/1985 | Buckler et al. |
| 5,234,923 A | 8/1993 | Poss et al. |
| 5,306,609 A | 4/1994 | Mihayashi et al. |
| 6,187,785 B1 | 2/2001 | Zefirov et al. |
| 6,468,996 B1 | 10/2002 | Jeppesen et al. |
| 6,514,968 B1 | 2/2003 | TenBrink |
| 6,569,849 B1 | 5/2003 | Jorgensen et al. |
| 6,770,656 B2 | 8/2004 | Halazy et al. |
| 6,835,513 B2 | 12/2004 | Jubran et al. |
| 6,849,640 B2 | 2/2005 | Ennis et al. |
| 6,864,025 B2 | 3/2005 | Law et al. |
| 7,018,988 B2 | 3/2006 | Halazy et al. |
| 7,071,206 B2 | 7/2006 | Zefirov et al. |
| 7,148,259 B1 | 12/2006 | Li et al. |
| 7,438,916 B2 | 10/2008 | Rathore et al. |
| 7,445,877 B2 | 11/2008 | Jubran et al. |
| 7,449,478 B2 | 11/2008 | Hsieh et al. |
| 7,807,704 B2 | 10/2010 | Thomas et al. |
| 7,834,063 B2 | 11/2010 | Turnbull et al. |
| 7,989,127 B2 | 8/2011 | Wu et al. |
| 8,268,575 B2 | 9/2012 | Imai et al. |
| 8,362,277 B2 | 1/2013 | McKnight et al. |
| 8,604,074 B2 | 12/2013 | McKnight et al. |
| 8,735,440 B2 | 5/2014 | McKnight et al. |
| 8,748,473 B2 | 6/2014 | McKnight et al. |
| 8,791,149 B2 | 7/2014 | McKnight et al. |
| 8,877,797 B2 | 11/2014 | McKnight et al. |
| 9,095,571 B2 | 8/2015 | McKnight et al. |
| 9,095,572 B2 | 8/2015 | McKnight et al. |
| 9,156,787 B2 | 10/2015 | McKnight et al. |
| 9,162,980 B2 | 10/2015 | McKnight et al. |
| 9,243,281 B2 | 1/2016 | McKnight et al. |
| 9,278,923 B2 | 3/2016 | McKnight et al. |
| 9,446,022 B2 | 9/2016 | McKnight et al. |
| 9,446,042 B2 | 9/2016 | McKnight et al. |
| 9,458,155 B2 | 10/2016 | Hung et al. |
| 9,616,048 B2 | 4/2017 | McKnight et al. |
| 9,645,139 B2 | 5/2017 | McKnight et al. |
| 9,701,676 B2 | 7/2017 | McKnight et al. |
| 2003/0171309 A1 | 9/2003 | Halazy et al. |
| 2003/0203296 A1 | 10/2003 | Law et al. |
| 2003/0207188 A1 | 11/2003 | Jubran et al. |
| 2003/0216427 A1 | 11/2003 | Halazy et al. |
| 2005/0124675 A1 | 6/2005 | Hsieh et al. |
| 2005/0277038 A1 | 12/2005 | Jubran et al. |
| 2006/0038170 A1 | 2/2006 | Brunschwiler et al. |
| 2007/0185152 A1 | 8/2007 | Yamashita et al. |
| 2007/0196395 A1 | 8/2007 | Mackerell et al. |
| 2007/0197524 A1 | 8/2007 | Brauer et al. |
| 2007/0203236 A1 | 8/2007 | Smith et al. |
| 2007/0275965 A1 | 11/2007 | Thomas et al. |
| 2007/0293558 A1 | 12/2007 | Gao et al. |
| 2008/0058383 A1 | 3/2008 | Jernstedt et al. |
| 2008/0255124 A1 | 10/2008 | Turnbull et al. |
| 2009/0163545 A1 | 6/2009 | Goldfarb |
| 2009/0236229 A1 | 9/2009 | Advincula |
| 2009/0246803 A1 | 10/2009 | Imai et al. |
| 2010/0022580 A1 | 1/2010 | Hung et al. |
| 2010/0305121 A1 | 12/2010 | Smith et al. |
| 2011/0003836 A1 | 1/2011 | McKnight et al. |
| 2011/0015217 A1 | 1/2011 | McKnight et al. |
| 2012/0022013 A1 | 1/2012 | Sinclair et al. |
| 2012/0022096 A1 | 1/2012 | McKnight et al. |
| 2012/0122924 A1 | 5/2012 | Curtin et al. |
| 2012/0172584 A1 | 7/2012 | Sauve et al. |
| 2013/0040977 A1 | 2/2013 | McKnight et al. |
| 2013/0184271 A1 | 7/2013 | McKnight et al. |
| 2013/0184300 A1 | 7/2013 | McKnight et al. |
| 2013/0184301 A1 | 7/2013 | McKnight et al. |
| 2013/0190273 A1 | 7/2013 | McKnight et al. |
| 2013/0190339 A1 | 7/2013 | McKnight et al. |
| 2014/0057900 A1 | 2/2014 | McKnight et al. |
| 2014/0094480 A1 | 4/2014 | McKnight et al. |
| 2014/0343018 A1 | 11/2014 | McKnight et al. |
| 2015/0051218 A1 | 2/2015 | Hung et al. |
| 2015/0057301 A1 | 2/2015 | McKnight et al. |
| 2015/0132783 A1 | 5/2015 | McKnight et al. |
| 2015/0290195 A1 | 10/2015 | McKnight et al. |
| 2016/0074361 A1 | 3/2016 | McKnight et al. |
| 2016/0206594 A1 | 7/2016 | McKnight et al. |
| 2016/0206596 A1 | 7/2016 | McKnight et al. |
| 2016/0272619 A1 | 9/2016 | McKnight et al. |
| 2016/0362372 A1 | 12/2016 | McKnight et al. |
| 2016/0362373 A1 | 12/2016 | McKnight et al. |
| 2017/0030897 A1 | 2/2017 | McKnight et al. |
| 2017/0157092 A1 | 6/2017 | McKnight et al. |

FOREIGN PATENT DOCUMENTS

| | | |
|---|---|---|
| EP | 1 094 063 | 4/2001 |
| EP | 1 591 511 | 11/2005 |
| EP | 2 236 511 A2 | 10/2010 |
| FR | 1167510 | 11/1958 |
| GB | 2 355 659 | 5/2001 |
| JP | H04-217657 A | 8/1992 |
| JP | 2007/223916 | 9/2007 |
| WO | WO 92/21660 | 12/1992 |
| WO | WO 96/34863 | 11/1996 |
| WO | WO 00/23425 | 4/2000 |
| WO | WO 00/78795 | 12/2000 |
| WO | WO 01/29028 | 4/2001 |
| WO | WO 01/71430 | 9/2001 |
| WO | WO 02/038142 | 5/2002 |
| WO | WO 02/060867 | 8/2002 |
| WO | WO 03/007069 | 1/2003 |
| WO | WO 03/007070 | 1/2003 |
| WO | WO 03/007071 | 1/2003 |
| WO | WO 03/032072 | 1/2003 |
| WO | WO 03/091247 | 11/2003 |
| WO | WO 2004/052885 | 6/2004 |
| WO | WO 2004/106335 | 9/2004 |
| WO | WO 2005/055951 | 6/2005 |
| WO | WO 2005/056522 | 6/2005 |
| WO | WO 2005/074971 | 8/2005 |
| WO | WO 2007/008541 | 1/2007 |
| WO | WO 2007/041697 | 4/2007 |
| WO | WO 2007/062399 | 5/2007 |
| WO | WO 2007/079239 | 7/2007 |
| WO | WO 2007/081091 | 7/2007 |
| WO | WO 2007/087425 | 8/2007 |
| WO | WO 2007/137227 | 11/2007 |
| WO | WO 2008/021745 | 2/2008 |
| WO | WO 2008/060190 | 5/2008 |
| WO | WO 2008/115098 | 9/2008 |
| WO | WO 2008/123796 | 10/2008 |
| WO | WO 2008/123800 | 10/2008 |
| WO | WO 2008/156105 | 12/2008 |
| WO | WO 2009/040517 | 4/2009 |
| WO | WO 2009/055828 | 4/2009 |
| WO | WO 2009/094668 | 7/2009 |
| WO | WO 2009/120717 | 10/2009 |
| WO | WO 2010/048446 | 4/2010 |
| WO | 2010-051501 A1 | 5/2010 |
| WO | WO 2010/051503 | 5/2010 |
| WO | WO 2010/081115 | 7/2010 |
| WO | 2011-015217 A1 | 2/2011 |
| WO | WO 2011/019417 | 2/2011 |
| WO | WO 2011/038162 | 3/2011 |
| WO | WO 2011/117668 | 9/2011 |
| WO | WO 2012/006419 | 1/2012 |

(56) References Cited

FOREIGN PATENT DOCUMENTS

| | | |
|---|---|---|
| WO | WO 2014/031125 | 2/2014 |
| WO | WO 2014/031986 | 2/2014 |
| WO | WO 2015/035051 | 3/2015 |

OTHER PUBLICATIONS

Naidoo; J. Med. Chem. 2014, 57, 3746-3754. (Year: 2014).*
Abad, J. et al., "Internal Oxidosqualenes: Determination of Absolute Configuration and Activity as Inhibitors of Purified Pig Liver Squalene Epoxidase," J. Org. Chem., 60(12), pp. 3648-3656 (Jun. 1995).
Abrous, D. et al., "Adult Neurogenesis: From Precursors to Network and Physiology," Physiol Rev, vol. 85, pp. 523-569 (2005).
Alexander, M. et al., "A Central Strategy for Converting Natural Products into Fluorescent Probes," ChemBioChem, 7(3), pp. 409-416 (Mar. 2006).
Altman, J., "Are New Neurons Formed in the Brains of Adult Mammals?" Science, 135, pp. 1127-1128 (Mar. 1962).
Altman, J., "Autoradiographic Investigation of Cell Proliferation in the Brains of Rats and Cats," Anat. Rec., 145, pp. 573-591 (Apr. 1963).
Altman, J., "Autoradiographic and Histological Evidence of Postnatal Hippocampal Neurogenesis in Rats," J. Comp. Neur., 124(3), pp. 319-335 (Jun. 1965).
Altman, J., "Autoradiographic and Histological Studies of Postnatal Neurogenesis: I. A Longitudinal Investigation of the Kinetics, Migration and Transformation of Cells Incorporating Tritiated Thymidine in Neonate Rats, with Special Reference to Postnatal Neurogenesis in Some Brain Regions," J. Comp. Neur., 126(3), pp. 337-389 (Mar. 1966).
Altman, J., "Autoradiographic and Histological Studies of Postnatal Neurogenesis: II. A Longitudinal Investigation of the Kinetics, Migration and Transformation of Cells Incorporating Tritiated Thymidine in Infant Rats, with Special Reference to Postnatal Neurogenesis in Some Brain Regions," J. Comp. Neur., 128(4), pp. 431-473 (Dec. 1966).
Altman, J., "Autoradiographic and Histological Studies of Postnatal Neurogenesis: IV. Cell Proliferation and Migration in the Anterior Forebrain, with Special Reference to Persisting Neurogenesis in the Olfactory Bulb," J. Comp. Neur., 137(4), pp. 433-457 (Dec. 1969).
Araki et al., "Increased Nuclear NAD Biosynthesis and SIRT1 Activation Prevent Axonal Degeneration" Science 305:1010-1013, Aug. 13, 2004.
AsInEx Chemical Library, Compound "9H-Carbazole-9-Ethanol, 3,6-dibromo-a-[[(3-chlorophenyl) amino]methyl]" (2001).
Asso, V. et al., "α-Naphthylaminopropan-2-ol Derivatives as BACE1 Inhibitors," ChemMedChem, 3(10), pp. 1530-1534 (Oct. 2008).
Awasthi, S. et al., "Modulation of Doxorubicin Cytotoxicity by Ethacrynic Acid", Int. J. Cancer, vol. 69, pp. 333-339 (1996).
Bachurin, S. et al., "Antihistamine Agent Dimebon as a Novel Neuroprotector and a Cognition Enhancer," Ann. N.Y. Acad Sci., 939, pp. 425-435 (Jun. 2001).
Bachurin, S. et al., "Mitochondria as a Target for Neurotoxins and Neuroprotective Agents," Ann. N.Y. Acad. Sci., 993, pp. 334-344 (May 2003).
Bachurin, S. et al., "Questions and Answers: Session VII: Oxidative Stress, Mitochondria, and Approaches to Neuroprotection," Ann. N.Y. Acad. Sci., 993, pp. 345-349 (May 2003).
Berg et al., "New Neuronal Growth Factors" Ann. Rev. Neurosci., 7: 149-170 (Jul. 1984).
Beyer, M. et al., "Synthesis of Novel Aromatic Nitroxides as Potential DNA Intercalators. An EPR Spectroscopical and DFT Computational Study," J. Org. Chem., 68(6), pp. 2209-2215 (Mar. 2003).
Boekelheide, V. et al., "Curariform Activity and Chemical Structure. VII. Some 1-Skatylisoquinoline Derivatives and a Novel Method for their Synthesis," J. Am. Chem. Soc., 72(5), pp. 2134-2137 (May 1950).

Boldrini, M. et al., "Antidepressants Increase Neural Progenitor Cells in the Human Hippocampus," Neuropsychopharmacology, 34(11), pp. 2376-2389 (Oct. 2009).
Bombrun, A. et al., "3,6-Dibromocarbazole Piperazine Derivatives of 2-Propanol as First Inhibitors of Cytochrome c Release via Bax Channel Modulation," J. Med. Chem., 46(21), pp. 4365-4368 (Oct. 2003).
Borrell-Pages, M. et al., "Huntington's Disease: From Huntington Function and Dysfunction to Therapeutic Strategies," Cell. Mol. Life Sci., 63(22), pp. 2462-2660 (Nov. 2006).
Brown, J. et al., "Transient Expression of Doublecortin during Adult Neurogenesis," The Journal of Comparative Neurology, 467(1), pp. 1-10 (Dec. 2003).
Browne, S. et al., "The Energetics of Huntington's Disease," Neurochemical Research, 29(3), pp. 531-546 (Mar. 2004).
Burd, G. et al., "Ultrastructural Characterization of Synaptic Terminals Formed on Newly Generated Neurons in a Song Control Nucleus of the Adult Canary Forebrain," The Journal of Comparative Neurology, 240(2), pp. 143-152 (Oct. 1985).
Burns, A. et al., "Dimebon in Alzheimer's Disease: Old Drug for New Indication," The Lancet, 372, pp. 179-180 (Jul. 2008).
Cao, R. et al., "Synthesis, Acute Toxicities, and Antitumor Effects of Novel 9-Substituted β-Carboline Derivatives," Bioorganic & Medicinal Chemistry, 12(17), pp. 4613-4623 (Sep. 2004).
Cao, R. et al., "Design, Synthesis and in Vitro and in Vivo Antitumor Activities of Novel β-Carboline Derivatives," European Journal of Medicinal Chemistry, 40(10), pp. 991-1001 (Oct. 2005).
Cao, R. et al., "DNA Binding Properties of 9-Substituted Harmine Derivatives," Biochemical and Biophysical Research Communications, 338(3), pp. 1557-1563 (Dec. 2005).
Cao, R. et al., "Synthesis and Cytotoxic Activities of 1-Benzylidine Substituted β-Carboline Derivatives," Bioorganic & Medicinal Chemistry Letters, 18(24), pp. 6558-6561 (Dec. 2008).
Cattaneo, E. et al., "Normal Huntington Function: An Alternative Approach to Huntington's Disease," Nature Reviews: Neuroscience, 6, pp. 919-930 (Dec. 2005).
Carter, R. et al., "Characterization of Progressive Motor Deficits in Mice Transgenic for the Human Huntington's Disease Mutation," The Journal of Neuroscience, 19(8), pp. 3248-3257 (Apr. 1999).
Cha, J. et al., "Altered Brain Neurotransmitter Receptors in Transgenic Mice Expressing a Portion of an Abnormal Human Huntington Disease Gene," Proc. Natl. Acad. Sci. USA, 95, pp. 6480-6485 (May 1998).
Cha, J., "Transcriptional Dysregulation in Huntington's Disease," TINS, 23(9), pp. 387-392 (Sep. 2000).
Chakraborti, A. et al., "Lithium Bromide, an Inexpensive and Efficient Catalyst for Opening of Epoxide Rings by Amines at Room Temperature under Solvent-Free Condition," Eur. J. Org. Chem., 2004(17), pp. 3597-3600 (Sep. 2004).
Cimini et al., "Expression of Peroxisome Proliferator-Activated Receptors (PPARs) and Retinoic Acid Receptors (RXRs) in Rat Cortical Neurons.", Neuroscience, vol. 130, pp. 325-337, 2005.
Davies, S. et al., "Formation of Neuronal Intranuclear Inclusions Underlies the Neurological Dysfunction in Mice Transgenic for the HD Mutation," Cell, 90, pp. 537-548 (Aug. 1997).
DeJesus-Cortes, H. et al., "Neuroprotective Efficacy of Aminopropyl Carbazoles in a Mouse Model of Parkinson Disease" PNAS, vol. 109, No. 42, pp. 17010-17015 (Oct. 16, 2012).
Distelmaier, F. et al., "Life Cell Quantification of Mitochondrial Membrane Potential at the Single Organelle Level," Cytometry A, 73(2), pp. 129-138 (Feb. 2008).
Di Santo, R. et al., "Design, Synthesis and QSAR Studies on N-Aryl Heteroarylisopropanolamines, a New Class of Non-Peptidic HIV-1 Protease Inhibitors," Bioorganic & Medicinal Chemistry, 10(8), pp. 2511-2526 (Aug. 2002).
Doody, R. et al., "Effect of Dimebon on Cognition, Activities of Daily Living, Behaviour, and Global Function in Patients with Mild-to-Moderate Alzheimer's Disease: A Randomised, Double-Blind, Placebo-Controlled Study," The Lancet, 372, pp. 207-215 (Jul. 2008).
Doody, R. et al., "Intermittent Preventive Antimalarial Treatment in Infancy," The Lancet, 372, pp. 1383-1384 (Oct. 2008).

(56) References Cited

OTHER PUBLICATIONS

Dow, R. et al., "Identification of Tricyclic Analogs Related to Ellagic Acid as Potent/Selective Tyrosine Protein Kinase Inhibitors," *J. Med. Chem.*, 37(14), pp. 2224-2231 (Jul. 1994).
Driscoll, I. et al., "The Aging Hippocampus: A Multi-Level Analysis in the Rat," *Neuroscience*, 139(4), pp. 1173-1185 (Mar. 2006).
Enyedy et al., "Discovery of Small-Molecule Inhibitors of Bcl-2 through Structure-Based Computer Screening," *J. Med. Chem.*, 44(25), pp. 4313-4324 (Dec. 6, 2001).
Eriksson, P. et al., "Neurogenesis in the Adult Human Hippocampus," *Nature Medicine*, 4(11), pp. 1313-1317 (Nov. 1998).
Fedele, V. et al., "Neurogenesis in the R6/2 Mouse Model of Huntington's Disease is Impaired at the Level of Neurod1," *Neuroscience*, 173, pp. 76-81 (Jan. 2011).
Fernandes, H. et al., "Mitochondrial Sensitivity and Altered Calcium Handling Underlie Enhanced NMDA-Induced Apoptosis in YAC128 Model of Huntington's Diase," *The Journal of Neuroscience*, 27(50), pp. 13614-13623 (Dec. 2007).
Ferris, R.M. et al., "Rimcazole (BW 234U), a Novel Antipsychotic Agent Whose Mechanism of Action Cannot be Explained by a Direct Blockade of Postsynaptic Dopaminergic Receptors in Brain," *Drug Development Research*, 9(3), pp. 171-188 (Nov. 1986).
Freireich, E. et al., "Quantitative Comparison of Toxicity of Anticancer Agents in Mouse, Rat, Hamster, Dog, Monkey, and Man," *Cancer Chemotherapy Reports*, 50(4), pp. 219-244 (May 1966).
Gennaro, A. et al., "Remington's Pharmaceutical Sciences," *Mack Publishing Company*, 17$^{th}$ Edition, pp. 1418-1419 (1985).
Getautis, V. et al., "Study of the Products from Reaction of 1(2)-Aminoanthraquinones with 1-Chloro-2,3-Epoxypropane," *Chemistry of Heterocyclic Compounds*, 41(4), pp. 426-436 (Apr. 2005).
Giancaspro et al., "Synthesis of Disubstituted Tetrahydrocarbazoles with Potential Antidepressive Activity," IL Farmaco, 44(5), 483-493, 1989.
Giancaspro et al., "Trypanocidal Activity of 1,2,3,4-Tetrahydrocarbazoles," Rev. Microbiol., Sao Paulo, 25(3):201-205, 1994.
Gil, J. et al., "Asialoerythropoetin is not Effective in the R6/2 Line of Huntington's Disease Mice," *BMC Neuroscience*, 5(17), pp. 1-10 (May 2004).
Gil, J. et al., "Reduced Hippocampal Neurogenesis in R6/2 Transgenic Huntington's Disease Mice," *Neurobiology of Disease*, 20, pp. 744-751 (Jun. 2005).
Gil, J. et al., "The R6 Lines of Transgenic Mice: A Model for Screening New Therapies for Huntington's Disease," *Brain Research Reviews*, 59(2), pp. 410-431 (Mar. 2009).
Godin, J. et al., "Huntingtin is Required for Mitotic Spindle Orientation and Mammalian Neurogenesis," *Neuron*, 67, pp. 392-406 (Aug. 2010).
Goehler, H. et al., "A Protein Interaction Network links GIT1, an Enhancer of Huntingtin Aggregation, to Huntington's Disease," *Molecular Cell*, 15, pp. 853-865 (Sep. 2004).
Goldberg, Y.P. et al., "Cleavage of Huntingtin by Apopain, a Proapoptotic Cysteine Protease, is Modulated by the Poyglutamine Tract," *Nature Genetics*, 13, pp. 442-449 (Aug. 1996).
Goldman, S. et al., "Neuronal Production, Migration, and Differentiation in a Vocal Control Nucleus of the Adult Female Canary Brain," *Proc. Natl. Acad. Sci. USA*, 80, pp. 2390-2394 (Apr. 1983).
Gross, C. "Neurogenesis in the Adult Brain: Death of a Dogma," *Nature Reviews*, 1, pp. 67-73 (Oct. 2000).
Haggquist, G. et al., "Intramolecular Triplet Energy Transfer. 3. A Carbazole-Naphthalene System Having Short Chain Length Methylene Spacer Units," *J. Phys. Chem.*, 97, pp. 9270-9273 (Sep. 1993).
Harbert, C. et al., "Neuroleptic Activity in 5-Aryltetrahydroγ-carbolines," *J. Med. Chem.*, 23(6), pp. 635-643 (Jun. 1980).
Hisada, K. et al., "Intramolecular Triplet Energy Transfer. 4. A Carbazole-Naphthalene System Having a Flexible Alkyl Spacer Doped in Poly(methyl methacrylate) Matrixes," *J. Phys. Chem. B*, 102, pp. 2640-2645 (Mar. 1998).

Jackson-Lewis, V. et al., "Protocol for the MPTP Mouse Model of Parkinson's Disease," *Nature Protocols*, 2, pp. 141-151 (Feb. 2007).
Jantas, D. et al., "Protective Effect of Memantine Against Doxorubicin Toxicity in Primary Neuronal Cell Cultures: Influence a Development Stage", *Neurotox Res.*, vol. 15, pp. 24-37 (2009).
Jin, K. et al., "Heparin-Binding Epidermal Growth Factor-Like Growth Factor: Hypoxia-Inducible Expresstion In Vitro and Stimulation of Neurogenesis In Vitro and In Vivo," *The Journal of Neuroscience*, vol. 22, Chapter 13, pp. 5365-5373 (Jul. 1, 2002).
Jorapur, Y. et al., "Potassium Carbonate as a Base for the N-alkylation of Indole and Pyrrole in Ionic Liquids," *Tetrahedron Letters*, 47(14), pp. 2435-2438 (Apr. 2006).
Jun, W. et al., "Inorganic-Organic Hybrid Photorefractive Materials Bearing the Bifunctional Chromophore," *Journal of Nonlinear Optical Physics & Materials*, 14(4), pp. 497-504 (Dec. 2005).
Kaewtong, C. et al., "Self-Assembly and Electrochemical Oxidation of Pollyamidoamine—Carbazole Dendron Surfmer Complexes: Nanoring Formation," *ASC Nano*, 2(8), pp. 1533-1542 (Aug. 2008).
Kamal et al., "Carbazole-pyrrolo [2,1-c] [1, 4] benzodiazepine conjugates: design, synthesis, and biological evaluation", MedChemComm, vol. 2, No. 8, pp. 780-788 (2001).
Kamnasaran, D. et al., "Disruption of the Neuronal PAS3 Gene in a Family Affected with Schizophrenia," *J. Med. Genet.*, 40(5), pp. 325-332 (May 2003).
Kamogawa, H. et al., "Syntheses of N-Substituted Carbazoles Involving Polymerizable Terminal Vinyl Groups," *Journal of Polymer Science*, 17(1), pp. 9-18 (Jan. 1979).
Kemp et al., "Pharmacologic Rescue of Motor and Sensory Function by the Neuroprotective Compound P7C3 Following Neonatal Nerve Injury," Neuroscience (2015), 284, 202-216.
Kempermann, G. et al., "More Hippocampal Neurons in Adult Mice Living in an Enriched Environment," *Nature*, 386, pp. 493-495 (Apr. 1997).
Kim, J. et al., "Mitochondrial Loss, Dysfunction and Altered Dynamics in Huntington's Disease," *Human Molecular Genetics*, 19(20), pp. 3919-3935 (Jul. 2010).
Kim, S. et al., "Treadmill Exercise Prevents Aging-Induced Failure of Memory through an Increase in Neurogenesis and Suppression of Apoptosis in Rat Hippocampus," *Experimental Gerontology*, 45(5), pp. 357-365 (May 2010).
Kim, T. et al., "Molecular Tripods Showing Fluorescence Enhancement upon Binding to Streptavidin," *Organic Letters*, 7(1), pp. 111-114 (Jan. 2005).
Kim, T. et al., "Self-Quenching Mechanism: the Influence of Quencher and Spacer on Quencher-fluorescein Probes," *Bull. Korean. Chem. Soc.*, 28(7), pp. 1221-1223 (2007).
Kohl, Z. et al., "Impaired Adult Olfactory Bulb Neurogenesis in the R6/2 Mouse Model of Huntington's Disease," *BMC Neuroscience*, 11, pp. 1-11 (Sep. 2010).
Kondratov et al., "Small molecules that dramatically alter multidrug resistance phenotype by modulating the substrate specificity of P-glycoprotein," Proceedings of the National Academy of Sciences of the United States of America (2001), 98(24), 14078-14083.
Krishnan, V. et al., "The Molecular Neurobiology of Depression," *Nature*, 455, pp. 894-902 (Oct. 2008).
Kuhn, G. et al., "Neurogenesis in the Dentate Gyrus of the Adult Rat: Age-Related Decrease of Neuronal Progenitor Proliferation," *The Journal of Neuroscience*, 16(6), pp. 2027-2033 (Mar. 1996).
Landree et al., "C75, a Fatty Acid Synthase Inhibitor, Modulates AMP-activated Protein Kinase to Alter Neuronal Energy Metabolism" J. Biol. Chem., 2004, v. 279, p. 3817-3827 (Jan. 30, 2004).
Lavedan, C. et al., "Effect of a Ciliary Neurotrophic Factor Polymorphism on Schizophrenia Symptom Improvement in an Iloperidone Clinical Trial," *Pharmacogenomics*, 9(3), pp. 289-301 (Mar. 2008).
Lavedan, C. et al., "Association of the NPAS3 Gene and Five Other Loci with Response to the Antipsychotic Iloperidone Identified in a Whole Genome Association Study," *Molecular Psychiatry*, 14(8), pp. 804-819 (Aug. 2009).
Lee, H. et al., "Structure-Activity Relationship Studies of the Chromosome Segregation Inhibitor, Incentrom A," *Bioorganic & Medicinal Chemistry Letters*, 18(6), pp. 4670-4674 (Aug. 2008).

(56) References Cited

OTHER PUBLICATIONS

Li, Z. et al., "Two Types of Nonlinear Optical Polyurethanes Containing the Same Isolation Groups: Syntheses, Optical Properties, and Influence of Binding Mode," *J Phys. Chem. B*, 113, pp. 14943-14949 (Oct. 2009).

Lione, L. et al., "Selective Discrimination Learning Impairments in Mice Expressing the Human Huntington's Disease Mutation," *The Journal of Neuroscience*, 19(23), pp. 10428-10437 (Dec. 1999).

Liu, X. et al., "Induction of Apoptotic Program in Cell-Free Extracts: Requirement for dATP and Cytochrome c," *Cell*, 86, pp. 147-157 (Jul. 1996).

Liu et al., "Synthesis and Spectroscopic and Electrochemical Properties of TTF-Derivatized Polycarbazole", Macromolecules, vol. 41, No. 6, pp. 2045-2048 (2011).

Loo, D. et al., "Apoptosis is Inducted by β-Amyloid in Cultured Central Nervous System Neurons," *Proc. Natl. Acad. Sci. USA*, 90, pp. 7951-7955 (Sep. 1993).

Lygaitis, R. et al., "Synthesis and Photophysical Properties of Bipolar Low-Molar-Mass Amorphous Materials," *Journal of Photochemistry and Photobiology A: Chemistry*, 167(2-3), pp. 163-168 (Oct. 2004).

MacMillan, et al., "Development of Proneurogenic, Neuroprotective Small Molecules", Journal of the American Chemical Society, vol. 133, No. 5, pp. 1428-1437 (2011).

Maegawa, Y. et al., "A Useful Procedure for Diiodination of Carbazoles and Subsequent Efficient Transformation to Novel 3,6-bis(triethoxysilyl) Carbazoles Giving Mesoporous Materials," *Tetrahedron Letters*, 47(39), pp. 6957-6960 (Sep. 2006).

Mahapatra, et al., "A Small Molecule Which Protects Newborn Neurons", ACS Chemical Neuroscience, vol. 1, No. 9, pp. 589 (2010).

Mangialasche, F. et al., "Alzheimer's Disease: Clinical Trials and Drug Development," *The Lancet*, 9, pp. 702-716 (Jul. 2010).

Mangiarini, L. et al., "Exon 1 of the *HD* Gene with an Expanded CAG Repeat is Sufficient to Cause a Progressive Neurological Phenotype in Transgenic Mice," *Cell*, 87, pp. 493-506 (Nov. 1996).

Martin, D. et al., "Apoptotic Changes in the Aged Brain are Triggered by Interleukin-1β-Induced Activation of p38 and Reversed by Treatment with Eicosapentaeonic Acid," *The Journal of Biological Chemistry*, 277(37), pp. 34239-34246 (Sep. 2002).

Mattos et al., "Multiple Binding Modes," in *3D QSAR in Drug Design: Theory, Methods and Applications*, ed. H. Kubinyi, Springer, pp. 243-244 (Dec. 31, 1993).

McGrath, J. et al., "Novel Carbazole Phenoxy-Based Methacrylates to Produce High-Refractive Index Polymers," *Polymer*, 47, pp. 4042-4057 (Mar. 2006).

Menalled, L. et al., "Mouse Models of Huntington's Disease," *TRENDS in Pharmacological Sciences*, 23(1), pp. 32-39 (Jan. 2002).

Morcuende, A. et al., "Microwave-Promoted Transformations: Fast and Chemoselective N-Acylation of Amino Alcohols Using Catalytic Amounts of Dibutyltin Oxide. Influence of the Power Output and the Nature of Acylating Agent on the Selectivity," *J. Org. Chem.*, 61(16), pp. 5264-5270 (Aug. 1996).

Murphy, K. et al., "Abnormal Synaptic Plasticity and Impaired Spatial Cognition in Mice Transgenic for Exon 1 of the Human Huntington's Disease Mutation," *The Journal of Neuroscience*, 20(13), pp. 5115-5123 (Jul. 2000).

Muruganantham et al., "Synthesis, anticonvulsant and antihypertensive activities of 8-substituted quinoline derivatives," Vel's College of Pharmacy, Biological & Pharmaceutical Bulletin. 27(10):1683-7 (2004).

Naidoo, J. et al., "Development of a Scalable Synthesis of P7C3-A20, a Potent Neuroprotective Agent" *Tetrahedron Letters*, vol. 54, pp. 4429-4431 (2013).

Naumova et al., CAPLUS Abstract of: Vestsi Akademii Navuk BSSR, Seryya Khimichnykh Navuk (1988), (4), 110-111)).

Negrin, C.M. et al., "In Vivo-In Vitro Study of Biodegradable Methadone Delivery Systems," *Biomaterials*, 22(6), pp. 563-570 (Mar. 2001).

Neitzert, H.C. et al., "Monitoring of the Initial Degradation of Oxadiazole Based Blue OLED's," *Journal of Non-Crystalline Solids*, 352, pp. 1695-1699 (Mar. 2006).

Newman, Robert A. et al., "Amelioration of Adriamycin and Daunorubicin Myocardial Toxicity by Adenosine", *Cancer Research*, vol. 41, pp. 3483-3488, Sep. 1981.

Nucifora, Jr., F. et al., "Interference by Huntingtin and Atrophin-1 with CBP-Mediated Transcription Leading to Cellular Toxicity," *Science*, 291, pp. 2423-2428 (Mar. 2001).

O'Brien, J. "A Promising New Treatment for Alzheimer's Disease?" *The Lancet*, 7, pp. 768-769 (Sep. 2008).

Okumura, H. et al., "Phenothiazine and Carbazole-Related Compounds Inhibit Mitotic Kinesin Eg5 and Trigger Apoptosis in Transformed Culture Cells," *Toxicology Letters*, 166(1), pp. 44-52 (Sep. 2006).

Olla, S. et al., "Indolyl-Pyrrolone as a New Scaffold for Pim1 Inhibitors," *Bioorganic & Medical Chemistry Letters*, 19(5), pp. 1512-1516 (Mar. 2009).

Pan, J. et al., "Synthesis of Carrier-Transporting Dendrimers with Perylenebis(dicarboximide)s as a Luminescent Core," *Eur. J. Org. Chem.*, 2006(4) pp. 986-1001 (Feb. 2006).

Panov, A. et al., "Early Mitochondrial Calcium Defects in Huntington's Disease are a Direct Effect of Polyglutamines," *Nature Neuroscience*, 5(8), pp. 731-736 (Aug. 2002).

Park, K. et al., "Promoting Axon Regeneration in the Adult CNS by Modulation of the PTEN/mTOR Pathway," *Science*, 322, pp. 963-966 (Nov. 2008).

Paton, J. et al., "Neurons Generated in the Adult Brain Are Recruited into Functional Circuits," *Science*, 225(4666), pp. 1046-1048 (Sep. 1984).

Pattison, L. et al., "Apoptotic Cascades as Possible Targets for Inhibiting Cell Death in Huntington's Disease," *J Neurol*, 253(9), pp. 1137-1142 (Sep. 2006).

Pereira, Olivia M., et al., "Photosensitization of Human Diploid Cell, Cultures by Intracellular Flavins and Protection by Antioxidants", *Photochemistry and Photobiology*, vol. 24, Issue 3, pp. 237-242 (Sep. 1976).

Perutz, M., "Glutamine Repeats and Neurodegenerative Diseases: Molecular Aspects," *TIBS*, 24, pp. 58-63 (Feb. 1999).

Petit, S. et al., "Structure-Activity Relationship Analysis of the Peptide Deformylase Inhibitor 5-Bromo-1H-indole-3-acetohydroxamic Acid," *ChemMedChem*, 4(2), pp. 261-275 (Feb. 2009).

Petruska, J. et al., "Analysis of Strand Slippage in DNA Polymerase Expansions of CAG/CTG Triplet Repeats Associated with Neurodegenerative Disease," *The Journal of Biological Chemistry*, 273(9), pp. 5204-5210 (Feb. 1998).

Phillips, W. et al., "Abnormalities of Neurogenesis in the R6/2 Mouse Model of Huntington's Disease are Attributable to the In Vivo Microenvironment," *The Journal of Neuroscience*, 25(50), pp. 11564-11576 (Dec. 2005).

Pickard, B. et al., "Disruption of a Brain Transcription Factor, NPAS3, is Associated with Schizophrenia and Learning Disability," *American Journal of Medical Genetics Part B*, 136B(1), pp. 26-32 (Jul. 2005).

Pickard, B. et al., "The *NPAS3* Gene—Emerging Evidence for a Role in Psychiatric Illness," *Annals of Medicine*, 38(6), pp. 439-448 (2006).

Pickard, B. et al., "Interacting Haplotypes at the *NPAS3* Locus Alter Risk of Schizophrenia and Bipolar Disorder," *Molecular Psychiatry*, 14(9), pp. 874-884 (Sep. 2009).

Pieper, A. et al., "The Neuronal PAS Domain Protein 3 Transcription Factor Controls FGF-Mediated Adult Hippocampal Neurogenesis in Mice," *PNAS*, 102(39), pp. 14052-14057 (Sep. 2005).

Pieper, A. et al., "Discovery of a Proneurogenic, Neuroprotective Chemical," *Cell*, 142, pp. 39-51 (Jul. 2010).

Pieper et al., "P7C3 and an unbiased Approach to Drug Discovery for Neurodegenerative Diseases," Chem. Soc. Rev.(2014), 19: 51-59.

(56) References Cited

OTHER PUBLICATIONS

Poesen, K. et al., "Novel Role for Vascular Endothelial Growth Factor (VEGF) Receptor-1 and its Ligand VEGF-B in Motor Neuron Degeneration," *The Journal of Neuroscience*, 28(42), pp. 10451-10459 (Oct. 2008).
Ponce, M. et al., "Synthesis and Isolation of Bromo-β-Carbolines Obtained by Bromination of β-Carboline Alkaloids," *J. Heterocyclic Chem.*, 38, pp. 1087-1095 (Sep.-Oct. 2001).
Pubchem SID 3976298 (deposit date Aug. 9, 2005).
Pubchem SID 7706058 (deposit date Sep. 26, 2005).
PubChem Compound, 1-[(3-chlorophenyl)amino]-3-(3,6-dibromo-9H-carbazol-9-yl)propan-2-ol, create date Jul. 28, 2005.
PubChem compound N-{4-[3-(3,6-dibromo-9H-carbazol-9-yl)-2-hydroxypropoxy]phenyl}acetamide, create date Sep. 15, 2005.
Racke et al., PPARs in Neuroinflammation, Hindawi Publishing (Special Issue), 107 pgs., 2008.
Ramamoorthy, "Synthesis of small molecular inhibitors targeting signal transduction pathways," *University of South Florida Thesis*, pp. 1-70 (Jun. 10, 2009).
Raoul, C et al., "Motoneuron Death Triggered by a Specific Pathway Downstream of Fas: Potentiation by ALS-Linked SOD1 Mutations" *Neuron*, vol. 35, pp. 1067-1083 (Sep. 12, 2002).
Ravlee et al., "Pharmacological evaluation of some new 6-amino/methyl pyridine derivatives," Chem. Pharm. Bull. 51(2): 162-170 (2003).
Rische, T. et al., "One-Pot Synthesis of Pharmacologically Active Diamines via Rhodium-Catalysed Carbonylative Hydroaminomethylation of Heterocyclic Allylic Amines," *Tetrahedron*, 55(32), pp. 9801-9816 (Aug. 1999).
Rubinsztein, D., "Lessons from Animal Models of Huntington's Disease," *TRENDS in Genetics*, 18(4), pp. 202-209 (Apr. 2002).
Rubinsztein, D. et al., "Huntington's Disease: Molecular Basis of Neurodegeneration," *Expert Reviews in Molecular Medicine*, 5(22), pp. 1-21 (Aug. 2003).
Sadri-Vakili, G. et al., "Mechanisms of Disease: Histone Modifications in Huntington's Disease," *Nature Clinical Practice: Neurology*, 2(6), pp. 330-338 (Jun. 2006).
Schmidt, H. et al., "The Role of Neurotrophic Factors in Adult Hippocampal Neurogenesis, Antidepressant Treatments and Animal Models of Depressive-Like Behavior," *Behavioural Pharmacology*, 18(5-6), pp. 391-418 (Sep. 2007).
Schwarcz, G. et al., "Open Label Evaluation of the Novel Antipsychotic Compound BW234U in Chronic Schizophrenics," *Drug Development Research*, vol. 5, pp. 387-393 (1985).
Stanfield, B. et al., "The Development of the Hippocampal Region," *Cerebral Cortex* (ed. Alan Peters and Edward G. Gones), vol. 7, pp. 91-131 (1988).
STN compounds registry Nos. 305862-95-7, 304893-66-1, 304880-74-8, 304878-30-6, 304868-62-0, 301353-98-0, 301353-96-8, 301160-69-0, 300805-47-7, 300588-31-2, 253448-99-6, 119091-28-0, 119091- 27-9, 331416-70-7, 331235-98-4, 331235-97-3, 328076-93-3, 327026-16-4, 317842-35-6, 314052-83-0, 313268-34-7, 313268-19-8, 313268-17-6, and 313268-16-5, entry date ranging from Nov. 6, 2000 to May 19, 2009.
STN Registry Entry 312599-43-2 entered Jan. 3, 2001.
STN Registry Entry 448231-97-8 entered Sep. 9, 2002.
Sun, W. et al., "Programmed Cell Death of Adult-Generated Hippocampal Neurons is Mediated by the Proapoptotic Gene Bax," *The Journal of Neuroscience*, 24(49), pp. 11205-11213 (Dec. 2004).
Sundararajan, C. et al., "Photolytic Release of Carboxylic Acids Using Linked Donor-Acceptor Molecules: Direct versus Mediated Photoinduced Electron Transfer to N-Alkyl-4-picolinium Esters," *Organic Letters*, 7(13), pp. 2631-2634 (Jun. 2005).
Suzdalev, K.F. et al., "Synthesis of Indole 2,3-Epoxypropyl Derivatives and their Reactions with Amines," *Russian Journal of Organic Chemistry*, 41(2), pp. 233-237 (Feb. 2005).
Tang, T-S et al., "Disturbed $Ca^{2+}$ Signaling and Apoptosis of Medium Spiny Neurons in Huntington's Disease," *PNAS*, 102(7), pp. 2602-2607 (Feb. 2005).

Tatton, N.A. et al., "In Situ Detection of Apoptotic Nuclei in the Substantia Nigra Compacta of 1-methyl-4-phenyl-1,2,3,6-tetrahydropyridine-treated Mice Using Terminal Deoxynucleotidyl Transferase Labelling and Acridine Orange Staining," *Neuroscience*, 77(4), pp. 1037-1048 (Apr. 1997).
Teles, A.V.F.F. et al., "Increase in Bax Expression and Apoptosis are Associated in Huntington's Disease Progression," *Neuroscience Letters*, 438(1), pp. 59-63 (Jun. 2008).
Terfloth et al., "Electronic Screening: Lead Finding from Database Mining," in *The Practice of Medicinal Chemistry*, ed. C. Wermuth, Academic Press, pp. 131-157 (Mar. 7, 1996).
Tesla, R. et al., "Neuroprotective Efficacy of Aminopropyl Carbazoles in a Mouse Model of Amyotrophic Lateral Sclerosis" *PNAS*, vol. 109, No. 42, pp. 17016-17021 (Oct. 16, 2012).
Thiel, M. et al., "Contributions to the Development of Psychotropic Substances, 3 Mitt: Diphenylamine Derivatives with Pyridyl-substituted Side Chains and Guanidyl," *Chemical Monthly*, 93(5), pp. 1080-1089 (1962).
Van Waarde, A. et al., "The Cholinergic System, sigma-1 Receptors and Cognition," *Behavioral Brain Research*, 221 (2), pp. 543-554 (Dec. 26, 2009).
van Praag, H. et al., "Running Increases Cell Proliferation and Neurogenesis in the Adult Mouse Dentate Gyrus," *Nature Neuroscience*, 2(3), pp. 266-270 (Mar. 1999).
Wang et al., "P7C3 Neuroprotective Chemicals Function by Activating the Rate-Limiting Enzyme in NAD Salvage," Cell 158, 11324-1334 (2014).
Wanker, E. et al., "HIP-I: A Huntingtin Interacting Protein Isolated by the Yeast Two-Hybrid System," *Human Molecular Genetics*, 6(3), pp. 487-495 (Mar. 1997).
Watanabe, T. et al., "Palladium-Catalyzed Direct Synthesis of Carbazoles via One-Pot N-Arylation and Oxidative Biaryl Coupling: Synthesis and Mechanistic Study," *J. Org. Chem.*, 74, pp. 4720-4726 (Jul. 2009).
Weissman, S. et al., "Ligand-Free Palladium-Catalyzed Cyanation of Aryl Halids," *J. Org. Chem.*, 70(4), pp. 1508-1510 (Jan. 2005).
Wermuth, C., "Molecular Variations Based on Isosteric Replacements," *The Practice of Medicinal Chemistry* (ed. Camille G. Wermuth), pp. 203-237 (1996).
Wilde, R. et al., "Acyl CoA:Cholesterol Acyltransferase (ACAT) Inhibitors: Heterocyclic Bioisosteres for the Urea Group in DuP 128," *Bioorganic & Medicinal Chemistry Letters*, 5(2), pp. 177-180 (Jan. 1995).
Wilen, S., *Tables of Resolving Agents and Optical Resolutions* (Ed. Ernest L. Eliel) pp. 268-298 (1972).
Wilen, S. et al, "Strategies in Optical Resolutions," *Tetrahedron*, 33, pp. 2725-2736 (1977).
Xuan, A.G. et al., "BDNF Improves the Effects of Neural Stem Cells on the Rat Model of Alzheimer's Disease with Unilateral Lesion of Fimbria-Fornix," *Neuroscience Letters*, 400(3), pp. 331-335 (Aug. 2008).
Xue, Y. et al., "Novel Hypoglycemic Compounds-synthesis of Glycine Derivatives and Research on the Role of PPARS," *Jiefangjun Yaoxue Xueao*, 25(1), pp. 5-10 (2009).
Yang, J. et al., "Prevention of Apoptosis by Bcl-2: Release of Cytochrome c from Mitochondria Blocked," *Science*, 275, pp. 1129-1132 (Feb. 1997).
Yin et al., "P7C3 Neuroprotective Chemicals Block Axonal Degeneration and Preserve Function after Traumatic Brain Injury" Cell Reports, 8, 1-10 (2014).
Yonemura, H. et al., "Spectroscopic Studies on Exchange Properties in Through-Ring Cyclodextrin Complexes of Carbazole-Viologen Linked Compounds: Effects of Spacer Chain Length," *J. Phys. Chem.*, 96, pp. 5765-5770 (Jul. 1992).
Yonemura, H. et al., "Effect of π-System on Long-Rang Photoinduced Electron Transfer in Through-Ring α-Cyclodextrin Complexes of Carbazole-Viologen Linked Compounds," *Tetrahedron Letters*, 39(38), pp. 6915-6918 (Sep. 1998).
Zeron, M. et al., "Mutant Huntingtin Enhances Excitotoxic Cell Death," *Molecular and Cellular Neuroscience*, 17(1), pp. 41-53 (Jan. 2001).
Zhang, H. et al., "Implantation of Neural Stem Cells Embedded in Hyaluronic Acid and Collagen Composite Conduit Promotes

(56) References Cited

OTHER PUBLICATIONS

Regeneration in a Rabbit Facial Nerve Injury Model," *Journal of Translational Medicine*, 6(67), pp. 1-11 (Nov. 2008).
Zherebtsov et al., CAPLUS Abstract of: SU 474533, From: Otkrytiya, Izobret., Prom. Obraztsy, Tovarnye Znaki 1975, 52(23), 51-2.
Zoidis, G. et al., "Design and Synthesis of 1,2-annulated Adamantane Piperidines with Anti-Influenza Virus Activity," *Bioorganic & Medicinal Chemistry*, 17(4), pp. 1534-1541 (Feb. 2009).
Zuccato, C. et al., "Huntingtin Interacts with REST/NRSF to Modulate the Transcription of NRSE-controlled Neuronal Genes," *Nature Genetics*, 35(1), pp. 76-83 (Sep. 2003).
PCT International Search Report based on PCT/US2010/020681 dated Jun. 17, 2010.
USPTO Office Action in U.S. Appl. No. 12/832,056 dated Feb. 9, 2012.
PCT International Search Report based on PCT/2011/043185 dated Apr. 10, 2012.
USPTO Office Action in U.S. Appl. No. 12/832,056 dated Jul. 11, 2012.
USPTO Office Action in U.S. Appl. No. 12/685,652 dated Jul. 19, 2012.
PCT International Search Report based on PCT/2012/052283 dated Oct. 24, 2012.
USPTO Notice of Allowance in U.S. Appl. No. 12/832,056 dated Nov. 20, 2012.
USPTO Office Action in U.S. Appl. No. 12/685,652 dated Mar. 20, 2013.
USPTO Office Action in U.S. Appl. No. 13/177,981 dated Apr. 16, 2013.
USPTO Office Action in U.S. Appl. No. 12/685,652 dated Apr. 26, 2013.
PCT International Preliminary Report on Patentability based on PCT/2011/043185 dated Jun. 25, 2013.
USPTO Office Action in U.S. Appl. No. 13/740,876 dated Jul. 12, 2013.
USPTO Office Action in U.S. Appl. No. 13/709,531 dated Jul. 17, 2013.
USPTO Office Action in U.S. Appl. No. 13/770,676 dated Sep. 6, 2013.
USPTO Office Action in U.S. Appl. No. 13/177,981 dated Nov. 18, 2013.
USPTO Office Action in U.S. Appl. No. 13/740,807 dated Dec. 5, 2013.
USPTO Office Action in U.S. Appl. No. 13/594,223 dated Jan. 13, 2014.
PCT International Search Report based on PCT/US13/56440 dated Jan. 22, 2014.
USPTO Office Action in U.S. Appl. No. 13/770,706 dated Jan. 27, 2014.
USPTO Office Action in U.S. Appl. No. 13/177,981 dated Mar. 21, 2014.
USPTO Office Action in U.S. Appl. No. 13/709,531 dated Apr. 4, 2014.
Extended European Search Report issued in European Application No. EP 11804335 dated Apr. 17, 2014.
USPTO Office Action in U.S. Appl. No. 13/177,981 dated Jun. 26, 2014.
USPTO Office Action in U.S. Appl. No. 13/594,223 dated Jun. 26, 2014.
USPTO Office Action in U.S. Appl. No. 13/709,531 dated Jul. 10, 2014.
PCT International Search Report based on PCT/US14/65058 dated Jan. 26, 2015.
PCT International Search Report based on PCT/US14/65054 dated Jan. 29, 2015.
USPTO Office Action in U.S. Appl. No. 14/100,515 dated Feb. 12, 2015.
USPTO Office Action in U.S. Appl. No. 13/594,223 dated Feb. 13, 2015.
USPTO Office Action in U.S. Appl. No. 13/594,223 dated Apr. 19, 2016.
Supplementary European Search Report issued in European Application No. EP 12883358 dated May 6, 2016.
Supplementary European Search Report issued in European Application No. EP 13830535 dated Jun. 24, 2016.
USPTO Office Action in U.S. Appl. No. 15/250,021 dated Mar. 22, 2017.
USPTO Office Action in U.S. Appl. No. 13/594,223 dated Mar. 23, 2017.
USPTO Office Action in U.S. Appl. No. 15/250,117 dated Mar. 23, 2017.
Ivashchenko, A.V.; Frolov et al., Izvestiya Vysshikh Uchebnyka Zavedenii, Khimiya i KhimicheskayaTekhnologiya, 52(10), pp. 55-60 (2009).
Kumar, Arun Babu et al., Bioorganic & Medicinal Chemistry Letters, 22(14), pp. 4740-4744 (2012).
USPTO Office Action in U.S. Appl. No. 13/974,642 dated Sep. 14, 2016.
USPTO Office Action in U.S. Appl. No. 13/594,223 dated Dec. 6, 2016.
USPTO Office Action in U.S. Appl. No. 14/996,596 dated Dec. 27, 2016.
Registry Entry 325696-14-8 IEntered STN: Mar. 5, 2001).
Jeppeson (CAPLUS Abstract 2000:277964 (Apr. 27, 2000)).
Naumova (CAPLUS Abstract 1989:94923 (1988)).
Kamagowa (CAPLUS Abstract 1979:138254 (1979)).
USPTO Office Action in U.S. Appl. No. 15/250,021 dated Aug. 22, 2017.

\* cited by examiner

A

B

C

NEUROPROTECTIVE COMPOUNDS AND USE THEREOF

CROSS-REFERENCE TO RELATED APPLICATIONS

This application is a U.S. National Phase application of International Application No. PCT/US2014/065054 filed Nov. 11, 2014, which claims the benefit of and priority to U.S. Provisional Patent Application Nos. 61/902,680 filed Nov. 11, 2013, 61/912,625 filed Dec. 6, 2013 and 62/002,961 filed May 26, 2014, the entire disclosures of all of which are hereby incorporated by reference.

STATEMENT REGARDING FEDERALLY SPONSORED RESEARCH

This invention was made with government support under Grant No. 5-R01-MH087986 awarded by the National Institute of Mental Health and Grant Nos. 1R21MH100086-01 and 5R01NS064159-05 awarded by the National Institute of Health; the Government has certain rights in the invention.

FIELD

This disclosure relates to neuroprotective compounds and their use in reducing neuronal cell death, promoting neurogenesis, preserving axonal integrity and/or reducing axonal degeneration associated with various diseases.

BACKGROUND

It is now accepted that the adult vertebrate brain fosters the birth and functional incorporation of newly formed neurons (Goldman and Nottebohm, Proc Natl Acad Sci USA 1983, 80: 2390-2394; Paton and Nottebohm, Science 1984, 225, 1046-1048; Burd and Nottebohm, J Comp Neurol 1985, 240:143-152). However, it was long thought that no new neurons could be added to the adult mammalian brain. This dogma was challenged in the 1960's when autoradiographic evidence of new neuron formation in the hippocampal dentate gyrus, olfactory bulb, and cerebral cortex of the adult rat was presented (Altman, J. Science 1962, 135, 1127-1128; Altman, J. J Comp Neurol 1966, 128:431-474; Altman, Anat Rec 1963, 145:573-591; Altman and Das, J. Comp. Neurol. 1965, 124, 319-335; Altman and Das, J Comp Neurol 1966, 126:337-390). It is now accepted that within all mammalian species, including humans (Eriksson et al., Nat. Med. 1998, 4(11), 1313-1317), there are two major reservoirs of neuronal stem cells, one located in the subgranular zone (SGZ) of the hippocampal dentate gyrus and another in the subventricular zone (SVZ) (Gross, Natl. Rev. 2000, 1, 67-72). Neural stem cells in the SVZ facilitate formation of new neurons that migrate rostrally to populate the olfactory bulb, while neural stem cells in the SGZ produce neurons that integrate locally in the granular layer of the dentate gyrus, a region of the hippocampus that exhibits lifelong structural and functional plasticity.

The process of new neuron formation in the adult mouse brain can be influenced by environmental, chemical and genetic variables. As demonstrated by Gage and colleagues, neurogenesis in the adult mouse brain is enhanced when animals are exposed to an enriched environment (Kempermann et al., Nature 1997, 386, 493-495) or able to exercise voluntarily (van Praag et al., Nat. Neuro-sci. 1999, 2, 266-270). More recently, anti-depressant drugs have been shown to enhance levels of adult neurogenesis in animals, including humans (Schmidt et al., Behav Pharmacol. 2007 September; 18(5-6):391-418; Boldrini et al., Neuropsychopharmacology 2009, 34, 2376-2389). Among many genes reported to impact adult neurogenesis is the gene encoding neuronal PAS domain protein 3 (NPAS3), a central nervous system (CNS)-specific transcription factor that has been associated with schizophrenia and bipolar disorder (Kamnasaran et al., J. Med. Genet. 2003, 40, 325-332; Pickard et al., Am. J. Med. Genet. B. Neuropsychiatr. Genet. 2005, 136B, 26-32; Pickard et al., Ann. Med. 2006, 38, 439-448; Pickard et al., Mol. Psychiatry 2009, 14, 874-884; Lavedan et al., *Pharmacogenomics* 2008, 9: 289-301). Animals missing both copies of the NPAS3 gene suffer a profound loss of adult hippocampal neurogenesis coupled with significant behavioral deficits (Pieper et al., Proc. Natl. Acad. Sci. USA 2005, 102, 14052-14057). Knowing that impaired post-natal neurogenesis elicits unfavorable phenotypic deficits, it is predicted that pro-neurogenic chemical compounds should exhibit favorable therapeutic benefits for a variety of neuropsychiatric and neurodegenerative diseases.

Neurodegenerative diseases currently affect millions of people worldwide, and the incidence of disease is rapidly increasing as the aging population expands. The magnitude and trend of this problem places a growing human and financial strain on healthcare systems, which is exacerbated by the absence of effective treatments for many of the most common afflictions.

Neurodegenerative diseases, such as amyotrophic lateral sclerosis (ALS) and Parkinson's disease (PD), traumatic brain injury (PDI) and normal age-related cognitive decline, feature, by definition, neuronal cell death. Thus, there remains a great need for small molecules that could prevent the death of neurons in a variety of in vivo contexts. Such neuroprotective agents could possess general utility for treating disorders associated with neuron cell death and other causes.

SUMMARY

This invention relates generally to compounds that promote survival of existing neurons, reduce neuronal cell death, protect neurons from axonal degeneration, and/or promote neurogenesis in the mammalian brain. For the purpose of simplicity these compounds are referred to as being neuroprotective. In certain embodiments, the compounds promote survival and integrity of neurons in the post-natal mammalian brain. In certain embodiments, the compounds are neuroprotective, e.g., they promote the survival, health, integrity, growth, development and/or function of neurons, and/or protect neurons from cell death, apoptosis and/or degeneration, and/or stimulate neurogenesis, particularly CNS, brain, cerebral, and hippocampal neurons. In certain embodiments, the compounds stimulate post-natal hippocampal neurogenesis, reduce neuronal cell death, and/or protect neurons from axonal degeneration, which while not wishing to be bound by theory, is believed to represent a therapeutic target useful for treating a variety of diseases.

Provided herein, in one aspect, is a method for reducing axonal degeneration and/or neuronal cell death, promoting neurogenesis, and/or maintaining neuron health or integrity. The method includes administering an effective amount of a compound of formula (I) (also referred to as "P7C3 class" of compounds), or a pharmaceutically acceptable salt thereof, to a patient in need thereof:

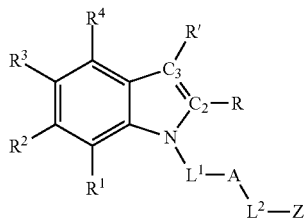

(I)

wherein:
each of $R^1$, $R^2$, $R^3$, and $R^4$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —NH($C_1$-$C_6$ alkyl), —N($C_1$-$C_6$ alkyl)$_2$, —NHC(O)($C_1$-$C_6$ alkyl), nitro, —C(O)O($C_1$-$C_6$ alkyl), —C(O)$NH_2$, —C(O)NH($C_1$-$C_6$ alkyl), —C(O)N($C_1$-$C_6$ alkyl)$_2$, —S(O)$_2$$NH_2$, —S(O)$_2$NH($C_1$-$C_6$ alkyl), and —S(O)$_2$N($C_1$-$C_6$ alkyl)$_2$;
R and R' are defined according to (1), (2), (3) or (4) below:
(1) R and R' together with $C_2$ and $C_3$, respectively, form a fused phenyl ring having formula (II):

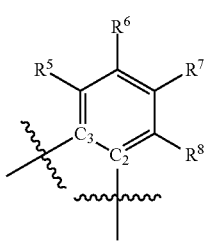

(II)

wherein each of $R^5$, $R^6$, $R^7$, and $R^8$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —NH($C_1$-$C_6$ alkyl), —N($C_1$-$C_6$ alkyl)$_2$, —NHC(O)($C_1$-$C_6$ alkyl), nitro, —C(O)O($C_1$-$C_6$ alkyl), —C(O)$NH_2$, —C(O)NH($C_1$-$C_6$ alkyl), —C(O)N($C_1$-$C_6$ alkyl)$_2$, —S(O)$_2$$NH_2$, —S(O)$_2$NH($C_1$-$C_6$ alkyl), and —S(O)$_2$N($C_1$-$C_6$alkyl)$_2$; or
(2) R and R' together with $C_2$ and $C_3$, respectively, form a fused heteroaryl ring containing 6 ring atoms, wherein from 1-2 independently selected ring atoms is N; and wherein said heteroaryl ring is optionally substituted with from 1-2 independently selected $R^b$; or
(3) R and R' together with $C_2$ and $C_3$, respectively, form a fused heterocyclic ring containing from 5-6 ring atoms, wherein from 1-2 of the ring atoms is independently selected from N, NH, N($C_1$-$C_6$ alkyl), NC(O)($C_1$-$C_6$ alkyl), O, and S; and wherein said heterocyclic ring is optionally substituted with from 1-3 independently selected $R^a$; or
(4) each of R and R' is, independently, hydrogen, $C_1$-$C_6$ alkyl, or $C_1$-$C_6$ haloalkyl; each of $L^1$ and $L^2$ is, independently, $C_1$-$C_3$ alkylene, which is optionally substituted with from 1-2 independently selected $R^c$;
A is:
(i) $CR^{41}R^{42}$, wherein each of $R^{41}$ and $R^{42}$ is independently selected from hydrogen, halo, $C_1$-$C_3$ alkyl, $OR^9$, wherein $R^9$ is hydrogen or $C_1$-$C_3$ alkyl that is optionally substituted with hydroxyl or $C_1$-$C_3$ alkoxy, or a double bond formed between A and one of $L^1$ and $L^2$; or
(ii) C=O; or
(iii) $C_3$-$C_5$cycloalkylene that is (a) substituted with 1 oxo; and (b) optionally further substituted with from 1-4 independently selected $R^a$; or
(iv) heterocycloalkylene containing from 3-5 ring atoms, wherein from 1-2 of the ring atoms is independently selected from N, NH, N($C_1$-$C_3$ alkyl), O, and S; and wherein said heterocycloalkylene is (a) substituted with 1 oxo; and (b) is optionally further substituted with from 1-4 independently selected $R^a$;
Z is:
(i) —$NR^{10}R^{11}$; or
(ii) —C(O)$NR^{10}R^{11}$; or
(iii) —$OR^{12}$; or
(iv) —S(O)$_n$$R^{13}$, wherein n is 0, 1, or 2; or
(v) heterocycloalkenyl containing from 5-6 ring atoms, wherein from 1-3 of the ring atoms is independently selected from N, NH, N($C_1$-$C_6$ alkyl), NC(O)($C_1$-$C_6$ alkyl), O, and S; and wherein said heterocycloalkenyl is optionally substituted with from 1-4 independently selected $R^a$; or
(vi) $C_6$-$C_{10}$ aryl that is optionally substituted with from 1-4 independently selected $R^b$; or
(vii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 independently selected $R^b$; or
(viii) $C_8$-$C_{14}$ arylcycloalkyl, wherein:
  (1) the aryl portion is optionally substituted with from 1-4 independently selected $R^b$, and
  (2) the cycloalkyl portion is optionally substituted with from 1-4 independently selected $R^a$; or
(ix) arylheterocyclyl containing from 8-14 ring atoms, wherein:
  (1) the aryl portion from is optionally substituted with from 1-4 independently selected $R^b$, and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$; or
(x) heteroarylheterocyclyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$; or
(xi) heteroarylcycloalkyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) the cycloalkyl portion is optionally substituted with from 1-4 independently selected $R^a$;

each of $R^{10}$ and $R^{11}$ is independently selected from the substituents delineated collectively in (a) through (l) below:
(a) hydrogen;
(b) $C_6$-$C_{10}$ aryl that is optionally substituted with from 1-4 $R^b$;
(c) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;
(d) $C_1$-$C_6$ alkyl or $C_1$-$C_6$ haloalkyl, each of which is optionally substituted with from 1-3 $R^d$;
(e) —C(O)($C_1$-$C_6$ alkyl), —C(O)($C_1$-$C_6$ haloalkyl), —C(O)O($C_1$-$C_6$ alkyl), —S(O)$_2$($C_1$-$C_6$ alkyl), —S(O)$_2$($C_6$-$C_{10}$ aryl), or —S(O)$_2$($C_1$-$C_{13}$ heteroaryl), wherein the $C_6$-$C_{10}$ aryl and $C_1$-$C_{13}$ heteroaryl are each independently optionally substituted with 1-4 $R^b$;
(f) $C_2$-$C_6$ alkenyl or $C_2$-$C_6$ alkynyl;
(g) $C_8$-$C_{14}$ arylcycloalkyl, wherein:
  (1) the aryl portion is optionally substituted with from 1-4 independently selected $R^b$, and
  (2) the cycloalkyl portion is optionally substituted with from 1-4 independently selected $R^a$;
(h) arylheterocyclyl containing from 8-14 ring atoms, wherein:
  (1) the aryl portion from is optionally substituted with from 1-4 independently selected $R^b$, and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
(i) heteroarylheterocyclyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
(j) heteroarylcycloalkyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) the cycloalkyl portion is optionally substituted with from 1-4 independently selected $R^a$;
(k) $C_3$-$C_8$ cycloalkyl or $C_3$-$C_8$ cycloalkenyl, each of which is optionally substituted with from 1-4 independently selected $R^a$; and
(l) $C_7$-$C_{12}$ aralkyl, wherein the aryl portion is optionally substituted with from 1-4 independently selected $R^b$, provided that one of $R^{10}$ and $R^{11}$ must be selected from (b), (c), (g), (h), (i), (j), and (k);
$R^{12}$ is:
(i) $C_6$-$C_{10}$ aryl that is optionally substituted with from 1-4 $R^b$; or
(ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$; or
(iii) $C_1$-$C_6$ alkyl or $C_1$-$C_6$ haloalkyl, each of which is substituted with from 1-3 $R^d$; or
(iv) $C_8$-$C_{14}$ arylcycloalkyl, wherein:
  (1) the aryl portion is optionally substituted with from 1-4 independently selected $R^b$, and
  (2) the cycloalkyl portion is optionally substituted with from 1-4 independently selected $R^a$; or
(v) arylheterocyclyl containing from 8-14 ring atoms, wherein:
  (1) the aryl portion from is optionally substituted with from 1-4 independently selected $R^b$, and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$; or
(vi) heteroarylheterocyclyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;

or
(vii) heteroarylcycloalkyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) the cycloalkyl portion is optionally substituted with from 1-4 independently selected $R^a$;
$R^{13}$ is:
(i) $C_6$-$C_{10}$ aryl that is optionally substituted with from 1-4 $R^b$; or
(ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$; or
(iii) $C_8$-$C_{14}$ arylcycloalkyl, wherein:
  (1) the aryl portion is optionally substituted with from 1-4 independently selected $R^b$, and
  (2) the cycloalkyl portion is optionally substituted with from 1-4 independently selected $R^a$;
or
(iv) arylheterocyclyl containing from 8-14 ring atoms, wherein:
  (1) the aryl portion from is optionally substituted with from 1-4 independently selected $R^b$, and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(v) heteroarylheterocyclyl containing from 8-14 ring atoms, wherein:

(1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;

or (vi) heteroarylcycloalkyl containing from 8-14 ring atoms, wherein:

(1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and (2) the cycloalkyl portion is optionally substituted with from 1-4 independently selected $R^a$;

$R^a$ at each occurrence is, independently selected from halo, hydroxyl, $C_1$-$C_6$ alkoxy, $C_1$-$C_6$ thioalkoxy, $C_1$-$C_6$ haloalkoxy, $C_1$-$C_6$ thiohaloalkoxy, oxo, thioxo, =NH, =N($C_1$-$C_6$ alkyl), $C_1$-$C_6$ alkyl, $C_1$-$C_6$ haloalkyl, —$NH_2$, —NH($C_1$-$C_6$ alkyl), —N($C_1$-$C_6$ alkyl)$_2$, —NHC(O)($C_1$-$C_6$ alkyl), and cyano;

$R^b$ at each occurrence is independently selected from the substituents delineated in (aa) through (dd) below:

(aa) $C_1$-$C_6$ alkoxy; $C_1$-$C_6$ haloalkoxy; $C_1$-$C_6$ thioalkoxy; $C_1$-$C_6$ thiohaloalkoxy; —O—($CH_2$)$_{1-3}$—[O($CH_2$)$_{1-3}$]$_{1-3}$—H; —$C_1$-$C_6$ alkyl, $C_1$-$C_6$ haloalkyl, —NH($C_1$-$C_6$ alkyl), —N($C_1$-$C_6$ alkyl)$_2$, —NHC(O)($C_1$-$C_6$ alkyl), wherein the alkyl portion of each is optionally substituted with from 1-3 independently selected $R^e$;

(bb) halo; hydroxyl; cyano; nitro; —$NH_2$; azido; sulfhydryl; $C_2$-$C_6$ alkenyl; $C_2$-$C_6$ alkynyl; —C(O)H; —C(O)($C_1$-$C_6$ alkyl); —C(O)($C_1$-$C_6$ haloalkyl); —C(O)OH; —C(O)O($C_1$-$C_6$ alkyl); —C(O)$NH_2$; —C(O)NH($C_1$-$C_6$ alkyl); —C(O)N($C_1$-$C_6$alkyl)$_2$; —$SO_2$($C_1$-$C_6$ alkyl); —$SO_2$$NH_2$; —$SO_2$NH($C_1$-$C_6$ alkyl); —$SO_2$N($C_1$-$C_6$ alkyl)$_2$;

(cc) $C_3$-$C_6$ cycloalkyl or heterocyclyl containing from 5-6 ring atoms, wherein from 1-2 of the ring atoms of the heterocyclyl is independently selected from N, NH, N($C_1$-$C_6$ alkyl), NC(O)($C_1$-$C_6$ alkyl), O, and S; and wherein each of said phenyl and heterocyclyl is optionally substituted with from 1-3 independently selected $R^a$; and (dd) phenyl or heteroaryl containing from 5-6 ring atoms, wherein from 1-2 of the ring atoms of the heteroaryl is independently selected from N, NH, N($C_1$-$C_3$ alkyl), O, and S; wherein each of said phenyl and heteroaryl is optionally substituted with from 1-3 substituents independently selected from halo; hydroxyl; cyano; nitro; —$NH_2$; —NH($C_1$-$C_6$ alkyl), —N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl;

$R^c$ at each occurrence is, independently selected from halo, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —NHC(O)($C_1$-$C_6$ alkyl), and cyano;

$R^d$ at each occurrence is, independently selected from hydroxyl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —NHC(O)($C_1$-$C_6$ alkyl), and cyano; and $R^e$ at each occurrence is, independently selected from hydroxyl, $C_1$-$C_6$ alkoxy; $C_1$-$C_6$ thioalkoxy; $C_1$-$C_6$ haloalkoxy; $C_1$-$C_6$ thiohaloalkoxy; —$NH_2$; —NH($C_1$-$C_6$ alkyl); —N($C_1$-$C_6$ alkyl)$_2$; —NHC(O)($C_1$-$C_6$ alkyl); cyano; —C(O)H; —C(O)($C_1$-$C_6$ alkyl); —C(O)($C_1$-$C_6$ haloalkyl); —C(O)OH; —C(O)O($C_1$-$C_6$ alkyl); —C(O)$NH_2$; —C(O)NH($C_1$-$C_6$ alkyl); —C(O)N($C_1$-$C_6$alkyl)$_2$; —$SO_2$($C_1$-$C_6$ alkyl); —$SO_2$$NH_2$; —$SO_2$NH($C_1$-$C_6$ alkyl); —$SO_2$N($C_1$-$C_6$alkyl)$_2$; and $L^3$-($C_1$-$C_6$ alkylene)-biotin, where in $L^3$ is a —O—, —NH—, —$NCH_3$—, —C(O)—, —C(O)NH—, —C(O)$NCH_3$—, —NHC(O)—, or —$NCH_3$C(O)—.

In some embodiments, one or more of (A), (B), or (C) apply:

(A) Provided that when R and R' are defined according to definition (3), then:

(i) each of $L^1$ and $L^2$ must be $C_1$-$C_3$ alkylene, which is optionally substituted with from 1-2 independently selected $R^c$ when A is $CH_2$; or (ii) -$L^1$-A-$L^2$- cannot be —$CH_2$—$CH_2$— when Z is 2-methylpyridyl; or (iii) Z must be other than heteroaryl containing from 5-14 (e.g., 5-6 or 6) ring atoms, wherein from 1-6 of the ring atoms is independently selected from N, NH, N($C_1$-$C_3$ alkyl), O, and S; and wherein said heteroaryl is optionally substituted with from 1-4 independently selected $R^b$; e.g., Z is other than substituted pyridyl, e.g., other than pyridyl substituted with $C_1$-$C_3$ alkyl (e.g., $CH_3$), e.g., other than 2 or 6-methylpyridyl.

(B) Each of $R^{10}$ and $R^{11}$ cannot be optionally substituted naphthyl (e.g., each of $R^{10}$ and $R^{11}$ cannot be unsubstituted naphthyl). In embodiments, each of $R^{10}$ and $R^{11}$ is other than optionally substituted naphthyl (e.g., unsubstituted naphthyl) when R and R' are defined according to definitions (1), (2), and (4); and A is $CR^{41}R^{42}$ (e.g., $CHOR^9$, e.g., CHOH), and each of $L^1$ and $L^2$ is $C_1$-$C_3$ alkylene (e.g., each of $L^1$ and $L^2$ is $CH_2$).

(C) $R^{12}$ and/or $R^{13}$ cannot be substituted phenyl. In embodiments, $R^{12}$ and/or $R^{13}$ cannot be substituted phenyl when R and R' are defined according to definition (1); and A is $CR^{41}R^{42}$ (e.g., $CHOR^9$, e.g., CHOH), and each of $L^1$ and $L^2$ is $C_1$-$C_3$ alkylene (e.g., each of $L^1$ and $L^2$ is $CH_2$).

In some embodiments, (A), (B), or (C) applies. In other embodiments, (A) and (B); or (A) and (C); or (B) and (C) applies. In still other embodiments, (A), (B), and (C) apply.

In certain embodiments, the compounds are of formula (III):

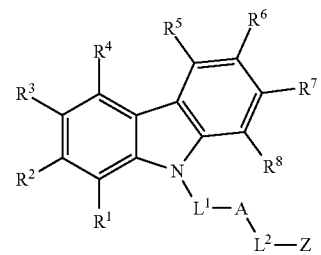

in which $R^1$, $R^2$, $R^3$, $R^4$, $L^1$, $L^2$, A, and Z can be as defined anywhere herein.

In some embodiments, one or more of the following can apply:

each of $L^1$ and $L^2$ is $CH_2$;

A is $CR^{A1}R^{A2}$, wherein one of $R^{A1}$ and $R^{A2}$ is halo (e.g., fluoro) or $OR^9$, and the other is hydrogen;

Z is $-NR^{10}R^{11}$; and each of $R^{10}$ and $R^{11}$ is independently selected from:
(a) hydrogen;
(b) $C_6$-$C_{10}$ aryl that is optionally substituted with from 1-4 $R^b$;
(c) heteroaryl containing from 5-14 ring atoms, wherein from 1-6 of the ring atoms is independently selected from N, NH, N($C_1$-$C_3$ alkyl), O, and S, and wherein said heteroaryl is optionally substituted with from 1-4 $R^b$; e.g., pyridyl optionally substituted with 1 $R^b$; e.g., 2-methoxypyridyl;
(d) $C_1$-$C_6$ alkyl or $C_1$-$C_6$ haloalkyl, each of which is optionally substituted with from 1-3 $R^d$;
(f) $C_2$-$C_6$ alkenyl or $C_2$-$C_6$ alkynyl.

In embodiments, one or more of the following may apply:
provided that $R^3$ and $R^6$ cannot both be hydrogen when A is $CH_2$, and R and R' are defined according to definition (1);
provided that $R^3$ cannot be hydrogen when A is $CH_2$, and R and R' are defined according to definition (2);
provided that $R^3$ and $R^6$ cannot both be chloro when A is $CH_2$, R and R' are defined according to definition (1), Z is $-OR^{12}$, and $R^{12}$ is unsubstituted phenyl;
provided that $R^3$ and $R^6$ cannot both be bromo when A is $CH_2$, R and R' are defined according to definition (1), Z is $-OR^{12}$, and $R^{12}$ is phenyl that is substituted with pyridyl or alkyl that is substituted with from 1-3 $R^e$;
provided that $R^3$ and $R^6$ cannot both be hydrogen when A is $CH(CH_3)$, R and R' are defined according to definition (1), Z is $NR^{10}R^{11}$, $R^{10}$ is $CH_3$, and $R^{11}$ is unsubstituted phenyl;
provided that when A is $CR^{A1}R^{A2}$, and one of $R^{A1}$ and $R^{A2}$ is OH (i.e., $R^9$ is H), then the other of $R^{A1}$ and $R^{A2}$ is $C_1$-$C_3$ alkyl.

In certain embodiments, one or more of the following apply, e.g., when A is CHOH and Z is $NR^{10}R^{11}$:
each of $R^3$ and $R^6$ is $CH_3$; and/or each of $R^3$ and $R^6$ is bromo; and/or each of $R^3$ and $R^6$ is chloro; and/or one of $R^3$ and $R^6$ is $CH_3$ (e.g., $R^6$), and the other is bromo (e.g., $R^3$);
each of $R^{10}$ and $R^{11}$ is other than hydrogen;
each of $R^{10}$ and $R^{11}$ is hydrogen;
one of $R^{10}$ and $R^{11}$ is heteroaryl (optionally substituted) as defined herein; and
$L^1$ and/or $L^2$ is $C_2$-$C_3$ alkylene (optionally substituted).

In certain embodiments, when $R^3$ and $R^6$ are both halo, one of $R^{A1}$ and $R^{A2}$ is OH and the other is hydrogen, Z is $-NHR^{10}$, and $R^{10}$ is $C_6$-$C_{10}$ aryl that is optionally substituted with 1 to 4 $R^b$, then $R^{10}$ is unsubstituted phenyl or phenyl substituted with 1 $R^b$.

In some embodiments, one of $R^{10}$ and $R^{11}$ must be (b) or (c).

The compound, in some embodiments, can be (+) or (−) (dextrorotatory) when in the presence of plane polarized light. In some embodiments, the (+) (dextrorotatory) compound can be substantially free of (e.g., containing less than about 5% of, less than about 2% of, less than about 1%, less than about 0.5%) a compound that is (levorotatory). In some embodiments, the (−) (levorotatory) compound can be substantially free of (e.g., containing less than about 5% of, less than about 2% of, less than about 1%, less than about 0.5%) a compound that is (+) (dextrorotatory).

In embodiments, the carbon attached to $R^{A1}$ and $R^{A2}$ is substituted with four different substituents (for purposes of clarification, these four substituents include $R^{A1}$ and $R^{A2}$) and is therefore a stereogenic center.

In certain embodiments, the carbon attached to $R^{A1}$ and $R^{A2}$ is (R) configured, meaning that the carbon attached to $R^{A1}$ and $R^{A2}$ has the (R) configuration (Cahn Ingold Prelog sequence rules notation). Such compounds are sometimes referred to herein as an "(R)-configured compound" (this term also includes compounds that further contain one or more stereogenic centers in addition to the (R)-$CR^{A1}R^{A2}$ stereogenic center). In other embodiments, the carbon attached to $R^{A1}$ and $R^{A2}$ is (S) configured, meaning that the carbon attached to $R^{A1}$ and $R^{A2}$ has the (S) configuration (Cahn Ingold Prelog sequence rules notation). Such compounds are sometimes referred to herein as an "(S)-configured compound" (this term also includes compounds that further contain one or more stereogenic centers in addition to the (S)-$CR^{A1}R^{A2}$ stereogenic center). In embodiments, the (R) configured compound (or salt, e.g., a pharmaceutically acceptable salt, thereof) is substantially free of (e.g., contains less than about 5% of, less than about 2% of, less than about 1%, less than about 0.5% of) a compound (or salt thereof as described herein) that is (S) configured at the carbon attached to $R^{A1}$ and $R^{A2}$ (i.e., a compound in which the carbon attached to $R^{A1}$ and $R^{A2}$ has the (S) configuration). For example, the (R) configured compound can be an (R)-enantiomer that is substantially free of its opposing (S) enantiomer. As another example, an (R) configured compound can be substantially free of a diastereomer in which the carbon attached to $R^{A1}$ and $R^{A2}$ has the (S) configuration. In certain embodiments, the (R) configured compound can be additionally in substantially pure form (e.g., contains less than about 5% of, less than about 2% of, less than about 1%, less than about 0.5% of other substances, including, for example, one or more of other compounds). In embodiments, the (S) configured compound (or salt, e.g., a pharmaceutically acceptable salt, thereof) is substantially free of (e.g., contains less than about 5% of, less than about 2% of, less than about 1%, less than about 0.5% of) a compound (or salt thereof as described herein) that is (R) configured at the carbon attached to $R^{A1}$ and $R^{A2}$ (i.e., a compound in which the carbon attached to $R^{A1}$ and $R^{A2}$ has the (R) configuration). For example, the (S) configured compound can be an (S)-enantiomer that is substantially free of its opposing (R) enantiomer. As another example, the (S) configured compound can be substantially free of a diastereomer in which the carbon attached to $R^{A1}$ and $R^{A2}$ has the (R) configuration. In certain embodiments, the (S) configured compound can be additionally in substantially pure form (e.g., contains less than about 5% of, less than about 2% of, less than about 1%, less than about 0.5% of other substances, including, for example, one or more of other compounds).

The compound of the present invention can include any one or more compounds selected from:
R-1-(3,6-Dibromo-9H-carbazol-9-yl)-3-(3-methoxyphenylamino)-propan-2-ol;
S-1-(3,6-Dibromo-9H-carbazol-9-yl)-3-(3-methoxyphenylamino)-propan-2-ol;
1-(3,6-dibromo-9H-carbazol-9-yl)-3-(2-iminopyridin-1 (2H)-yl)propan-2-ol;
1-(3,6-dibromo-9H-carbazol-9-yl)-3-(phenylthio)propan-2-ol;
N-(3-(3,6-dibromo-9H-carbazol-9-yl)-2-hydroxypropyl)-N-(3-methoxyphenyl)acetamide;
5-((3,6-dibromo-9H-carbazol-9-yl)methyl)-3-(3-methoxyphenyl)-oxazolidin-2-one;
N-(3-(3,6-dibromo-9H-carbazol-9-yl)-2-fluoropropyl)-3-methoxyaniline;

1-(3,6-dibromo-9H-carbazol-9-yl)-3-(3-methoxyphenylamino)-propan-2-one;
N-(3-(3,6-dibromo-9H-carbazol-9-yl)-2-methoxypropyl)-3-methoxyaniline;
1-(3,6-Dimethyl-9H-carbazol-9-yl)-3-(3-methoxyphenylamino)propan-2-ol;
1-(3-Bromo-6-methyl-9H-carbazol-9-yl)-3-(3-methoxyphenylamino)-propan-2-ol;
1-(3,6-Dichloro-9H-carbazol-9-yl)-3-(3-methoxyphenylamino)propan-2-ol;
1-(5-bromo-2,3-dimethyl-1H-indol-1-yl)-3-(phenylamino)propan-2-ol;
1-(3,6-Dibromo-9H-pyrido[3,4-b]indol-9-yl)-3-(phenylamino)propan-2-ol;
1-(3-Azidophenylamino)-3-(3,6-dibromo-9H-carbazol-9-yl)propan-2-ol;
1,3-Bis(3,6-dibromo-9H-carbazol-9-yl)propan-2-ol;
1-(9H-Carbazol-9-yl)-3-(3,6-dibromo-9H-carbazol-9-yl)propan-2-ol;
3-(3,6-Dibromo-9H-carbazol-9-yl)-2-hydroxy-N-(3-methoxyphenyl)-propanamide;
Ethyl 5-(2-Hydroxy-3-(3-methoxyphenylamino)propyl)-8-methyl-3,4-dihydro-1H-pyrido[4,3-b]indole-2(5H)-carboxylate;
4-(3,6-dibromo-9H-carbazol-9-yl)-1-(phenylamino)butan-2-ol;
N-(3-(3,6-dibromo-9H-carbazol-9-yl)propyl)aniline;
1-(3,6-dibromo-9H-carbazol-9-yl)-4-(phenylamino)butan-2-ol;
1-(3,6-dibromo-9H-carbazol-9-yl)-3-(pyridin-2-ylamino)propan-2-ol;
1-(3,6-dibromo-9H-carbazol-9-yl)-3-((3-methoxyphenyl)(methyl)-amino)propan-2-ol;
3-(3,6-dibromo-9H-carbazol-9-yl)-1-(3-methoxyphenylamino)-1-(methylthio)propan-2-one;
3-amino-1-(3-(3,6-dibromo-9H-carbazol-9-yl)-2-hydroxypropyl)pyridinium;
1-(3,6-dibromo-9H-carbazol-9-yl)-3-(pyrimidin-2-ylamino)propan-2-ol;
N-(3-(3,6-dibromo-9H-carbazol-9-yl)-2-fluoropropyl)-3-methoxy-N-methylaniline;
1-(3,6-dibromo-9H-carbazol-9-yl)-3-methoxypropan-2-ol;
1-(3,6-dibromo-9H-carbazol-9-yl)-4-phenylbutan-2-ol;
1-(3,6-dibromo-9H-carbazol-9-yl)-3-(1H-indol-1-yl)propan-2-ol;
3-(1-(3-(3,6-dibromo-9H-carbazol-9-yl)-2-hydroxypropyl)-1H-1,2,3-triazol-4-yl)propan-1-ol;
1-(3,6-dibromo-9H-carbazol-9-yl)-3-(3-ethoxyphenylamino)propan-2-ol;
1-(3,6-dibromo-9H-carbazol-9-yl)-3-(3,5-dimethyl-1H-pyrazol-1-yl)propan-2-ol;
1-(3,6-dibromo-9H-carbazol-9-yl)-3-(phenylsulfinyl)propan-2-ol;
1-(3,6-dibromo-9H-carbazol-9-yl)-3-(phenylsulfonyl)propan-2-ol;
1-(3-bromo-9H-carbazol-9-yl)-3-(3-methoxyphenylamino)propan-2-ol;
N-(5-(3-(3-(3,6-dibromo-9H-carbazol-9-yl)-2-hydroxypropylamino)phenoxy)pentyl)-2-(7-(dimethylamino)-2-oxo-2H-chromen-4-yl)acetamide;
1-(3,6-dibromo-9H-carbazol-9-yl)-3-phenoxypropan-2-ol;
N-(2-(3-(3,6-dibromo-9H-carbazol-9-yl)-2-hydroxypropoxy)ethyl)-acetamide;
1-(3,6-dibromo-9H-carbazol-9-yl)-3-(pyridin-3-ylamino)propan-2-ol;
1-(3,6-dibromo-9H-carbazol-9-yl)-3-(pyridin-4-ylamino)propan-2-ol;
1-(2,8-dimethyl-3,4-dihydro-1H-pyrido[4,3-b]indol-5(2H)-yl)-3-(phenylamino)propan-2-ol;
N-(3-(3,6-dibromo-9H-carbazol-9-yl)-2,2-difluoropropyl)-3-methoxyaniline;
1-(3,6-dibromo-9H-carbazol-9-yl)-3-phenoxypropan-2-ol;
1-(3,6-dibromo-9H-carbazol-9-yl)-3-(phenylamino)propan-2-ol;
1-(3,6-dibromo-9H-carbazol-9-yl)-3-(o-tolylamino)propan-2-ol;
1-(3,6-dibromo-9H-carbazol-9-yl)-3-(m-tolylamino)propan-2-ol;
1-(3,6-dibromo-9H-carbazol-9-yl)-3-(2-methoxyphenylamino)propan-2-ol;
1-(3,6-dibromo-9H-carbazol-9-yl)-3-(naphthalen-1-ylamino)propan-2-ol;
1-(4-bromophenylamino)-3-(3,6-dichloro-9H-carbazol-9-yl)propan-2-ol;
1-(4-bromophenylamino)-3-(3,6-dibromo-9H-carbazol-9-yl)propan-2-ol;
1-(3,6-dibromo-9H-carbazol-9-yl)-3-(4-ethoxyphenylamino)propan-2-ol;
1-(4-chlorophenylamino)-3-(3,6-dibromo-9H-carbazol-9-yl)propan-2-ol;
1-(3,6-dibromo-9H-carbazol-9-yl)-3-(phenethylamino)propan-2-ol;
1-(3,6-dibromo-9H-carbazol-9-yl)-3-(2-hydroxyethylamino)propan-2-ol;
1-(3,6-dibromo-9H-carbazol-9-yl)-3-(2,4-dimethoxyphenylamino)propan-2-ol;
1-(3,6-dibromo-9H-carbazol-9-yl)-3-(2,3-dimethylphenylamino)propan-2-ol;
1-(2-chlorophenylamino)-3-(3,6-dibromo-9H-carbazol-9-yl)propan-2-ol;
1-(tert-butylamino)-3-(3,6-dibromo-9H-carbazol-9-yl)propan-2-ol;
1-(3,6-dibromo-9H-carbazol-9-yl)-3-(isopropylamino)propan-2-ol;
1-(3,6-dibromo-9H-carbazol-9-yl)-3-(4-methoxyphenylamino)propan-2-ol;
1-(3,6-dibromo-9H-carbazol-9-yl)-3-(3-methoxyphenylamino)propan-2-ol;
1-(3,6-dibromo-9H-carbazol-9-yl)-3-(m-tolylamino)propan-2-ol;
1-(3,6-dibromo-9H-carbazol-9-yl)-3-(3,5-dimethylphenylamino)propan-2-ol;
1-(3,6-dibromo-9H-carbazol-9-yl)-3-(3,4-dimethylphenylamino)propan-2-ol;
1-(3,6-dibromo-9H-carbazol-9-yl)-3-(3,4-dimethylphenylamino)propan-2-ol;
1-(3,6-dibromo-9H-carbazol-9-yl)-3-(2,5-dimethylphenylamino)propan-2-ol;
1-(4-bromophenylamino)-3-(2,3-dimethyl-1H-indol-1-yl)propan-2-ol;
1-(2,3-dimethyl-1H-indol-1-yl)-3-(4-methoxyphenylamino)propan-2-ol;
1-(2,3-dimethyl-1H-indol-1-yl)-3-(4-ethoxyphenylamino)propan-2-ol;
1-(2,3-dimethyl-1H-indol-1-yl)-3-(p-tolylamino)propan-2-ol;
1-(2,3-dimethyl-1H-indol-1-yl)-3-(phenylamino)propan-2-ol oxalate;
1-(1H-indol-1-yl)-3-(4-methoxyphenylamino)propan-2-ol hydrochloride;
1-(1H-indol-1-yl)-3-(phenylamino)propan-2-ol oxalate;
1-(3,4-dihydro-1H-carbazol-9(2H)-yl)-3-(m-tolylamino)propan-2-ol;
1-(9H-carbazol-9-yl)-3-(phenylamino)propan-2-ol;

1-(3,6-dichloro-9H-carbazol-9-yl)-3-(phenylamino)propan-2-ol;
1-(9H-carbazol-9-yl)-3-(p-tolylamino)propan-2-ol;
1-(3,6-dichloro-9H-carbazol-9-yl)-3-(p-tolylamino)propan-2-ol;
1-(3,6-dibromo-9H-carbazol-9-yl)-3-(p-tolylamino)propan-2-ol;
N-(4-(3-(9H-carbazol-9-yl)-2-hydroxypropoxy)phenyl)acetamide;
1-(9H-carbazol-9-yl)-3-phenoxypropan-2-ol;
1-(9H-carbazol-9-yl)-3-(4-methoxyphenylamino)propan-2-ol;
1-(benzylamino)-3-(9H-carbazol-9-yl)propan-2-ol;
methyl 4-(3-(9H-carbazol-9-yl)-2-hydroxypropoxy)benzoate;
1-(9H-carbazol-9-yl)-3-(4-methoxyphenoxy)propan-2-ol;
1-amino-3-(3,6-dibromo-9H-carbazol-9-yl)propan-2-ol;
(S)-1-(3,6-dibromo-9H-carbazol-9-yl)-3-phenoxypropan-2-ol;
(R)-1-(3,6-dibromo-9H-carbazol-9-yl)-3-phenoxypropan-2-ol;
3,6-dibromo-9-(2-fluoro-3-phenoxypropyl)-9H-carbazole;
1-(3,6-dibromo-9H-carbazol-9-yl)-3-(3-methoxyphenylamino)-2-methylpropan-2-ol;
1-(2,8-dimethyl-3,4-dihydro-1H-pyrido[4,3-b]indol-5(2H)-yl)-3-(3-methoxyphenylamino)propan-2-ol;
1-(4-azidophenylamino)-3-(3,6-dibromo-9H-carbazol-9-yl)propan-2-ol;
1-(3-azido-6-bromo-9H-carbazol-9-yl)-3-(3-methoxyphenylamino)propan-2-ol;
1-(3,6-dibromo-9H-carbazol-9-yl)-3-(4-methoxyphenoxy)propan-2-ol;
1-(3,6-dichloro-9H-carbazol-9-yl)-3-(phenylsulfonyl)propan-2-ol;
3,6-dibromo-9-(2-fluoro-3-(phenylsulfonyl)propyl)-9H-carbazole;
S)-1-(3,6-dibromo-9H-carbazol-9-yl)-3-(phenylsulfonyl)propan-2-ol;
(R)-1-(3,6-dibromo-9H-carbazol-9-yl)-3-(phenylsulfonyl)propan-2-ol;
1-(3,6-dicyclopropyl-9H-carbazol-9-yl)-3-(phenylamino)propan-2-ol;
1-(3,6-diiodo-9H-carbazol-9-yl)-3-(phenylamino)propan-2-ol;
1-(3,6-diethynyl-9H-carbazol-9-yl)-3-(3-methoxyphenylamino) propan-2-ol;
9-(2-hydroxy-3-(3-methoxyphenylamino)propyl)-9H-carbazole-3,6-dicarbonitrile;
N-(3-(3,6-dibromo-9H-carbazol-9-yl)-2-fluoropropyl)aniline;
3,6-dibromo-9-(2,2-difluoro-3-phenoxypropyl)-9H-carbazole;
N-(3-(3,6-dibromo-9H-carbazol-9-yl)-2-fluoropropyl)-4-methoxyaniline;
N-(2-bromo-3-(3,6-dibromo-9H-carbazol-9-yl)propyl)-N-(4-methoxyphenyl)-4-nitrobenzenesulfonamide;
Ethyl 2-(4-(3-(3,6-dibromo-9H-carbazol-9-yl)-2-fluoropropylamino)phenoxy)acetate; and
N-(3-(3,6-dibromo-9H-carbazol-9-yl)-2-fluoropropyl)-4-(2-(2-methoxyethoxy)ethoxy)aniline;
N-(2-(2-(4-(3-(3,6-dibromo-9H-carbazol-9-yl)-2-fluoropropylamino)phenoxy)acetamido)ethyl)-5-(2-oxohexahydro-1H-thieno[3,4-d]imidazol-4-yl)pentanamide;
2-(4-(3-(3,6-dibromo-9H-carbazol-9-yl)-2-fluoropropylamino)phenoxy)-N,N-dimethylacetamide;
2-(4-(3-(3,6-dibromo-9H-carbazol-9-yl)-2-fluoropropylamino)phenoxy)-N-(2-hydroxyethyl)acetamide;
1-(bis(4-bromophenyl)amino)-3-(phenylamino)propan-2-ol;
(E)-3,6-dibromo-9-(3-phenoxyallyl)-9H-carbazole;
(E)-3,6-dibromo-9-(3-phenoxyprop-1-en-1-yl)-9H-carbazole;
1-(3,6-bis(trifluoromethyl)-9H-carbazol-9-yl)-3-(phenylamino)propan-2-ol;
1-(2,8-Dibromo-10,11-dihydro-5H-dibenzo[b,f]azepin-5-yl)-3-(3-methoxyphenylamino)propan-2-ol;
1-(3,6-Dibromo-9H-carbazol-9-yl)-3-(3-methoxyphenylthio)propan-2-ol;
1-(3,6-Dibromo-9H-carbazol-9-yl)-3-(4-methoxyphenylthio)propan-2-ol;
3,6-Dibromo-9-(2-fluoro-3-(3-methoxyphenylthio)propyl)-9H-carbazole;
3,6-Dibromo-9-(2-fluoro-3-(4-methoxyphenylthio)propyl)-9H-carbazole;
3,6-Dibromo-9-(2-fluoro-3-(3-methoxyphenylsulfonyl)propyl)-9H-carbazole;
1-(3,6-Dibromo-9H-carbazol-9-yl)-3-(3-methoxyphenylsulfonyl)propan-2-ol;
3,6-Dibromo-9-(2-fluoro-3-(4-methoxyphenylsulfonyl)propyl)-9H-carbazole;
1-(3,6-Dibromo-9H-carbazol-9-yl)-3-(4-methoxyphenylsulfonyl)propan-2-ol;
3-(3-(3,6-Dibromo-9H-carbazol-9-yl)-2-hydroxypropylthio)phenol;
4-(3-(3,6-Dibromo-9H-carbazol-9-yl)-2-hydroxypropylthio)phenol;
3-(3-(3,6-Dibromo-9H-carbazol-9-yl)-2-hydroxypropylsulfonyl)phenol;
4-(3-(3,6-Dibromo-9H-carbazol-9-yl)-2-hydroxypropylsulfonyl)phenol;
1-(3-Aminophenylthio)-3-(3,6-dibromo-9H-carbazol-9-yl)propan-2-ol;
1-(4-Aminophenylthio)-3-(3,6-dibromo-9H-carbazol-9-yl)propan-2-ol;
1-(3,6-dibromo-9H-carbazol-9-yl)-3-phenoxypropan-2-amine;
N-Benzyl-2-(3-(3-(3,6-dibromo-9H-carbazol-9-yl)-2-hydroxypropylthio)-phenoxy)acetamide;
N-Benzyl-2-(4-(3-(3,6-dibromo-9H-carbazol-9-yl)-2-hydroxypropylthio)-phenoxy)acetamide;
3-(3-(3,6-Dibromo-9H-carbazol-9-yl)-2-fluoropropylsulfonyl)phenol; N-Benzyl-2-(3-(3-(3,6-dibromo-9H-carbazol-9-yl)-2-hydroxypropylsulfonyl)-phenoxy)acetamide;
4-(3-(3,6-Dibromo-9H-carbazol-9-yl)-2-fluoropropylsulfonyl)phenol;
5-(5-(3-(3-(3,6-dibromo-9H-carbazol-9-yl)-2-hydroxypropylamino)phenoxy)pentylcarbamoyl)-2-(6-hydroxy-3-oxo-3H-xanthen-9-yl)benzoic acid;
1-(8-bromo-3,4-dihydro-1H-pyrido[4,3-b]indol-5(2H)-yl)-3-phenoxypropan-2-ol;
1-(8-bromo-2-cyclopropyl-3,4-dihydro-1H-pyrido[4,3-b]indol-5(2H)-yl)-3-phenoxypropan-2-ol;
8-bromo-5-(2-hydroxy-3-phenoxypropyl)-3,4-dihydro-1H-pyrido[4,3-b]indole-2(5H)-carbonitrile;
8-bromo-5-(2-fluoro-3-phenoxypropyl)-2,3,4,5-tetrahydro-1H-pyrido[4,3-b]indole;
1-(cyclohexylamino)-3-(3,6-dibromo-9H-carbazol-9-yl)propan-2-ol;
(9-(2-hydroxy-3-(phenylthio)propyl)-9H-carbazole-3,6-dicarbonitrile;
9-(2-hydroxy-3-phenoxypropyl)-9H-carbazole-3,6-dicarbonitrile;
R-N-(3-(3,6-dibromo-9H-carbazol-9-yl)-2-fluoropropyl)-3-methoxyaniline S-N-(3-(3,6-dibromo-9H-carbazol-9-yl)-2-fluoropropyl)-3-methoxyaniline
N-(2-(3,6-dibromo-9H-carbazol-9-ylethyl)aniline;
2-(6-Amino-3-imino-3H-xanthen-9-yl)-4-(6-(5-(3-(3-(3,6-dibromo-9H-carbazol-9-yl)-2-hydroxypropylamino)phenoxy)pentylamino)-6-oxohexylcarbamoyl)benzoic acid AND 2-(6-amino-3-imino-3H-xanthen-9-yl)-5-(6-(5-(3-(3-(3,6-dibromo-9H-carbazol-9-yl)-2-hydroxypropylamino)phenoxy)pentylamino)-6-oxohexylcarbamoyl)benzoic acid;
1-(8-bromo-2-methyl-3,4-dihydro-1H-pyrido[4,3-b]indol-5(2H)-yl)-3-phenoxypropan-2-ol;
6-((4-bromophenyl)(2-hydroxy-3-phenoxypropyl)amino)nicotinonitrile;
1-(3-(3,6-dibromo-9H-carbazol-9-yl)-2-hydroxypropyl)pyridin-2(1H)-one;
9-(2-hydroxy-3-phenoxypropyl)-9H-carbazole-3-carbonitrile;
tert-butyl (5-(4-((3-(3,6-dibromo-9H-carbazol-9-yl)-2-hydroxypropyl)sulfonyl) phenoxy)pentyl)carbamate;
6-bromo-9-(2-hydroxy-3-phenoxypropyl)-9H-carbazole-3-carbonitrile;
6-bromo-9-(2-hydroxy-3-phenoxypropyl)-9H-carbazole-3-carboxamide;
1-(3,6-dibromo-9H-carbazol-9-yl)-3-(pyridin-2-yloxy)propan-2-ol;
methyl 6-bromo-9-(2-hydroxy-3-phenoxypropyl)-9H-carbazole-3-carboxylate;
6-bromo-9-(2-hydroxy-3-phenoxypropyl)-9H-carbazole-3-carboxylic acid;
6-bromo-9-(2-hydroxy-3-phenoxypropyl)-9H-pyrido[2,3-b]indole-3-carbonitrile;
9-(2-hydroxy-3-phenoxypropyl)-9H-pyrido[2,3-b]indole-3-carbonitrile;
tert-butyl 3-(2-(2-(2-(3-((3-(3,6-dibromo-9H-carbazol-9-yl)-2-hydroxypropyl)amino)phenoxy)ethoxy)ethoxy)ethoxy)propanoate;
1-(3,6-dibromo-1,4-dimethoxy-9H-carbazol-9-yl)-3-(phenylamino)propan-2-ol;
1-(3,6-dibromo-1,8-dimethyl-9H-carbazol-9-yl)-3-(phenylamino)propan-2-ol;
2-(3,6-dibromo-9H-carbazol-9-yl)acetic acid;
1-(6-bromo-3-methoxy-1-methyl-9H-carbazol-9-yl)-3-(phenylamino)propan-2-ol;
1-(4,6-dibromo-3-methoxy-1-methyl-9H-carbazol-9-yl)-3-(phenylamino)propan-2-ol;
1-(3,6-dibromo-4-methoxy-9H-carbazol-9-yl)-3-(phenylamino)propan-2-ol;
9-(2-hydroxy-3-phenoxypropyl)-9H-pyrido[3,4-b]indole-3-carboxylic acid;
6-bromo-9-(2-hydroxy-3-phenoxypropyl)-9H-pyrido[3,4-b]indole-3-carboxylic acid;
ethyl 6-bromo-9-(2-hydroxy-3-phenoxypropyl)-9H-pyrido[3,4-b]indole-3-carboxylate;
9-(2-fluoro-3-phenoxypropyl)-9H-carbazole-3,6-dicarbonitrile;
9-(2-hydroxy-2-methyl-3-phenoxypropyl)-9H-carbazole-3,6-dicarbonitrile;
1-(cyclohexyloxy)-3-(3,6-dibromo-9H-carbazol-9-yl)propan-2-ol;
(E)-N-(3-(3,6-dibromo-9H-carbazol-9-yl)prop-1-en-1-yl)-1,1,1-trifluoro-N-(3-methoxyphenyl)methanesulfonamide;
1-(3,6-dibromo-9H-pyrido[2,3-b]indol-9-yl)-3-phenoxypropan-2-ol;
1-(3,6-dibromo-9H-carbazol-9-yl)-3-((6-methoxypyridin-2-yl)amino)propan-2-ol;
1-(8-bromo-5H-pyrido[4,3-b]indol-5-yl)-3-phenoxypropan-2-ol;
6-bromo-9-(2-hydroxy-3-phenoxypropyl)-9H-pyrido[3,4-b]indole-3-carboxamide;
8-bromo-5-(2-hydroxy-3-phenoxypropyl)-5H-pyrido[4,3-b]indole 2-oxide;
8-bromo-5-(2-hydroxy-3-phenoxypropyl)-5H-pyrido[3,2-b]indole 1-oxide;
(6-bromo-9H-pyrido[3,4-b]indol-3-yl)methanol;
ethyl 6-bromo-9H-pyrido[3,4-b]indole-3-carboxylate;
tert-butyl (3-(3,6-dibromo-9H-carbazol-9-yl)-2-fluoropropyl)carbamate;
2-(3,6-dibromo-9H-carbazol-9-yl)-N-methylacetamide;
3-(3,6-dibromo-9H-carbazol-9-yl)-2-fluoropropan-1-amine hydrochloride;
N-(3-(3,6-dibromo-9H-carbazol-9-yl)-2-fluoropropyl)acetamide;
2-(3,6-dibromo-9H-carbazol-9-yl)propanamide;
6-bromo-9H-pyrido[3,4-b]indole-3-carbonitrile;
6-bromo-3-methyl-9H-pyrido[3,4-b]indole;
methyl (2-(3,6-dibromo-9H-carbazol-9-yl)acetyl)carbamate;
N-(3-(3,6-dibromo-9H-carbazol-9-yl)-2-fluoropropyl)-1,1,1-trifluoro-N-(3-methoxyphenyl)methanesulfonamide;
N-(3-(3,6-dibromo-9H-carbazol-9-yl)-2-fluoropropyl)-6-methoxypyridin-2-amine;
N-(3-(3,6-dibromo-9H-carbazol-9-yl)-2-hydroxypropyl)-1,1,1-trifluoro-N-(3-methoxyphenyl)methanesulfonamide;
1-(3,6-dibromo-9H-carbazol-9-yl)3-((4-methoxybenzyl)(3-methoxyphenyl)amino)propan-2-ol;
N-(3-(3,6-dibromo-9H-carbazol-9-yl)-2-hydroxypropyl)-2,2,2-trifluoroacetamide;
tert-butyl (3-(3,6-dibromo-9H-carbazol-9-yl)-2-hydroxypropyl)carbamate;
5-(2-hydroxy-3-phenoxypropyl)-5H-pyrimido[5,4-b]indole-2-carboxylic acid;
N-(3-(3,6-dibromo-9H-carbazol-9-yl)-2-hydroxypropyl)acetamide;
ethyl (3-(3,6-dibromo-9H-carbazol-9-yl)-2-hydroxypropyl)carbamate;
6-bromo-9-(3-(4-bromophenoxy)-2-hydroxypropyl)-9H-carbazole-3-carbonitrile;
methyl 9-(2-hydroxy-3-phenoxypropyl)-9H-pyrido[3,4-b]indole-3-carboxylate;
N-(3-(3-bromo-6-methyl-9H-carbazol-9-yl)-2-fluoropropyl)-6-methoxypyridin-2-amine;
or a salt (e.g., a pharmaceutically acceptable salt) thereof.

In certain embodiments, the compound or salt is 1-(3,6-dibromo-9H-carbazol-9-yl)-3-(phenylamino)propan-2-ol ("P7C3"), N-(3-(3,6-dibromo-9H-carbazol-9-yl)-2-fluoropropyl)-3-methoxyaniline ("P7C3-A20" or "A20"), N-(3-(3,6-dibromo-9H-carbazol-9-yl)-2-fluoropropyl)-6-methoxypyridin-2-amine ("P7C3-S243"), and/or (−)-N-(3-(3,6-dibromo-9H-carbazol-9-yl)-2-fluoropropyl)-6-methoxypyridin-2-amine ("(−)-P7C3-S243").

In one embodiment, the compound is (−)-P7C3-S243, or a pharmaceutically acceptable salt thereof. It has been surprisingly discovered that the (−)-P7C3-S243, also known as (S)-P7C3-S243, enantiomer displays high activity in the in vivo hippocampal neurogenesis screening assay, while the (+)- or (R)-enantiomer shows little activity. This is unexpected especially given that the hydroxy series of P7C3 compounds show higher activity in the opposite enantiomer. More specifically, higher activity was previously observed in the enantiomer series illustrated in the structure A below. Thus it would have been reasonably expected that the fluorinated P7C3 compounds, such as P7C3-S243 would be active in the same enantiomeric series. In contrast and surprisingly, the active P7C3-S243 enantiomer is the opposite to that of the structure A compounds. It will be recognized that the R/S designation of the compounds represented by structure A will differ depending on the priority of the X substituent according to established rules of chemical nomenclature.

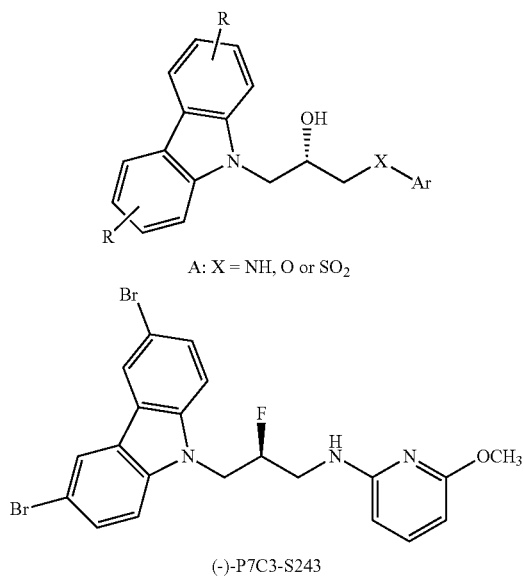

A: X = NH, O or SO₂

(-)-P7C3-S243

Furthermore, both the racemic P7C3-S243 and the (−) enantiomer of P7C3-S243 display activity in protection of mice from MPTP toxicity, a model of Parkinson's disease, and protect rats from toxicity associated with 6-hydroxydopamine (6-OHDA), an alternative model of Parkinson's disease. Importantly, unlike the MPTP model of Parkinson's disease, the 6-OHDA rat model is associated with a motor neuron deficit. In contrast, MPTP treatment does not cause a behavioral phenotype in mice. Thus, it was previously unknown if the protection offered in the MPTP model would translate into reduction of disease symptoms including motor function. Significantly, both A20 and P7C3-S243 display robust protective effect in the 6-OHDA rat model. The racemic P7C3-S243 and the (−) enantiomer of P7C3-S243 also protect mice from cognitive deficit after blast-mediated traumatic brain injury (TBI).

Surprisingly, the racemic P7C3-S243 and the (−) enantiomer of P7C3-S243, also protects neurons from axonal degeneration or injury such as in blast-mediated TBI in mice. This is unexpected because previously P7C3 class of compounds were reported to block cell death, but axonal degeneration or injury is a unique process distinct from cell death, while vitally important to normal functioning of the brain. As such, P7C3-S243 and its analogs or derivatives can be used to treat various diseases caused by or associated with axonal degeneration, such as TBI, concussive injury, crush injury, peripheral neuropathy, diabetic neuropathy, chemotherapy induced neuropathy, and retinal neurodegeneration.

Another surprising finding is that treatment with (−)-P7C3-S243 is not only effective against acute injury, but also after an extended period (e.g., 1 month, 2 months, 3 months, 4 months, 5 months, 6 months, 7 months, 8 months, 9 months, 10 months, 11 months, 1 year, 2 years, 3 years, or any period longer or shorter than these durations) following an injury. Thus, treatment with the P7C3-class of neuroprotective agents can be of therapeutic value for patients suffering from the long term consequences of TBI, who also may have missed the opportunity for acute therapeutic intervention shortly after injury. While not wishing to be bound by theory, one hypothesis is that this protective effect is due to the ability of the compound to enhance the net magnitude of hippocampal neurogenesis, which is important in learning and memory. In contrast, the protective effect immediately after injury is likely due to protecting the brain from axonal degeneration.

In some embodiments, the above compounds (such as a formula (I) or (III) compound, or (−)-P7C3-S243), or a pharmaceutically acceptable salt thereof, can be used to treat a disease such as schizophrenia, major depression, bipolar disorder, normal aging, epilepsy, traumatic brain injury and/or a visual symptom associated therewith, post-traumatic stress disorder, Parkinson's disease, Alzheimer's disease, Down syndrome, spinocerebellar ataxia, amyotrophic lateral sclerosis, Huntington's disease, stroke, radiation therapy, chronic stress, abuse of a neuro-active drug, retinal degeneration, spinal cord injury, peripheral nerve injury, physiological weight loss associated with various conditions, cognitive decline and/or general frailty associated with normal aging and/or chemotherapy, chemotherapy induced neuropathy, concussive injury, crush injury, peripheral neuropathy, diabetic neuropathy, post-traumatic headache, multiple sclerosis, retinal degeneration and dystrophy (such as Leber congenital amaurosis, retinitis pigmentosa, cone-rod dystrophy, microphthalmia, anophthalmia, myopia, and hyperopia), spinal cord injury, traumatic spinal cord injury, peripheral nerve injury (such as peripheral nerve crush injury, neonatal brachial plexus palsy, and traumatic facial nerve palsy), retinal neuronal death related diseases (such as glaucoma and age related macular degeneration, diabetic retinopathy, retinal blood vessel occlusions, retinal medication toxicity (such as what amino glycosides or plaquenil can cause), retinal trauma (e.g., post-surgical), retinal infections, choroidal dystrophies, retinal pigmentary retinopathies, inflammatory and cancer mediated auto immune diseases that result in retinal neuronal cell death), Autism, Stargardt disease, Kearns-Sayre syndrome, Pure neurosensory deafness, Hereditary hearing loss with retinal diseases, Hereditary hearing loss with system atrophies of the nervous system, Progressive spinal muscular atrophy, Progressive bulbar palsy, Primary lateral sclerosis, Hereditary forms of progressive muscular atrophy and spastic paraplegia, Frontotemporal dementia, Dementia with Lewy bodies, Corticobasal degeneration, Progressive supranuclear palsy, Prion disorders causing neurodegeneration, Multiple system atrophy (olivopontocerebellar atrophy), Hereditary spastic paraparesis, Friedreich ataxia, Non-Friedreich ataxia, Spinocerebellar atrophies, Amyloidoses, Metabolic-related (e.g., Diabetes) neurodegenerative disorders, Toxin-related neurodegenerative disorders, Multiple sclerosis, Charcot Marie Tooth, Diabetic neuropathy, Metabolic neuropathies, Endocrine neuropathies, Orthostatic hypotension, Creutzfeldt-Jacob Disease, Primary progressive aphasia, Frontotemporal Lobar Degeneration, Cortical blindness, Shy-Drager Syndrome (Multiple, System Atrophy with Orthostatic Hypotension), Diffuse cerebral cortical atrophy of non-Alzheimer type, Lewy-body dementia, Pick disease (lobar atrophy), Thalamic degeneration, Mesolimbocortical dementia of non-Alzheimer type, Nonhuntingtonian types of chorea and dementia, Cortical-striatal-spinal degeneration, Dementia-Parkinson-amyotrophic lateral sclerosis complex, Cerebrocerebellar degeneration, Cortico-basal ganglionic degeneration, Familial dementia with spastic paraparesis or myoclonus, and Tourette syndrome.

In certain embodiments, the above compounds (such as a formula (I) or (III) compound, or (−)-P7C3-S243), or a pharmaceutically acceptable salt thereof, can be used to treat TBI or a symptom associated with TBI. Such treatment can be administered acutely after injury, and/or after an extended period (e.g., 1 month, 2 months, 3 months, 4 months, 5 months, 6 months, 7 months, 8 months, 9 months, 10 months, 11 months, 1 year, 2 years, 3 years, or any period longer or shorter than these durations) following an injury to alleviate a long term symptom associated with TBI.

Also disclosed herein is a compound of formula (I) or (III) or (−)-P7C3-S243, or a pharmaceutically acceptable salt thereof, for use in the treatment of one or more of the above diseases.

A further aspect relates to use of the compound or salt disclosed herein in the manufacture of a medicament for the treatment of one or more of the above diseases.

Also provided herein is a pharmaceutical composition comprising a compound of formula (I) or (III) or (−)-P7C3-S243, or a pharmaceutically acceptable salt thereof, and a pharmaceutically acceptable carrier.

The present disclosure features compositions (e.g., pharmaceutical compositions) that include a compound of formula (I) or (III) or (−)-P7C3-S243, as well as methods of making, identifying, and using such compounds. New insight into the mechanisms by which the P7C3 class of neuroprotective agents protect neurons is also provided. Other features and advantages are described in, or will be apparent from, the present specification and accompanying drawings.

BRIEF DESCRIPTION OF THE DRAWINGS

(FIG. 16A) Daily IP administration of P7C3-S243 for 11 days in divided daily doses for the total amount indicated dose-dependently preserved memory in the probe test of the Barnes maze in blast-injured mice, as measured by the most stringent measure of percent time in escape area (5 cm radius around the escape hole). Treatment with an intermediate dose (3 mg/kg/d) of the active (−)-P7C3-S243 enantiomer preserved normal performance to the level displayed by sham-injured mice. By contrast, mice treated with the same dose of the less active (+)-P7C3-S243 enantiomer showed the same deficit as injured mice treated with vehicle. (FIG. 16B) Daily administration of P7C3-S243 was initiated at progressively later time periods after injury in order to define the window of therapeutic efficacy. Whereas both 3 and 30 mg/kg/d doses preserved normal function when treatment was initiated 24 hours after injury, only the 30 mg/kg/d dose was efficacious when treatment was initiated at 36 hours. When treatment was initiated 48 hours after injury, no protective efficacy was noted at any dose. (FIG. 16C) Oral (PO) administration of the highly active (−)-P7C3-S243 enantiomer preserved normal hippocampal dependent memory at 3, 10 and 30 mg/kg/day doses. Every group shown consisted of 25 male C57/BI6 mice, aged 12-14 weeks, and data was collected and scored in an automated manner blind to treatment group. Data are represented as mean±SEM. Significance was determined by two way ANOVA with Bonferroni post-hoc analysis. p-value labeled as *<0.05, <0.01, *<0.001, and ****<0.0001 compared to blast-injured animals treated with vehicle. See also FIGS. 21, 22, 23, 24, 25, and 26.

(FIG. 17A) LTP induced by 12 theta burst stimulation (TBS) is significantly decreased in animals that sustained blast-induced TBI 14 days prior to testing. (FIG. 17B) This deficit was not rescued in animals treated with low dose P7C3-S243 (0.3 mg/kg/d) starting 24 hours after injury, but was rescued by treatment with higher doses of (FIG. 17C) 3 and (FIG. 17D) 30 mg/kg/d P7C3-S243. LTP at 1 hour after 12 TBS is summarized by quantification of the initial slope in FIG. 17E. (FIG. 17F) The blast-injury induced PPF deficit of 50 ms inter-pulse interval was also rescued in animals treated with the two higher doses (3 and 30 mg/kg/d) of P7C3-S243. Data are represented as mean±SEM. Statistics were determined by one-way ANOVA with Tukey's post hoc test.

(FIG. 18A) Representative pictures from the CA1 stratum radiatum show prominent silver staining of degenerating axons 12 days after blast-injury, in the absence of loss of NeuN staining or other cell death (H+E). Images shown are representative of typical images from 5 animals in each group, and demonstrate that 3 and 30 mg/kg/day doses of P7C3-S243, initiated 24 hours after blast-injury, effectively block axonal degeneration. Similar protective efficacy is seen in animals treated with 3 mg/kg/day of the highly active enantiomer (−)-P7C3-S243, but not when animals are treated with the less active enantiomer (+)-P7C3-S243. Scale bar=2.5 μm. (FIG. 18B) Optical densitometry of light transmitted through silver-stained CA1 stratum radiatum from all animals in each group was used to quantify the protective effect. The specific tissue area was manually delineated, and signal was quantified for 18 sections for each of the 5 animals, spaced 480 μm apart. Here, a greater value indicates that more light was able to pass unimpeded through the section by virtue of less silver staining, which reflects less axonal degeneration. Data are represented as mean±SEM. P-value *<0.05, determined by-two way ANOVA with Bonferroni post-hoc analysis. See also FIGS. 27, 28, 29 and 30.

(FIG. 20A) Representative pictures from the cerebellar molecular layer show prominent silver staining of degenerating axons 12 days after blast-injury, in the absence of loss of NeuN staining or other cell death (H+E). Images shown are representative of typical images from 5 animals in each group, and demonstrate that 3 and 30 mg/kg/day doses of P7C3-S243, initiated 24 hours after blast-injury, effectively block axonal degeneration. Similar protective efficacy is seen in animals treated with 3 mg/kg/day of the highly active enantiomer (−)-P7C3-S243, but not when animals are treated with the less active enantiomer (+)-P7C3-S243. Scale bar=2.5 μm. (FIG. 20B) Optical densitometry of light transmitted through silver-stained cerebellar molecular layer from all animals in each group was used to quantify the protective effect. The specific tissue area was manually delineated, and signal was quantified for 18 sections for each of the 5 animals, spaced 480 μm apart. Here, a greater value indicates that more light was able to pass unimpeded through the section by virtue of less silver staining, which reflects less axonal degeneration. (FIG. 20C) Seven days after blast-injury, mice show a trend towards impaired balance and coordination with increased foot slips that did not achieve statistical significance. By 28 days, however, blast-injured mice showed a two-fold increase in the number of foot slips relative to sham-injured mice. When daily oral treatment with 6 mg/kg/day of the active enantiomer (−)-P7C3-S243 was initiated 24 hours after blast-injury, however, mice performed normally in this task. Every group shown consisted of 25 male C57/BI6 mice, aged 12-14 weeks, and data was collected and scored in an automated manner blind to treatment group. Significance was determined by 2 way ANOVA with Bonferroni post-hoc analysis. Data are represented as mean±SEM. p-value labeled as \*\*<0.01 and \*\*\*\*<0.0001 compared to blast-injured animals treated with vehicle. See also FIG. 27.

(FIG. 21A) Administration of P7C3-A20 or P7C3-S243 (10 mg/kg/d administered IP in divided daily doses for 11 days), within 30-60 seconds after blast-mediated TBI, preserves hippocampal-dependent spatial memory in the Barnes maze 11 days after injury. Animals subjected to sham-injury and administered vehicle, or the same doses of P7C3-A20 or P7C3-S243, spent ≈60% of their time in the escape quadrant, in contrast to blast-injured vehicle controls, which spent ≈20% of their time in the escape quadrant. This same treatment with P7C3-A20 or P7C3-S243 immediately after blast-injury rescued memory to normal levels in sham-injured mice. In both blast-injured and sham-injured groups, treatment with (−)-P7C3-S243 showed a nonsignificant trend in increasing time spent in the escape quadrant. 12 male C57/BI6 mice aged 12-14 weeks were tested per group, and data was collected and scored in an automated manner blind to treatment group. Significance was determined by 2 way ANOVA with Bonferroni post-hoc analysis. p-value labeled as \*<0.05, \*\*<0.01, \*\*\*<0.001, compared to blast-injured animals treated with vehicle. (FIG. 21B) Blood-brain-barrier permeability is compromised at 6 hours after blast injury, and returns to normal 24 hours after injury. Daily treatment with P7C3-S243 (10 mg/kg/d) for four days does not affect blood brain barrier permeability. 5 male C57/BI6 mice aged 12-14 weeks were tested per group. Significance was measured using two way ANOVA. Data are represented as mean±SEM. p-value labeled as \*\*\*\*<0.0001, compared to uninjured animals treated with vehicle.

(FIG. 22A) Daily IP administration of P7C3-S243 for 11 days in divided daily doses as indicated dose-dependently preserved performance in the probe test of the Barnes maze in blast-injured mice, as measured by the percent target entry. This metric is defined as the number of times a mouse pokes its nose into the correct hole out of the total number of times it pokes its nose into any hole. Treatment with an intermediate dose (3 mg/kg/d) of the active (−)-P7C3-S243 enantiomer preserved normal performance in this measure to the level displayed by sham-injured mice. By contrast, mice treated with the less active (+)-P7C3-S243 enantiomer showed the same deficit as blast-injured mice treated with vehicle. (FIG. 22B) Daily administration of P7C3-S243 was initiated at progressively later time periods after injury, in order to define the window of therapeutic efficacy. Whereas both 3 and 30 mg/kg/d doses preserved a normal percent target entry when treatment was initiated 24 hours after injury, only the higher dose was significantly protective when daily treatment was initiated at 36 hours. When treatment was initiated 48 hours after injury, no protective efficacy was noted at any dose. (FIG. 22C) Oral (PO) administration of the highly active (−)-P7C3-S243 enantiomer showed potent preservation of percent target entry at 3, 10 and 30 mg/kg/day doses. Every group shown consisted of 25 male C57/BI6 mice, aged 12-14 weeks, and data was collected and scored in an automated manner blind to treatment group. Data are represented as mean±SEM. Significance was determined by two-way ANOVA with Bonferroni post-hoc analysis. p-value labeled as \*<0.05, \*\*<0.01, \*\*\*<0.001, and \*\*\*\*<0.0001 compared to blast-injured animals treated with vehicle.

(FIG. 23A) Daily IP administration of racemic P7C3-S243 for 11 days in divided daily doses as indicated dose-dependently preserved performance in the probe test of the Barnes maze in blast-injured mice, as measured by the percent quadrant time. This metric is defined as the percentage of time the mouse spends in the quadrant containing the escape hole. Treatment with an intermediate dose (3 mg/kg/d) of the active (−)-P7C3-S243 enantiomer completely preserved normal performance in this assay to the level displayed by sham-injured mice. Mice treated with the less active (+)-P7C3-S243 enantiomer showed some protection at the margin of statistical significance, but not to the degree effected by equivalent doses of racemic P7C3-S243 or (−)-P7C3-S243. (FIG. 23B) Daily administration of racemic P7C3-S243 was initiated at progressively later time periods after injury, in order to define a window of therapeutic efficacy. Whereas 3 and 30 mg/kg/d doses preserved a normal percent quadrant time when treatment was initiated 24 hours after injury, only the higher dose was significantly protective when daily treatment was initiated 36 hours after injury. When treatment was initiated 48 hours after injury, no protective efficacy in this assay was noted at any dose of racemic P7C3-S243. (FIG. 23C) Oral (PO) administration of the highly active (−)-P7C3-S243 enantiomer showed potent preservation of percent quadrant time at 3, 10 and 30 mg/kg/day doses. Every group shown consisted of 25 male C57/BI6 mice, aged 12-14 weeks, and data was collected and scored in an automated manner blind to treatment group. Data are represented as mean±SEM. Significance was determined by two-way ANOVA with Bonferroni post-hoc analysis. p-value labeled as \*<0.05, \*\*<0.01, \*\*\*<0.001, and \*\*\*\*<0.0001 compared to blast-injured animals treated with vehicle.

(FIG. 24A) Speed did not differ as a function of blast-injury or treatment initiated 24 hours after injury. (FIG. 24B) Speed did not differ as a function of compound administered (IP) 36 or 48 hours after injury. (FIG. 24C) Speed did not differ as a function of oral (PO) administration of compound to blast-injured animals. Every group shown consisted of 25 male C57/BI6 mice, aged 12-14 weeks, and data was collected and scored in an automated manner blind to treatment group. Data are represented as mean±SEM.

(FIG. 25A) Distance traveled did not differ as a function of blast-injury or treatment (IP) initiated 24 hours after injury. (FIG. 25B) Distance traveled did not differ as a function of compound administered (IP) 36 or 48 hours after injury. (FIG. 25C) Distance traveled did not differ as a function of oral (PO) administration of compound to blast-injured animals. Every group shown consisted of 25 male C57/BI6 mice, aged 12-14 weeks, and data was collected and scored in an automated manner blind to treatment group. Data are represented as mean±SEM.

(FIG. 26A) Mice subjected to blast-mediated TBI and then treated with vehicle, 0.3 mg/kg/day P7C3-S243, or 3 mg/kg/day (+)-P7C3-S243 learned significantly more poorly than did sham-injured mice. When treatment with 1, 3, 10 or 30 mg/kg/day P7C3-S243 (IP), or 3 mg/kg/day (−)-P7C3-S243 (IP), was initiated 24 hours after injury, however, all groups learned the task equally well. (FIG. 26B) Daily administration of P7C3-S243 was initiated at progressively later time periods after injury, in order to define a window of therapeutic efficacy. Whereas 3 and 30 mg/kg/day doses preserved a normal percent latency to escape when treatment was initiated 24 hours after injury, only the higher dose was protective when treatment was initiated at 36 hours. However, some protective efficacy was also seen at the lower dose of 3 mg/kg/day (IP) when treatment was initiated at this time point. When treatment was initiated 48 hours after injury, protective efficacy was noted at 30 mg/kg/day (IP) P7C3-S243. (FIG. 26C) Oral (PO) administration of the highly active (−)-P7C3-S243 enantiomer preserved of normal percent latency to escape at 1, 3, 10 and 30 mg/kg/day doses. Every group shown consisted of 25 male C57/Bl6 mice, aged 12-14 weeks, and data was collected and scored in an automated manner blind to treatment group. Data are represented as mean±SEM. Significance was determined by two-way ANOVA with Bonferroni post-hoc analysis. p-value labeled as *<0.05, <0.01, *<0.001, and ****<0.0001 compared to blast-injured animals treated with vehicle.

(FIG. 27A) Shown at 80× magnification for clarity of morphology (scale bar=5 µm) is prominent silver staining of degenerating axons in CA1, corpus callosum, thalamus, cortex, olfactory bulb, striatum, dentate gyrus and cerebellum of blast-injured animals treated with vehicle, low dose (0.3 mg/kg/day) P7C3-S243, or intermediate dose (3 mg/kg/day) of the less active enantiomer (+)-P7C3-S243. Silver staining shows no evidence of axonal degeneration in sham-injured mice treated with vehicle, or in blast-injured mice treated with 3 or 30 mg/kg/day doses of P7C3-S243. Blast-injured mice were also protected from axonal degeneration by treatment with 3 mg/kg/day dose of the highly active enantiomer (−)-P7C3-S243. No axonal degeneration was observed in the hypothalamus as a result of blast-injury. Images shown are representative of brain slices from 5 animals in each group. (FIG. 27B) Same as (FIG. 27A), with lower power (40×, scale bar=2.5 µm) images showing breadth of axonal staining. (FIG. 27C) Optical densitometry of light transmitted through the indicated silver stained regions from all animals in each group was used to quantify the protective effect. The specific tissue area was manually delineated, and signal was quantified for 18 sections for each of the 5 animals, spaced 480 µm. Here, a greater value indicates that more light was able to pass unimpeded through the section by virtue of less silver staining, which indicates less axonal degeneration. Data are represented as mean±SEM. P-value *<0.05, *<0.01, **<0.001 determined by-two way ANOVA with Bonferroni post-hoc analysis.

(FIG. 31A) This diagram shows the methodology of tissue processing for toluidine blue and TEM. Both hemispheres of the hippocampus (red rectangles) were used for evaluation of pathology. (FIG. 31B) Toluidine blue staining showed that blast-injury vehicle-treated mice accumulate chromatolytic and pyknotic neurons in the CA1 region, and that initiation of daily oral treatment of blast-injured mice with (−)-P7C3-S243 prevents this pathology. Pictures shown are representative of 4 animals for each condition, and are from different animals than the pictures shown in FIG. 19. Scale bar=20 µm. (FIG. 31C) TEM showing protection against myelin degeneration (red arrows) and mitochondrial swelling (blue arrows) in stratum radiatum of blast-injury mice treated with 30 mg/kg/day (−)-P7C3-S243. These pictures are from different animals than the pictures in FIG. 19. Scale bar=500 nm.

(FIG. 33A) Hippocampal neurons exposed to 6-OHDA showed significant MTT reduction after 24 hrs at 50 µM, 75 µM and 100 µM doses, compared to control neurons treated with DMSO+Ascorbic acid (*$p<0.05$,* $p<0.001$, $p<0.0001$ respectively; one-way ANOVA). 10 µM P7C3-S243 conferred significant protection of hippocampal neurons exposed to 50 µM 6-OHDA ($p<0.005$ using an unpaired t-test). (FIG. 33B) The average number of hippocampal neurons in the 10 µM P7C3-S243 treatment group was not different from the average number of hippocampal neurons treated with medium alone or with DMSO+Ascorbic acid (one-way ANOVA). (FIG. 33C) Cortical neurons exposed to 6-OHDA showed significant MTT reduction after 24 hrs at 50 µM, 75 µM and 100 µM doses, compared to control neurons treated with DMSO+Ascorbic acid (*$p<0.0001$,$p<0.0001$, $p<0.0001$ respectively; one-way ANOVA). (FIG. 33D) 10 µM P7C3-S243 conferred significant protection of cortical neurons exposed to 50 µM and 75 µM 6-OHDA(**$p<0.0001$, *$p<0.05$ respectively, unpaired t-test). The average number of cortical neurons in the 10 µM P7C3-S243 treatment group was not different from the average number of cortical neurons treated with medium alone or with DMSO+Ascorbic acid (one-way ANOVA). Experiments were performed two independent times, with 8-12 replicates of each sample both times.

(FIG. 34A) Schematic of the experimental design illustrates that rats received a unilateral stereotactic injection of 6-OHDA or saline in the medial forebrain bundle (MFB), followed by daily injection of P7C3-S243 for 7 days. Open field and cylinder tests were performed 8-10 days after 6-OHDA injection, and the amphetamine circling test was conducted on day 11. Rats were transcardially perfused on day 14, and brain tissue was processed for neurochemistry and immunohistochemistry analysis. (FIG. 34B) Graphical illustration of the site of stereotaxic injection in the median forebrain bundle (MFB) shows dopaminergic fibers connecting the striatum and the substantia nigra pars compacta (SNc). (FIG. 34C) Amphetamine-circling test showed a significant increase in ipsilateral (toward the lesion site) rotations of 6-OHDA-exposed animals that received vehicle compared to sham-injured animals that received vehicle ($p<0.005$; one-way ANOVA), and also to 6-OHDA-exposed animals that were treated with P7C3-S243 (*$p<0.001$; one-way ANOVA). (FIG. 34D) Cylinder test showed a significant decrease in the total amount of rearings of 6-OHDA-exposed animals that received vehicle compared to sham-injured animals that received vehicle ($p<0.005$; one-way ANOVA), and also to 6-OHDA-exposed animals that were treated with P7C3-S243 (*$p<0.001$; one-way ANOVA). (FIG. 34E) Open field test showed a significant decrease in the total distance traveled of 6-OHDA-exposed animals that received vehicle compared to sham-injured animals that received vehicle (*$p<0.001$; one-way ANOVA), and also to 6-OHDA-exposed animals that were treated with P7C3-S243 ($p<0.0001$; one-way ANOVA). (FIG. 34F) Representative immunohistochemistry of tyrosine hydroxylase (TH) in the SNc shows that the non-injected side (left) shows no reduction in TH-positive cells in any group, while the injected side (right) shows prominent reduction in TH staining only in rats that were exposed to 6-OHDA and then administered vehicle. Scale bars=250 µm. (FIG. 34G) Quantification of TH-positive cells shows a significant decrease in rats that were exposed to 6-OHDA and then administered vehicle compared to sham-injured rats that received vehicle ($p<0.0001$; one-way ANOVA), and also a significant increase in rats that were exposed to 6-OHDA and then treated with P7C3-S243 compared to the 6-OHDA-Vehicle group (**$p<0.0001$; one-way ANOVA). (FIG. 34H) HPLC analysis of striatal concentration of dopamine, DOPAC, and homovanillic acid showed a significant decrease in rats that were exposed to 6-OHDA and then administered vehicle compared to sham-injured rats that received vehicle, and also a significant increase in rats that were exposed to 6-OHDA and then treated with P7C3-S243 compared to the 6-OHDA-Vehicle group. No difference was found in the concentration of serotonin in all groups (one-way ANOVA). For all experiments in FIG. 34, n=10 per group except for the HPLC analysis, for which n=7.

(FIG. 35A) Hippocampal neurons exposed to 10 µM MPP$^+$ showed significant MTT reduction after 24 hrs compared to neurons treated with DMSO (**$p<0.0001$; one-way ANOVA). MPP$^+$-exposed neurons that were also treated with 10 µM P7C3-A20 or 10 µM P7C3-S243 showed significant protection compared to neurons treated with MPP$^+$ alone ($p<0.005$; one-way ANOVA). (FIG. 35B) Cortical neurons exposed to 10 µM MPP$^+$ showed significant MTT reduction after 24 hrs compared to neurons treated with DMSO (**$p<0.0001$; one-way ANOVA). MPP$^+$-exposed neurons that were also treated with 10 µM P7C3-S243 showed significant protection compared to neurons treated with MPP$^+$ alone ($p<0.005$; one-way ANOVA). Experiments were performed 2 independent times with 8-12 replicates of each sample both times.

(FIG. 36A) Schematic of the experimental design illustrates that rats were pretreated for 3 days with either P7C3-A20 or P7C3-S243, and then administered either 6-OHDA or saline by stereotactic injection in the medial forebrain bundle (MFB), followed by 7 more days of treatment with either P7C3-A20 or P7C3-S243. Open field and cylinder tests were performed between days 8-10, and the amphetamine circling test was performed on day 11. Rats were transcardially perfused on day 14, and brain tissue was processed for neurochemistry and immunohistochemistry analysis. (FIG. 36B) Amphetamine-circling test showed a significant increase in ipsilateral (to the lesion site) rotations of 6-OHDA-exposed animals that received vehicle compared to sham-injured animals that received vehicle (*$p<0.001$; one-way ANOVA), and also to 6-OHDA-exposed animals that were treated with either P7C3-A20 or P7C3-S243 ($p<0.005$; one-way ANOVA). (FIG. 36C) Cylinder test showed a significant decrease in the total amount of rearings of 6-OHDA-exposed animals that received vehicle compared to sham-injured animals that received vehicle (**$p<0.005$; one-way ANOVA), and also to 6-OHDA-exposed animals that were treated with either P7C3-A20 or P7C3-S243 (*$p<0.05$; one-way ANOVA). (FIG. 36D) Open field test showed a significant decrease in the total distance traveled of 6-OHDA-exposed animals that received vehicle compared to sham-injured animals that received vehicle (***$p<0.001$; one-way ANOVA), and also to 6-OHDA-exposed animals that were treated with either P7C3-A20 or P7C3-S243 (*$p<0.05$; one-way ANOVA. (FIG. 36E) Representative immunohistochemistry of tyrosine hydroxylase (TH) in the SNc shows that the non-injected side (left) shows no reduction in TH-positive cells in any group, while the injected side (right) shows prominent reduction in TH staining only in rats that were exposed to 6-OHDA and then administered vehicle. Scale bars=250 µm. (FIG. 36F) Quantification of TH-positive cells shows a significant decrease in rats that were exposed to 6-OHDA and then administered vehicle compared to sham-injured rats that received vehicle (****$p<0.0001$; one-way ANOVA), and also a significant increase in rats that were exposed to 6-OHDA and then treated with either P7C3-A20 or P7C3-S243 group compared to 6-OHDA-Vehicle group (*$p<0.05$, ****$p<0.0001$; one-way ANOVA). n=10 per group FIGS. 37A-37B. Treatment of 6-OHDA-exposed rats with P7C3-S243 preserves both TH and NeuN staining, illustrating that TH staining corresponds to neuronal survival.

DETAILED DESCRIPTION

Figure 1:
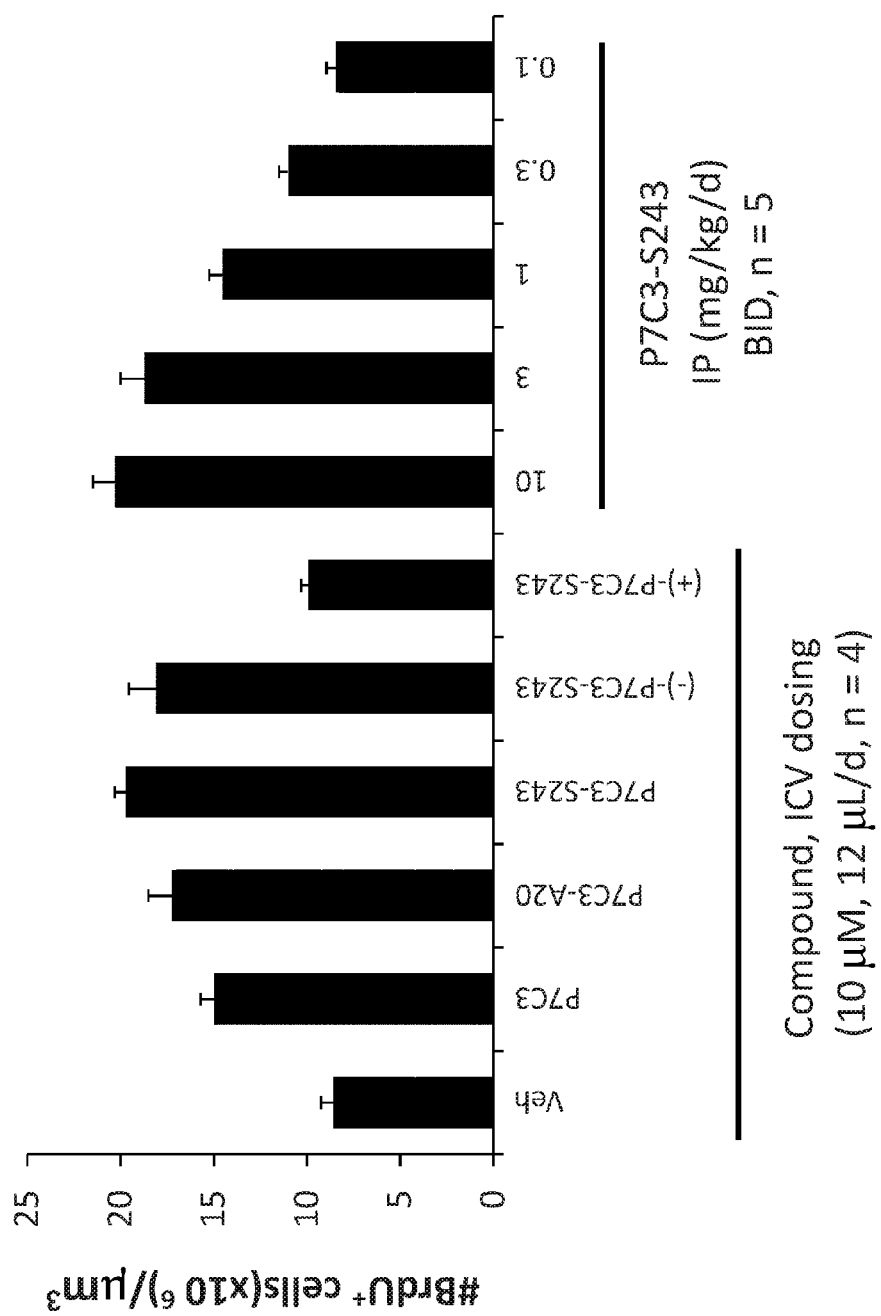
FIG. 1 shows efficacy of P7C3 derivatives in an in vivo mouse model of neurogenesis. Compounds were administered as indicated for 7 days along with daily injection of BrdU. Data are expressed as mean±SEM.

A number of small molecules with in vivo neuroprotective properties (the "P7C3 class of compounds") have been previously identified and disclosed in U.S. Pat. No. 8,362,277; U.S. Publication No. 2011/0015217; U.S. Publication No. 2012/0022096; U.S. Publication No. 2013/0040977 and U.S. application Ser. No. 14/339,772 filed Jul. 24, 2014, all of which are hereby incorporated herein by reference in their entirety, in particular the compounds disclosed in the Examples section.

It has now been surprisingly discovered that the neuroprotective activity appears to reside in one enantiomer of certain compounds. For example, the (−)-P7C3-S243 enantiomer displays high activity in the in vivo hippocampal neurogenesis screening assay, while the (+)-enantiomer shows little activity. This is unexpected especially given that the hydroxy series of P7C3 compounds show higher activity in the opposite enantiomer. More specifically, higher activity was previously observed in the enantiomer series illustrated in the structure A below. Thus it would have been reasonably expected that the fluorinated P7C3 compounds, such as P7C3-S243 would be active in the same enantiomeric series. In contrast and surprisingly, the active P7C3-S243 enantiomer is the opposite to that of the structure A compounds. It will be recognized that the R/S designation of the compounds represented by structure A will differ depending on the priority of the X substituent according to established rules of chemical nomenclature.

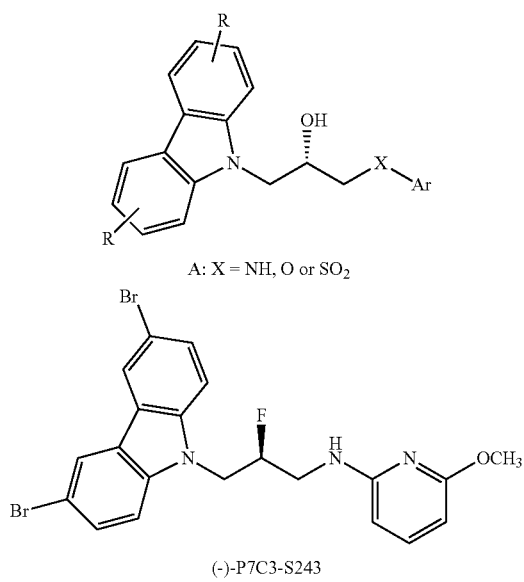

A: X = NH, O or SO$_2$ (-)-P7C3-S243

Furthermore, both the racemic P7C3-S243 and the (−) enantiomer of P7C3-S243 display activity in protection of mice from MPTP toxicity, a mice model of Parkinson's disease, and protect rats from toxicity associated with 6-hydroxydopamine (6-OHDA), an alternative model of Parkinson's disease (FIGS. 33-37). Importantly, unlike the MPTP model of Parkinson's disease, the 6-OHDA rat model is associated with a motor neuron deficit. In contrast, MPTP treatment does not cause a behavioral phenotype in mice. Thus, it was previously unknown if the protection offered in the MPTP model would translate into reduction of disease symptoms including motor function. Significantly, both A20 and P7C3-S243 display robust protective effect in the 6-OHDA rat model. The racemic P7C3-S243 and the (−) enantiomer of P7C3-S243 also protect mice from cognitive deficit after blast-mediated traumatic brain injury (TBI). Thus, (−)-P7C3-S243 is useful in treating Parkinson's disease, TBI, as well as other neuropsychiatric and neurodegenerative diseases.

In addition, the P7C3 series of compounds, in particular (−)-P7C3-S243, are surprisingly found to reduce or block axonal degeneration independently of neuronal cell death. This axonal rescue is associated with preservation of related measures of synaptic transmission, hippocampal-dependent learning and memory, and motor coordination. These compounds also protect neuronal myeling sheaths and mitochondria in a neurodegenerative disease model. As axonal degeneration almost always precedes cell death, these compounds can achieve therapeutic effect at earlier time points than previously believed in all forms of neurodegenerative diseases (e.g., prior to or at the early onset of the disease). Thus, the P7C3 class of compounds, such as P7C3-S243 can serve as a chemical scaffold upon which new drugs can be designed to treat patients with acute and chronic conditions of axonal degradation, such as occurs in traumatic brain injury, various neuropathies including chemotherapy induced neuropathy and peripheral neuropathy or other diseases. Such an agent would have broad applicability, as axon degeneration proceeds through unique mechanisms distinct from cell death, and most forms of neurodegenerative disease involve degradation of synapses and axons preceding loss of neuronal cell bodies.

Various compounds, such as those having one or more common substituents on P7C3-S243 and/or (−)-P7C3-S243 are also within the scope of this invention.

Definitions

Unless defined otherwise, all technical and scientific terms used herein have the meaning commonly understood by one of ordinary skill in the art to which the disclosure pertains. The Definitions section at paragraphs [1001]-[1031] of U.S. Publication No. 2013/0040977 is incorporated herein by reference. Specific terminology is defined below.

As used in the specification and the appended claims, the singular forms "a," "an," and "the" include plural referents unless the context clearly dictates otherwise.

As used herein, the term "about" means within 20%, more preferably within 10% and most preferably within 5%.

The terms "neuroprotective" and "neuroprotective activity" refer to an activity in promoting the survival, health, integrity, growth, development and/or function of neurons, and/or protecting neurons from cell death, apoptosis and/or degeneration, and/or stimulating neurogenesis, particularly CNS, brain, cerebral, and hippocampal neurons.

The term "neurogenesis" refers to the process by which neurons are generated from neural stem cells and progenitor cells, which is responsible for populating the growing brain with neurons. While neurogenesis generally is most active during pre-natal development, in some embodiments the compounds disclosed herein can stimulate or promote postnatal neurogenesis such as hippocampal neurogenesis.

The terms "treating" and "treatment" as used herein refer to reduction in severity and/or frequency of symptoms, elimination of symptoms and/or underlying cause, and improvement or remediation of damage.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing and/or that it is included on the Inactive Ingredient Guide prepared by the U.S. Food and Drug administration.

As used herein, the term "patient" or "individual" or "subject" refers to any person or mammalian subject for whom or which therapy is desired, and generally refers to the recipient of the therapy to be practiced according to the disclosure.

The term "substituent" refers to a group "substituted" on, e.g., an alkyl, haloalkyl, cycloalkyl, heterocyclyl, heterocycloalkenyl, cycloalkenyl, aryl, or heteroaryl group at any atom of that group, replacing one or more hydrogen atom therein. In one aspect, the substituent(s) on a group are independently any one single, or any combination of two or more of the permissible atoms or groups of atoms delineated for that substituent. In another aspect, a substituent may itself be substituted with any one of the above substituents. Further, as used herein, the phrase optionally substituted" means unsubstituted (e.g., substituted with an H) or substituted. It is understood that substitution at a given atom is limited by valency. Common substituents include halo, straight chain or branched chain alkyl, alkenyl, alkynyl, cycloalkyl, aryl, heteroaryl, heterocyclyl, alkylsulfonyl, nitro, cyano, —COOR, —C(O)NRR', —OR, —SR, —NRR', and oxo, such as mono- or di- or tri-substitutions with moieties such as trifluoromethoxy, chlorine, bromine, fluorine, methyl, methoxy, pyridyl, furyl, triazyl, piperazinyl, pyrazoyl, imidazoyl, and the like, each optionally containing one or more heteroatoms such as halo, N, O, S, and P. R and R' are independently hydrogen, alkyl, haloalkyl, alkenyl, alkynyl, cycloalkyl, cycloalkylalkyl, aryl, aralkyl, heterocyclyl, heterocyclylalkyl, heteroaryl or heteroarylalkyl, Unless otherwise noted, all groups described herein optionally contain one or more common substituents, to the extent permitted by valency.

Compound Forms and Salts

The compounds of the present disclosure may contain one or more asymmetric centers and thus occur as racemates and racemic mixtures, enantiomerically enriched mixtures, single enantiomers, individual diastereomers and diastereomeric mixtures. All such isomeric forms of these compounds are expressly included in the present disclosure. The compounds of the present disclosure may also contain linkages (e.g., carbon-carbon bonds, carbon-nitrogen bonds such as amide bonds) wherein bond rotation is restricted about that particular linkage, e.g. restriction resulting from the presence of a ring or double bond. Accordingly, all cis/trans and E/Z isomers and rotational isomers are expressly included in the present disclosure. The compounds of the present disclosure may also be represented in multiple tautomeric forms, in such instances, the present disclosure expressly includes all tautomeric forms of the compounds described herein, even though only a single tautomeric form may be represented. All such isomeric forms of such compounds are expressly included in the present disclosure.

Optical isomers can be obtained in pure form by standard procedures known to those skilled in the art, and include, but are not limited to, diastereomeric salt formation, kinetic resolution, and asymmetric synthesis. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, N Y, 1962); Wilen, S. H. Tables of Resolving Agents and Optical Resolutions p. 268 (E. L. Eliel, Ed., Univ. of Notre Dame Press, Notre Dame, Ind. 1972), each of which is incorporated herein by reference in their entireties. It is also understood that the present disclosure encompass all possible regioisomers, and mixtures thereof, which can be obtained in pure form by standard separation procedures known to those skilled in the art, and include, but are not limited to, column chromatography, thin-layer chromatography, and high-performance liquid chromatography.

The compounds of the present disclosure include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include $C_{1-6}$ alkyl esters of carboxylic acid groups, which, upon administration to a subject, are capable of providing active compounds.

Pharmaceutically acceptable salts of the compounds of the present disclosure include those derived from pharmaceutically acceptable inorganic and organic acids and bases. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient.

Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the present disclosure and their pharmaceutically acceptable acid addition salts. Salts derived from appropriate bases include alkali metal (e.g., sodium), alkaline earth metal (e.g., magnesium), ammonium and $N$-$(alkyl)_4^+$ salts. The present disclosure also envisions the quaternization of any basic nitrogen-containing groups of the compounds disclosed herein. Water or oil-soluble or dispersible products may be obtained by such quaternization. Salt forms of the compounds of any of the formulae herein can be amino acid salts of carboxyl groups (e.g. L-arginine, -lysine, -histidine salts).

Lists of suitable salts are found in Remington's Pharmaceutical Sciences, 17th ed., Mack Publishing Company, Easton, Pa., 1985, p. 1418; Journal of Pharmaceutical Science, 66, 2 (1977); and "Pharmaceutical Salts: Properties, Selection, and Use A Handbook; Wermuth, C. G. and Stahl, P. H. (eds.) Verlag Helvetica Chimica Acta, Zurich, 2002 [ISBN 3-906390-26-8] each of which is incorporated herein by reference in their entireties.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

In addition to salt forms, the present disclosure provides compounds which are in a prodrug form. Prodrugs of the compounds described herein are those compounds that undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present disclosure which is administered as an ester (the "prodrug"), but then is metabolically hydrolyzed to the carboxylic acid, the active entity. Additional examples include peptidyl derivatives of a compound of the present disclosure.

The present disclosure also includes various hydrate and solvate forms of the compounds.

The compounds of the present disclosure may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present disclosure, whether radioactive or not, are intended to be encompassed within the scope of the present disclosure.

Synthesis

The compounds of the present disclosure can be conveniently prepared in accordance with the procedures outlined in the Examples sections of U.S. Pat. No. 8,362,277; U.S. Publication No. 2011/0015217; U.S. Publication No. 2012/0022096; U.S. Publication No. 2013/0040977 and U.S. application Ser. No. 14/339,772 filed Jul. 24, 2014, all of which are hereby incorporated herein by reference in their entirety, in particular the Examples section. The compounds can also be prepared from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds described herein.

Synthetic chemistry transformations (including protecting group methodologies) useful in synthesizing the compounds described herein are known in the art and include, for example, those such as described in R. C. Larock, *Comprehensive Organic Transformations*, 2d.ed., Wiley-VCH Publishers (1999); P. G. M. Wuts and T. W. Greene, *Protective Groups in Organic Synthesis,* 4th Ed., John Wiley and Sons (2007); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The processes described herein can be monitored according to any suitable method known in the art. For example, product formation can be monitored by spectroscopic means, such as nuclear magnetic resonance spectroscopy (e.g., $^1H$ or $^{13}C$), infrared spectroscopy (FT-IR), spectrophotometry (e.g., UV-visible), or mass spectrometry (MS), or by chromatography such as high performance liquid chromatography (HPLC) or thin layer chromatography (TLC).

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis,* 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of compounds can be carried out by any of numerous methods known in the art. An example method includes preparation of the Mosher's ester or amide derivative of the corresponding alcohol or amine, respectively. The absolute configuration of the ester or amide is then determined by proton and/or $^{19}F$ NMR spectroscopy. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent compositions can be determined by one skilled in the art.

Pharmaceutical Compositions

The term "pharmaceutically acceptable carrier" refers to a carrier or adjuvant that may be administered to a subject (e.g., a patient), together with a compound of the present disclosure, and which does not destroy the pharmacological activity thereof and is nontoxic when administered in doses sufficient to deliver a therapeutic amount of the compound.

Pharmaceutically acceptable carriers, adjuvants and vehicles that may be used in the compositions of the present disclosure include, but are not limited to, ion exchangers, alumina, aluminum stearate, lecithin, self-emulsifying drug delivery systems (SEDDS) such as d-a-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts, or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The compositions for administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, losenges or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

The amount administered depends on the compound formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 3, 10 or 30 to about 30, 100, 300 or 1000 mg, according to the particular application. In a particular embodiment, unit dosage forms are packaged in a multipack adapted for sequential use, such as blisterpack, comprising sheets of at least 6, 9 or 12 unit dosage forms. The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The following are examples (Formulations 1-4) of capsule formulations.

Capsule Formulations

| Capsule Formulation | Formulation 1 mg/capsule | Formulation 2 mg/capsule | Formulation 3 mg/capsule | Formulation 4 mg/capsule |
|---|---|---|---|---|
| Compound (solid solution) | 100 | 400 | 400 | 200 |
| Silicon Dioxide | 0.625 | 2.5 | 3.75 | 1.875 |
| Magnesium Stearate NF2 | 0.125 | 0.5 | 0.125 | 0.625 |
| Croscarmellose Sodium NF | 11.000 | 44.0 | 40.0 | 20.0 |
| Pluronic F68 NF | 6.250 | 25.0 | 50.0 | 25.0 |
| Silicon Dioxide NF | 0.625 | 2.5 | 3.75 | 1.875 |
| Magnesium Stearate NF | 0.125 | 0.5 | 1.25 | 0.625 |
| Total | 118.750 | 475.00 | 475.00 | 475.00 |
| Capsule Size | No. 4 | No. 0 | No. 0 | No. 2 |

Preparation of Solid Solution

Crystalline compound (80 g/batch) and the povidone (NF K29/32 at 160 g/batch) are dissolved in methylene chloride (5000 mL). The solution is dried using a suitable solvent spray dryer and the residue reduced to fine particles by grinding. The powder is then passed through a 30 mesh screen and confirmed to be amorphous by x-ray analysis.

The solid solution, silicon dioxide and magnesium stearate are mixed in a suitable mixer for 10 minutes. The mixture is compacted using a suitable roller compactor and milled using a suitable mill fitted with 30 mesh screen. Croscarmellose sodium, Pluronic F68 and silicon dioxide are added to the milled mixture and mixed further for 10 minutes. A premix is made with magnesium stearate and equal portions of the mixture. The premix is added to the remainder of the mixture, mixed for 5 minutes and the mixture encapsulated in hard shell gelatin capsule shells.

Use

In one aspect, methods for treating (e.g., controlling, relieving, ameliorating, alleviating, or slowing the progression of) or methods for preventing (e.g., delaying the onset of or reducing the risk of developing) one or more diseases, disorders, or conditions caused by, or associated with, aberrant (e.g., insufficient) neurogenesis, accelerated neuron cell death and/or axonal degeneration in a subject in need thereof are featured. The methods include administering to the subject an effective amount of a compound of formula (I) (and/or a compound of any of the other formulae described herein) or a salt (e.g., a pharmaceutically acceptable salt) thereof as defined anywhere herein to the subject.

In another aspect, the use of a compound of formula (I) (and/or a compound of any of the other formulae described herein) or a salt (e.g., a pharmaceutically acceptable salt) thereof as defined anywhere herein in the preparation of, or for use as, a medicament for the treatment (e.g., controlling, relieving, ameliorating, alleviating, or slowing the progression of) or prevention (e.g., delaying the onset of or reducing the risk of developing) of one or more diseases, disorders, or conditions caused by, or associated with, aberrant (e.g., insufficient) neurogenesis, exacerbated neuronal cell death and/or axonal degeneration is featured.

In embodiments, the one or more diseases, disorders, or conditions can include neuropathies, nerve trauma, and neurodegenerative diseases. In embodiments, the one or more diseases, disorders, or conditions can be diseases, disorders, or conditions caused by, or associated with aberrant (e.g., insufficient) neurogenesis (e.g., aberrant hippocampal neurogenesis as is believed to occur in neuropsychiatric diseases), accelerated death of existing neurons and/or axonal degeneration. Examples of the one or more diseases include, but are not limited to, schizophrenia, major depression, bipolar disorder, normal aging, epilepsy, traumatic brain injury and/or a visual symptom associated therewith, post-traumatic stress disorder, Parkinson's disease, Alzheimer's disease, Down syndrome, spinocerebellar ataxia, amyotrophic lateral sclerosis, Huntington's disease, stroke, radiation therapy, chronic stress, abuse of a neuroactive drug, retinal degeneration, spinal cord injury, peripheral nerve injury, physiological weight loss associated with various conditions, cognitive decline and/or general frailty associated with normal aging and/or chemotherapy, chemotherapy induced neuropathy, concussive injury, crush injury, peripheral neuropathy, diabetic neuropathy, post-traumatic headache, multiple sclerosis, retinal degeneration and dystrophy (such as Leber congenital amaurosis, retinitis pigmentosa, cone-rod dystrophy, microphthalmia, anophthalmia, myopia, and hyperopia), spinal cord injury, traumatic spinal cord injury, peripheral nerve injury (such as peripheral nerve crush injury, neonatal brachial plexus palsy, and traumatic facial nerve palsy), retinal neuronal death related diseases (such as glaucoma and age related macular degeneration, diabetic retinopathy, retinal blood vessel occlusions, retinal medication toxicity (such as what amino glycosides or plaquenil can cause), retinal trauma (e.g., post-surgical), retinal infections, choroidal dystrophies, retinal pigmentary retinopathies, inflammatory and cancer mediated auto immune diseases that result in retinal neuronal cell death), Autism, Stargardt disease, Kearns-Sayre syndrome, Pure neurosensory deafness, Hereditary hearing loss with retinal diseases, Hereditary hearing loss with system atrophies of the nervous system, Progressive spinal muscular atrophy, Progressive bulbar palsy, Primary lateral sclerosis, Hereditary forms of progressive muscular atrophy and spastic paraplegia, Frontotemporal dementia, Dementia with Lewy bodies, Corticobasal degeneration, Progressive supranuclear palsy, Prion disorders causing neurodegeneration, Multiple system atrophy (olivopontocerebellar atrophy), Hereditary spastic paraparesis, Friedreich ataxia, Non-Friedreich ataxia, Spinocerebellar atrophies, Amyloidoses, Metabolic-related (e.g., Diabetes) neurodegenerative disorders, Toxin-related neurodegenerative disorders, Multiple sclerosis, Charcot Marie Tooth, Diabetic neuropathy, Metabolic neuropathies, Endocrine neuropathies, Orthostatic hypotension, Creutzfeldt-Jacob Disease, Primary progressive aphasia, Frontotemporal Lobar Degeneration, Cortical blindness, Shy-Drager Syndrome (Multiple, System Atrophy with Orthostatic Hypotension), Diffuse cerebral cortical atrophy of non-Alzheimer type, Lewy-body dementia, Pick disease (lobar atrophy), Thalamic degeneration, Mesolimbocortical dementia of non-Alzheimer type, Nonhuntingtonian types of chorea and dementia, Cortical-striatal-spinal degeneration, Dementia-Parkinson-amyotrophic lateral sclerosis complex, Cerebrocerebellar degeneration, Cortico-basal ganglionic degeneration, Familial dementia with spastic paraparesis or myoclonus, and Tourette syndrome. The resultant promotion of neurogenesis or survival of existing neurons (i.e., a resultant promotion of survival, growth, development, function and/or generation of neurons) may be detected directly, indirectly or inferentially from an improvement in, or an amelioration of one or more symptoms of the disease or disorder caused by or associated with aberrant neurogenesis, survival of existing neurons and/or preservation of axonal integrity. Suitable assays which directly or indirectly detect neural survival, growth, development, function and/or generation are known in the art, including axon regeneration in rat models (e.g. Park et al., Science. 2008 Nov. 7; 322:963-6), nerve regeneration in a rabbit facial nerve injury models (e.g. Zhang et al., J Transl Med. 2008 Nov. 5; 6(1):67); sciatic nerve regeneration in rat models (e.g. Sun et al., Cell Mol Neurobiol. 2008 Nov. 6); protection against motor neuron degeneration in mice (e.g. Poesen et al., J. Neurosci. 2008 Oct. 15; 28(42):10451-9); rat model of Alzheimer's disease, (e.g. Xuan et al., Neurosci Lett. 2008 Aug. 8; 440(3):331-5); animal models of depression (e.g. Schmidt et al., Behav Pharmacol. 2007 September; 18(5-6):391-418; Krishnan et al., Nature 2008, 455, 894-902); and/or those exemplified herein.

Administration

The compounds and compositions described herein can, for example, be administered orally, parenterally (e.g., subcutaneously, intracutaneously, intravenously, intramuscularly, intraarticularly, intraarterially, intrasynovially, intrasternally, intrathecally, intralesionally and by intracranial injection or infusion techniques), by inhalation spray, topically, rectally, nasally, buccally, vaginally, via an implanted reservoir, by injection, subdermally, intraperitoneally, transmucosally, or in an ophthalmic preparation, with a dosage ranging from about 0.01 mg/kg to about 1000 mg/kg, (e.g., from about 0.01 to about 100 mg/kg, from about 0.1 to about 100 mg/kg, from about 1 to about 100 mg/kg, from about 1 to about 10 mg/kg) every 4 to 120 hours, or according to the requirements of the particular drug. The interrelationship of dosages for animals and humans (based on milligrams per meter squared of body surface) is described by Freireich et al., Cancer Chemother. Rep. 50, 219 (1966). Body surface area may be approximately determined from height and weight of the patient. See, e.g., Scientific Tables, Geigy Pharmaceuticals, Ardsley, N.Y., 537 (1970). In certain embodiments, the compositions are administered by oral administration or administration by injection. The methods herein contemplate administration of an effective amount of compound or compound composition to achieve the desired or stated effect. Typically, the pharmaceutical compositions of the present disclosure will be administered from about 1 to about 6 times per day or alternatively, as a continuous infusion. Such administration can be used as a chronic or acute therapy.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of the present disclosure may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

In some embodiments, the compounds described herein can be coadministered with one or more other therapeutic agents. In certain embodiments, the additional agents may be administered separately, as part of a multiple dose regimen, from the compounds of the present disclosure (e.g., sequentially, e.g., on different overlapping schedules with the administration of one or more compounds of formula (I) (including any subgenera or specific compounds thereof)). In other embodiments, these agents may be part of a single dosage form, mixed together with the compounds of the present disclosure in a single composition. In still another embodiment, these agents can be given as a separate dose that is administered at about the same time that one or more compounds of formula (I) (including any subgenera or specific compounds thereof) are administered (e.g., simultaneously with the administration of one or more compounds of formula (I) (including any subgenera or specific compounds thereof)). When the compositions of the present disclosure include a combination of a compound of the formulae described herein and one or more additional therapeutic or prophylactic agents, both the compound and the additional agent can be present at dosage levels of between about 1 to 100%, and more preferably between about 5 to 95% of the dosage normally administered in a monotherapy regimen.

The compositions of the present disclosure may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

The compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The compositions of the present disclosure may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The compositions of the present disclosure may also be administered in the form of suppositories for rectal administration. These compositions can be prepared by mixing a compound of the present disclosure with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the compositions of the present disclosure is useful when the desired treatment involves areas or organs readily accessible by topical application. For application topically to the skin, the composition should be formulated with a suitable ointment containing the active components suspended or dissolved in a carrier. Carriers for topical administration of the compounds of the present disclosure include, but are not limited to, mineral oil, liquid petroleum, white petroleum, propylene glycol, polyoxyethylene polyoxypropylene compound, emulsifying wax and water. Alternatively, the composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The compositions of the present disclosure may also be topically applied to the lower intestinal tract by rectal suppository formulation or in a suitable enema formulation.

In some embodiments, topical administration of the compounds and compositions described herein may be presented in the form of an aerosol, a semi-solid pharmaceutical composition, a powder, or a solution. By the term "a semi-solid composition" is meant an ointment, cream, salve, jelly, or other pharmaceutical composition of substantially similar consistency suitable for application to the skin. Examples of semi-solid compositions are given in Chapter 17 of The Theory and Practice of Industrial Pharmacy, Lachman, Lieberman and Kanig, published by Lea and Febiger (1970) and in Remington's Pharmaceutical Sciences, 21st Edition (2005) published by Mack Publishing Company, which is incorporated herein by reference in its entirety.

Topically-transdermal patches are also included in the present disclosure. Also within the present disclosure is a patch to deliver active chemotherapeutic combinations herein. A patch includes a material layer (e.g., polymeric, cloth, gauze, bandage) and the compound of the formulae herein as delineated herein. One side of the material layer can have a protective layer adhered to it to resist passage of the compounds or compositions. The patch can additionally include an adhesive to hold the patch in place on a subject. An adhesive is a composition, including those of either natural or synthetic origin, that when contacted with the skin of a subject, temporarily adheres to the skin. It can be water resistant. The adhesive can be placed on the patch to hold it in contact with the skin of the subject for an extended period of time. The adhesive can be made of a tackiness, or adhesive strength, such that it holds the device in place subject to incidental contact, however, upon an affirmative act (e.g., ripping, peeling, or other intentional removal) the adhesive gives way to the external pressure placed on the device or the adhesive itself, and allows for breaking of the adhesion contact. The adhesive can be pressure sensitive, that is, it can allow for positioning of the adhesive (and the device to be adhered to the skin) against the skin by the application of pressure (e.g., pushing, rubbing,) on the adhesive or device.

The compositions of the present disclosure may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

A composition having the compound of the formulae herein and an additional agent (e.g., a therapeutic agent) can be administered using any of the routes of administration described herein. In some embodiments, a composition having the compound of the formulae herein and an additional agent (e.g., a therapeutic agent) can be administered using an implantable device. Implantable devices and related technology are known in the art and are useful as delivery systems where a continuous, or timed-release delivery of compounds or compositions delineated herein is desired. Additionally, the implantable device delivery system is useful for targeting specific points of compound or composition delivery (e.g., localized sites, organs). Negrin et al., Biomaterials, 22(6):563 (2001). Timed-release technology involving alternate delivery methods can also be used in the present disclosure. For example, timed-release formulations based on polymer technologies, sustained-release techniques and encapsulation techniques (e.g., polymeric, liposomal) can also be used for delivery of the compounds and compositions delineated herein.

The present disclosure will be further described in the following examples. It should be understood that these examples are for illustrative purposes only and are not to be construed as limiting the present invention in any manner.

EXAMPLES

Example 1

Discovery of (−)-P7C3-S243 as a Neuroprotective Compound and its Effect in MPTP Toxicity Model of Parkinson's Disease Abstract. This study identified (−)-P7C3-S243 as a neuroprotective aminopropyl carbazole with improved drug-like properties compared to previously reported compounds in the P7C3 class. It protects developing neurons in a mouse model of hippocampal neurogenesis and protects mature neurons within the substantia nigra in a mouse model of Parkinson's disease. Furthermore, it protects dopaminergic neurons from toxicity associated with 6-OHDA in a rat model of Parkinson's disease and additionally improves motor function in that model. A short, enantioselective synthesis provides (−)-P7C3-S243 in optically pure form. It is non-toxic, orally bioavailable, metabolically stable and crosses the blood-brain barrier. As such, it represents a valuable lead compound for the development of drugs to treat neurodegenerative diseases and traumatic brain injury.

Introduction. Neurodegenerative diseases currently affect millions of people worldwide, and the incidence of disease is rapidly increasing as the aging population expands. The magnitude and trend of this problem places a growing human and financial strain on healthcare systems, which is exacerbated by the absence of effective treatments for many of the most common afflictions.[i] Neurodegenerative diseases, such as amyotrophic lateral sclerosis (ALS) and Parkinson's disease (PD), traumatic brain injury (PDI) and normal age-related cognitive decline, feature, by definition, neuronal cell death. Accordingly, we have searched for small molecules that could prevent the death of neurons in a variety of in vivo contexts. We hypothesize that such neuroprotective agents could possess general utility for treating disorders associated with neuron cell death.

Rather than focusing on pre-defined molecular targets thought to be related to specific neurodegenerative diseases, we searched for small molecules with in vivo neuroprotective properties. In 2010 we reported the results of an unbiased, in vivo screen designed to identify such agents. This assay involved administration of compounds concurrent with exposure to bromodeoxyuridine (BrdU), which marked newly born neurons through incorporation into newly synthesized DNA. The neuroprotective efficacy of compounds was gauged by evaluating their protective effect on newborn neurons within the hippocampus over a 1 week period. Under the assay conditions, around 40% of newborn neural precursor cells in the hippocampus of untreated or vehicle-treated mice underwent apoptotic cell death within one week of their birth. Our screen revealed an aminopropyl carbazole, which we named P7C3, that approximately doubled the number of surviving newborn hippocampal cells at this time point.[ii] Additional experiments demonstrated that P7C3 and derivatives thereof increased the number of new neurons by blocking apoptotic cell death rather than by increasing cell proliferation. Subsequent chemical optimization yielded P7C3-A20, a derivative with improved potency and toxicity profile[iii] and which is available on large scale.[iv] Recently, we and others have shown that the P7C3 class of compounds are broadly protective of mature neurons, with potent efficacy in multiple models of neurodegenerative disease. For instance, we discovered that P7C3 and P7C3-A20 protect neurons in the substantia nigra of mice in a mouse model of Parkinson's disease involving the neurotoxin 1-methyl-4-phenyl-1,2,3,6-tetrahydropyridine (MPTP).[v] Similarly, we found that they minimize motor neuron cell death in the spinal cord of G93A SOD1 transgenic mice, a common model of ALS.[vi] More recently, P7C3-A20 was found to protect rat cerebral cortical neurons in the moderate fluid percussion model of traumatic brain injury.[vii] Finally, P7C3 demonstrated neuroprotective effects in a rat model of age-related cognitive decline[2] and a zebrafish model of retinal degeneration.[viii] In all of these cases, administration of P7C3 or P7C3-A20 protected mature neurons from cell death. Moreover, in cases where neuron death was associated with behavioral or learning deficits, neuroprotective efficacy was reflected in an improvement in learning and memory.

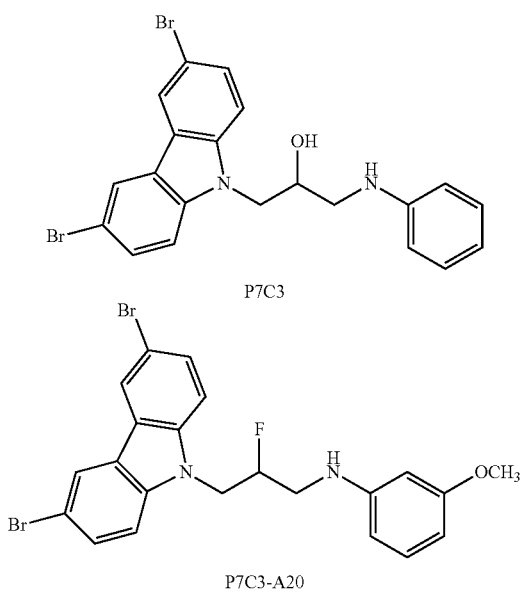

P7C3

P7C3-A20

While P7C3-A20 is active, orally available, brain penetrant and non-toxic, even at doses in excess of the minimally efficacious dose, we recognized the opportunity to design a molecule with improved drug-like properties. In particular, we sought to replace the aniline moiety of P7C3-A20 with an alternative heterocycle, increase the polarity of the compound, and synthesize the drug lead as a single enantiomer. Few marketed drugs contain aniline moieties, and most chiral drugs are produced in optically active form. Here we describe the discovery and evaluation of (−)-P7C3-S243, a neuroprotective agent with improved physicochemical properties. It appears non-toxic and more efficacious than P7C3-A20 in animal models of Parkinson's disease. It therefore represents an optimized neuroprotective agent emerging from the P7C3 class of compounds.

Results. Our most robust assay involves monitoring neuroprotection of newborn hippocampal neurons in mice because this assay gives a simultaneous readout of efficacy, acute toxicity and cell permeability. For this reason, all analogs of P7C3 were evaluated initially by infusing them directly into the left lateral ventricle of environmentally-deprived[ix] live mice using a subcutaneously implanted osmotic minipump. Compounds were delivered intracerebroventricularly (ICV) over a 7 day period at a concentration of 10 µM (12 µL/d).[x] Coincident with ICV administration of drug, mice were dosed daily with the thymidine analog bromodeoxyuridine (BrdU, IP, 50 mg/kg) to mark newly born hippocampal neural precursor cells. At the end of the 1 week dosing, animals were sacrificed and transcardially perfused. Brain slices were stained with antibodies to BrdU, and the number of surviving neural precursor cells was quantified by counting the number of BrdU+ cells in the hippocampal dentate gyrus. To avoid complications arising from the surgical implantation of the pump, we quantified neurogenesis in the hemisphere opposite to compound infusion. Finally, to obtain consistent data across many animals, the number of BrdU+ cells was normalized to the volume of the dentate gyrus.

Our initial objective was to replace the aniline ring with a heterocyclic ring. Previous studies had shown that the N-phenyl ring of P7C3 could be replaced with a 2-pyridyl group (1), but not 3- or 4-pyridyl, while maintaining activity in the in vivo hippocampal neuroprotection assay.[3] Moreover, we had discovered that fluorination of the central methylene and substitution of N-aryl ring improved activity, but neither change alone had substantial impact. For example, 2 (i.e. methoxy-P7C3) and 3 (i.e. fluoro-P7C3) showed similar activity as P7C3. However, fluorinating the anisidine congener, 2, to provide P7C3-A20 substantially improved activity in the hippocampal neuroprotection assay. In this context, we targeted P7C3-S243 (13), a fluorinated compound containing a methoxy-substituted 2-aminopyridine. Following the approach we described for the large-scale synthesis of P7C3-A20,[4] terminal epoxide 4 was opened with 4-Nosyl-protected (Ns, 4-nitrobenzene sulfonyl) 2-methoxy-6-amino aniline. Surprisingly, when the resultant amino alcohol 6 was subjected to fluorination conditions with MorphoDast, analysis by HPLC/MS indicated the formal loss of methanol. We speculated that the pyridine nitrogen displaced an activated alcohol, and the cyclized pyridinium salt (not shown) was demethylated to yield the aminopyridone 7.

We next considered an approach involving amination of a primary amine. To this end, epoxide 5 was opened with sodium azide, the resulting secondary alcohol (8) was fluorinated to provide azido fluoride 9, and the azide was reduced with triphenylphosphine to yield the fluoroamine 10. Reaction of this amine with iodopyridine 11[xi] in the presence of CuI and diketone ligand 12 provided the desired analog, P7C3-S243 in high yield on multi-gram scale.[xii] Alternative conditions featuring Pd catalysts or lacking the diketone ligand provided less than 20% of the intended product. In a similar manner, amino alcohol 14 was arylated to provide 15, the hydroxy congener of P7C3-S243. The aminoalcohol 14 proved much less reactive than the fluoroamine 10, resulting in incomplete conversion. Moreover, in this case added diketone ligand only improved the yield around 10%, suggesting that the amino alcohol itself can serve as a ligand for Cu.

Figure 4:
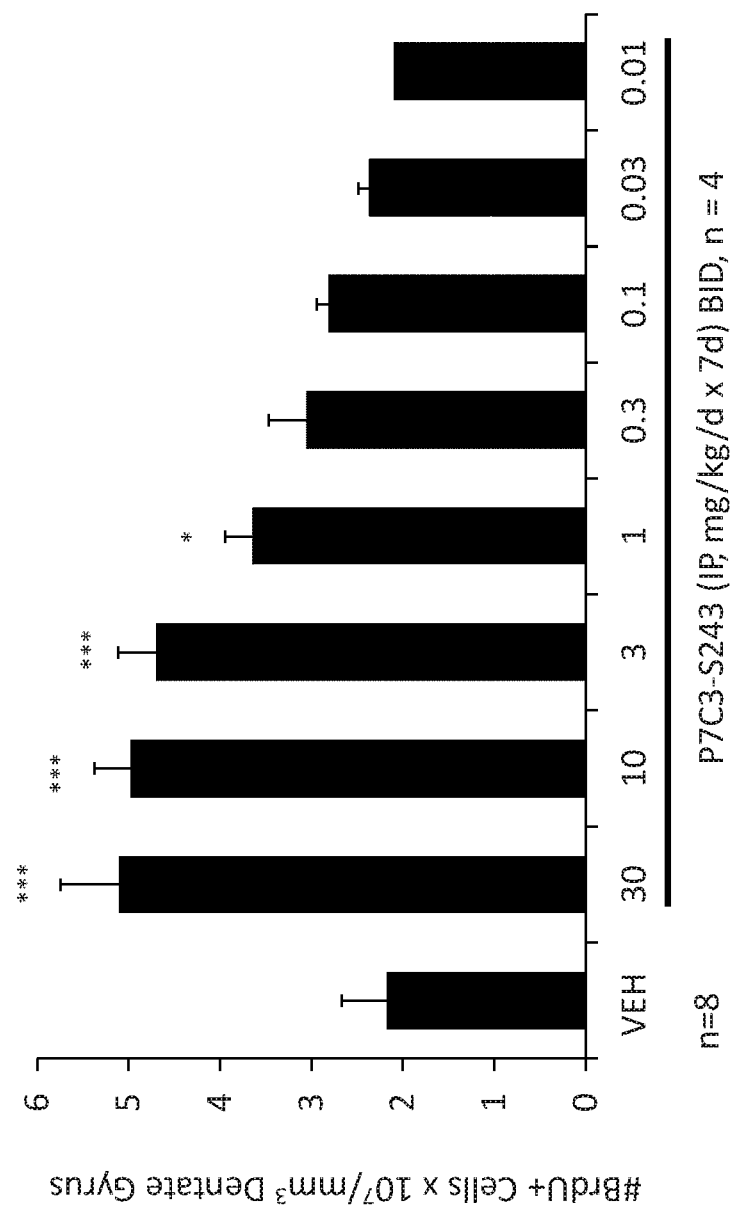
FIG. 4 shows neuroprotective activity of P7C3-S243 rather than increased cell proliferation. Adult mice were administered a bolus of BrdU (150 mg/kg) to label newborn neurons, and 24 hours later, twice-daily IP treatment was begun with vehicle or compound for 7 days. At the end of the 7 days, the number of surviving BrdU-labeled neurons was quantified. Importantly, under the conditions of this experiment, newborn neurons were labeled prior to exposure to drug, so any increase in number of neurons can be attributed to neuroprotective activity rather than proliferative effects. P7C3-S243 showed protection down to 1 mg/kg/day dose. Data shown are mean+/−SEM. P values are shown for comparison to VEH treated group, and were obtained by one-way ANOVA with Dunnet's post-hoc test, using GraphPad Prism 5.0. Asterisks indicate $p<0.01$ (*) or $p<0.0001$ (***).

As described above, compounds were administered to mice ICV over a 1 week period concurrent with IP dosing of BrdU to label newborn hippocampal neurons. FIG. 1 (data shown are the mean+/−SEM) shows that P7C3-S243 approximately doubled the number of surviving newborn hippocampal neurons over this time period, and displayed an activity superior to P7C3 and comparable to P7C3-A20. Several of the synthetic intermediates also displayed neuroprotective activity in this assay. While the azide (9) was inactive under the conditions of this experiment, the primary amines 10 and 14 as well as the N-pyridyl amino alcohol (15) showed a 30% increase in the number of BrdU+ cells compared to vehicle. However, these intermediates were less potent than P7C3-S243 and even slightly less active than our initial hit, P7C3. We originally adopted intracerebroventricular delivery to avoid complications related to brain penetration. Nonetheless, ICV is clearly not an ideal method of dosing. Fortunately, P7C3-S243 showed a smooth dose-response when it was administered intraperitoneally. It was active at a dose of 1 mg/kg/d, and reached its ceiling of efficacy at 10 mg/kg/d, results which parallel those found in the MPTP model of Parkinson's disease (see below). Control experiments demonstrated that the increase in BrdU+ neurons within the hippocampus was due to neuroprotection rather than increased cell proliferation (FIG. 4).

Specifically, in FIG. 4, adult mice were administered a bolus of BrdU (150 mg/kg) to label newborn neurons, and 24 hours later, twice-daily IP treatment was begun with vehicle or compound for 7 days. At the end of the 7 days, the number of surviving BrdU-labeled neurons was quantified.

Importantly, under the conditions of this experiment, newborn neurons were labeled prior to exposure to drug, so any increase in number of neurons can be attributed to neuroprotective activity rather than proliferative effects. As shown in FIG. 4, P7C3-S243 showed protection down to 1 mg/kg/day dose. Data shown are mean+/−SEM. P values are shown for comparison to VEH treated group, and were obtained by one-way ANOVA with Dunnet's post-hoc test, using GraphPad Prism 5.0. Asterisks indicate $p<0.01$ (*) or $p<0.0001$ (***).

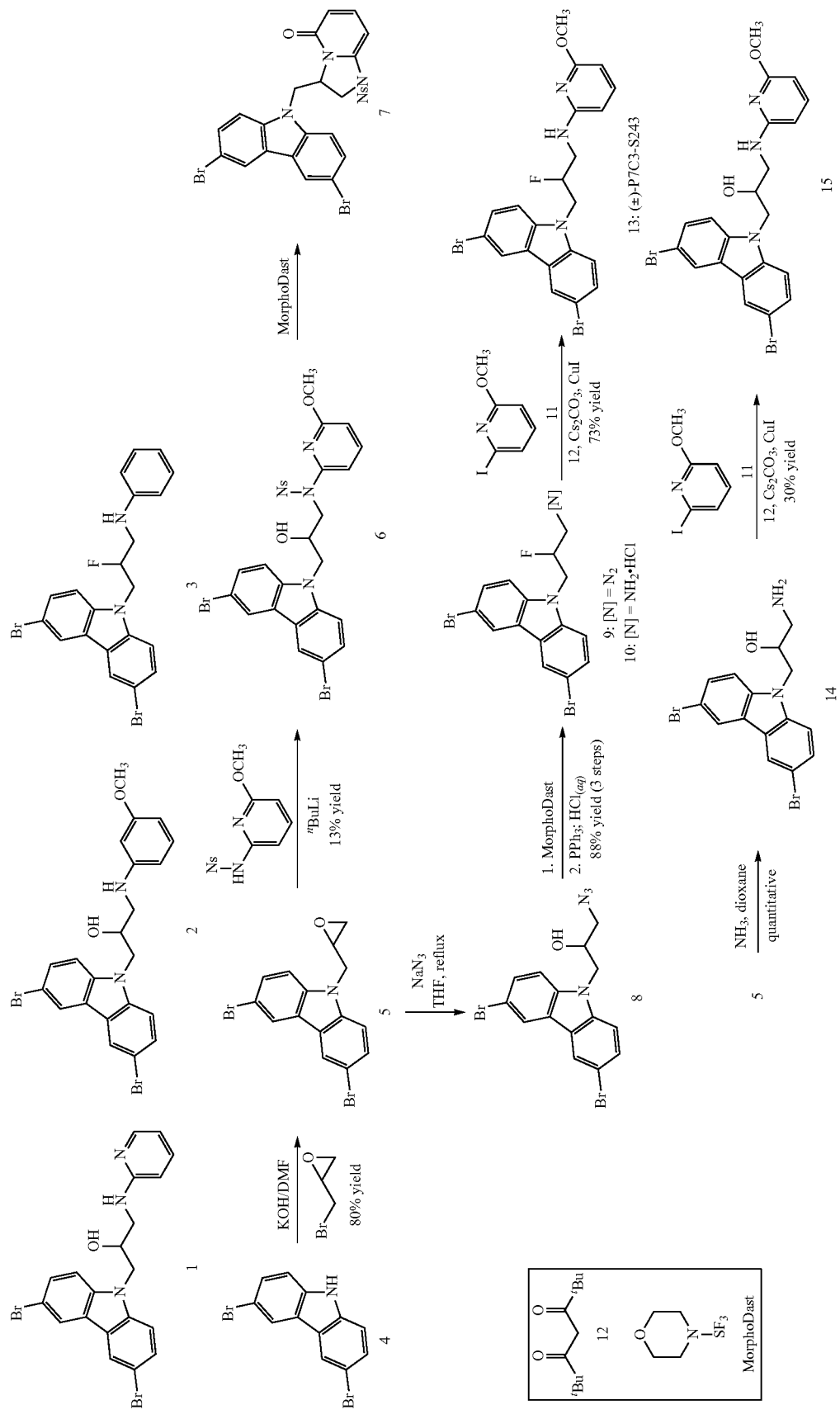

Previous work had demonstrated that the preponderance of neuroprotective activity may have resided in a single enantiomer of the P7C3 class of compounds. The enantiomers of 16, 17 and 18 that are shown in Scheme 2 were the more active of each pair, suggesting a specific protein-binding partner. We also determined that the tertiary alcohol 19 was more active than P7C3, suggesting the presence of a hydrophobic binding site into which the methyl group could project.[3] These observations prompted the question of which, if either, enantiomer of fluorinated analogs such as P7C3-A20 and P7C3-S243 would display higher potency. In particular, we sought to determine if fluorine would act as a polar group and occupy the binding site favored by the hydroxyl group of 16, 17 and 18 or if it would act as a hydrophobic group and bind similarly to 19. Unfortunately, previous attempts to fluorinate an optically active precursor to P7C3-A20 provided material between 0 and 20% ee. This observation came as a surprise because common fluorination agents such as MorphoDast, typically convert one enantiomer of a secondary alcohol to the opposite enantiomer of fluoride. Generally, it is thought that the alcohol is activated by reaction with the sulfur reagent to generate an intermediate of the form —$OSF_2(NR_2)$, which is then displaced, with stereochemical inversion, by fluoride ion. Overall, this process leads to inversion of stereochemistry at the reacting center. In the case of the P7C3 scaffold, it is possible that the carbazole nitrogen could cyclize to yield an aziridinium ion, which, upon ring-opening with fluoride, would generate P7C3-A20 with net retention of stereochemistry. Thus, a combination of these two mechanisms—one proceeding with stereochemical inversion, the other with stereochemical retention—could yield a mixture of enantiomers. An alternative, and not mutually exclusive, mechanism to explain the lack of stereospecificity in the fluorination could involve ionization of the activated alcohol to generate an achiral cation which would be trapped by fluoride to yield racemic product.

Condensation of dibromocarbazole (4) with the 3-Ns protected glycidol derivative 20 provided the epoxide (S)-5 in 97% yield and 96% ee.[xiii] Epoxide ring-opening with azide was quantitative, and provided a substrate for fluorination (+)-8. Comparison with material formed from a Mitsunobu reaction with S-glycidol demonstrated that, as described by Sharpless and co-workers, sulfonate 20 reacted by direct displacement of the leaving group rather than by epoxide opening/epoxide closure.[xiv]

Consistent with previous results, we found that reaction with MorphoDast was not stereospecific: recovered azido-flouride 9 was only 63% ee. We speculate that the common invertive mechanistic pathway was compromised by an intramolecular displacement with the carbazole nitrogen, yielding an aziridinium ion intermediate (not shown). This pathway would occur with overall retention, and lower the observed optical purity. In contrast, we discovered that the reagent combination perfluorobutane sulfonylfluoride and TBAT (tetrabutylammonium difluorotriphenylsilicate) yielded the desired fluoride with clean inversion.[xv] Subsequent processing as before provided optically active P7C3-S243 in 95% ee. Recrystallization from isopropanol enriched the optical purity to 99% ee. Direct synthesis of the single enantiomer provides a practical and operational advantage over separation of the racemate using chromatography. While separation may be effective, it is limited to a maximum 50% yield and becomes more challenging on larger scales due to the requirement for larger HPLC columns and increased solvent use, among other difficulties.

It should be noted that the synthesis of (−)-P7C3-S243 required unconventional approaches because standard reaction conditions proved ineffective. For example, the synthesis of the (+3,6-dibromo-9-(oxiran-2-ylmethyl)-9H-carbazole intermediate could reasonably have been anticipated to have been accomplished using optically active epichlorohydrin or epibromohydrin. However, under these conditions, racemic product was formed. The special reagent 3-nitrobenzenesulfonyl glycidol was required. Similarly, installation of the fluoride of (−)-P7C3-S243 proved surprisingly difficult. Using conditions analogous to those we developed for P7C3-A20 (Naidoo, et al. Tetrahedron Lett, 2013, 4429), we observed an unanticipated cyclization of the aminopyridine rather than the desired fluorination. Using a different substrate, an azide, we were able to effect fluorination. However, common reagents including DAST and MorphoDast generated P7C3-S243 as a mixture of R and S isomers. This observation required the use of unusual reaction conditions (C4F9SO2F/[Bu$_4$N][Ph$_3$SiF$_2$]), conditions which have not previously been used for compounds containing only a single stereogenic center.

Scheme 2. Stereoselective synthesis of P7C3-S243

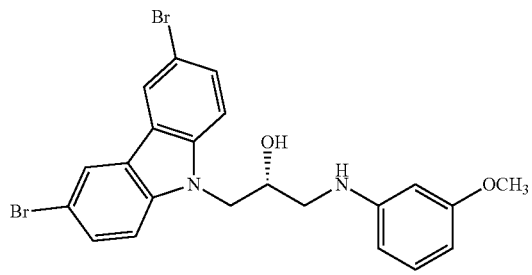

16

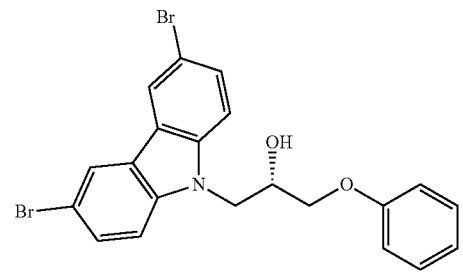

17

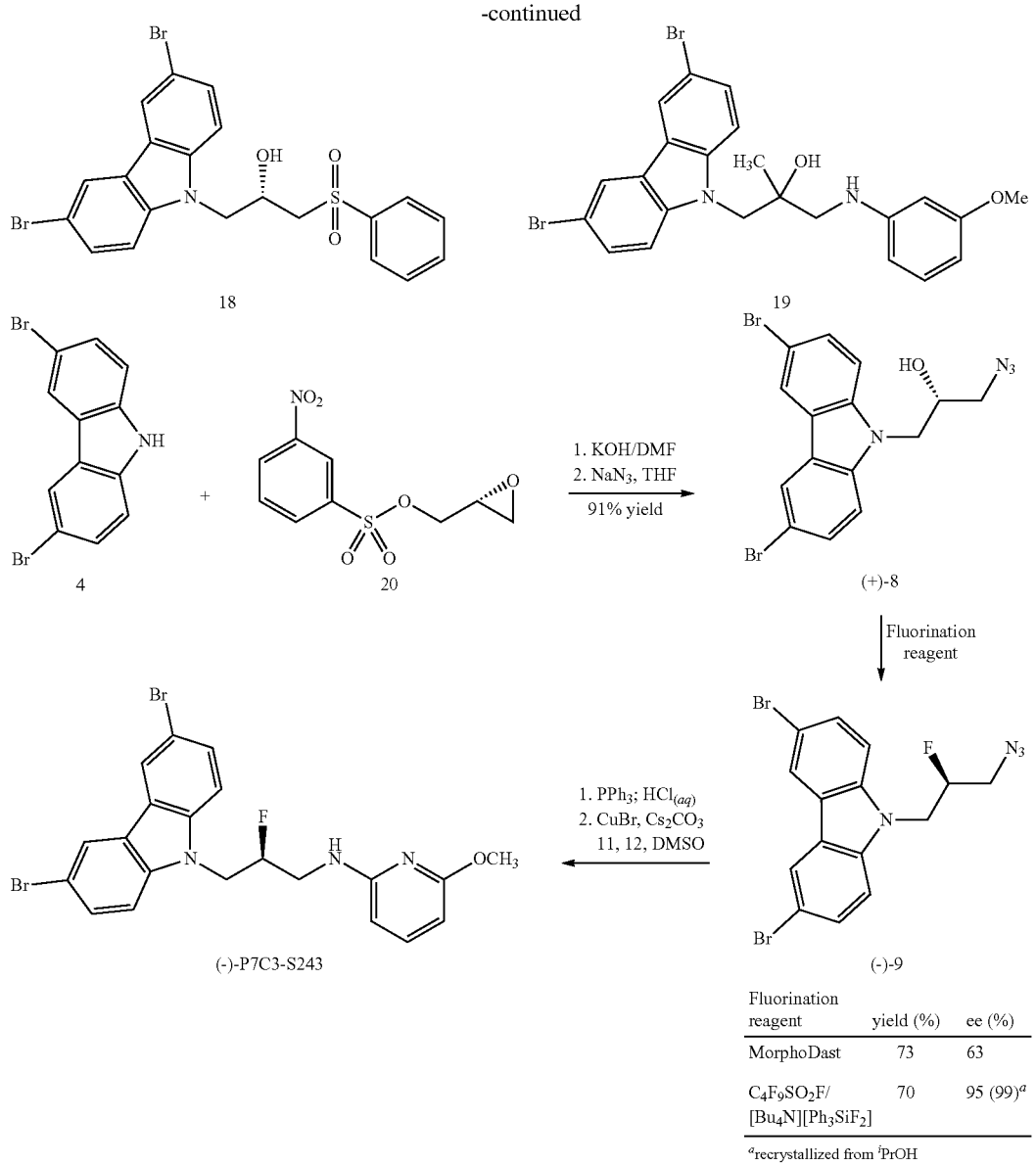

It was unclear at the outset whether the R or S enantiomer would show activity. Previous work had demonstrated the enantiomeric preference for neuroprotective compounds with a central hydroxyl group. However, the presence of a methyl group was also known to increase activity. Taken together, the data suggests that the binding pocket for the P7C3 class of compounds contains one pocket that prefers polar groups, and perhaps donates or accepts a hydrogen bond. Additionally, there appeared to be a binding site for lipophilic groups such as a methyl group. Conceivable, the same pocket could accommodate either a methyl group or a hydroxyl group. In this context, it was unclear if the fluoride would mimic a hydroxyl since both are electronegative, and therefore form polar bonds, and can accept hydrogen bonds. Alternatively, fluoride is generally considered lipophilic, and could therefore more closely resemble a methyl group and occupy the binding site distinct from the hydroxyl group. For these reasons, it proved impossible to predict if the R or S enantiomer would be more active or even if there would be a difference between them.

Figure 2:
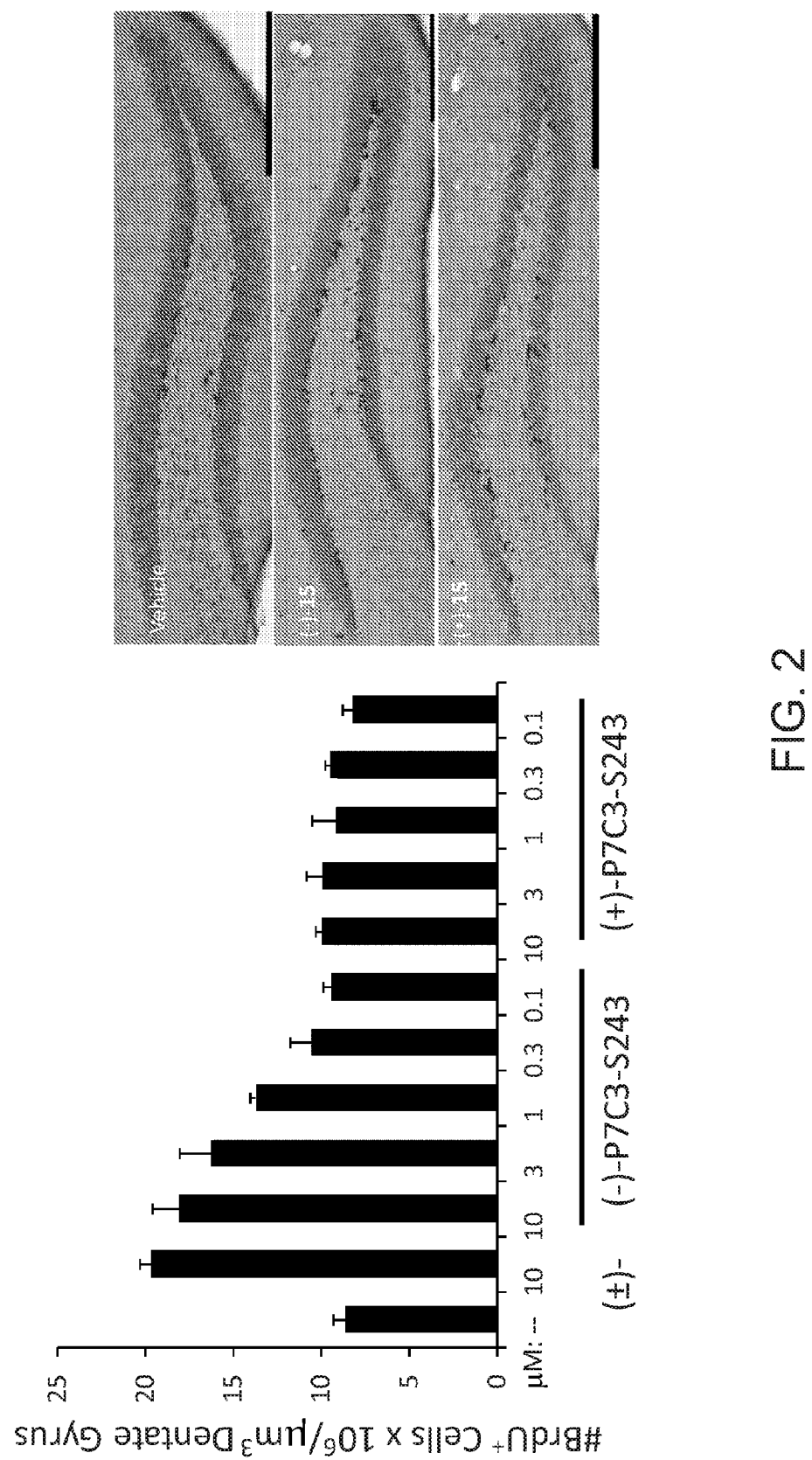
FIG. 2 shows enantiomer-specific efficacy of P7C3-S243 in a mouse model of neurogenesis. Compound was administered ICV at the indicated concentration (0.5 mL/h) for 7 days, during which time mice were dosed IP daily with BrdU (50 mg/kg/d) to label newborn hippocampal neurons. Graph shows are the mean±SEM. N=4 or 5 for each group. Images are of representative stained sections. Bar=0.3 mm.
Figure 5:
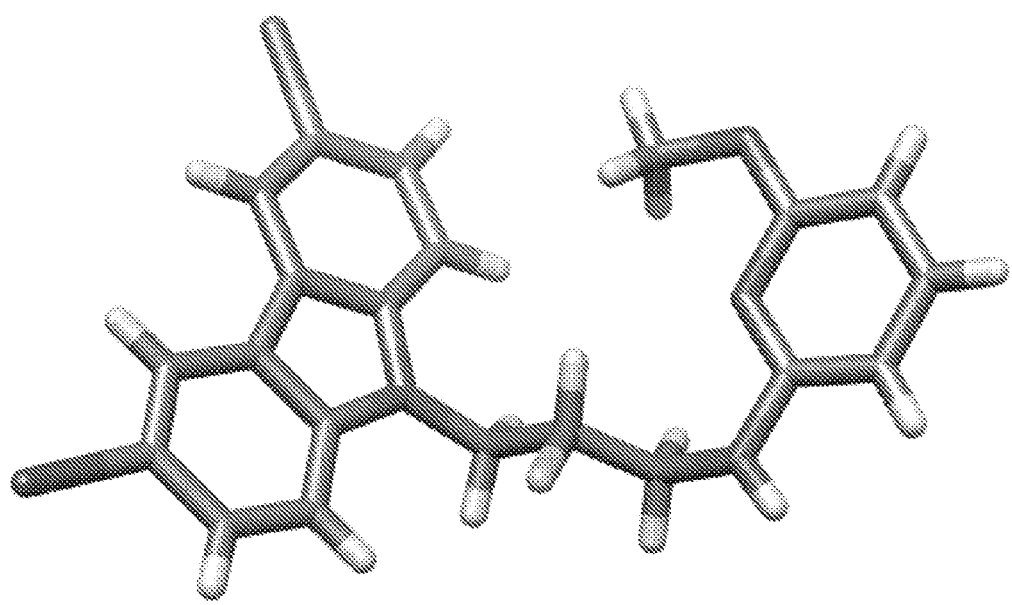
FIG. 5 shows X-ray crystal structure of (−)-(S)-P7C3-S243.

The pure enantiomers of P7C3-S243 were first evaluated in the mouse model of hippocampal neuroprotection following ICV dosing. Referring to FIG. 2, compound was administered ICV at the indicated concentration (0.5 µL/h) for 7 days, during which time mice were dosed IP daily with BrdU to label newborn hippocampal neurons. Data shown in FIG. 2 upper panel are the mean+/−SEM. N=4 or 5 for each group. Images shown in FIG. 2 lower panel are of representative stained sections. Bar=0.3 mm. As shown in FIG. 2, (−)-P7C3-S243 is highly active, whereas its enantiomer shows no neuroprotective activity in this assay. X-ray crystallographic analysis of a single crystal of (−)-P7C3-S243 revealed it to be the S enantiomer (FIG. 5). Interestingly, the more active fluoride is enantiomeric to the more active enantiomer in the hydroxyl series (16-18). This observation implies that the binding partner for the P7C3 class of neuroprotective chemicals contains both a hydrophobic pocket, which can be occupied by the fluoride or methyl group, and a polar pocket, which preferentially accommodates a hydroxyl group.

The mouse model of neurogenesis involves protecting newborn hippocampal neurons from premature apoptotic cell death. We also sought to determine if P7C3-S243 could protect mature neurons from cell death. In this context, we had previously demonstrated that P7C3 and P7C3-A20 could protect mature dopaminergic neurons within the substantia nigra (SNc) from toxicity associated with MPTP.[5] This mouse model of Parkinson's disease entails treating mice for 5 days with a toxic dose of MPTP (30 mg/kg/d) to initiate cell death within the substantia nigra. In the brain, MPTP is oxidized to 1-methyl-4-phenylpyridinium cation (MPP$^+$), which is selectively transported into dopaminergic neurons within the SNc.[xh] Within these cells, MPP$^+$ acts as a mitochondrial poison, generating a pathology that resembles that of Parkinsonian patients.[xvii] Under our assay conditions, treatment with drug was initiated a full 24 hours after the final dose of MPTP. This dosing regime ensures that any effect of the P7C3 class of compounds can be attributed to neuroprotective activity rather than to simply blocking the uptake or metabolism of MPTP.[xviii] Mice were administered drug twice daily for 21 days, after which time they were sacrificed by transcardial perfusion. Fixed brains were sectioned through the SNc at 30-μM intervals. Every fourth section was stained with antibodies specific to tyrosine hydroxylase (TH). The TH enzyme catalyzes the oxidation of L-tyrosine to L-DOPA, which is the first step in the biosynthesis of dopamine. Accordingly, the number of TH+ cells provides a quantification of the neuroprotective efficacy of P7C3 derivatives following MPTP exposure. Importantly, all microscopic analyses were performed blinded to treatment group.

Figure 3:
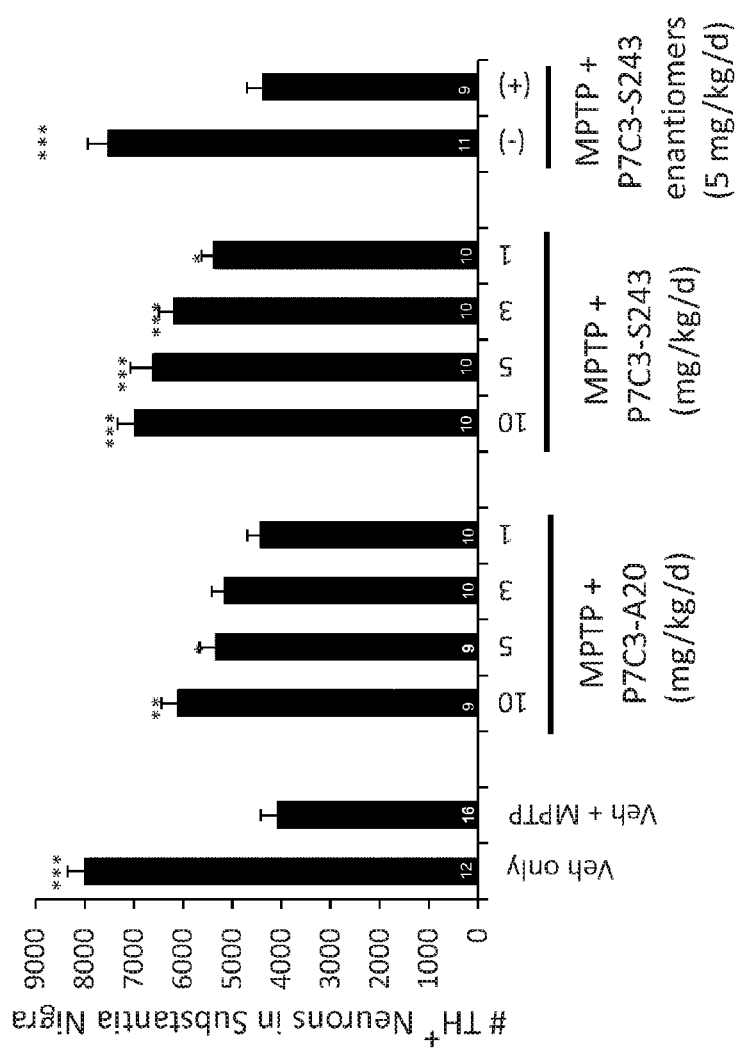
FIG. 3 shows neuroprotection in the MPTP model of Parkinson's disease. Mice were administered MPTP (30 mg/k/d) for 5 days. On the 6$^{th}$ day, treatment with drug was initiated at the indicated dose (IP, BID, 21 d). Bars indicate number of tyrosine hydroxylase positive cells detected by immunohisotochemical staining of the substantial nigra. Error bars indicate SEM. Asterisks indicate $p<0.01$ (*), $p<0.001$ () or $p<0.0001$ (*) relative to Veh+MPTP group. Numbers of mice in each group are shown within the bars.
Figure 3:
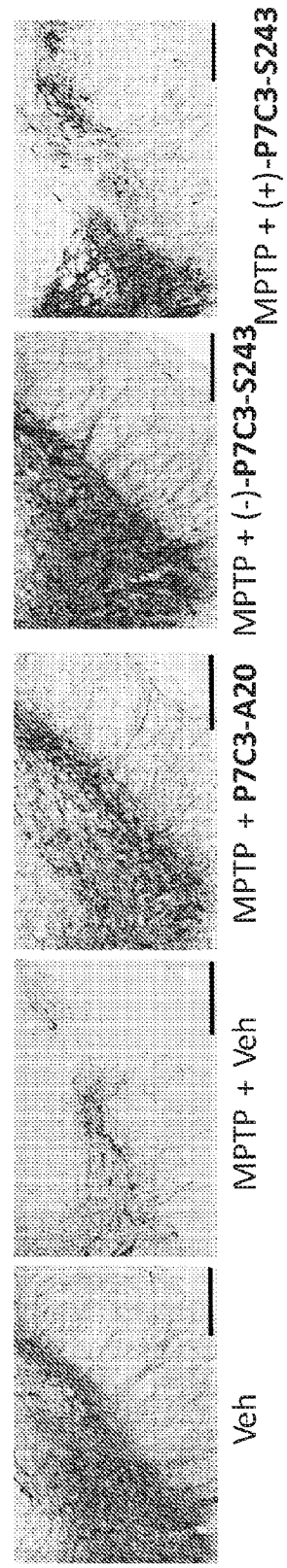

To test efficacy of P7C3-S243 in the MPTP model of Parkinson's disease, mice were administered MPTP (30 mg/k/d) for 5 days. On the 6$^{th}$ day, treatment with drug was initiated at the indicated dose (IP, BID, 21 d). In FIG. 3 upper panel, bars indicate number of tyrosine hydroxylase positive cells detected by immunohistochemical staining of the substantia nigra; error bars indicate SEM; asterisks indicate $p<0.01$ (*), $p<0.001$ () or $p<0.0001$ (*) relative to the Veh+MPTP group; number of mice in each group are shown within the bars. In FIG. 3 lower panel, representative immunohistochemical pictures of TH staining in the SNc are shown for 5 mg/kg/d treatment groups; bar=300 μM. As shown in FIG. 3, MPTP effects an approximately 50% reduction in the number of TH+ neurons under the chronic dosing protocol described above. Consistent with our earlier reports, P7C3-A20 shows marked neuroprotective activity, showing significant neuroprotective effect when administered at 5 mg/kg/d and protection resulting in around 75% rescue at the 10 mg/kg/d dose.[5] Encouragingly, P7C3-S243 demonstrated even higher neuroprotective activity than P7C3-A20, with the former showing significant activity at a dose of 1 mg/kg/d and rescuing over 85% of the TH+ neurons at the highest dose tested (10 mg/kg/d). Moreover, the enantiomeric specificity observed in the MPTP model of Parkinson's disease mirrored that observed in the mouse model of neurogenesis. Specifically, (−)-P7C3-S243 was strongly protective while the (+)-enantiomer was indistinguishable from vehicle treatment under the conditions of the assay. In this side-by-side experiment, P7C3-S243 appears at least as effective as P7C3-A20, a compound that has proven efficacy in several animal models of neurodegenerative disease.

The pharmacokinetic and toxicity profiles of P7C3-S243 were evaluated using both in vivo and in vitro methods. Having observed near complete metabolic stability in the presence of murine hepatocytes ($T_{1/2}>240$ min), we monitored plasma and brain levels of the compound following IV, oral and IP dosing. As shown in Table 1, P7C3-S243 showed a dose-proportional increase in brain levels following IP dosing. Plasma bioavailability was higher via IP dosing compared to PO, but partitioning into the brain was superior when the compound was administered by oral gavage. We have noted the same effect with P7C3-A20, and thus comparable brain levels are achieved by either IP or oral gavage. By all routes of administration, P7C3-S243 was metabolically stable.

TABLE 1

Pharmacokinetic properties of P7C3-S243

| Administration | Dose (mg/kg) | AUC$_{(brain)}$ (μg * min/g)$^a$ | % F (plasma/brain) | AUC$_{brain}$: AUC$_{plasma}$ | $T_{1/2}$ (h) |
|---|---|---|---|---|---|
| IV | 10 | 671 ± 14 | — | 1.1 | 7.4 |
| IP | 10 | 189 ± 35 | 66/28 | 0.45 | >24 |
| IP | 20 | 319 ± 68 | 90/48 | 0.28 | 15 |
| PO | 20 | 388 ± 29 | 38/58 | 0.81 | 9.6 |

$^a$mean ± SEM.

(−)-P7C3-S243 did not show significant toxicity towards 3 human cancer cell lines tested (IC$_{50}$>10 μM vs H2122, H2009 and HCC44). Likewise, we observed <15% inhibition of the hERG channel at 50 μM using a patch clamp assay. Several cytochrome P450's were insensitive to (−)-P7C3-S243 (3A4, 2C9, 3D6, 2C8, 2B6) while CYP1A2 and CYP2C19 showed modest IC$_{50}$ values of 20 and 1.9 μM, respectively. Given the high protein binding of P7C3-S243, free concentrations of drug are unlikely to reach those concentrations. Finally, (−)-P7C3-S243 was screened through the NIH's Psychoactive Drug Screening Program, and no compelling binding partners were identified. Of 47 neuronal receptors and channels tested, only the μ-opioid receptor (IC$_{50}$=8.2 μM) and the peripheral benzodiazepine receptor (also known as translocator protein, TSPO, IC$_{50}$=0.35 μM) showed any ligand displacement. The binding affinity of the former is clearly too weak to be causative for the biological activity we observe, provided that the in vitro data are predictive of binding in vivo. The relevance of binding to TSPO is less clear, however. While total brain concentration remains in the low μM range for several hours after dosing, free concentration is much lower. Moreover, while we see enantiomeric specificity in the neurogenesis (FIG. 2) and MPTP assays (FIG. 3), both enantiomers of P7C3-S243 bind TSPO with similarly weak affinity (0.35 and 0.68 μM). A wide structural range of chemicals have been found to bind TSPO, from the eponymous benzodiazepines to cholesterol to porphyrins,[xix] suggesting that it might represent a non-specific binding partner for small molecules. Finally, a tight binding inhibitor of this protein showed no toxicity in phase I and II clinical trials for amyotrophic lateral sclerosis and is currently in phase II trials for spinal muscular atrophy.[xx] Overall, the clean receptor binding results (not shown) are consistent with our observation that long-term treatment with P7C3-A20 (up to 40 mg/kg/d for 21 d) or P7C3-S243 (up to 10 mg/kg/d for 21 d) has no negative impact on weight, behavior or appearance of treated animals.

We have discovered a novel class of potent neuroprotective agents known as the P7C3 series of aminopropyl carbazoles. We have now synthesized and characterized an optimized member of this series which lacks an aniline moiety. Moreover, it exhibits improved polarity and is readily available as a single enantiomer. These characteristics improve its drug-like properties compared to previously reported analogs. Here we demonstrate that the (−)-P7C3-S243 potently blocks neurons cell death under two conditions: apoptosis of newborn hippocampal neurons and MPTP-mediated killing of dopaminergic neurons in the substantia nigra. The latter effect is notable for almost complete protection in this model of Parkinson's disease. Future reports will describe the effect of this neuroprotective chemical in a rat model of Parkinson's disease and mouse models of traumatic brain injury. Taken together, the results suggest that (−)-P7C3-S243 is a promising candidate for treating some of the most devastating neurological disorders—disorders that are likely to increase in prevalence and which currently lack effective therapies.

Experimental Section

In Vivo Neuroprotection Assay. Test compounds were evaluated as described previously.[2] Compounds were infused intracerebroventricularly (i.c.v.) into the left lateral ventricle of four adult (12 week old) wild-type C57BL/J6 mice by means of surgically implanted Alzet osmotic minipumps that delivered solution into animals at a constant rate of 0.5 μl/hour for 7 days. Alternatively, compounds were administered intraperitoneally twice daily. Bromodeoxyuridine (BrdU) was injected intraperitoneally at 50 mg/kg/day for six days during pump infusion. Twenty-four hours after the final BrdU administration, mice were sacrificed by transcardial perfusion with 4% paraformaldehyde at pH 7.4, and their brains were processed for immunohistochemical detection of incorporated BrdU in the SGZ. Dissected brains were immersed in 4% paraformaldehyde overnight at 4° C., then cryoprotected in sucrose before being sectioned into 40 μm thick free-floating sections. Unmasking of BrdU antigen was achieved through incubating tissue sections for two hours in 50% formamide/2×SSC at 65° C., followed by a five minute wash in 2×SSC and subsequent incubation for thirty minutes in 2M HCl at 37° C. Sections were processed for immunohistochemical staining with mouse monoclonal anti-BrdU (1:100). The number of BrdU+ cells in the entire dentate gyrus SGZ in the contralateral hemisphere (opposite side of surgically implanted pump) was quantified by counting BrdU+ cells within the SGZ and dentate gyrus in every fifth section throughout the entire hippocampus and then normalizing for dentate gyrus volume.

MPTP Assay. As previously reported,[5] adult male C57Bl/6 mice were individually housed for one week and then injected daily for 5 days with 30 mg/kg/day (i.p.) free base MPTP (Sigma). On day 6, 24 hours after receiving the fifth and final dose of MPTP, daily treatment with compound was initiated. Mice received twice daily doses of each compound (or vehicle) for the following 21 days, after which mice were sacrificed by transcardial perfusion with 4% paraformaldehyde. Brains were dissected, fixed overnight in 4% paraformaldehyde, and cryoprotected in sucrose for freezing by standard procedures. Frozen brains were sectioned through the striatum and SNc at 30 μM intervals, and every fourth section (spaced 120 μM apart) was stained with antibodies directed against tyrosine hydroxylase (TH) (Abcam, rabbit anti-TH, 1:2500). Diaminobenzidine was used as a chromagen, and tissue was counter-stained with hematoxylin to aid in visualization of the neuroanatomy. Images were analyzed with a Nikon Eclipse 90i motorized research microscope with Plan Apo lenses coupled with Metamorph Image Acquisition software (Nikon). TH+ neurons were counted with Image J software (NIH) in every section by 2 blinded investigators and results were averaged and multiplied by the sectioning interval to determine the total number of TH+ neurons per SNc.

Pharmacokinetic Analysis. P7C3-S243 was formulated in 5% DMSO/10% cremophor EL (Sigma, St. Louis, Mo.)/85% D5W (5% dextrose in water, pH 7.2). Adult mice were dosed IV, IP or via oral gavage (P0) in a total volume of 0.2 ml. Animals were sacrificed at varying times after dosing by inhalation overdose of $CO_2$. Whole blood was collected with an ACD solution (sodium citrate) coated syringe and needle. The blood was subsequently centrifuged at 9300×g for 10 min to isolate plasma. Plasma was stored at −80° C. until analysis. Brains were isolated from mice immediately after sacrifice, rinsed extensively with PBS, blotted dry, weighed, and snap frozen in liquid nitrogen. Lysates were prepared by homogenizing the brain tissue in a 3-fold volume of PBS (weight of brain in g×3=volume of PBS in ml added). Total lysate volume was estimated as volume of PBS added+volume of brain in ml. One hundred μl of either plasma or brain was processed by addition of 200 μl of acetonitrile containing 0.15% formic acid to precipitate plasma or tissue protein and release bound drug. This mixture was vortexed 15 sec then centrifuged at 13,120×g for 5 min and the supernatant analyzed directly by HPLC/MS/MS. Standard curves were prepared by addition of compound to blank plasma or blank brain lysate. A value of 3-fold above the signal obtained from blank plasma or brain lysate was designated the limit of detection (LOD). The limit of quantitation (LOQ) was defined as the lowest concentration at which back calculation yielded a concentration within 20% of theoretical. Pharmacokinetic parameters were calculated using the noncompartmental analysis tool of WinNonLin (Pharsight). Bioavailability was calculated as $AUC_{oral}/AUC_{iv} \times Dose_{iv}/Dose_{oral} \times 100$ (AUC is area under the concentration time curve). The Brain:Blood ratio was calculated using AUC values.

Chemistry. (S)-3,6-dibromo-9-(oxiran-2-ylmethyl)-9H-carbazole: A stirred solution of 3,6-dibromocarbazole (6.27 g, 19.3 mmol) and crushed potassium hydroxide pellets (1.30 g, 23.2 mmol) in dimethylformamide (100 ml) was cooled in ice before the slow drop wise addition of (R)-glycidyl-3-nitrobenzenesulfonate, (20) (5.01 g, 19.3 mmol). The ice bath was removed and the reaction was stirred overnight at ambient temperature. The reaction mixture was diluted with water and washed several times with water and then brine. The organic layer was dried over $Na_2SO_4$, filtered, and concentrated to give epoxide in quantitative yield. Crude material was carried forward. $^1H$ NMR ($CDCl_3$, 400 MHz): δ 8.13 (d, J=2.0 Hz, 2H), 7.57 (dd, J=8.7, 1.8 Hz, 2H), 7.39-7.31 (m, 2H), 4.65 (dd, J=16.0, 2.5 Hz, 1H), 4.28 (dd, J=16.1, 5.0 Hz, 1H), 3.32 (ddd, J=5.2, 2.6, 1.3 Hz, 1H), 2.82 (t, J=4.3 Hz, 1H), 2.50 (dd, J=4.7, 2.6 Hz, 1H). HPLC conditions: ChiralPak AD-H column, flow-rate=1.0 ml/min, 1% IPOH/hexanes. Retention time of peak 1(major) is 24.3-34.0 minutes and retention time of peak 2 (minor) is 48.4-58.6 minutes; ee=95.9%. $[α]_D^{20}$=+5.737 (c=0.244, THF)

(S)-1-azido-3-(3,6-dibromo-9H-carbazol-9-yl)propan-2-ol: Tetrahydrofuran (65 ml) and a 20% aqueous solution of sodium azide (75 ml) were charged to a round bottom flask containing (S)-3,6-dibromo-9-(oxiran-2-ylmethyl)-9H-carbazole (7.79 g, 20.4 mmol). The reaction was heated to 75° C. A further 20 ml of a 20% aqueous solution of sodium azide was added after 24 hours to ensure completion of reaction. The mixture was condensed under reduced pressure, diluted with EtOAc and washed twice with water. The organic layer was dried over $Na_2SO_4$, filtered, and concentrated to give crude azido-alcohol in 91% yield, which was used without additional purification. $^1H$ NMR ($CDCl_3$, 400 MHz): δ 8.06 (d, J=1.9 Hz, 2H), 7.53 (dd, J=8.7, 2.0 Hz, 2H), 7.28 (d, J=8.4 Hz, 2H), 4.26 (dd, J=6.1, 1.6 Hz, 2H), 4.23-4.14 (m, 1H), 3.44 (dd, J=12.6, 4.3 Hz, 1H), 3.30 (dd, J=12.6, 5.6 Hz, 1H), 2.48 (s, 1H). ESI m/z: 466.6 ([M+HCOO]$^-$, $C_{15}H_{12}Br_2N_4O$ requires 421.94. $[\alpha]_D^{20}$=+3.18 (c=0.26, THF).

(R)-9-(3-azido-2-fluoropropyl)-3,6-dibromo-9H-carbazole: Tetrabutylammonium difluorotriphenylsilicate (TBAT, 9.50 g, 17.6 mmol) was charged to a round bottom flask containing (S)-1-azido-3-(3,6-dibromo-9H-carbazol-9-yl)propan-2-ol (7.41 g, 17.5 mmol). Diisopropylethylamine (7.75 ml, 44.5 mmol) and toluene (140 ml) was added. Perfluoro-1-butanesulfonyl fluoride (PBSF, 6.91 ml, 38.5 mmol) was added dropwise and the reaction was stirred overnight at ambient temperature. The mixture was concentrated and purified by an automated chromatography system (SiO$_2$, 50% DCM/hexanes) which gave 5.198 g of the fluoro-azide in 70% yield. $^1$H NMR (CDCl$_3$, 400 MHz): δ 8.14 (t, J=2.3 Hz, 2H), 7.64-7.52 (m, 2H), 7.32 (dd, J=8.7, 1.8 Hz, 2H), 5.12-4.85 (m, 1H), 4.54 (ddt, J=17.9, 5.4, 2.4 Hz, 2H), 3.58 (ddd, J=17.7, 13.5, 4.5 Hz, 1H), 3.40 (ddd, J=24.1, 13.5, 4.7 Hz, 1H). ESI m/z: 468.7 ([M+HCOO]$^-$, $C_{15}H_{11}Br_2FN_4$ requires 423.93. HPLC conditions: ChiralPak AD-H column, flowrate=1.0 ml/min, 0.5% IPOH/hexanes. Peak 1 (minor) has a retention time of 25.0-29.1 minutes and peak 2 (major) has a retention time of 29.4-40.7 minutes. ee=96.16%

(S)-3-(3,6-dibromo-9H-carbazol-9-yl)-2-fluoropropan-1-amine: THF (80 ml) was added to a round bottom flask containing (R)-9-(3-azido-2-fluoropropyl)-3,6-dibromo-9H-carbazole (5.096 g, 12.0 mmol) and triphenylphosphine (3.241, 12.3 mmol). The reaction was heated at 65° C. overnight. Water was added to the cooled reaction and stirred for six hours, before it was condensed. The viscous mixture was diluted with EtOAc and washed twice with water and then brine. The organic layer was dried over Na$_2$SO$_4$, filtered, and concentrated giving a yellow waxy residue.

Minimal cold DCM was added to the waxy residue before the dropwise addition of 1M HCl which precipitated the hydrochloride salt. The slurry was stirred for about 20 minutes before it was filtered, washed with DCM several times and finally with hexanes. The powdery solid (5.29 g) was air dried and contained less than 1% of PPh$_3$O byproduct.

The salt was then free-based by adding a saturated solution of sodium bicarbonate (90.0 ml) to a milky mixture of salt (5.29 g) in DCM (90.0 ml) with Et$_3$N (3.0 ml). The solution was stirred for an hour until the organic layer was translucent. The separated organic layer combined with organic extracts was dried over Na$_2$SO$_4$, filtered, and concentrated to give of the free amine as an off-white solid. $^1$H NMR (CDCl$_3$, 400 MHz): δ 8.15 (d, J=2.0 Hz, 2H), 7.57 (dd, J=8.8, 1.9 Hz, 2H), 7.36 (d, J=8.7 Hz, 2H), 4.85 (dtt, J=47.9, 6.1, 4.4 Hz, 1H), 4.67-4.39 (m, 2H), 3.22-2.78 (m, 2H). ESI m/z: 398.7 ([M+1]$^+$, $C_{15}H_{13}Br_2FN_2$ requires 397.94

(−)-P7C3-S243: (S)-N-(3-(3,6-dibromo-9H-carbazol-9-yl)-2-fluoropropyl)-3-methoxyaniline: (S)-9-(3-amino-2-fluoropropyl)-3,6-dibromo-9H-carbazole (72.2 mg, 0.18 mmol), 2-iodo-6-methoxypyridine (45.4 mg, 0.19 mmol), copper iodide (2.9 mg, 0.015 mmol) and cesium carbonate (119.4 mg, 0.36 mmol) were added to an oven dried vial, which was nitrogen purged for 10 minutes. DMSO (0.36 ml) and 2,2,6,6-tetramethyl-3,5-heptanedione (4 µl, 0.019 mmol) were then added. The reaction was heated at 40° C. for three hours. The cooled mixture was diluted with EtOAc and washed thrice with a solution of 9:1 saturated NH$_4$Cl: NH$_4$OH and then thrice with water and then brine. The organic layer was dried over Na$_2$SO$_4$, filtered and concentrated. The well dried solid was dissolved in methylene chloride and passed through a short silica plug, which removed the small amount of unreacted amine. The filtrate was condensed to give white solid, which was purified by automated flash chromatography system in 50-80% methylene chloride/hexanes. Isolated yield=61%, ee=96%. Recrystallization to enhance ee was carried out by heating a solution of 15.8 mg of purified product in 1.0 ml of isopropanol. Overall Yield=59%, ee=98.5%

$^1$H NMR (CDCl$_3$, 400 MHz): δ 8.16 (d, J=1.9 Hz, 2H), 7.56 (d, J=1.9 Hz, 2H), 7.35-(t, J=7.8 Hz, 1H), 7.30 (d, J=8.7 Hz, 1H), 6.04 (dd, J=32.7, 8.0 Hz, 2H), 5.29-5.02 (dm, 1H), 4.65-4.46 (m, 3H), 3.87-3.74 (m, 1H), 3.70 (s, 3H), 3.66-3.49 (m, 1H). ESI m/z: 506.7 ([M+1]$^+$, $C_{22}H_{19}Br_2FN_2O$ requires 504.98

HPLC conditions: ChiralPak IA column, flowrate=1.0 ml/min, 100% MeOH. Peak 1 (major) has a retention time of 8.37-10.02 minutes and peak 2 (minor) has a retention time of 10.26-11.26 minutes. $[\alpha]_D^{20}$=−9.48 (c=0.464, THF)

Abbreviations

ALS, amyotrophic lateral sclerosis; PD, Parkinson's disease; TBI, traumatic brain injury; BrdU, bromodeoxyuridine; MPTP, 1-methyl-4-phenyl-1,2,3,6-tetrahydropyridine; SOD, superoxide dismutase; ICV, intracerebroventricularly; IP, Intraperitoneal; PO, per os (by mouth); TH, tyrosine hydroxylase; SNc, substantia nigra; AUC, area under the curve.

Example 2

The P7C3-Class of Neuroprotective Molecules Protects Mice from Blast-Mediated Traumatic Brain Injury Abstract. Improvised explosive devices (IEDs) widely used in modern warfare have increased the prevalence of blast-mediated traumatic brain injury (TBI) in soldiers. TBI causes neuronal damage in the brain resulting in chronic cognitive and motor neurological symptoms (1), as well as a range of vision problems (23). Sadly, there is a lack of effective pharmacologic therapeutic options for these patients. The P7C3-series of aminopropyl carbazole neuroprotective molecules (2-6), however, has been shown to have both neuroprotective and functional protective efficacy in the moderate fluid percussion injury model in rats (22). When administered 30 minutes after injury, these agents blocked death of mature cortical neurons, enhanced hippocampal neurogenesis by blocking death of newborn hippocampal neurons, and preserved outcome measures of both sensorimotor (spontaneous forelimb task) and cognitive function (Morris water maze). Here, we show that these agents also offer protective efficacy in mice subjected to blast injury. Our hope is that the chemical scaffold represented by the P7C3-class of neuroprotective molecules will provide a basis for optimizing and advancing new pharmacologic agents for protecting patients against the early and chronic consequences of TBI.

Figure 6:
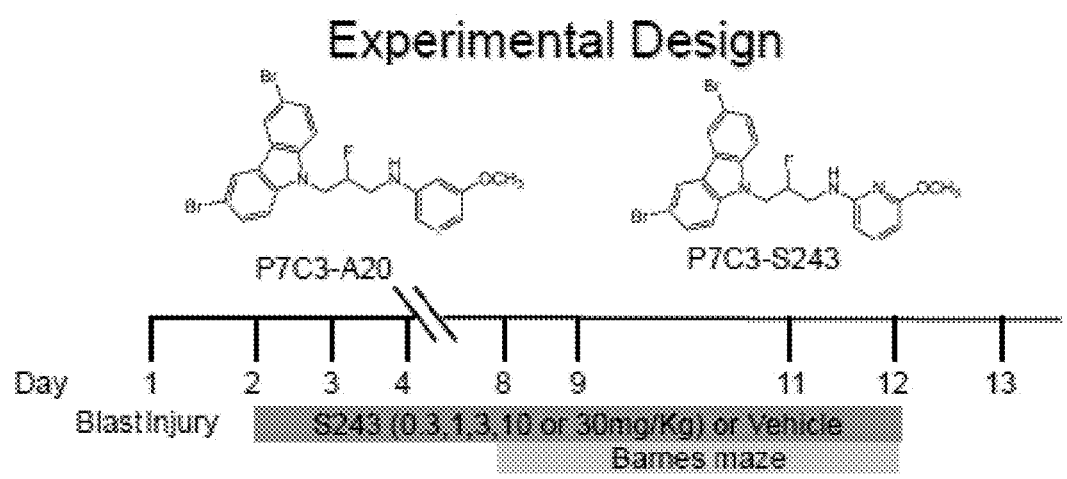
FIG. 6 shows experimental design of drug administration after blast injury to induce TBI. 24 hours after blast injury, treatment was initiated at the indicated level in divided twice-daily intraperitoneal dosage. After behavioral testing, mice were sacrificed for immunohistochemistry.

Results. P7C3-S243 is the most recently characterized highly active member of the P7C3-series of neuroprotective compounds, and differs from the previous lead agent (P7C3-A20) by elimination of the aniline ring. As shown in FIG. 6, 24 hours after blast injury, treatment was initiated at the indicated level in divided twice-daily intraperitoneal dosage. After behavioral testing, mice were sacrificed for immunohistochemistry.

Figure 7:
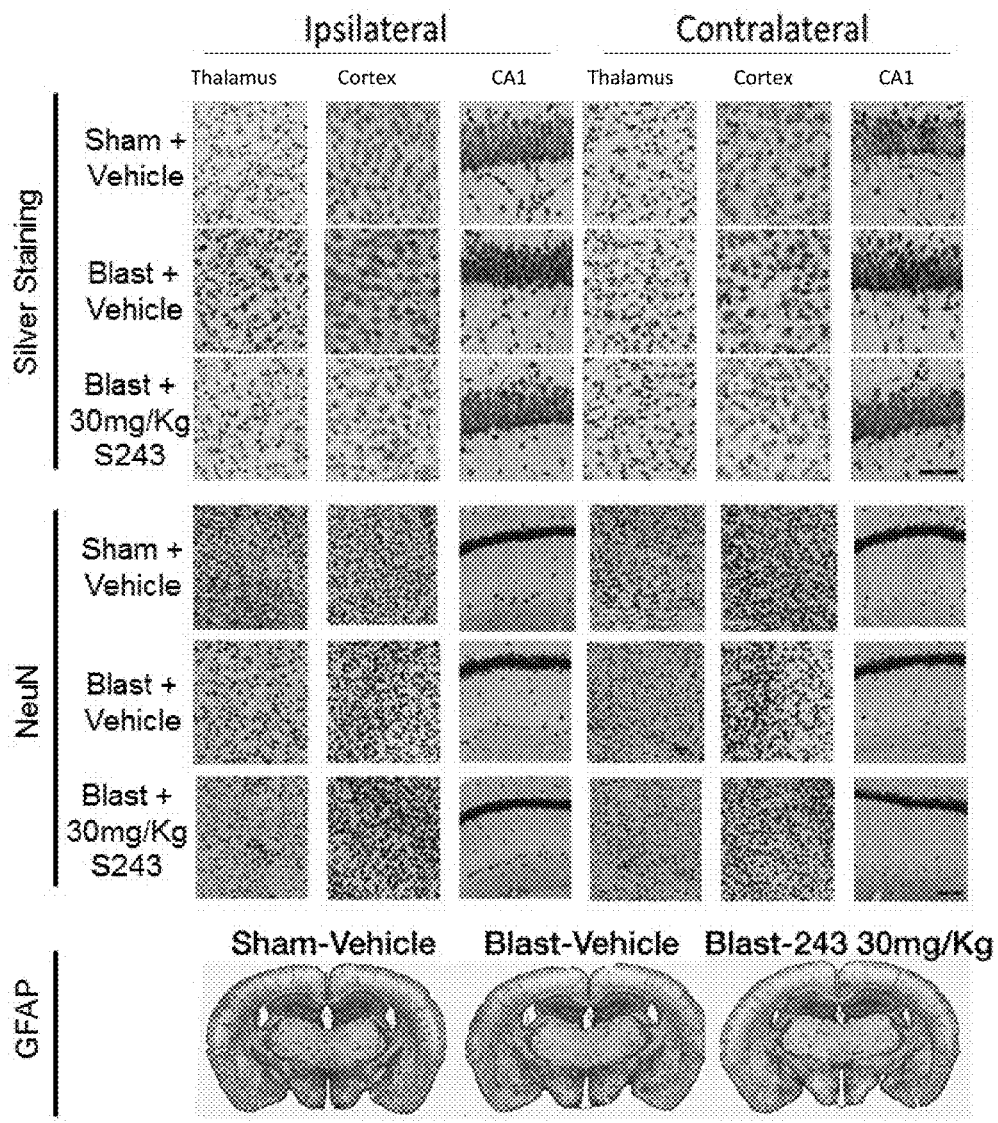
FIG. 7 shows silver staining from the ipsilateral and contralateral thalamus, cortex and CA1 regions 14 days after blast injury or sham compared to treatment with S243 begun 24 hours after injury.

Referring to FIG. 7, silver staining from the indicated regions 14 days after injury or sham shows axonal and cellular degeneration in blast-injured animals that is ameliorated by treatment with S243 begun 24 hours after injury. Immunohistochemical staining for NeuN in adjacent regions shows no obvious frank neuronal cell loss at this time point. No differences in GFAP signal are noted between groups. Data shown is representative of 5 animals per condition.

Figure 8A:
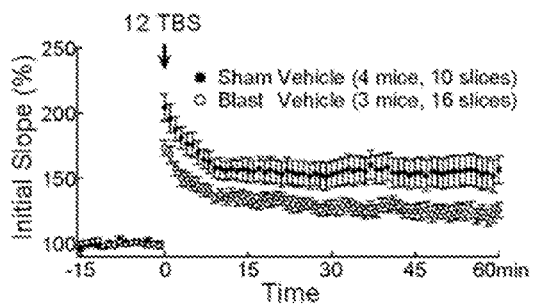
FIGS. 8A-8F show hippocampal electrophysiology showing treatment with P7C3-S243 rescues blast-mediated TBI-induced deficits in long term potentiation (LTP) and paired-pulse facilitation (PPF) in the hippocampal CA1 Schaffer-collateral pathway.
Figure 8B:
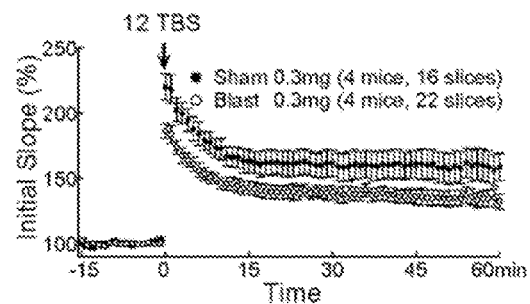
Figure 8C:
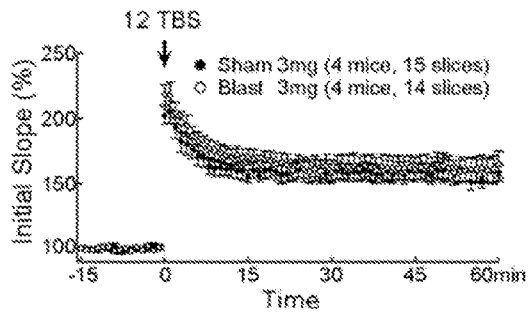
Figure 8D:
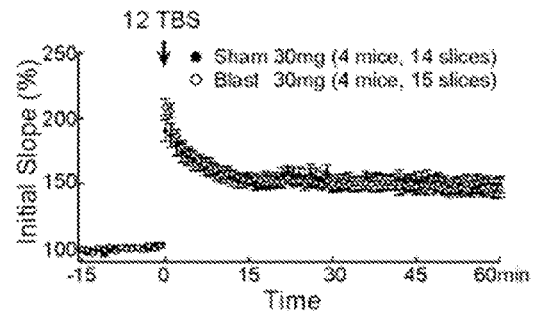
Figure 8E:
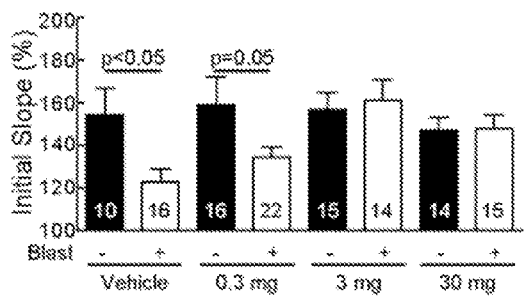
Figure 8F:
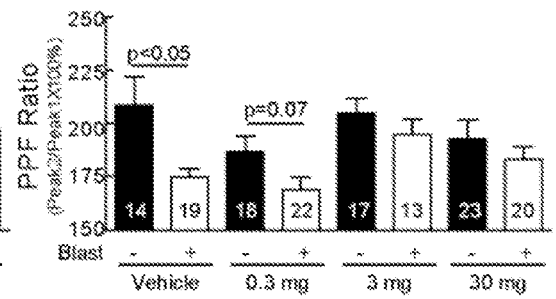

FIGS. 8A-8F show treatment with P7C3-S243 rescues blast-mediated TBI-induced deficits in long term potentiation (LTP) and paired-pulse facilitation (PPF) in the hippocampal CA1 Schaffer-collateral pathway. FIG. 8A: LTP induced by 12 theta burst stimulation (TBS) is significantly decreased in animals that have sustained blast-induced TBI 14 days prior to testing. FIG. 8B: This deficit was not rescued in animals treated with low dose P7C3-S243 (0.3 mg/kg/d) starting 24 hours after injury, but was rescued by treatment with higher doses of (FIG. 8C) 3 and (FIG. 8D) 30 mg/kg/d P7C3-S243. LTP at 1 hour after 12 TBS is summarized by quantification of the initial slope in FIG. 8E. FIG. 8F: Blast-mediated TBI-induced deficit in PPF of 50 ms inter-pulse interval was also rescued in animals treated with the two higher doses (3 and 30 mg/kg/d) of P7C3-S243. Statistics were determined by one-way ANOVA with Tukey's multiple comparisons test.

Figure 9:
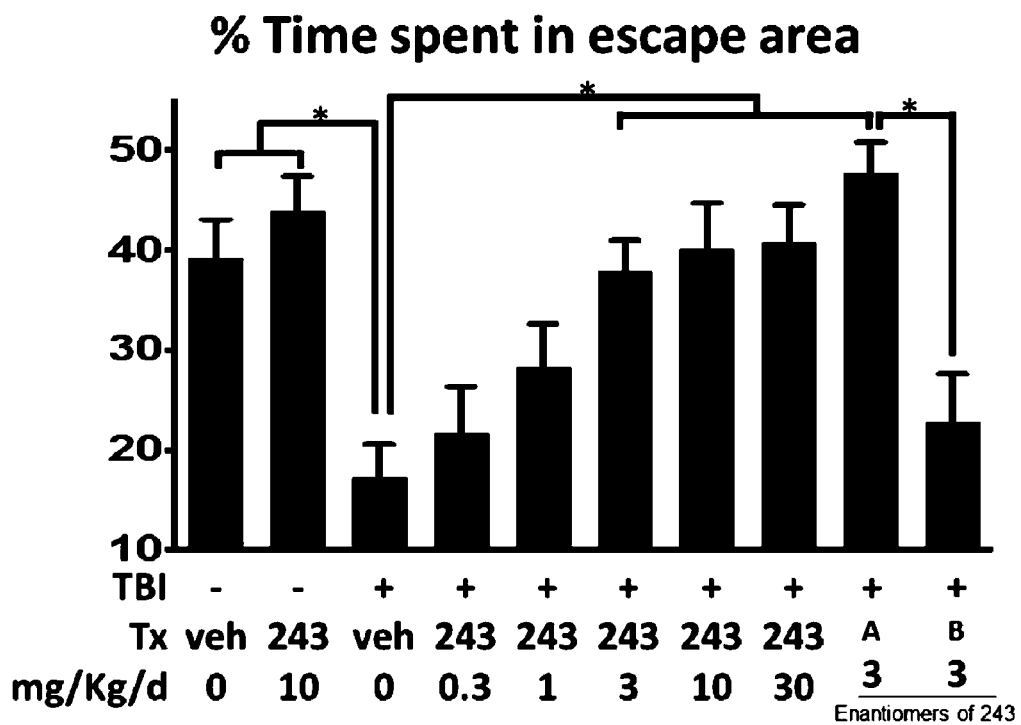
FIG. 9 shows Barnes Maze Probe Test following blast-induced TBI showing protective effect of P7C3-S243 and its (−)-enantiomer (labeled as enantiomer A).

As shown in FIG. 9, blast-induced TBI impairs performance in the probe test (*, p=0.004), and mice are protected by P7C3-S243 at 3 (*p=0.015), 10 (*p=0.0025) and 30 (*p=0.0015) mg/kg/d. Compound A ((−)-S243) was protective (*p<0.001), while B ((+)-enantiomer) was inactive. 25 animals were used per group. Statistics were determined by one-way ANOVA with Bonferroni's multiple comparison test.

Figure 10:
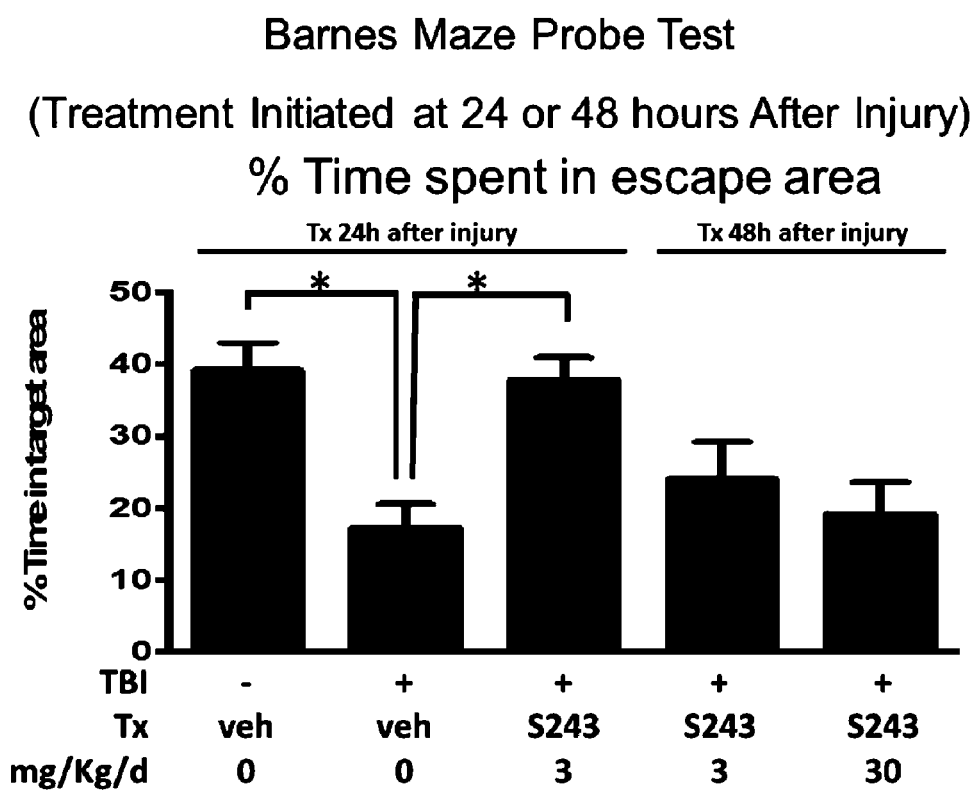
FIG. 10 shows Barnes Maze Probe Test following blast-induced TBI showing protective effect of P7C3-S243.
Figure 11A:
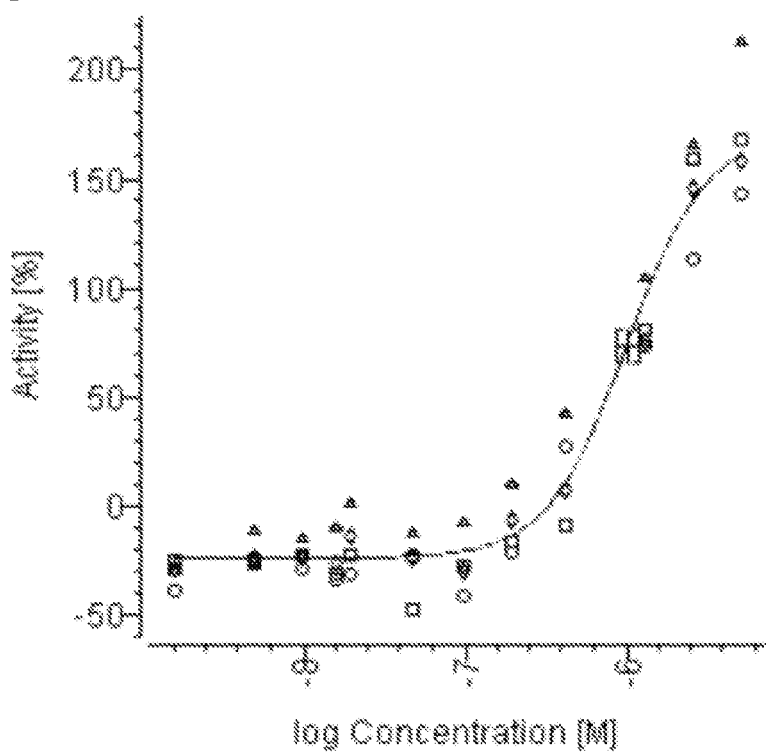
FIG. 11 shows protection of cultured U2OS cells from doxorubicin-mediated toxicity by active variants of P7C3. Left panel shows dose-responsive activity of the "A20" variant of P7C3 in protection of U2OS cells from doxorubicin-mediated cell toxicity. Right panel shows no Dox:Tox protective activity from the inactive S4 variant of P7C3.
Figure 11B:
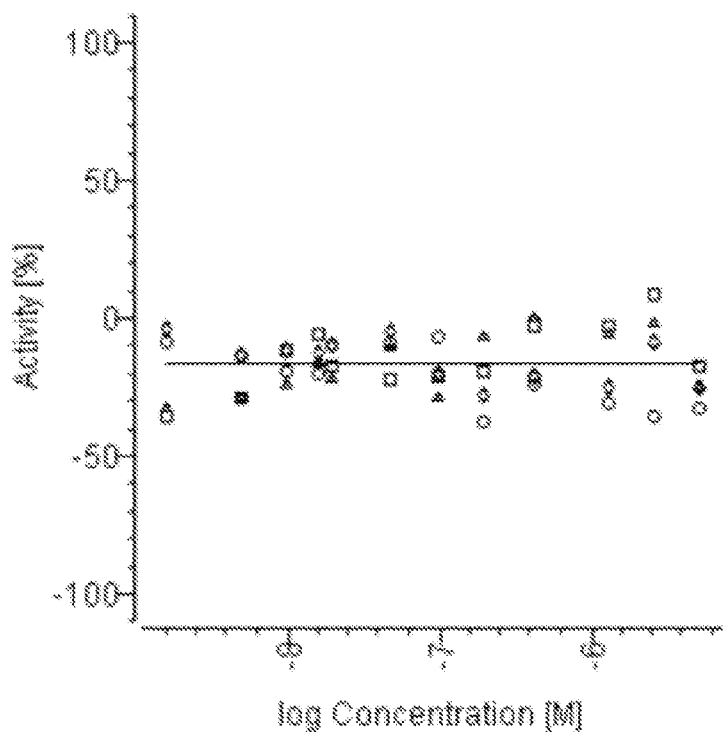
Figure 12:
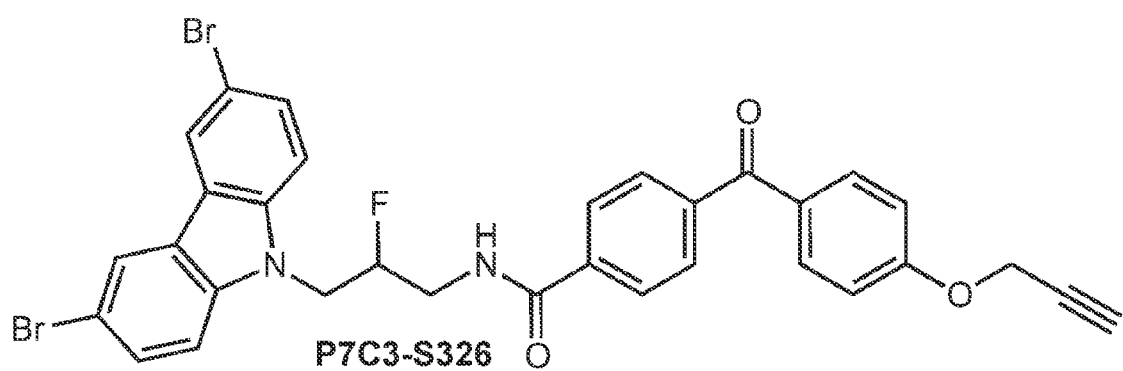
FIG. 12 shows chemical structure of P7C3-5326 variant of P7C3 carrying benzophenone and alkyne moieties.
Figure 13:
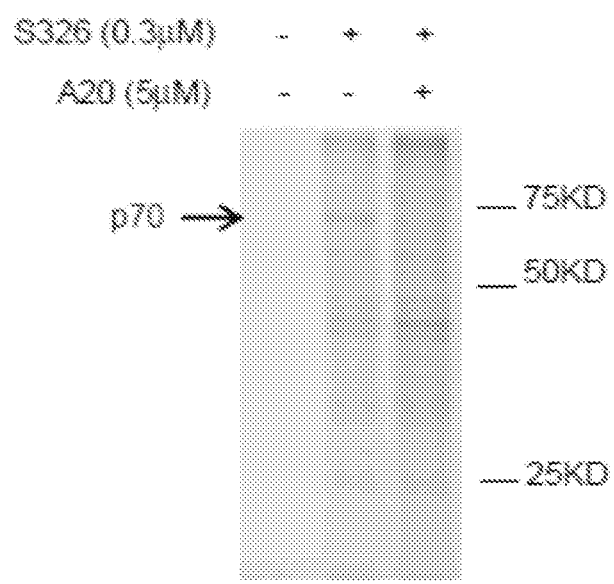
FIG. 13 shows photo-crosslinking of 70 kD polypeptide by P7C3-5326. Left lane of gel shows photo-crosslinking products of cells that were not exposed to a competing variant of P7C3. Right lane of gel shows photo-crosslinking products of cells that were co-exposed to >10-fold excess of the active "A20" variant of P7C3. Note that non-specific, crosslinked bands are not competed by the "A20" variant, but that crosslinking of the 70 kD band was competed.
Figure 14:
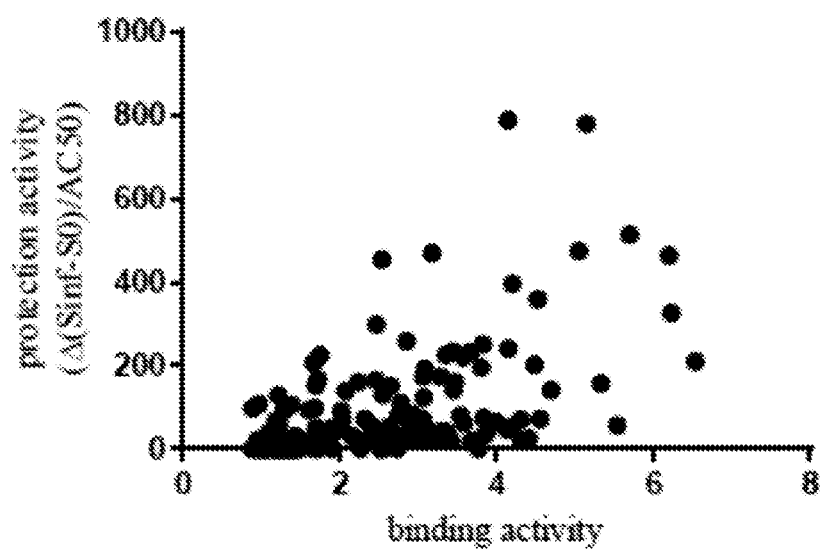
FIG. 14 shows scatter plot showing correlation between Dox:Tox protection and competition for crosslinking of the 70 kD band by P7C3-S326. 168 chemical derivatives of P7C3 were scored in both assays.
Figure 15:
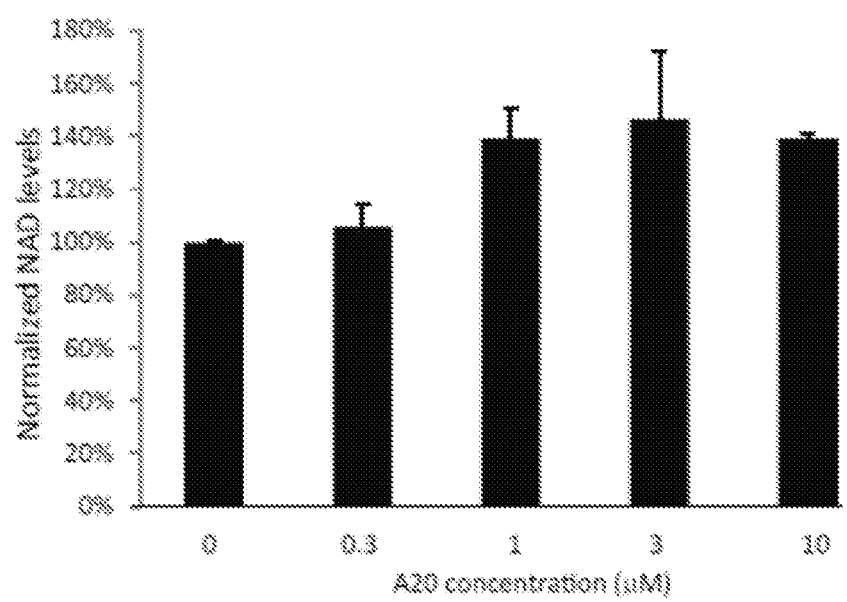
FIG. 15 shows enhancement of intracellular levels of NAD in response to the active "A20" variant of P7C3. Cultured cells were exposed to varying levels of "A20" (X-axis) for 12 hrs. Intracellular levels of NAD (Y-axis) were monitored by mass spectrometry. Maximal enhancement of NAD (20-30%) was achieved at the same level of compound (3 uM) required for maximal Dox:Tox protection.

FIG. 10 shows that blast-induced TBI impairs performance in the probe test (*, p=0.004), and mice are protected by administration of P7C3-S243 at 3 mg/kg/d dose initiated 24 hours after injury (*p=0.015). By contrast, administration of P7C3S243 at 3 or 30 mg/kg/d doses 48 hours after injury had no protective efficacy in this assay. 25 animals were used per group. Statistics were determined by one-way ANOVA with Bonferroni's multiple comparison test.

P7C3-S243, the most recently improved member of the P7C3-series of neuroprotective aminopropyl carbazoles, dose-dependently preserves hippocampal-dependent cognition after blast-mediated TBI with enantiomeric specificity when treatment is initiated 24 hours after injury. Protective efficacy is lost when treatment is initiated 48 hours after injury, thus defining the window of therapeutic opportunity for preserving acute impairments in learning after blast-mediated TBI. Preservation of hippocampal-dependent cognition correlated with preservation of electrophysiologic measures of LTP and PPF in the hippocampus.

As has been observed in patients, blast-mediated TBI in mice is associated with axonal degeneration in the absence of obvious widespread neuron cell death. This axonal damage is ameliorated by treatment with P7C3-S243 (or like compounds), providing new insight into the mechanisms by which the P7C3-class of neuroprotective agents protect neurons. In addition, the ability to block axonal degeneration offers new opportunities for therapeutic treatment of patients with forms of nervous system disease or injury that involve axonal degeneration. This includes many forms of neurodegenerative disease that involve a component of axonal degeneration that is visibly distinct from cell death/degeneration of the cell body. Other forms of nervous system disorders that primarily involve axonal degeneration may also be treated by P7C3-S243 (or like compounds).

One particularly surprising finding is that P7C3-S243 may be effective in treating vision problems after TBI, such as reading complaints, light sensitivity, saccadic dysfunction, accomdoative dysfunction, convergence insufficiency, strabismus, pursuit abnormalities, fixation deficits and visual field deficits. Visual problems after TBI are quite common and there is not treatment. The thalamus is a part of the brain through which visual information is transmitted/processed as it goes from the retina at the front of the brain back to the visual cortex on the other side of the brain. We saw dramatic increase in degenerating axons in the thalamus by silver staining, which can be related to the visual problems experiences by patients. P7C3-S243 helps protect the thalamus from this axonal degeneration, and thus, may provide a new way to treat visual problems associated with TBI.

In summary, the active (−)-enantiomer of P7C3-S243 may form the basis for development of a new drug to treat patients suffering from traumatic brain injury. (−)-P7C3-S243 can also be used to treat both acute and chronic visual problems experienced with great frequency by patients after both blast and non-blast forms of TBI.

Experimental

Barnes maze: The Barnes maze evaluates cognition based on time spent in the escape area. There are 20 holes around the periphery of the round tabletop, one of which contains an escape chamber (shown in red), into which the animal is motivated to seek shelter after being placed on the open tabletop. The escape area is defined as 5 cm around the hole, and time spent in the escape area during the probe test is used to measure hippocampal-dependent memory, which is dependent on visual cue around the table.

References 1 (a) Lees, A. J.; Hardy, J.; Revesz, T.: Parkinson's Disease. *The Lancet* 2009, 373, 2055. (b) Hebert, L. E.; Scherr, P. A.; Bienias, J. L.; Bennett, D. A.; Evans, D. A.: State-Specific Projections through 2025 of Alzheimer Disease Prevalence. *Neurology* 2004, 62, 1645.

2 Pieper, A. A.; Xie, S.; Capota, E.; Estill, S. J.; Zhong, J.; Long, J. M.; Becker, G. L.; Huntington, P.; Goldman, S. E.; Shen, C.-H.; Capota, M.; Britt, J. K.; Kotti, T.; Ure, K.; Brat, D. J.; Williams, N. S.; MacMillan, K. S.; Naidoo, J.; Melito, L.; Hsieh, J.; De, B. J.; Ready, J. M.; McKnight, S. L.: Discovery of a Proneurogenic, Neuroprotective Chemical. *Cell* 2010, 142, 39.

3 MacMillan, K. S.; Naidoo, J.; Liang, J.; Melito, L.; Williams, N. S.; Morlock, L.; Huntington, P. J.; Estill, S. J.; Longgood, J.; Becker, G. L.; McKnight, S. L.; Pieper, A. A.; De Brabander, J. K.; Ready, J. M.: Development of Proneurogenic, Neuroprotective Small Molecules. *J. Am. Chem. Soc.* 2011, 133, 1428.

4 Naidoo, J.; Bemben, C. J.; Allwein, S. R.; Liang, J.; Pieper, A. A.; Ready, J. M.: Development of a Scalable Synthesis of P7C3-A20, a Potent Neuroprotective Agent. *Tetrahedron Lett* 2013, 54, 4429.

5 De Jesús-Cortés, H.; Xu, P.; Drawbridge, J.; Estill, S. J.; Huntington, P.; Tran, S.; Britt, J.; Tesla, R.; Morlock, L.; Naidoo, J.; Melito, L. M.; Wang, G.; Williams, N. S.; Ready, J. M.; McKnight, S. L.; Pieper, A. A.: Neuroprotective Efficacy of Aminopropyl Carbazoles in a Mouse Model of Parkinson Disease. *Proc. Natl. Acad. Sci.* 2012, 109, 17010.

6 Tesla, R.; Wolf, H. P.; Xu, P.; Drawbridge, J.; Estill, S. J.; Huntington, P.; McDaniel, L.; Knobbe, W.; Burket, A.; Tran, S.; Starwalt, R.; Morlock, L.; Naidoo, J.; Williams, N. S.; Ready, J. M.; McKnight, S. L.; Pieper, A. A.: Neuroprotective Efficacy of Aminopropyl Carbazoles in a Mouse Model of Amyotrophic Lateral Sclerosis. *Proc. Natl. Acad. Sci.* 2012, 109, 17016.

7 Blaya, M. O.; Bramlett, H.; Nadoo, J.; Pieper, A. A.; Dietrich, W. D., 3rd: Neuroprotective Efficacy of a Proneurogenic Compound after Traumatic Brain Injury. *J Neurotrauma* 2013, doi:10.1089/neu.2013.3135.

8 Asai-Coakwell, M.; March, L.; Dai, X. H.; DuVal, M.; Lopez, I.; French, C. R.; Famulski, J.; De Baere, E.; Francis, P. J.; Sundaresan, P.; Sauve, Y.; Koenekoop, R. K.; Berry, F. B.; Allison, W. T.; Waskiewicz, A. J.; Lehmann, O. J.: Contribution of Growth Differentiation Factor 6-Dependent Cell Survival to Early-Onset Retinal Dystrophies. *Hum Mol Genet* 2013, 22, 1432.

9 Mice housed alone and without objects such as nesting material show decreased hippocampal neurogenesis, magnifying the effect of neuroprotective compounds.

10 Rough calculations suggest that test compounds would reach approximately 100 nM concentration by the end of the testing period if all material remained in the brain.

11 Struk, L.; Sosnicki, J. G.: Noncryogenic Synthesis of Functionalized 2-Methoxypyridines by Halogen-Magnesium Exchange Using Lithium Dibutyl(Isopropyl)Magnesate and Lithium Chloride. *Synthesis* 2012, 44, 735.

12 Das, P.; De Brabander, J. K.: A Room Temperature Copper Catalyzed N-Selective Arylation of—Amino Alcohols with Iodoanilines and Aryl Iodides. *Tetrahedron* 2013, 69, 7646.

13 Similar observations have been made by the De Brabander group with regard to the work published in ref. 12.

14 Bombrun, A.; Gerber, P.; Casi, G.; Terradillos, O.; Antonsson, B.; Halazy, S.: 3,6-Dibromocarbazole Piperazine Derivatives of 2-Propanol as First Inhibitors of Cytochrome C Release Via Bax Channel Modulation. *J. Med. Chem.* 2003, 46, 4365.

15 Klunder, J. M.; Onami, T.; Sharpless, K. B.: Arenesulfonate Derivatives of Homochiral Glycidol: Versatile Chiral Building Blocks for Organic Synthesis. *J. Org. Chem.* 1989, 54, 1295.

16 Zhao, X.; Zhuang, W.; Fang, D.; Xue, X.; Zhou, J.: A Highly Efficient Conversion of Primary or Secondary Alcohols into Fluorides with N-Perfluorobutanesulfonyl Fluoride-Tetrabutylammonium Triphenyldifluorosilicate. *Synlett* 2009, 779.

17 (a) Javitch, J. A.; D'Amato, R. J.; Strittmatter, S. M.; Snyder, S. H.: Parkinsonism-Inducing Neurotoxin, N-Methyl-4-Phenyl-1,2,3,6-Tetrahydropyridine: Uptake of the Metabolite N-Methyl-4-Phenylpyridine by Dopamine Neurons Explains Selective Toxicity. *Proc. Natl. Acad. Sci. U.S.A* 1985, 82, 2173. (b) D'Amato, R. J.; Lipman, Z. P.; Snyder, S. H.: Selectivity of the Parkinsonian Neurotoxin Mptp: Toxic Metabolite Mpp+ Binds to Neuromelanin. *Science* 1986, 231, 987.

18 Fukuda, T.: Neurotoxicity of MPTP. *Neuropathology* 2001, 21, 323.

19 Jackson-Lewis, V.; Przedborski, S.: Protocol for the MPTP Mouse Model of Parkinson's Disease. *Nat. Protoc.* 2007, 2, 141.

20 Rupprecht, R.; Papadopoulos, V.; Rammes, G.; Baghai, T. C.; Fan, J.; Akula, N.; Groyer, G.; Adams, D.; Schumacher, M.: Translocator Protein (18 Kda) (Tspo) as a Therapeutic Target for Neurological and Psychiatric Disorders. *Nat. Rev. Drug Discovery* 2010, 9, 971.

21 (a) Bordet, T.; Berna, P.; Abitbol, J.-L.; Pruss, R. M.: Olesoxime (Tro19622): A Novel Mitochondrial-Targeted Neuroprotective Compound. *Pharmaceuticals* 2010, 3, 345. (b) Sunyach, C.; Michaud, M.; Arnoux, T.; Bernard-Marissal, N.; Aebischer, J.; Latyszenok, V.; Gouarne, C.; Raoul, C.; Pruss, R. M.; Bordet, T.; Pettmann, B.: Olesoxime Delays Muscle Denervation, Astrogliosis, Microglial Activation and Motoneuron Death in an Als Mouse Model. *Neuropharmacology* 2012, 62, 2346.

22. Goldstein, L. E. et al. Science Translational Medicine 134, 60 (2012).

23. Goodrich et al., Optometry and Vision Science 90, 2, 105 (2013).

Example 3

Additional Compounds

Additional compounds were synthesized and tested using the above-described in vivo neuroprotection assay. Their structure and neuroprotective activity, as suggested by the number of BrdU+ cells, are shown in Table 2 below.

TABLE 2

| Structure | compound name | # cell (E6)/ mm^3 | SEM |
|---|---|---|---|
| NA | vehicle | 14.5 | 1.08 |
| 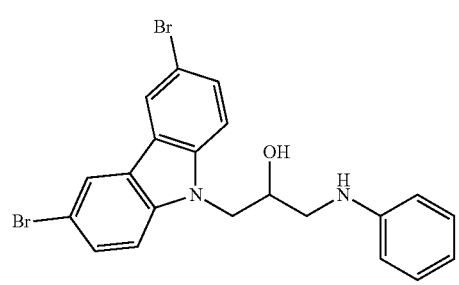 | P7C3 | 30 | 1.42 |

TABLE 2-continued

| Structure | compound name | # cell (E6)/ mm^3 | SEM |
|---|---|---|---|
| (structure) | P7C3-S318 | 20.8 | 1.5 |
| (structure) | P7C3-S324 | 27 | 1.8 |
| (structure) | P7C3-S325 | 30.6 | 3.2 |
| (structure) | P7C3-S326 | 25 | 1.5 |

Example 4

P7C3 Neuroprotective Chemicals Block Axonal Degeneration and Preserve Function after Traumatic Brain Injury Summary. The P7C3 class of neuroprotective aminopropyl carbazoles has recently been shown to block neuronal cell death in rodent models of neurodegeneration. We now show that active P7C3 molecules additionally preserve axonal integrity after injury, independently of blocking neuronal cell death, in a rodent model of blast-mediated traumatic brain injury (TBI). This protective quality is likely linked to the ability of P7C3 molecules to activate nicotinamide phosphoribosyltransferase (NAMPT), the rate-limiting enzyme in nicotinamide adenine dinucleotide (NAD) salvage, which is described in U.S. Provisional Patent Application No. 61/993,328 filed May 15, 2014, the entire disclosure of which is hereby incorporated by reference. Initiation of daily treatment with our recently reported lead agent, P7C3-S243, one day after blast-mediated TBI blocks widespread axonal degeneration in mice, and preserves normal synaptic activity, learning and memory, and motor coordination. Optimized variants of P7C3 thus offer hope for identifying neuroprotective agents for conditions involving axonal damage, neuronal cell death, or both, such as occurs in TBI.

Introduction

Traumatic brain injury (TBI) has emerged as the signature injury of military conflict, estimated to affect 20% of the 2.3 million servicemen and women deployed since 2001. Blast exposure from explosive devices affects soldiers and civilians around the globe, placing them at increased risk for TBI associated with long-term neurologic complications, including cognitive and motor decline, as well as neuropathological features similar to Alzheimer's disease (Hoge et al., 2008; Wolf et al., 2009; Shively et al., 2012; Goldstein et al., 2012). While the mechanisms of injury from exposure to the blast-generated shockwave are incompletely understood, the associated sheer forces are known to lead to widespread, diffuse and progressive axonal injury (Nakagawa et al., 2011; Magnuson et al., 2012). Unfortunately, just as there are currently no pharmacologic agents that arrest neuron cell death in any of the wide spectrum of neurodegenerative diseases, such as Alzheimer's disease, Parkinson's disease, Huntington's disease or amyotrophic lateral sclerosis, there are also currently no treatment options for patients with TBI beyond supportive and rehabilitative care.

The lack of pharmacologic strategies to block neuron cell death relates to the failure of target-directed drug discovery programs to develop neuroprotective therapeutics. Phenotypic screening, by contrast, offers the opportunity for discovery of new compounds with a desired biologic effect without bias concerning mechanism (Pieper et al., 2014). With this in mind, we previously implemented an in vivo phenotypic screen in living mice to identify new small drug-like molecules that safely increased the net magnitude of postnatal hippocampal neurogenesis. We designed the screen to capture agents that would either enhance proliferation or block death of newborn hippocampal neural precursor cells (Pieper et al., 2010), and identified an aminopropyl carbazole, named 'P7C3,' that was fortuitously endowed with favorable pharmacokinetic properties (Pieper et al., 2010). It was subsequently demonstrated that P7C3 achieved its proneurogenic effect by virtue of blocking death of neural precursor cells, and we have also demonstrated additional protective benefit of P7C3 molecules, specifically the highly active analog P7C3-A20, in blocking neuronal cell death and improving neurologic outcomes in a variety of rodent models of neurodegeneration (MacMillan et al., 2010; Naidoo and De Jesús-Cortés et al., 2013; Walker et al., 2014; De Jesus-Cortes et al., 2012; Tesla et al., 2012; Blaya et al., 2014).

Recently, we reported the synthesis and characterization of an optimized member of the P7C3 class, (−)-P7C3-S243, which exhibits improved polarity and lacks the aniline moiety present in other members of the P7C3 class, as described in U.S. Provisional Patent Application No. 61/912,625 filed Dec. 6, 2013, the entire disclosure of which is hereby incorporated by reference. This analog is readily available as a single enantiomer with selective neuroprotective activity (Naidoo and De Jesús-Cortés et al., 2014). Because blast exposure in rodent models results in a phenotype that recapitulates the consequences of blast-mediated TBI experiences by humans (Goldstein et al., 2012; Mohan et al., 2013), this animal model is suitable for evaluating the efficacy of neuroprotective agents. Here, we describe protective efficacy of P7C3-S243 in the mouse model of blast-induced TBI, which has also led to the discovery of a new protective quality of the P7C3-class—the ability to block axonal degeneration independent of cell death.

Results

To test the neuroprotective efficacy of P7C3-A20 and P7C3-S243, we employed a model of blast-induced TBI in which the blast wave is propagated following rupture of a mylar membrane (Mohan et al., 2013). Briefly, anesthetized mice are placed in an enclosed blast chamber constructed from an air tank partitioned into two sides. A sealed mylar membrane covers a small port between the two halves of the tank. When the pressure is increased in the side without the mouse, the membrane ruptures at ≈22 kilopascal (kPa), generating a blast wave that travels through the mouse's head. The head of the mouse is untethered and located in a padded holder, while the body is shielded from the blast by a metal tube. In all cases, the left side of the head faces the blast wave. As previously reported (Mohan et al., 2013), the intensity of the blast wave in our system is 149.8±2.09 kPa, and the duration of the total pressure (Blast wave+wind gust) is ≈10-15 milliseconds.

Figure 21:
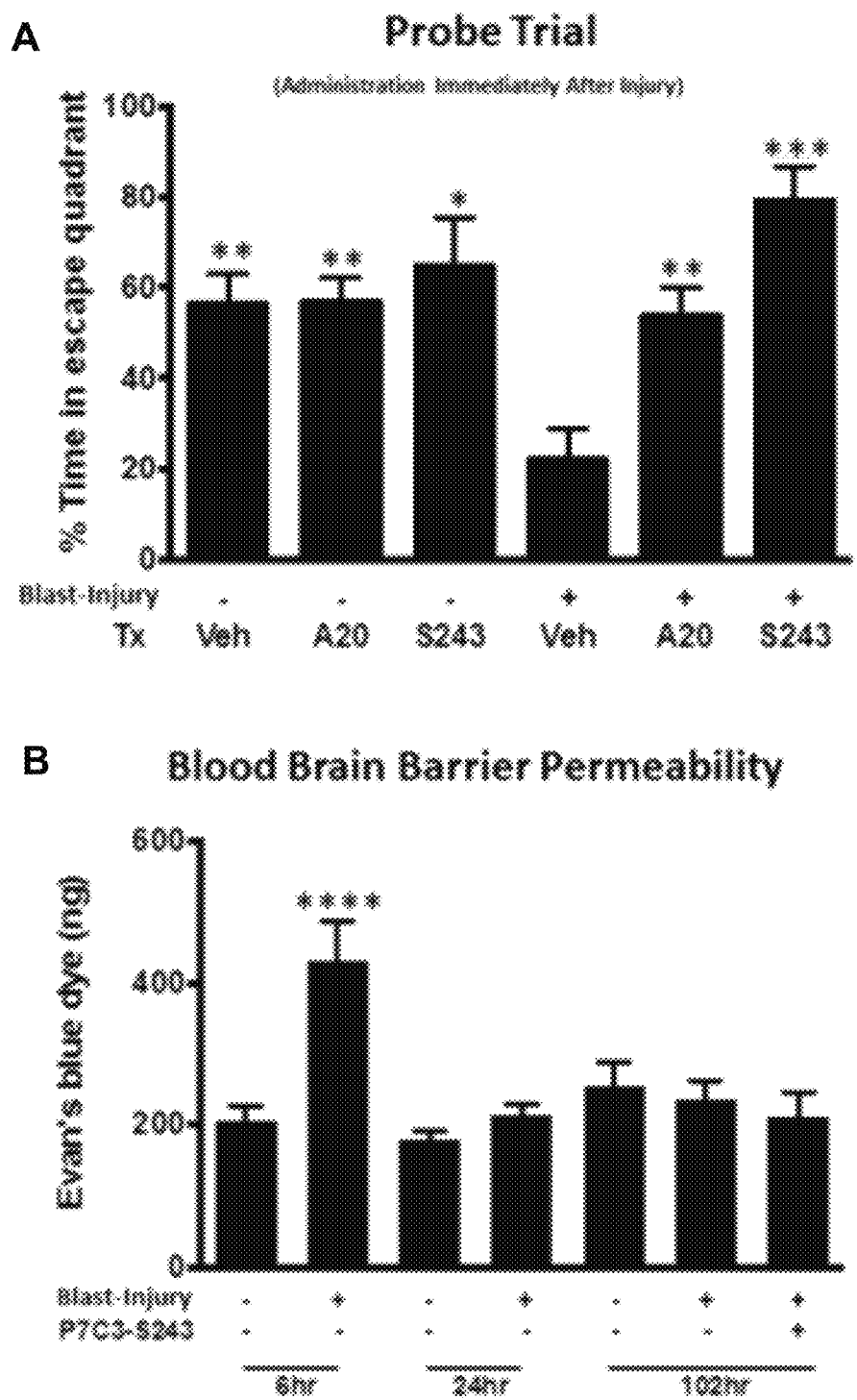
FIGS. 21A-21B. Protective Efficacy of Immediate Administration of P7C3-S243 and Dynamics of Blood Brain-Barrier Integrity after Blast-Injury.

We first evaluated hippocampal-dependent memory in the Barnes maze task after blast-injury, with immediate administration of test compounds. The Barnes maze consists of a circular table with holes equally spaced around the perimeter. One of these holes contains an escape cup, such that the mouse can enter the hole and hide in the cup to avoid exposure on the table. Testing in the Barnes maze was initiated 7 days after blast-injury. To begin, mice underwent 4 days of training, during which time they were allowed to find and enter the escape hole, and rest in the protective cup. By the 4th day of training, mice typically learn how to rapidly locate the escape hole, based on visual cues permanently positioned around the table throughout training. After 4 days of training, the cup is removed and the ability of the mouse to remember where the cup was previously located is assessed in the 'probe test.' Memory is reflected by measuring the amount of time the mouse spends in the area around where the cup was previously located. Sham-injured animals that were intraperitoneally administered daily vehicle, P7C3-A20, or P7C3-S243 spent 55-60% of their time in the quadrant that contained the escape hole, known as the 'escape quadrant,' during the probe test (FIG. 21A), indicating that normal memory is not affected by P7C3 compounds in this task. By contrast, blast-injured animals administered vehicle were notably impaired, spending only ≈25% of their time in the escape quadrant, which would be expected by chance alone (FIG. 21A). Daily treatment with P7C3-A20 or P7C3-S243 immediately after injury, however, restored the time spent in the escape quadrant to normal levels seen in uninjured mice (FIG. 21A).

Delayed Initiation of Treatment with P7C3-S243 Preserves Learning and Memory after Blast-Mediated TBI On the basis of the promising results seen with administration of P7C3-A20 or P7C3-S243 immediately after injury, we sought to determine whether P7C3-S243 could offer protective efficacy when treatment was initiated later. Because TBI can disrupt the blood-brain barrier (BBB), we first examined BBB integrity over time by means of the Evans blue assay. Evans blue is an azo dye with tight affinity for albumin, such that in serum virtually all Evans blue is albumin-bound. Normally, serum albumin cannot cross the BBB. However, when the BBB is compromised, albumin and its bound Evans blue can enter the CNS. The magnitude of Evans blue accumulation in the brain can then be spectrophotometrically determined in order to monitor disruption of the BBB (Uyama et al., 1988; Hawkins and Egleton, 2006). With this technique, we observed significant disruption of the BBB 6 hours after blast-injury, with integrity of the BBB recovering to normal 18 hours later (FIG. 21B). BBB integrity remained intact 102 hours after injury, and 3 days of daily treatment with P7C3-S243 did not compromise BBB integrity in sham-injured mice.

We next tested whether P7C3-S243 could preserve function when treatment was initiated 24 hours after blast-injury, when the BBB was intact. We have previously reported that P7C3-S243 readily enters the brains of mice with intact BBBs (Naidoo and De Jesús-Cortés et al., 2014). We reasoned that this time point for starting treatment represented an important milestone, as most patients would be expected to access treatment within 24 hours of their injury. Every group consisted of 25 male C57/BI6 wild type mice, aged 12-14 weeks, and data was collected and analyzed in an automated manner blind to treatment group. The most stringent measure of performance in the Barnes maze probe test is percent time in the escape area, defined as a 5 cm radius surrounding the escape hole. Sham-injured animals treated with vehicle or 10 mg/kg/day P7C3-S243, spent ≈39-43% of their time in the escape area, as opposed to only ≈15% for injured animals treated with vehicle (FIG. 16A). Daily treatment with P7C3-S243 initiated 24 hours after injury dose dependently preserved performance in this measure, with 3, 10 and 30 mg/kg/day doses showing complete protection, and 1 mg/kg/day partial, though not statistically significant, protection (FIG. 16A). Administration of the active enantiomer (−)-P7C3-S243 at 3 mg/kg/day showed complete protection, while the same dose of the less active enantiomer, (+)-P7C3-S243, showed no efficacy (FIG. 16A).

Next, we sought to define the time window of treatment efficacy by initiating daily IP administration of P7C3-S243 at later points after injury. Whereas both 3 and 30 mg/kg/d doses preserved normal function when treatment was initiated 24 hours after injury, only the 30 mg/kg/d dose was partially efficacious when initiated 36 hours after injury (FIG. 16B). When initiated 48 hours after injury, no protective efficacy was noted at any dose (FIG. 16B). Thus, acute memory deficits after blast-mediated TBI can be effectively mitigated when treatment with P7C3-S243 is initiated within 36 hours. Finally, we tested whether oral administration of the highly active (−)-P7C3-S243 enantiomer could achieve protective effect. Indeed, initiation of daily oral administration of (−)-P7C3-S243 at 24 hours after injury preserved memory at 3, 10 and 30 mg/kg/day doses (FIG. 16C).

Figure 22:
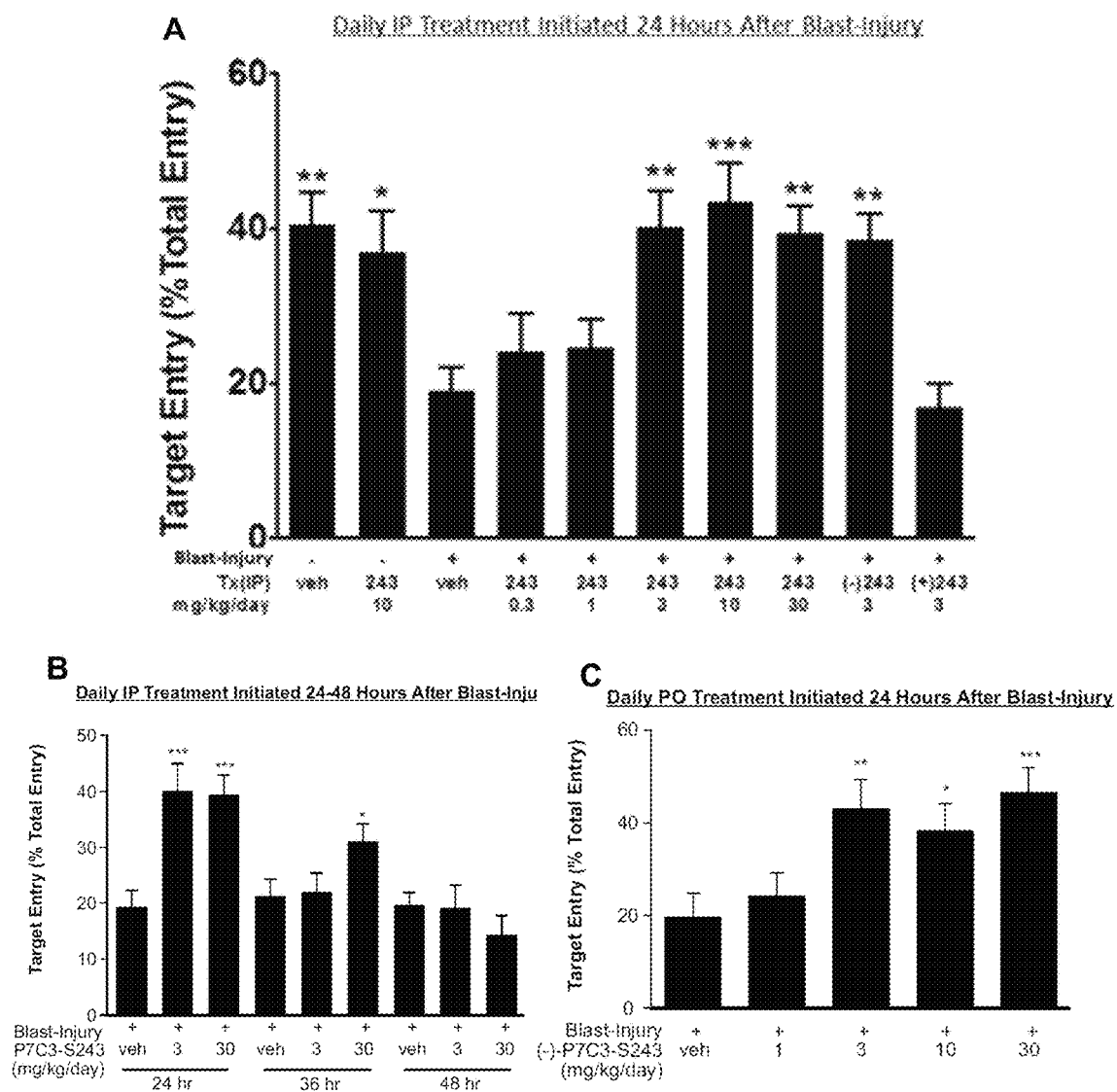
FIGS. 22A-22C. Target Entry in Barnes Maze Probe Test Data, Related to FIG. 16.
Figure 23:
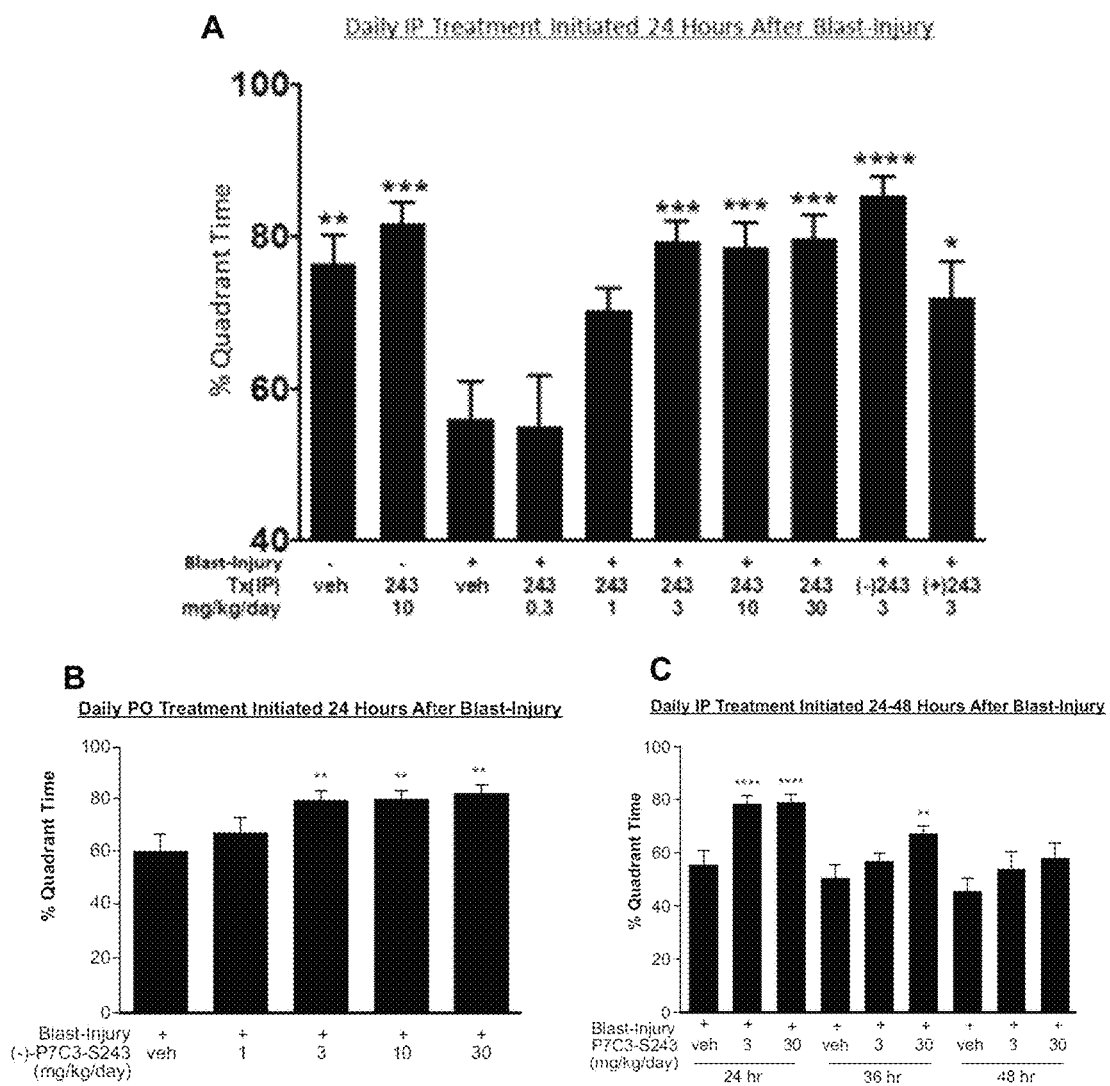
FIGS. 23A-23C. Quadrant Time in Barnes Maze Probe Test Data, Related to FIG. 16.

In addition to measuring time spent in the 5 cm radius around the escape hole in the probe test, we also tested other commonly used measures of memory. Specifically, we determined the percent of nose pokes into the correct hole, defined as 'target entry', and the percent of time spent in the quadrant of the maze containing the escape hole, defined as 'percent quadrant time.' Monitoring of target entry in the treatment groups showed the same protective effects as with the escape area measure (FIG. 22). Similar findings were also obtained with the metric of % quadrant time, with the exception that 3 mg/kg/day of the less active (+)-P7C3-S243 enantiomer achieved some measure of protective efficacy at the margin of statistical significance (FIG. 23). This modest effect indicates that low-level activity may reside in (+)-P7C3-S243.

Figure 24:
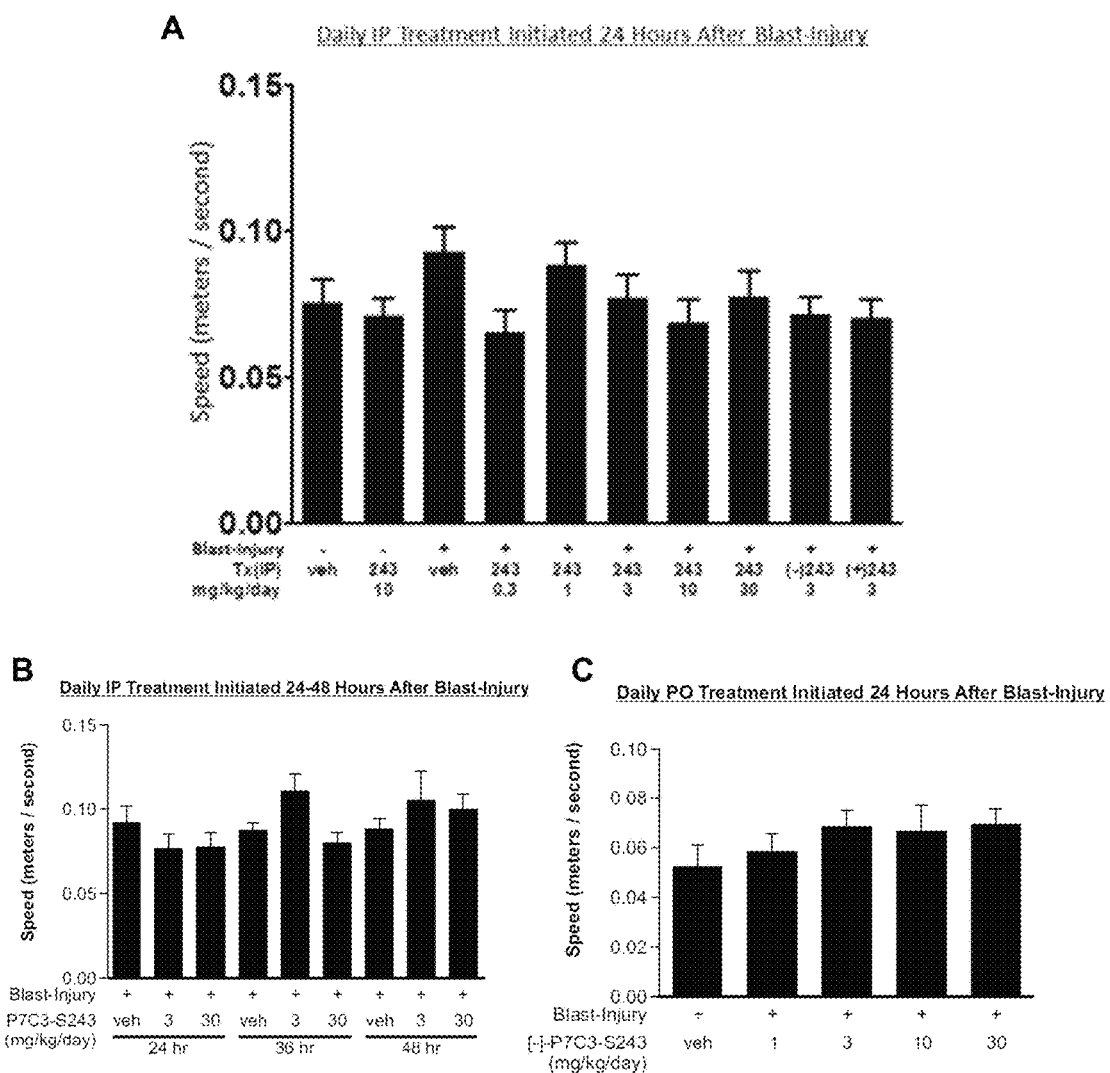
FIGS. 24A-24C. Speed in Barnes Maze Probe Test Data, Related to FIG. 16.
Figure 25:
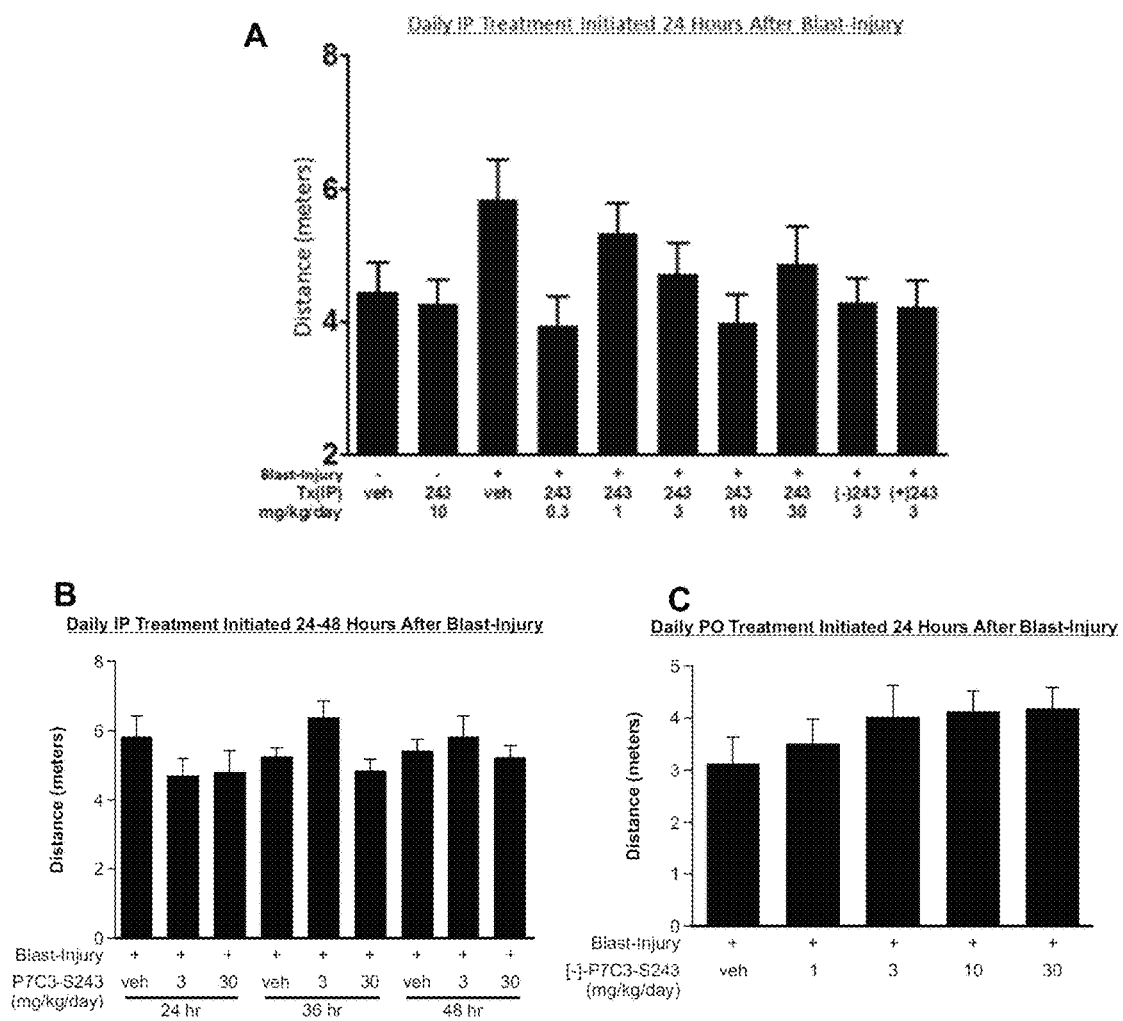
FIGS. 25A-25C. Distance Traveled in Barnes Maze Probe Test Data, Related to FIG. 16.
Figure 26:
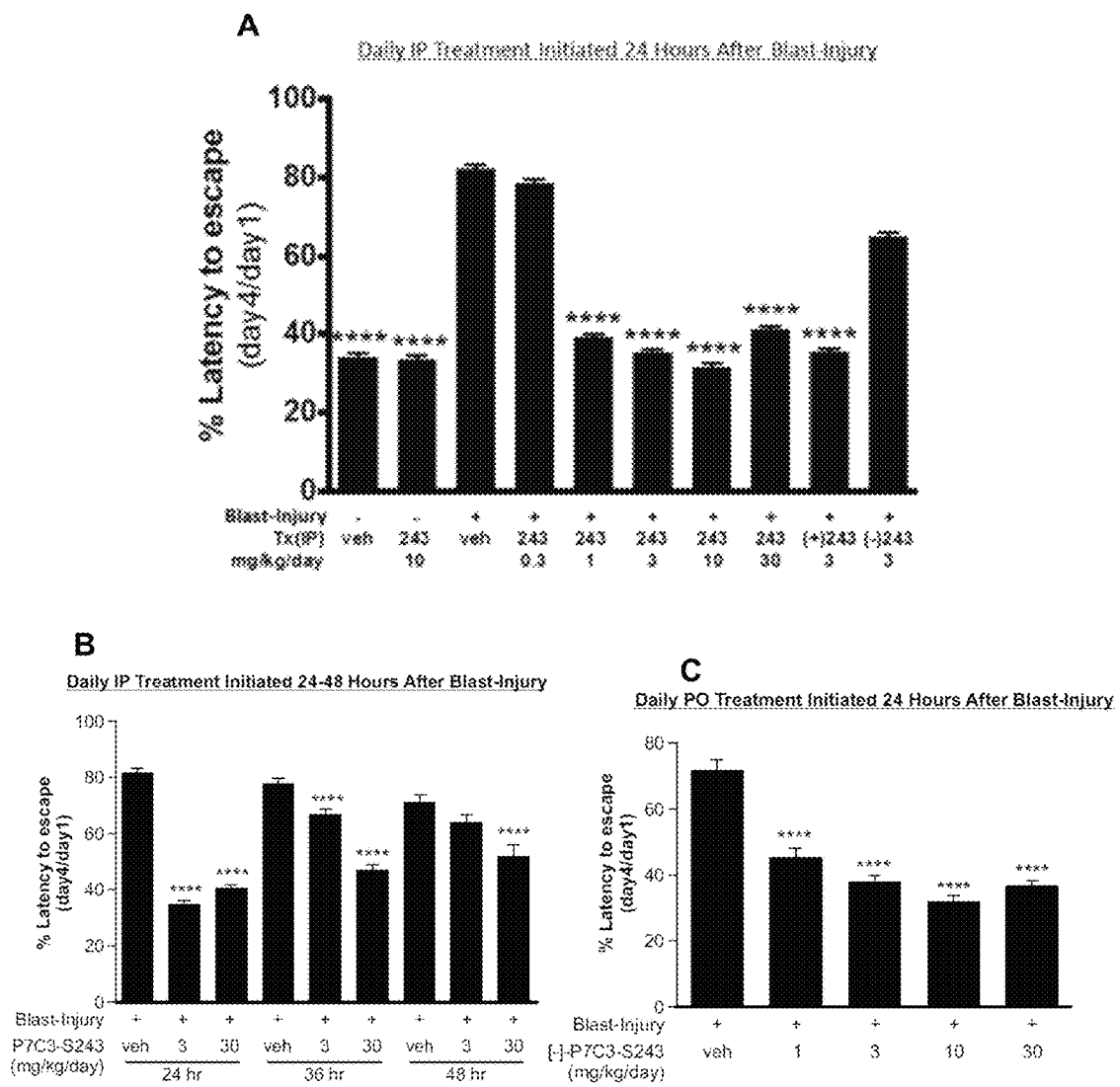
FIGS. 26A-26C. P7C3-S243 Enhances Learning in the Barnes Maze, Related to FIG. 16. Learning was assessed as the percent latency to escape, defined as the percentage of time the mouse took to enter the escape hole on day 4 out of the time that it required on day 1.

As controls in the Barnes maze, we examined the ability of animals to physically participate in the task, as well as to learn the task over the 4 day training period. Physical participation was defined as speed and distance traveled, and none of the groups differed significantly in these measures (FIGS. 24 and 25). Learning was assessed as the percent latency to escape, defined as the percentage of time the mouse took to enter the escape hole on day 4 out of the time originally required on day 1. All animals were able to learn, though mice subjected to blast-mediated TBI and then treated with vehicle, 0.3 mg/kg/day P7C3-S243, or 3 mg/kg/day of the less active enantiomer (+)-P7C3-S243 learned significantly worse than sham-injury mice (FIG. 26A). When treatment with 1, 3, 10 or 30 mg/kg/day P7C3-S243, or 3 mg/kg/day (−)-P7C3-S243, was initiated 24 hours after injury, however, mice learned the task as well as sham-injury mice (FIG. 26A). Notably, the 1 mg/kg/day dose failed to improve memory in the probe test (FIG. 16A), yet still facilitated learning during the training period.

Initiation of administration of 3 and 30 mg/kg/day doses of P7C3-S243 at 36 hours after injury improved learning (FIG. 26B), even though the 3 mg/kg/day dose did not improve memory in the probe test (FIG. 16B). Similarly, 30 mg/kg/day P7C3-S243 restored normal learning when treatment was initiated 48 hours after injury (FIG. 26C), despite having no effect on memory in the probe test (FIG. 16C). Finally, oral administration of 1 mg/kg/day (−)-P7C3-S243, which did not preserve memory in the probe test (FIG. 16C), also restored normal learning (FIG. 26C). Taken together, it can be concluded that treatment with P7C3-S243 mitigates acute neurocognitive deficits after blast-mediated TBI, and improves learning during the training period of the Barnes maze at doses lower than required for the more challenging task of preserving memory.

P7C3-S243 Preserves Hippocampal Synaptic Function after Blast-Mediated TBI

Figure 16:
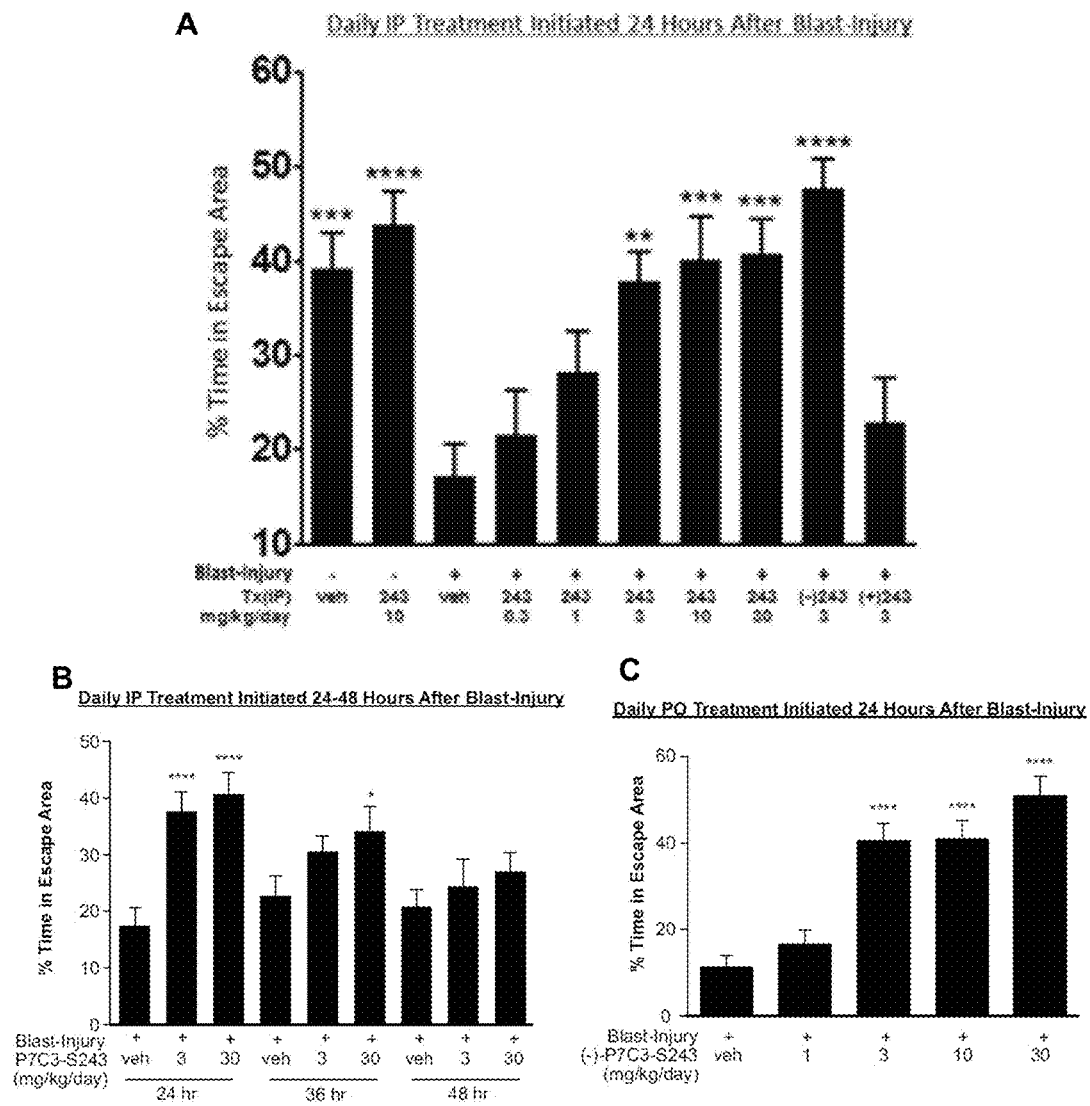
FIGS. 16A-16C. P7C3-S243 Preserves Memory after Blast-Mediated TBI.
Figure 17:
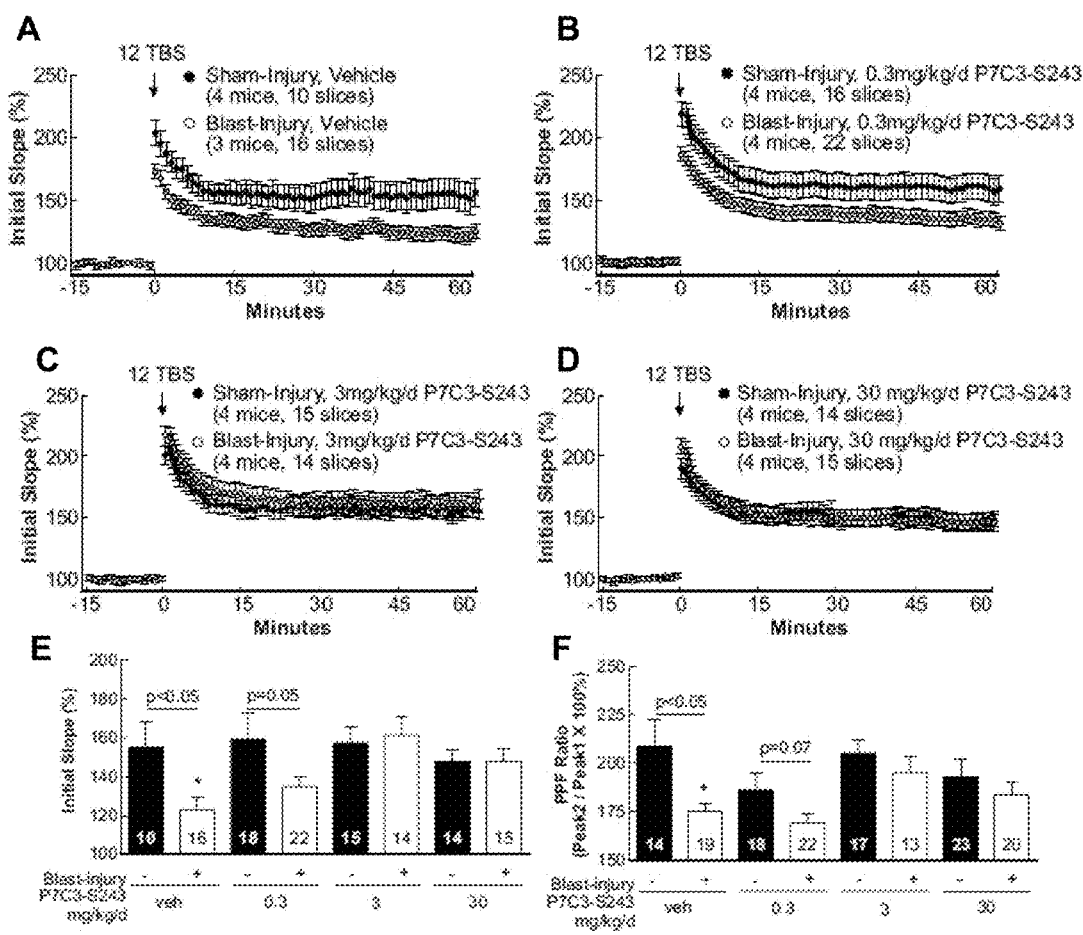
FIGS. 17A-17F. P7C3-S243 Preserves Hippocampal Synaptic Transmission after Blast-Mediated TBI. Treatment with P7C3-S243 rescues blast-injury-induced deficits in long-term potentiation (LTP) and paired-pulse facilitation (PPF) in the hippocampal CA1 Schaffer-collateral pathway.

To test our hypothesis that performance in the Barnes maze was associated with hippocampal function, we investigated synaptic plasticity in the hippocampus. Specifically, we measured both long-term potentiation (LTP) and paired pulse facilitation (PPF) in brain slices derived from mice exposed to blast-injury as a function of treatment with different doses of P7C3-S243 for 9 days, initiated 24 hours after injury, in animals not subjected to behavioral testing. The stimulating electrode activated CA3 Schaeffer collateral axons, and the recording electrode was placed in the stratum radiatum of the CA1 region, where Schaffer collateral axons synapse with dendrites from CA1 pyramidal cells. As shown in FIG. 17, blast-injury induced significant deficits in both measures, and low dose (0.3 mg/kg/day) P7C3-S243 had no effect. This dose also did not preserve memory in the Barnes maze probe test (FIG. 16). However, treatment with higher doses (3 and 30 mg/kg/day) of P7C3-S243, which did preserve normal memory after injury (FIG. 16), preserved both LTP and PPF in the hippocampus (FIG. 17). Thus, dose-dependent protective efficacy of P7C3-S243 in behavioral tasks of learning and memory correlated with hippocampal function.

P7C3-S243 Blocks Axonal Degeneration after Blast-Mediated TBI

Figure 18:
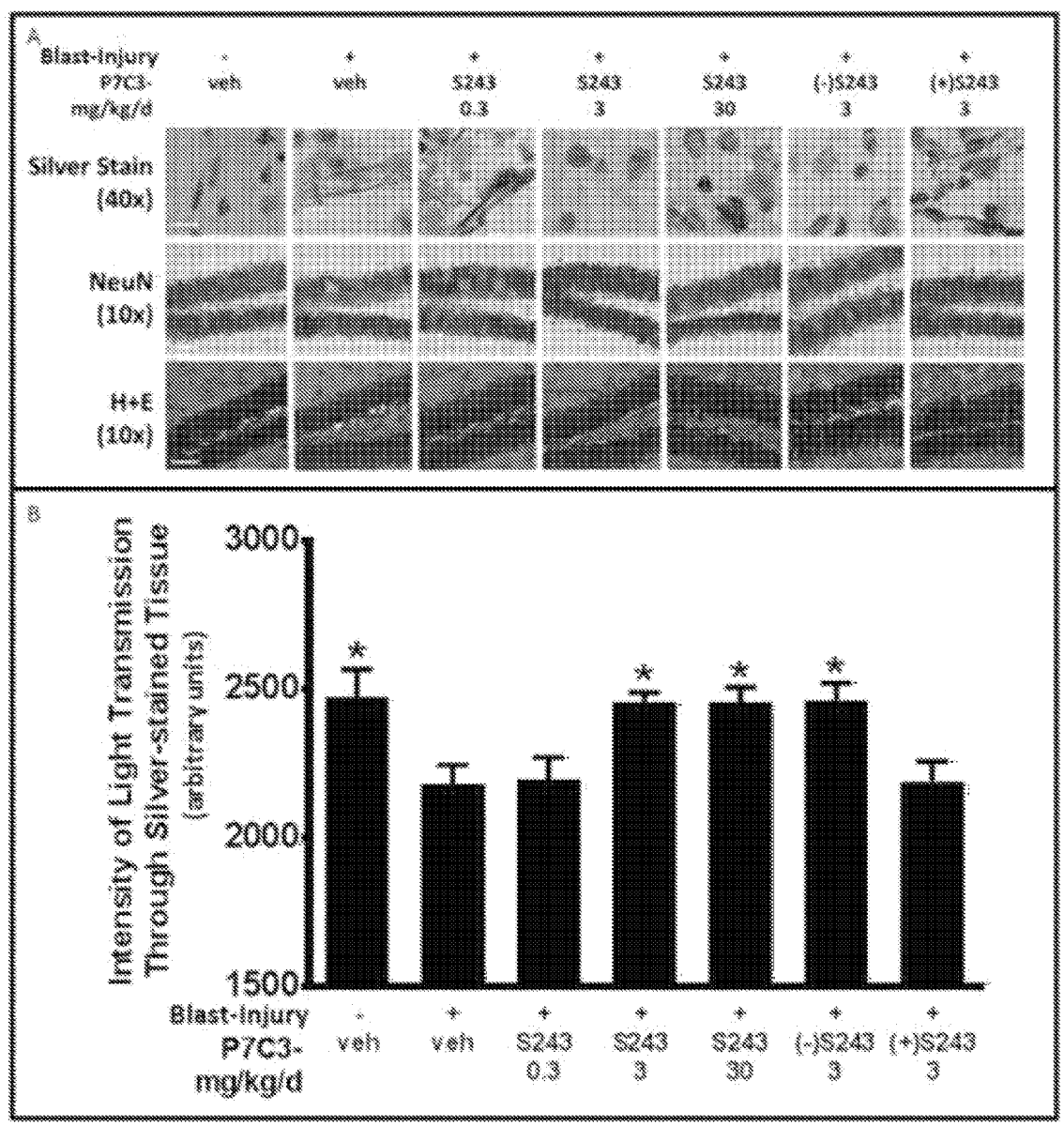
FIGS. 18A-18B. P7C3-S243 Blocks Axonal Degeneration after Blast-Mediated TBI.
Figure 27A:
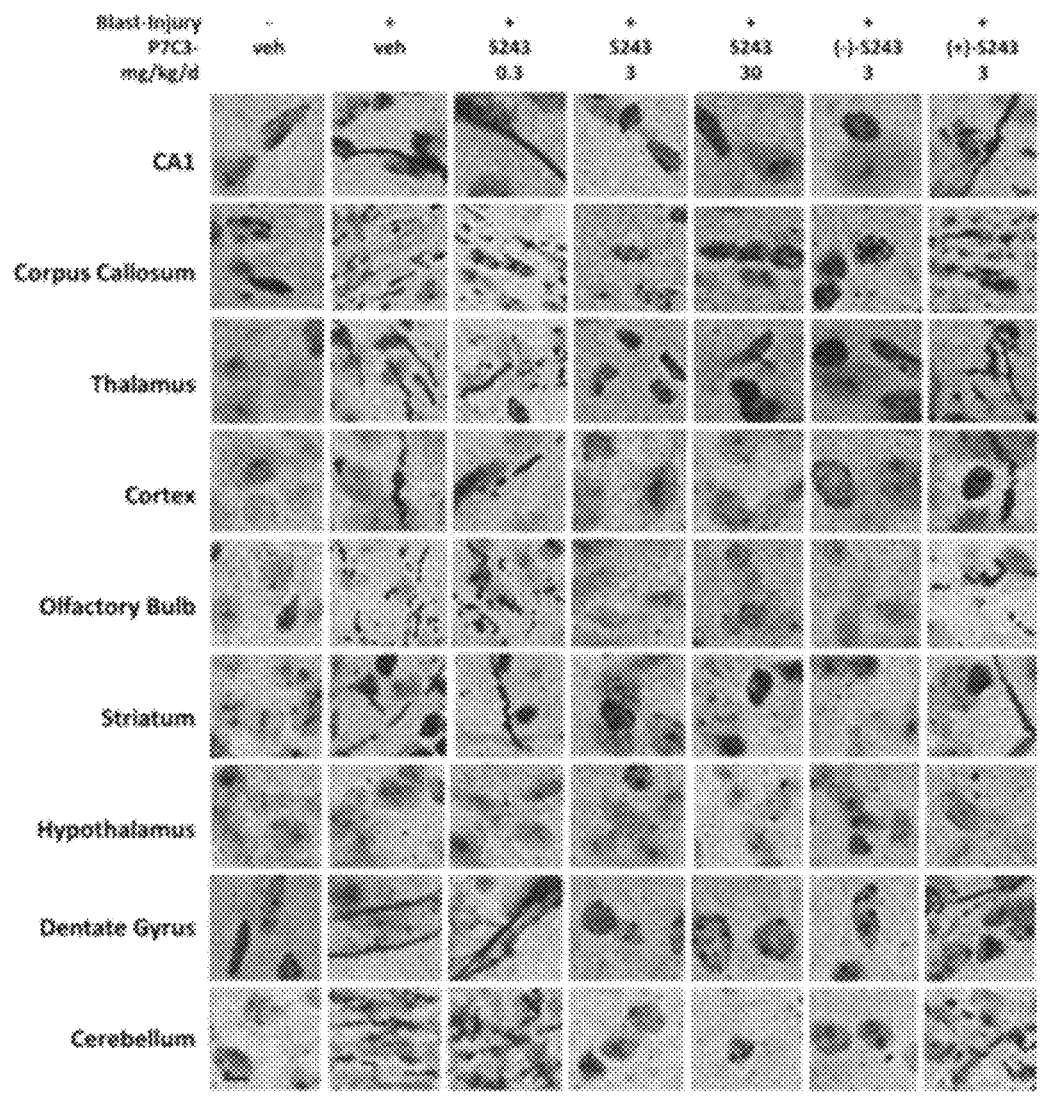
FIGS. 27A-27C. Silver Staining Reveals Widespread Axonal Degeneration after Blast-Injury, related to FIG. 18.
Figure 27B:
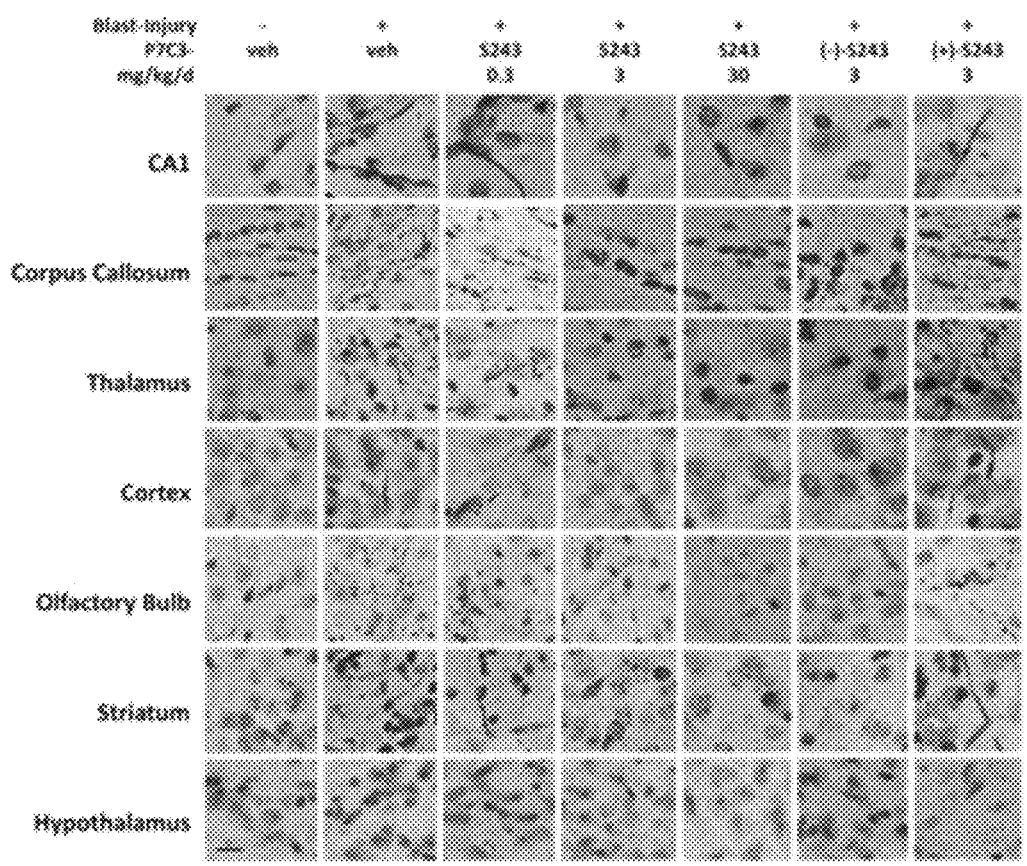
Figure 27C:
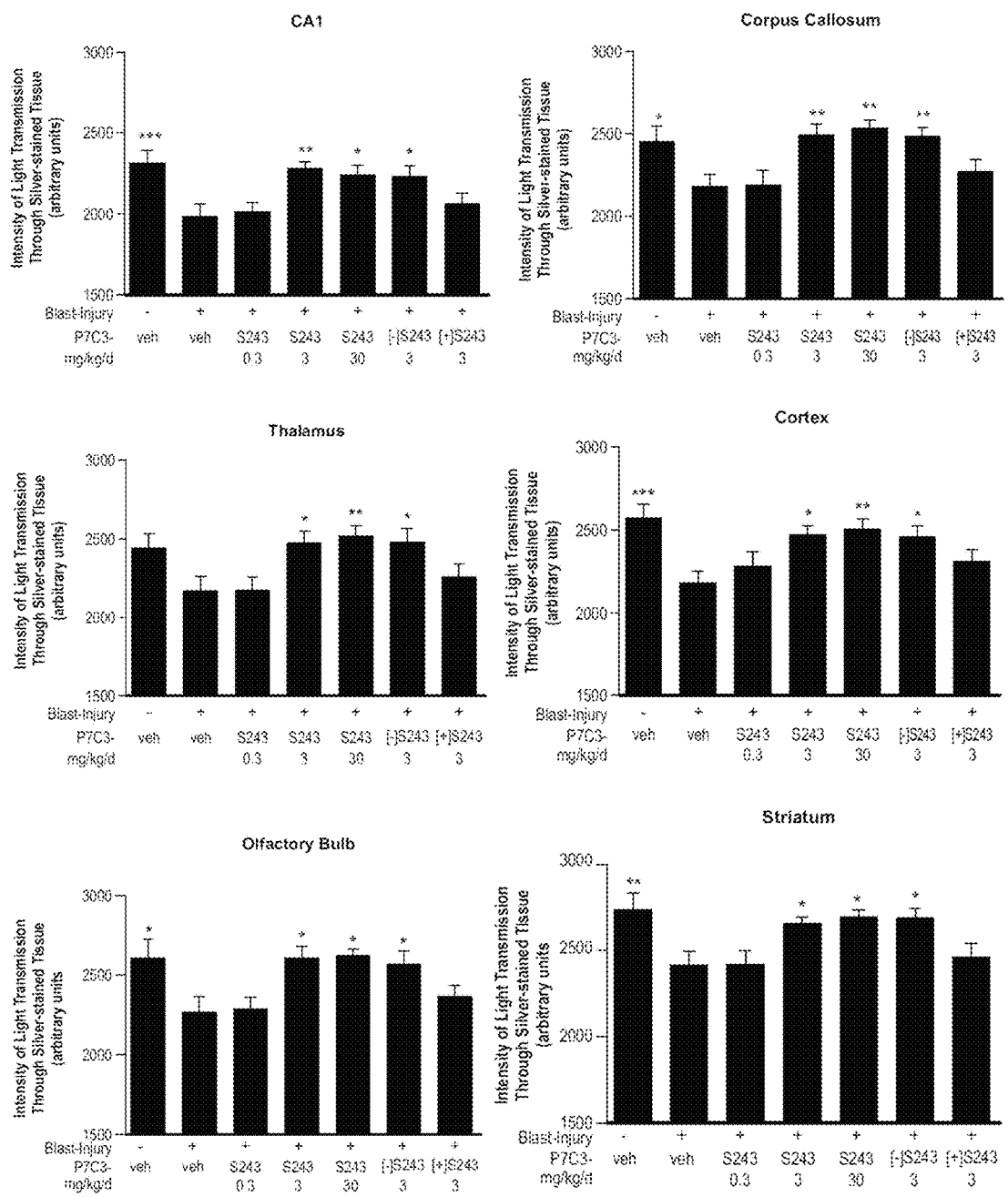
Figure 28:
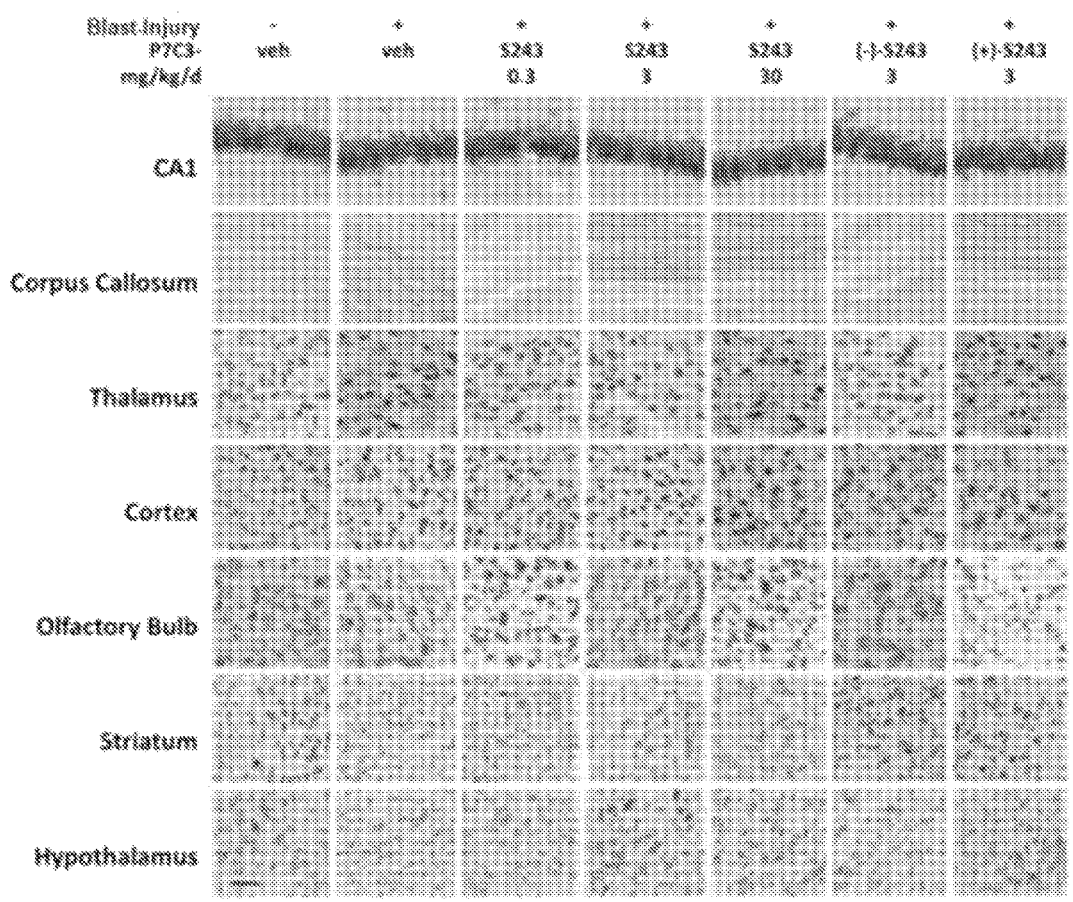
FIG. 28. NeuN Staining Reveals No Neuronal Cell Death in the Brain after Blast-Injury, related to FIG. 18. Immunohistochemical staining for NeuN shows no evidence of neuronal cell loss after blast-mediated TBI in CA1, corpus callosum, thalamus, cortex, olfactory bulb, striatum, or hypothalamus. Images shown are representative of brain slices from 5 animals in each group, directly adjacent to those shown in FIG. 27. Scale bar=5 µm.
Figure 29:
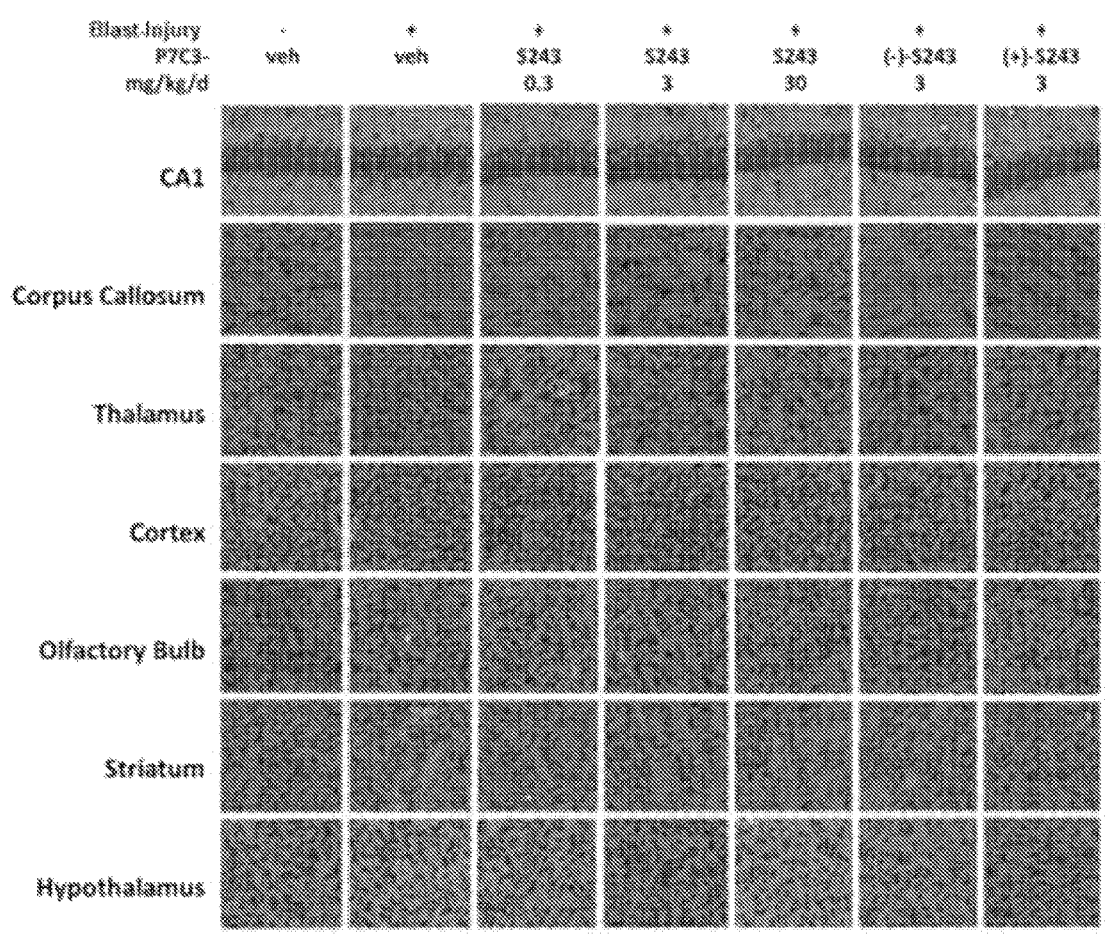
FIG. 29. Hematoxylin and Eosin Staining Reveals No Cell Loss in the Brain after Blast-Injury, related to FIG. 18. Hematoxylin and eosin staining shows no evidence of cell loss after blast-mediated TBI in CA1, corpus callosum, thalamus, cortex, olfactory bulb, striatum, or hypothalamus. Images shown are representative of brain slices from 5 animals in each group, directly adjacent to those shown in FIG. 27. Scale bar=5 µm.

Histologic examination of brain tissue 12 days after blast-injury revealed prominent axonal degeneration in the absence of cell death or acute inflammation. As shown in FIG. 18A, silver staining of degenerating axons was markedly increased in the CA1 stratum radiatum, without loss of cell bodies in the dentate gyrus. Optical densitometry of silver-stained tissue was used to quantify the magnitude of staining, such that greater impedance of light through the section reflected greater axonal degeneration (FIG. 18B). This analysis showed that degeneration of axons was blocked by treatment with P7C3-S243 at doses of 3 and 30 mg/kg/day when initiated 24 hours after injury. Treatment with 3 mg/kg/day of (−)-P7C3-S243 also offered complete protection from axonal degeneration, whereas the same dose of the less active enantiomer (+)-P7C3-S243 did not. Similar protective efficacy of 3 and 30 mg/kg/day of P7C3-S243 was also observed outside the hippocampus, including corpus callosum, thalamus, cortex, olfactory bulb, striatum and cerebellum (FIG. 27). Again, axonal degeneration in these regions occurred in the absence of death of neurons (FIG. 28) or other cell types (FIG. 29).

Figure 30:
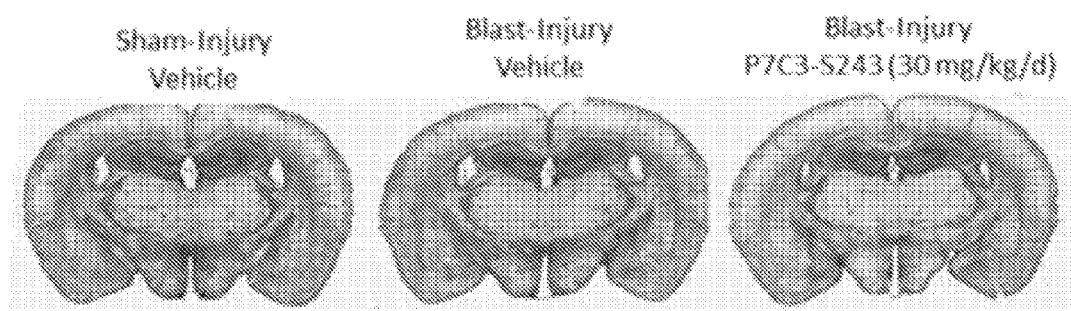
FIG. 30. Immunohistochemical Staining for glial fibrillary acidic protein (GFAP) reveals no Evidence for Inflammation after Blast-Injury, related to FIG. 18. GFAP staining shows no elevation after blast-injury, thus providing no evidence of neuroinflammation. Images shown are representative of brain slices from 5 animals in each group, directly adjacent to those shown in FIG. 29.

As neurodegenerative processes can be associated with neuroinflammation, we examined GFAP staining. Surprisingly, we did not observe elevated GFAP after blast-injury (FIG. 30A). As immunohistochemical staining was conducted 12 days after injury, we looked earlier for changes in relative gene expression in the inflammatory IL-1 pathway, which has been suggested to be active in some mouse models of TBI (Lloyd et al., 2008; Clausen et al., 2009). We examined IL-1 pathway expression in the hippocampus 2 and 24 hours after blast-injury, and saw no meaningful changes (Tables 3 and 4 below). Our data thus show that widespread axonal damage and degeneration, in the absence of acute inflammation or widespread cell death, is the predominant neuropathologic feature in the brains of mice in our model of blastmediated TBI at these early time points, which if reflective of the pathology observed in humans with mild TBI.

TABLE 3

| Gene | Fold Change Blast/Sham | t-Test p value | Average raw $C_t$, blast | Average raw $C_t$, sham |
| --- | --- | --- | --- | --- |
| IL-1α | −2.24 | 0.101177 | 31.61 | 29.39 |
| IL-1β | 1.17 | 0.166437 | 32.77 | 31.94 |
| IL1R1 | 1.28 | 0.207558 | 26.53 | 25.83 |
| IL1RAP | 1.05 | 0.539049 | 24.62 | 23.64 |
| IL1RAN | 2.71 | 0.230179 | 34.40 | 34.79 |

TABLE 4

| Gene | Fold Change Blast/Sham | t-Test p value | Average raw $C_t$, blast | Average raw $C_t$, sham |
| --- | --- | --- | --- | --- |
| IL-1α | −1.02 | 0.792652 | 29.83 | 29.85 |
| IL-1β | −1.71 | 0.193353 | 33.06 | 32.33 |
| IL1R1 | 1.02 | 0.794696 | 26.44 | 26.53 |
| IL1RAP | 1.01 | 0.850761 | 23.89 | 23.95 |
| IL1RAN | 1.10 | 0.587179 | 34.69 | 34.88 |

Figure 19:
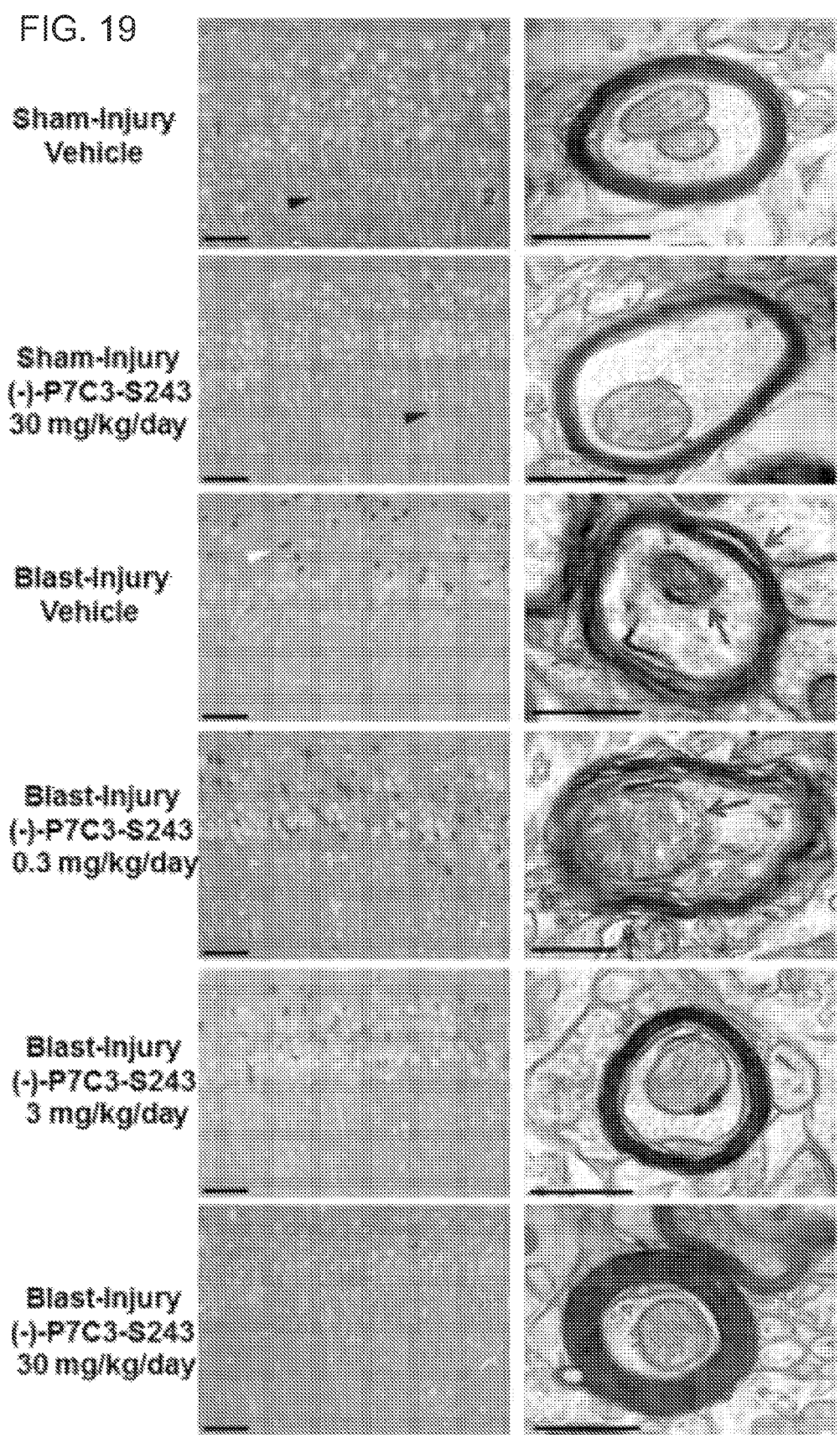
FIG. 19. Toluidine Blue Staining and Transmission Electron Microscopy. Visualization of Hippocampal Protection by orally administered (−)-P7C3-S243 after Blast-Injury Daily oral administration (PO) of the highly active enantiomer (−)-P7C3-S243 for 14 days, starting 24 hours after injury, dose-dependently preserved CA1 morphology, myelin and mitochondrial structures in the hippocampus after blast-injury. Two weeks after either sham or blast-injury, animals were perfused and processed for ultrastuctural pathology. Toluidine blue-stained semithin sections (left panel) of sham-injured mice treated with vehicle or (−)-P7C3-S243 showed normal CA1 histology, with densely packed neurons in the stratum pyramidale (1) and profuse dendritic profiles in the stratus radiatum (2; black arrows). Blast-injured animals treated with vehicle showed accumulation of chromatolytic and pyknotic neurons (white arrow) throughout the stratum pyramidale, as well as fewer dendrites in the stratum radiatum. There is no protection in CA1 morphology at the lowest concentration of blast-injured animals treated with 0.3 mg/kg/d of (−)-P7C3-S243. However, treatment at a dose of 3 mg/kg/day (−)-P7C3-S243 lowered the abundance of chromatolytic and pyknotic neurons, as well as a more densely packed stratum pyramidale. At the highest concentration (30 mg/kg/day) of (−)-P7C3-S243, there is complete preservation of CA1 morphology after blast-mediated TBI. Transmission electron micrographs (TEM; right panel) of immediately adjacent ultrathin sections showed normal myelin and axonal mitochondrial structures in the stratum radiatum of sham-injury mice treated with vehicle or (−)-P7C3-S243. Blast-injured mice treated with vehicle or 0.3 mg/kg/day of (−)-P7C3-S243 showed degeneration of myelin sheath (red arrows), along with abnormal outer membrane and internal cristae structures within neuronal mitochondria (blue arrows). At 3 and 30 mg/kg/day doses, however, both myelin and neuronal mitochondria were preserved. Pictures shown are representative of 4 animals per condition. Scale bars: Toluidine blue: 50 um; TEM: 500 nm. See also FIG. 31.
Figure 31:
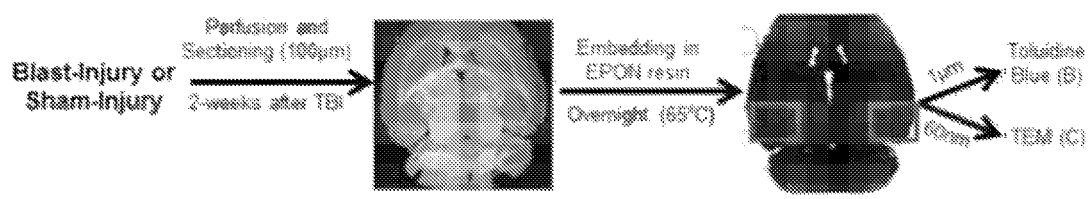
FIGS. 31A-31C. Schematic of tissue processing after either sham- or blast-injury, related to FIG. 19.
Figure 31:
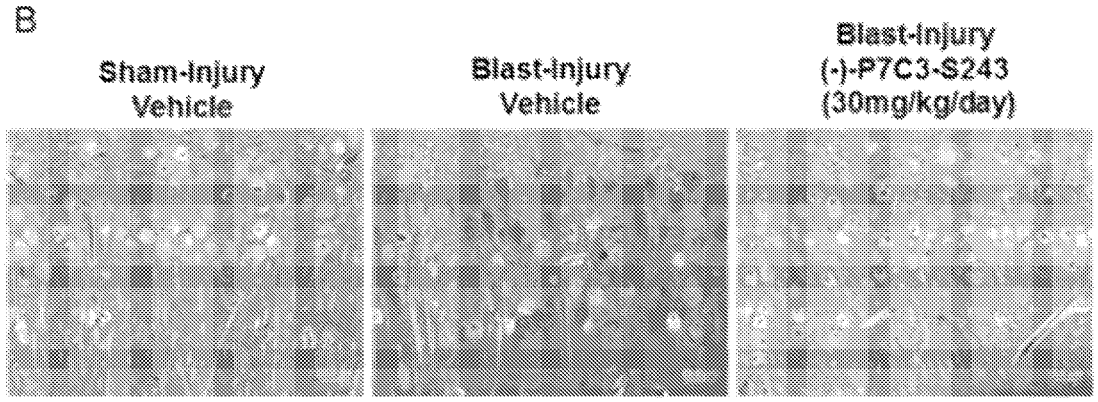
Figure 31:
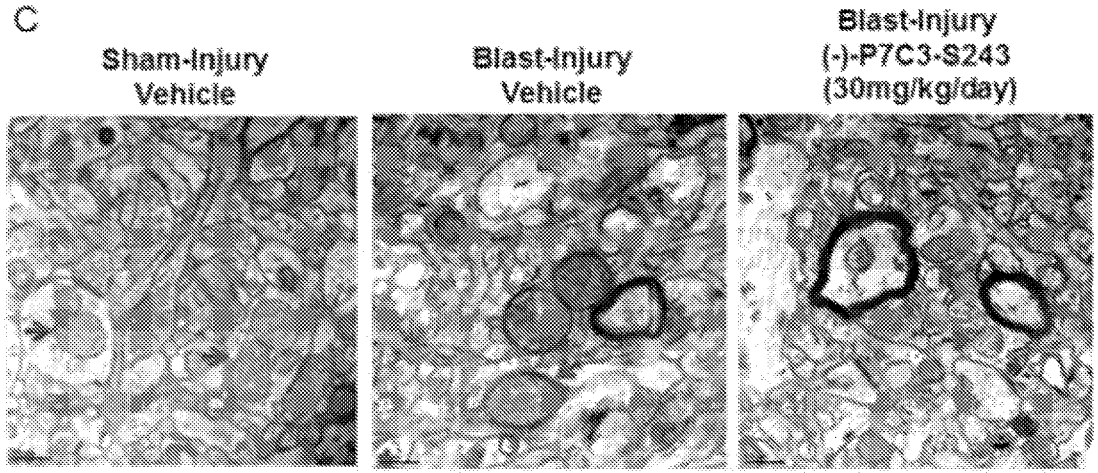

To further examine hippocampal structural pathology, we turned to ultrathin (1 μM) section histology using toluidine blue staining, as well as transmission electron microscopy (TEM) (FIG. 31). As shown in FIG. 19, sham-injury mice treated with vehicle displayed densely packed pyramidal neurons in CA1 stratum pyramidale, with abundant dendritic extensions into the stratum radiatum. These parameters did not change in sham-injured mice treated with orally administered (−)-P7C3-S243 (30 mg/kg/d). In blast-injured animals, however, we observed accumulation of chromatolytic and pyknotic neurons in the CA1 stratum pyramidale, accompanied by decreased dendritic extensions in the stratum radiatum, indicating general ongoing pathologic processes associated with neurodegeneration and consistent with our electrophysiologic data in FIG. 17. In blast-injured animals treated with low-dose (0.3 mg/kg/day) oral (−)-P7C3-S243, these same pathologic features were present (FIG. 19). Initiation of treatment 24 hours after injury with an intermediate dose (3 mg/kg/day) of oral (−)-P7C3-S243, however, appeared to decrease the abundance of pyknotic pathology in the CA1 stratum pyramidale and partially preserve dendritic extension into the stratum radiatum in blast-injured mice. A higher dose (30 mg/kg/d) of oral (−)-P7C3-S243 fully preserved all structural aspects of this region in blast-injured mice.

The stratum radiatum is where CA3 Schaeffer collateral axons synapse with dendrites of CA1 pyramidal cells. This was the circuit we investigated electrophysiologically (FIG. 17), and we next turned to TEM to further characterize blast-injury induced axonal degeneration. As shown in FIG. 19, we observed normally myelinated axons in the stratum radiatum of sham-injury mice treated with vehicle or orally administered (−)-P7C3-S243 (30 mg/kg/d). These axons contained intact and healthy-appearing mitochondria. In blast-injured animals treated with vehicle or low dose (0.3 mg/kg/day) oral (−)-P7C3-S243, however, we observed degenerating axons with characteristic unraveling of the myelin sheath. In addition, neuronal mitochondria contained within these degenerating axons showed both swelling and degenerating outer membrane and internal cristae. Initiation of treatment 24 hours after injury with an intermediate dose (3 mg/kg/d) of oral (−)-P7C3-S243 achieved partial resolution of pathological signs in both axons and neuronal mitochondria, and treatment with the higher oral dose (30 mg/kg/d) achieved full protection (FIG. 19).

Figure 20:
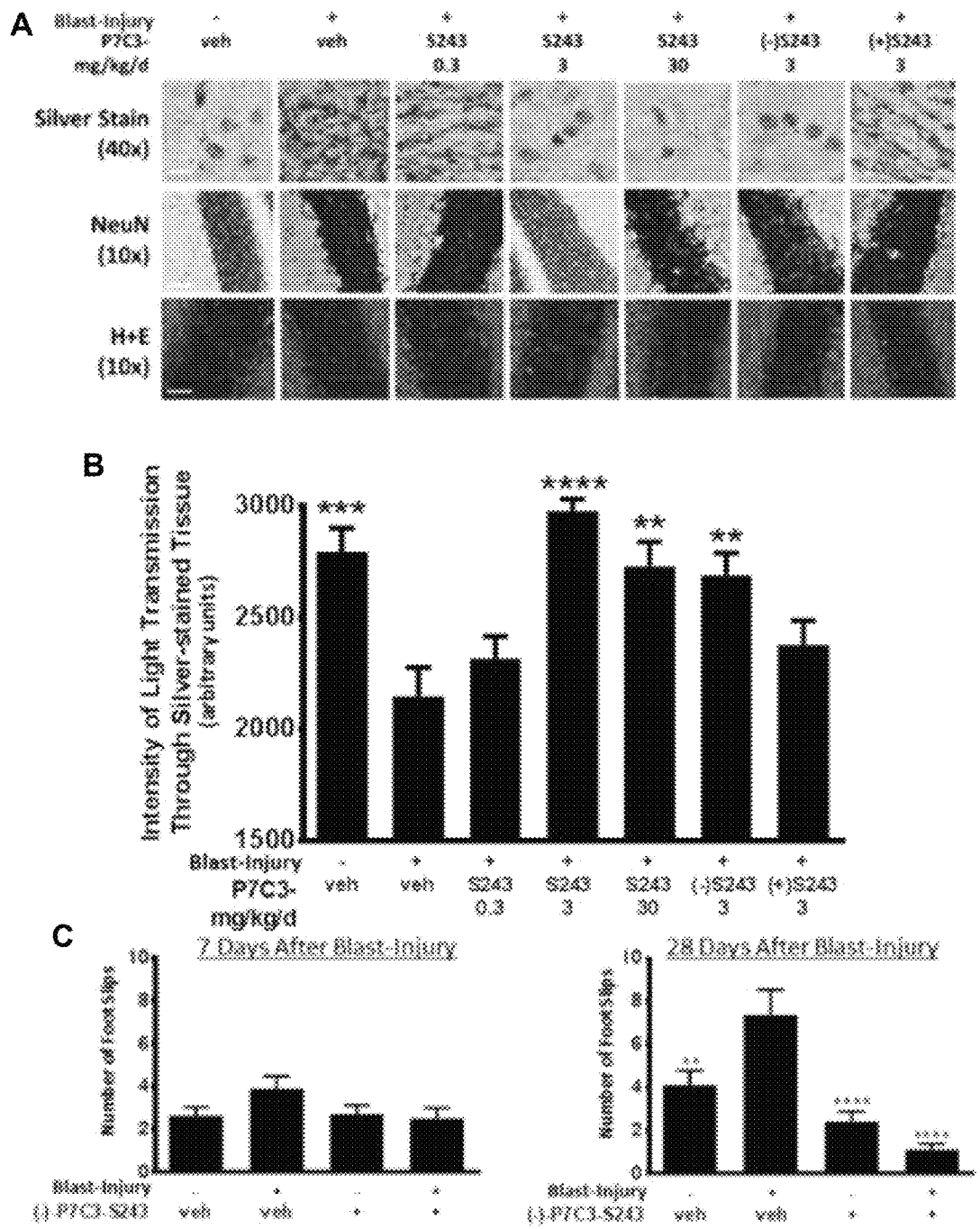
FIGS. 20A-20C. P7C3-S243 Blocks Cerebellar Axonal Degeneration and Preserves Balance and Coordination.

P7C3-S243 Preserves Cerebellar Function and Axonal Integrity after Blast-Mediated TBI Extensive axonal degeneration was also observed in the molecular layer of the cerebellum in blast-injured mice treated with vehicle or low dose (0.3 mg/kg/day) P7C3-S243, again in the absence of cell death (FIGS. 20A, 20B). As in other brain regions, axonal degeneration was blocked in the molecular layer by treatment with 3 and 30 mg/kg/day P7C3-S243, as well as 3 mg/kg/day of the highly active enantiomer (−)-P7C3-S243, but not by treatment with the same dose of the less active enantiomer (+)-P7C3-S243 (FIGS. 20A, 20B). Because the cerebellum controls coordination, we next assayed their balance and coordination, using standard procedures (Luong et al., 2011). Mice were trained to cross an 80 cm long beam over 2 days, and then sham or blast-injured on day 3. Daily oral administration of (−)-P7C3-S243 was initiated 24 hours later, and animals were tested 7 and 28 days after injury. Mice were videotaped during the test, and then analyzed for the number of foot slips by observers blind to treatment group. Seven days after blast-injury, mice showed a trend towards increased number of foot slips, which did not reach statistical significance. By 28 days after injury, however, blast-injured mice displayed a two-fold increase in number of foot slips. This behavioral deficit was normalized by daily oral treatment with (−)-P7C3-S243, initiated 24 hours after injury. Thus, protective efficacy for cerebellar axonal degeneration after injury by (−)-P7C3-S243 correlated with preservation of motor coordination.

Discussion

Here, we show for the first time that the P7C3 class of neuroprotective chemicals specifically blocks axonal degeneration independently of blocking neuron cell death. Briefly, administration of P7C3-S243, initiated 24 hours after blast-mediated TBI, potently preserves axonal integrity throughout the brain. This axonal rescue is associated with preservation of related measures of synaptic transmission, hippocampal-dependent learning and memory, and motor coordination. We thus propose that P7C3-S243 serves as a chemical scaffold upon which new drugs can be designed to treat patients with acute and chronic conditions of axonal degradation, such as occurs in TBI or other neurodegenerative diseases. Such an agent would have broad applicability, as axon degeneration proceeds through unique mechanisms distinct from cell death (Yan et al., 2010), and most forms of neurodegenerative disease involve degradation of synapses and axons preceding loss of neuronal cell bodies (Li et al., 2001; Raff et al., 2002; Coleman and Yao, 2003; Fischer et al., 2004; Gunawardena and Goldstein, 2005; Luo and O'Leary, 2005).

How might P7C3-S243 act to protect axons? In U.S. Provisional Patent Application No. 61/993,328 filed May 15, 2014, the entire disclosure of which is hereby incorporated by reference, we show that active P7C3 variants bind and enhance activity of the enzyme nicotinamide phosphoribosyltransferase (NAMPT). NAMPT synthesizes nicotinamide mononucleotide (NMN) from nicotinamide, the rate-limiting step in nicotinamide adenine dinucleotide (NAD) salvage (Preiss and Handler, 1958), and NAD is known to play a vital role in axon degeneration. For example, the Wallerian degeneration slow (WIdS) strain of mice is resistant to axonal degeneration after injury (Lunn et al., 1989) by virtue of a triplicated fusion gene resulting in over-expression of nicotinamide mononucleotide adenylyl-transferase 1 (NM-NAT1) (Araki et al., 2004), the enzyme that converts NMN into NAD. Furthermore, it has also been shown that treatment with NAD and NAD precursors, including nicotinamide, nicotinic acid mononucleotide and NMN, or overexpression of NAMPT, achieves axonal protection in vitro (Araki et al., 2004; Sasaki et al., 2006; Wang et al., 2005). Thus, active variants of P7C3 may protect from axonal degeneration by enhancing intracellular production of NAD through enhancing NAMPT activity. In conclusion, it is our hope that the P7C3 family of neuroprotective chemicals will form the basis for a new class of therapeutics applicable to a variety of conditions of nerve cell dysfunction currently lacking treatment options.

Experimental Procedures

Animals. Approval for animal experiments was obtained from the University of Iowa Institutional Animal Care and Use Committee. Mice were singly housed in the University of Iowa vivarium in a temperature-controlled environment with lights on 0600-1800. Mice had ad libitum access to water and standard chow. 8-week old C57BL6 wilt-type mice were obtained from Jackson Laboratories.

Blast-Mediated Traumatic Brain Injury. Mice were anesthetized with ketamine/xylazine (1 mg/kg and 0.1 mg/kg respectively) and placed in an enclosed blast chamber (50 cm long and 33 cm wide) constructed from an air tank partitioned into two sides. One side was pressurized with a 13 cm opening between the partitions, covered with a Mylar membrane. The unpressurized partition contained a restraint 10 cm from the Mylar membrane into which the mouse was placed. The head was freely moving while a metal tube shielded the body. Compressed air was forced in to the pressurized partition until the Mylar membrane bursts at 22 kPa. The blast wave impacts the test animal inside a foam-lined restraint to reduce blunt impact trauma of the head against the metal tube. The left side of the head was closest the origin of the blast wave. Sham-injured animals were anesthetized in the same way and not subjected to the blast.

Barnes Maze. The Barnes maze test assesses spatial learning and memory. It was conducted on a gray circular surface 91 cm in diameter with 20 holes 5 cm in diameter around the perimeter raised to a height of 90 cm (Stoelting Co.). The surface was brightly lit and open in order to motivate the test animal to learn the location of a dark escape chamber recessed under one of the 20 holes. The maze was placed inside a black circular curtain with four different visual cues (with different shapes and colors) for orientation to the permanent location of the escape chamber. Four days of training comprised of four trials per day were conducted for each animal. An area extending 4 cm from the escape hole in all directions was used as the target area for measurements (percent time in escape area, percent latency to escape and nose pokes). A probe trial was conducted on the subsequent day during which the escape chamber was removed and measurements were made to confirm the animal's memory based upon spatial cues. Measurements were made utilizing Anymaze video tracking software (Stoelting Co.), and analysis was conducted blind to treatment group.

P7C3 class of compounds formulation. Compound formulation was conducted using previously described methods (Pieper et al 2010, Naidoo and De Jesús-Cortés et al. 2014).

Immunohistochemistry. Formaldehyde-perfused and fixed mouse cerebrum, brainstem and cerebellum were cryoprotected with 0.1 M phosphate buffer (PB, pH 7.4) containing 20% sucrose for 72 hours, and rapidly frozen in isopentane pre-cooled to −70° C. with dry ice. All brains were stored in a freezer at −80° C. before sectioning. Serial sections (40 µm) were cut coronally through the cerebrum, approximately from bregma 3.20 mm to bregma −5.02 mm and the brainstem and cerebellum, approximately from bregma −5.52 mm to bregma −6.96 mm (cf. the Mouse Brain in Stereotaxic Coordinates by Paxinos & Franklin, 1997). Every 1st-12th sections of each series of 12 sections (interval: 480 µm) were collected separately. All sections were stored free-floating in FD sections storage solution (FD Neurotechnologies, Columbia, Md.) at −20° C. before further processing.

For hematoxilin & eosin (H&E) staining, sections were mounted on 1"×3" Superfrost Plus microscope slides and stained with FD hematoxylin & eosin (FD Neurotechnologies).

For silver staining, sections were collected in 0.1 M phosphate buffer (pH 7.4) containing 4% paraformaldehyde and fixed for 5 days at 4° C. Sections were then processed for the detection of neurodegeneration with FD NeuroSilver Kit II (FD Neurotechnologies) according to the manufacturer's instructions (for detailed procedures, cf. the manual of PK301, available at www.fdneurotech.com). Subsequently, all sections were mounted on slides, dehydrated in ethanol, cleared in xylene, and coverslipped with Permount (Fisher Scientific, Fair Lawn, N.J.).

For NeuN- and GFAP-immunoreactivity, we first inactivated the endogenous peroxidase activity with 0.6% hydrogen peroxidase, and then sections were incubated free-floating for 43 hours at 4° C. in 0.01 M phosphate-buffered saline (PBS, pH 7.4) containing 1% normal blocking serum, 0.3% Triton X-100 (Sigma, St. Louis, Mo.) and either a biotin-conjugated monoclonal mouse anti-NeuN IgG (1:600; Millipore, Billerica, Mass.) or rat anti-GFAP IgG (1:10,000; Invitrogen, Carlsbad, Calif.). The immunoreaction product was visualized according to the avidin-biotin complex method with the Vectastin elite ABC kit (Vector Lab., Burlingame, Calif.). In brief, sections were incubated in PBS containing normal blocking serum, Triton-X and biotinylated rabbit anti-rat IgG (for GFAP) for 1 hour, and then in PBS containing avidin-biotinylated horseradish peroxidase complex for another hour. This was followed by incubation of sections for 6-10 minutes in 0.05 M Tris buffer (pH 7.2) containing 0.03% 3',3'-diaminobenzidine (Sigma) and 0.0075% H2O2 (Sigma). All steps were carried out at room temperature except indicated, and each step was followed by washes in PBS. After thorough rinses in distilled water, all sections were mounted on slides, dehydrated in ethanol, cleared in xylene, and coverslipped in Permount (Fisher Scientific, Fair Lawn, N.J.). All images were taken with an Aperio ScanScope (Leica biosystems)

Electrophysiology. Single-housed, naïve 7- to 9-week-old male C57BL/6J mice received intraperitoneal injections of P7C3-S243 (0.3, 3, or 30 mg/kg/day) or vehicle 24 h following a single sham- or blast-Injury. On the tenth day after injury, coronal hippocampal slices (400 µm) were prepared, in accordance with the University of Iowa guidelines. Briefly, hippocampal slices were cut using a Vibratome 1000 Plus (Vibratome, St. Louis, Mo.) in ice-cold slicing buffer (in mM: 127 NaCl, 26 NaHCO3, 1.2 KH2PO4, 1.9 KCl, 1.1 CaCl2, 2 MgSO4, 10 D-Glucose) bubbled with 95% O2 and 5% CO2. Slices were then transferred to a holding chamber containing oxygenated artificial cerebrospinal fluid (ACSF; in mM: 127 NaCl, 26 NaHCO3, 1.2 KH2PO4, 1.9 KCl, 2.2 CaCl2, 1 MgSO4, 10 D-Glucose) for 30 min at 34 C and for another 30 min at 22° C. for recovery, and then transferred to a submersion recording chamber continually perfused with 32° C. oxygenated ACSF (rate: 2 ml/min). Slices were equilibrated for at least 15 min before each recording.

ACSF-filled glass electrodes (resistance <1 MΩ) were positioned in the stratum radiatum of area CA1 for extracellular recording. Synaptic responses were evoked by stimulating Schaffer collaterals with 0.2 ms pulses once every 15 s. The stimulation intensity was systematically increased to determine the maximal field excitatory postsynaptic potential (fEPSP) slope and then adjusted to yield 40-60% of the maximal (fEPSP) slope. Experiments with maximal fEPSPs of less than 0.5 mV, with large fiber volleys, or with substantial changes in the fiber volley during recording were rejected. LTP was induced by 12TBS (12 bursts, each of 4 pulses at 100 Hz).

Field EPSPs were recorded (AxoClamp 900A amplifier, Axon Instruments, Foster City, Calif.), filtered at 1 kHz, digitized at 10 kHz (Axon Digidata 1440), and stored for off-line analysis (Clampfit 10). Initial slopes of fEPSPs were expressed as percentages of baseline averages. In summary graphs, each point represents the average of 4 consecutive responses. The time-matched, normalized data were averaged across experiments.

Quantification of silver-stained tissue: Optical densitometry for quantification procedures were modified from published methodology (Baldock and Poole et al. 1993). Images were captured with an upright microscope (Zeiss AxioImager.M2) equipped with a monochromatic digital camera (Zeiss AxioCam MRm Rev.3) and processed with the Zen imaging software (Zeiss 2012, Blue edition). The microscope light intensity and camera exposure were held constant. The operator outlined areas of interest around specific brain regions and recorded the intensity of light passing through the slide. Degenerating axons allowed less light to pass through the section due to their uptake of silver stain, so lower light intensity correlated with increased degeneration. Operator performing quantification was blinded to condition and treatment.

IL-1 pathway examination with RT$^2$ Profiler PCR Array. 1 µg total RNA (from whole hippocampus) was used for cDNA synthesis for 2 hours post TBI samples via RT$^2$ first strand kit (SAbioscience 330401). 2 ug total RNA (from whole hippocampus) was used for cDNA synthesis for 24 hours post TBI samples. RT$^2$ syber green mastermix (SAbioscience 330522) and RT$^2$ profiler PCR array (Inflammatory Response & Autoimmunity PCR Array, Cat. No. PAMM-077Z, Qiagen) were used for real time PCR following manufacturer's instruction. Housekeeping genes used as endogenous controls include ACTB, B2M, GAPDH, GUSB, HSP90AB1.

Toluidine blue staining and transmission electron microscopy (TEM). Mice were transcardially perfused with Karnovsky's fixative solution (2% formaldehyde, 2.5% glutaraldehyde, 0.2M sodium cacodylate buffer, 1 mM CaCl2, 2 mM MgCl2, and 42.8 mM NaCl, pH 7.4) two weeks after either sham- or blast-Injury and with or without specified compound treatment. Harvested brains were incubated in Karnovsky's overnight at 4° C. Whole brains were cut in the horizontal plane (100 µm) using a vibratome (Leica 1500). Sections that contained the hippocampus were selected, washed with 0.1M sodium cacodylate buffer and then post fixed with 1% osmium fixative for 1 hr. After washing in 0.1M sodium cacodylate buffer, sections were dehydrated in a series of ethanol (50%, 75%, 95% and 100% ethanol) followed by embedding in EPON resin overnight at 65° C. For toluidine blue staining, semithin sections (1 µm) were cut with an ultramicrotome (Leica UC6) and stained with toluidine blue. Pictures were taken using an upright microscope (Zeiss Axio Imager.M2) with a color camera (AxioCam ICc5). For TEM, ultrathin sections (60 nm) adjacent to the semithin sections were cut with an ultramicrotome, loaded onto a Formvar 200-mesh Ni grid, and counterstained with uranyl acetate and lead citrate. Specimens were examined using a JEOL JEM 1230 electron microscope with a Gatan UltraScan 1000 2 k×2 k CCD camera. See also FIG. 31.

Blood brain barrier (BBB) permeability assay. To analyze the permeability of the BBB, we used an Evan's blue dye (EBD) method modified from Uyama et al. (1988). EBD, which binds albumin, is incapable of crossing an intact blood-brain barrier. One hour prior to sacrifice, freshly prepared 2% EBD (Sigma) in phosphate-buffered saline (PBS) was administered at a 4 ml/kg dose via the retro-orbital venous sinus. Animals were sacrificed and perfused 6 hours, 24 hours, and 102 hours following blast-Injury with cold PBS. Brains were frozen at −20° C. until all time points were complete to accurately compare each group. To quantify the extravasation of albumin-bound EBD in each brain, tissue was weighed and incubated for 30 minutes at room temperature in 50% Tricholoracetic acid (TCA) in PBS at a 3:1 µl/mg ratio. Samples were sonicated at 40% amplitude and centrifuged for 20 minutes at 10,000 rpm. Supernatants were transferred to new tubes and 100% ethanol was added in a 1:3 ratio. Fluorescence was measured using a SpectraMax M2$^e$ (Molecular Devices) in 100 µl of samples plated on a 96-well plate at excitation wavelength of 620 nm and an emission wavelength of 680 nm.

Foot slip assay. We used standard procedures described by Luong et al. (2011) to measure motor balance coordination. During the training period, mice were trained to cross the 80 cm beam to enter a black box with nesting material 3 times a day over 2 consecutive days. Mice were then sham-or blast-Injured on the next day. 24 hrs after injury, daily administration with (−)-P7C3-S243 or vehicle was initiated. Animals were then tested 7 and 28 days after injury. Mice performance was videotaped during the test and foot slips were analyzed by an observer blind to condition and treatment group.

Statistics. GraphPad Prism 6 software was used to perform all statistical analyses.

References

Araki, T., Sasaki, Y., and Milbrandt, J. (2004). Increased nuclear NAD biosynthesis and SIRT1 activation prevent axonal degeneration. Science 305, 1010-3.

Blaya, M. O., Bramlett, H. M., Naidoo, J., Pieper, A. A., and Dietrich, W. D. (2014). Neuroprotective efficacy of a proneurogenic compound after traumatic brain injury. J. Neurotrauma 31, 476-86.

Clausen, F., Hanell, A., Bjork, M., Hillered, L., Mir, A. K., Gram, H., and Marklund, N. (2009). Neutralization of interleukin-1beta modifies the inflammatory response and improves histological and cognitive outcome following traumatic brain injury in mice. Eur. J. Neurosci. 30, 385-96.

Coleman, P. D., and Yao, P. J. (2003). Synaptic slaughter in Alzheimer's disease. Neurobiol. Aging 24, 1023-7.

De Jesús-Cortés, H., Xu, P., Drawbridge, J., Estill, S. J., Huntington, P., Tran, S., Britt, J. K., Tesla, R., Morlock, L., Naidoo, J., Melito, L. M., Wang, G., Williams, N. S., Ready, J. M., McKnight, S. L., and Pieper, A. A. (2012). Neuroprotective efficacy of aminopropyl carbazoles in a mouse model of Parkinson disease. Proc. Natl. Acad. Sci. USA 109, 17010-5.

Fischer, L. R., Culver, D. G., Tennant, P., Davis, A. A., Wang, M., Castellano-Sanchez, A., Khan, J., Polak, M. A., and Glass, J. D. (2004). Amyotrophic lateral sclerosis is a distal axonopathy: evidence in mice and man. Exp. Neurol. 185, 232-40.

Goldstein, L. E., Fisher, A. M., Tagge, C. A., Zhang, X-L., Veliske, L., Sullivan, J. A., Upreti, C., Kracht, J. M., Ericsson, M., Wojnarowicz, M. W., Goletiani, C. J., Maglakelidze, G. M., Casey, N., Moncaster, J. A., Minaeva, O., Moir, R. D., Nowinski, C. J., Stern, R. A., Cantu, R. C., Geiling, J., Blusztajn, J. K., Wolozin, B. L., Ikezu, T., Stein, T. D., Budson, A. E., Kowall, N. W., Chargin, D., Sharon, A., Saman, S., Hall, G. F., Moss, W. C., Cleveland, R. O., Tanzi, R. E., Stanton, P. K., and McKee, A. C. (2012). Chronic traumatic encephalopathy in blastexposed military veterans and a blast neurotrauma mouse model. Sci. Trans. Med. 134, 1-16.

Gunawardena, S. and Goldstein, L. S. (2005). Polyglutamine diseases and transport problems: deadly traffic jams on neuronal highways. Arch. Neurol. 62, 46-51.

Hawkins, B. T. and Egleton, R. D. (2006). Fluorescence imaging of blood-brain barrier disruption. J. Neurosci. Meth. 151, 262-7.

Hoge, C. W., McGurk, D., Thomas, J. L., Cox, A. L., Engel, C. C., and Castro, C. A. (2008). Mild traumatic brain injury in U. S. soldiers returning from Iraq. N.Engl. J. Med. 385, 453-63.

Li, H., Li, S. H., Yu, Z. X., Shelbourne, P., Li, X. J. (2001). Huntingtin aggregate-associated axonal degeneration is an early pathological event in Huntington's disease mice. J. Neurosci. 21, 8473-81.

Lloyd, E., Somera-Molina, K., Van Eldik, L. J., Waterson, D. M., and Wainwright, M. S. (2008). Suppression of acute proinflammatory cytokine and chemokine upregulation by post-injury administration of a novel small molecule improves long-term neurologic outcome in a mouse model of traumatic brain injury. J. Neuroinflammation 5, 5-28.

Lunn, E. R., Perry, V. H., Brown, M. C., Rosen, H., and Gordon, S. (1989). Absence of Wallerian degeneration does not hinder regeneration in peripheral nerve. Eur. J. Neurosci. 1, 27-33.

Luong, T. N., Carlisle, H. J., Southwell, A., and Patterson, P. H. (2011). Assessment of motor balance and coordination in mice using the balance beam. J. Vis. Exp. 10.

MacMillan, K. S., Naidoo, J., Liang, J., Melito, L., Williams, N. S., Morlock, L., Huntington, P. J., Estill, S. J., Longgood, J., Becker, G. L., McKnight, S. L., Pieper, A. A., De Brabander, J. K., and Ready, J. M. (2010). Development of proneurogenic, neuroprotective small molecules. J. Am. Chem. Soc. 133, 1428-37.

Magnuson, J., Leonessa, F., and Ling, G. S. (2012). Neuropathology of explosive blast traumatic brain injury. Curr. Neurol. Neurosci. Rep. 12, 570-9.

Mohan, K., Kecova, H., Hernandez-Merino, E., Kardon, R. H., and Harper, M. M. (2013). Retina ganglion cell damage in an experimental rodent model of blast-mediated traumatic brain injury. Invest. Opthalmol. Vis. Sci. 54, 3440-50.

Naidoo, J., Bemben, C. J., Allwein, S. R., Liang, J., Pieper, A. A., and Ready, J. M. (2013). Development of a scalable synthesis of P7C3-A20, a potent neuroprotective agent. Tett. Lett. 54, 4429-4431.

Naidoo, J., De Jesús-Cortés, H., Huntington, P., Estill, S., Morlock, L. K., Starwalt, R., Mangano, T. J., Williams, N. S., Pieper, A. A. and Ready, J. M. (2014). Discovery of a neuroprotective chemical, (S)—N-(3,6-dibromo-9H-carbazol-9-yl)-2-fluoropropyl)-6-methoxypyridin-2-amine [(−)P7C3-S243], with improved druglike properties. J. Med. Chem. 57, 3746-54.

Nakagawa, A., Manley, G. T., Gean, A. D., Ohtani, K., Armonda, R., Tsukamoto, A., Yamamoto, H., Takayama, K., and Tominaga, T. (2011). Mechanisms of primary blastinduced traumatic brain injury: Insights from shockwave research. J. Neurotrauma 28, 1101-19.

Pieper, A. A., Wu, X., Han, T. W., Estill, S. J., Dang, Q., Wu, L. C., Reece-Fincanon, S., Dudley, C. A., Richardson, J. A., Brat, D. J., and McKnight, S. L. (2005). The neuronal PAS domain protein 3 transcription factor controls FGF-mediated adult hippocampal neurogenesis in mice. Proc. .Natl. Acad. Sci. USA 102, 14052-14057.

Pieper, A. A., Xie, S., Capota, E., Estill, S. J., Zhong, J., Long, J. M., Becker, G. L., Huntington, P., Goldman, S. E., Shen, C—H., Capota, M., Britt, J. K., Kotti, T., Ure, K., Brat, D. J., Williams, N. S., MacMillan, K. S., Naidoo, J., Melito, L., Hsieh, J., De Brabander, J., Ready, J. M., McKnight, S. L. (2010). Discovery of a proneurogenic, neuroprotective chemical. Cell 142, 39-51.

Pieper, A. A., McKnight, S. L., and Ready, J. M. (2014). P7C3 and an unbiased approach to drug discovery for neurodegenerative diseases. Chem. Soc. Rev. February 11 [EPub ahead of print].

Preiss, J., and Handler, P. (1958). Biosynthesis of diphosphopyridine nucleotide. I. Identification of Intermediates. J. Biol. Chem. 233, 488-92.

Raff, M. C., Whitmore, A. V., and Finn, J. T. (2002). Axonal self-destruction and neurodegeneration. Science 296, 868-71.

Sasacki, Y., Araki, T., and Milbrandt, J. (2006). Stimulation of nicotinamide adenine dinucleotide biosynthetic pathways delays axonal degeneration after axotomy. J. Neurosci. 26, 8484-91.

Shively, S. I., Scher, A. I., Perl, D. P., and Diaz-Arrastia, R. (2012). Dementia resulting from traumatic brain injury: what is the pathology? Arch. Neurol. 69, 1245-51.

Tesla, R., Wolf, H. P., Xu, P., Drawbridge, J., Estill, S. J., Huntington, P., McDaniel, L., Knobbe, W., Burket, A., Tran, S., Starwalt, R., Morlock, L., Naidoo, J., Williams, N. S., Ready, J. M., McKnight, S. L., and Pieper, A. A. (2012). Neuroprotective efficacy of aminopropyl carbazoles in a mouse model of amyotrophic lateral sclerosis. Proc. Natl. Acad. Sci. USA 109, 17016-21.

Uyama, O., Okamura, N., Yanase, M., Narita, M., Kawabata, K. and Sugita, M. (1988). Quantitative evaluation of vascular permeability in the gerbil brain after transient ischemia using Evans blue fluorescence. J.Cereb. Blood Flow Metab. 8, 282-4.

Walker, A. K., Rivera, P. D., Wang, Q., Chuang, J-C., Tran, S., Osborne-Lawrence, S., Estill, S. J., Starwalt, R., Huntington, P., Morlock, L., Naidoo, J., Williams, N. S., Ready, J. M., Eisch, A. J., Pieper, A. A. and Zigman, J. M.

(2014). The P7C3 class of neuroprotective compounds exerts antidepressant efficacy in mice by increasing hippocampal neurogenesis. Mol. Psych. April 22 [EPub ahead of print].

Wang, J. Zhai, Q., Chen, Y., Lin, E., Gu, W. McBurney, W., and He, Z. (2005). A local mechanism mediates NAD-dependent protection of axon degeneration. J. Cell Biol. 170, 349-55.

Wolf, S. J., Bebarta, V. S., Bonnett, C. J., Bonnett, P. T., Pons, S. V., and Cantrill, S. V. (2009). Blast injuries. Lancet 374, 405-15.

Yan, T., Feng, Y., and Zhai, Q. (2010). Axon degeneration: Mechanisms and implications of a distinct program from cell death. Neurochem. Int. 56, 529-34.

Example 5

(−)-P7C3-S243 Treatment Reverses Cognitive Decline Chronically in TBI Model

Figure 32:
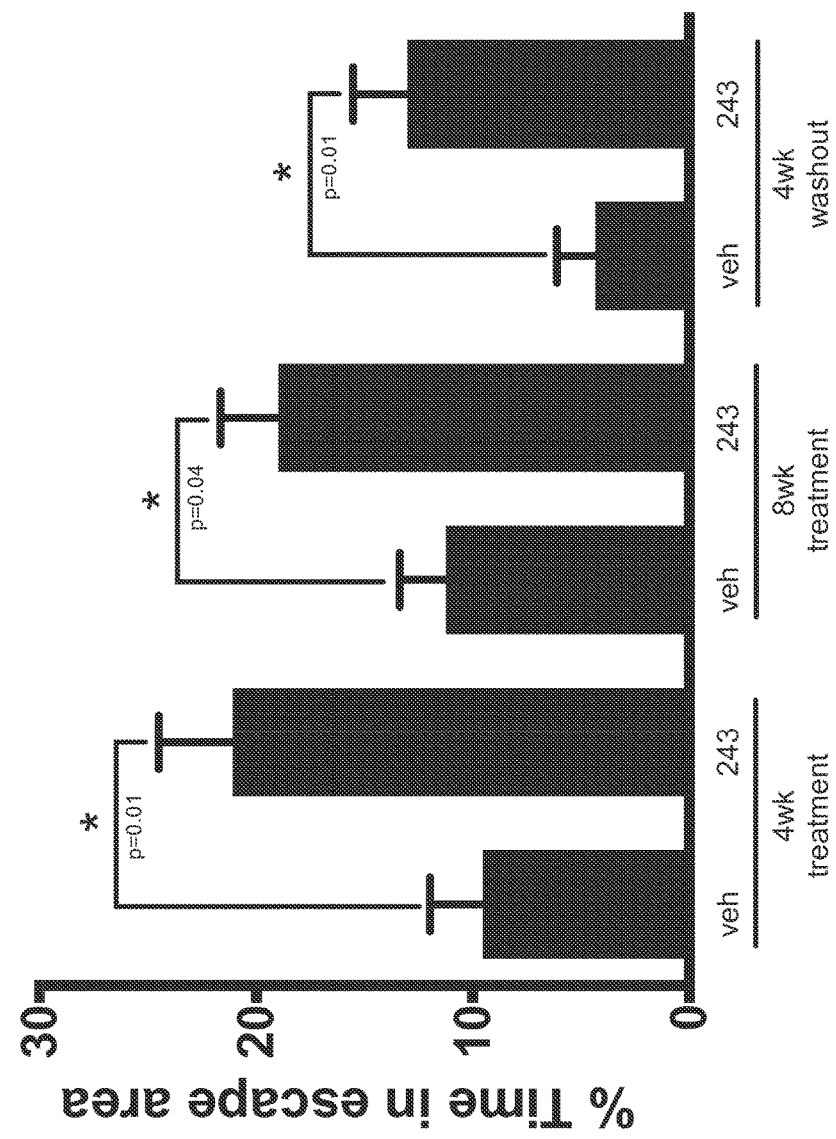
FIG. 32. (−)-P7C3-S243 treatment reverses cognitive decline chronically after blast mediated TBI. 10 months after a single blast injury, daily treatment with 3 mg/kg/day of (−)-P7C3-S243 was initiated. After both 4 and 8 weeks of daily treatment, mice showed sustained improvement in cognitive function, as measured by time spent in the escape area (5 cm radius around the escape hole) in the Barnes maze task of hippocampal-dependent learning and memory. After 8 weeks of treatment, mice were completely withdrawn from treatment with vehicle or compound. The group that had previously received 8 weeks of daily treatment showed sustained improvement in cognition relative to the group that received vehicle. There were 10 wild type male mice in (−)-P7C3-S243 (243)-treated group, and 9 mice wild type male mice in the vehicle (veh)-treated group. Statistical p values were determined by Student's t test of veh vs 243 groups.
Figure 33:
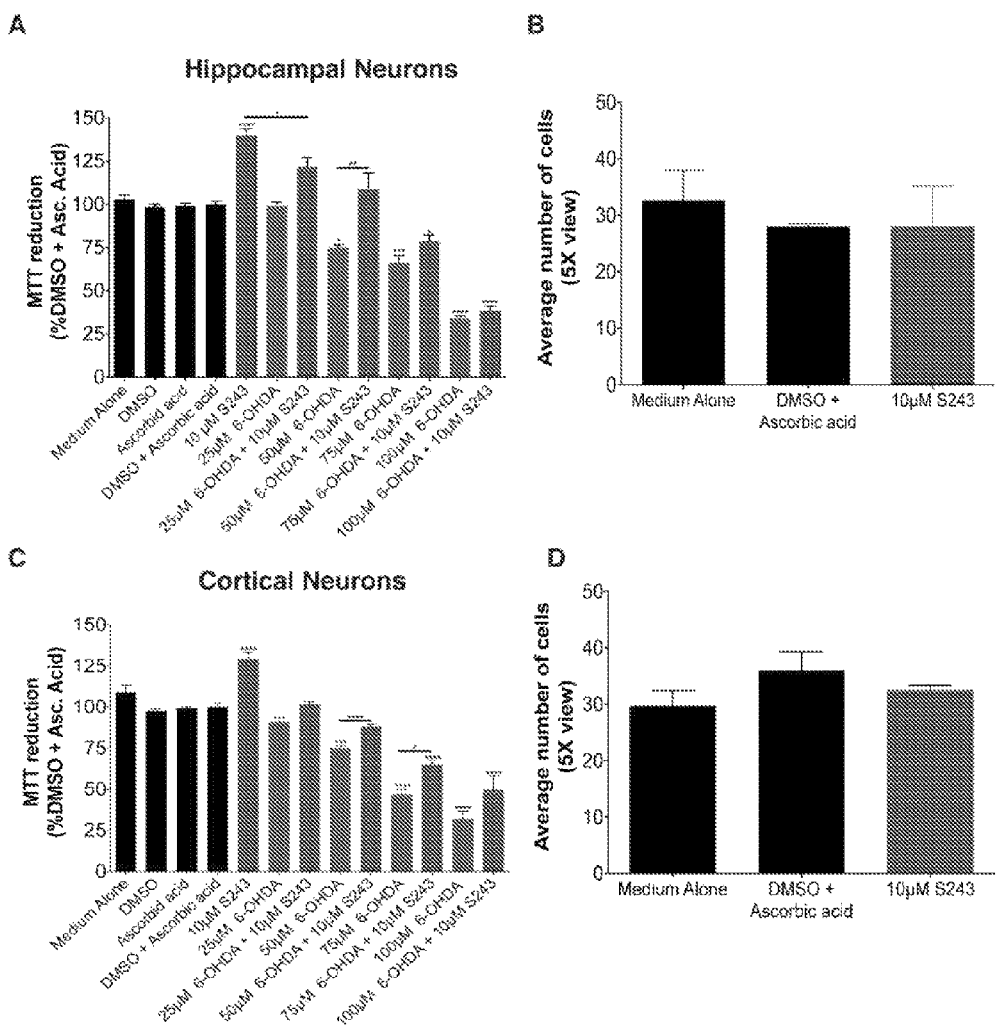
FIGS. 33A-33D. P7C3-S243 protects cultured hippocampal and cortical neurons from 6-OHDA toxicity.
Figure 34:
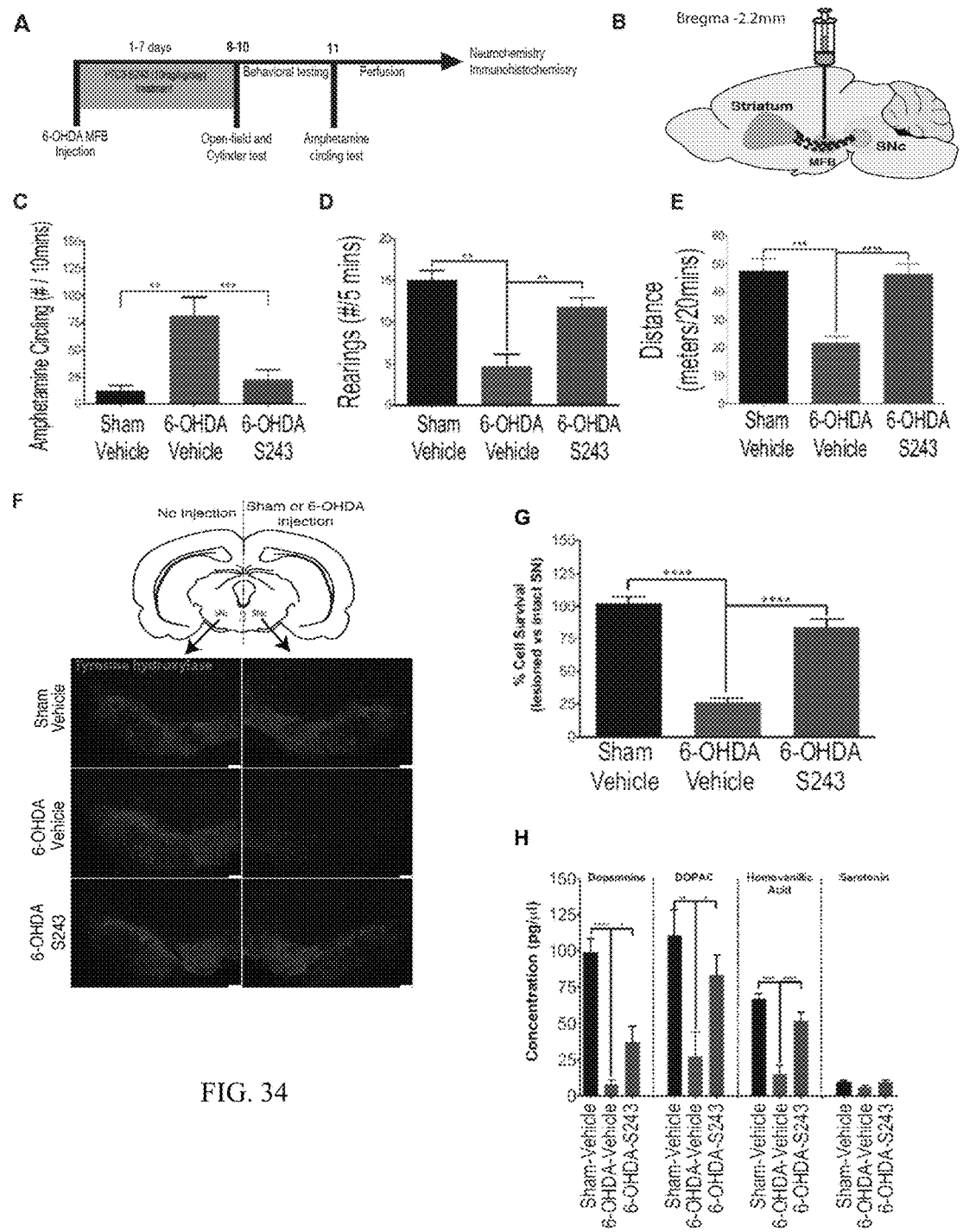
FIGS. 34A-34H. Treatment with P7C3-S243 (10 mg/kg/day) protects rats from 6-OHDA toxicity.
Figure 35:
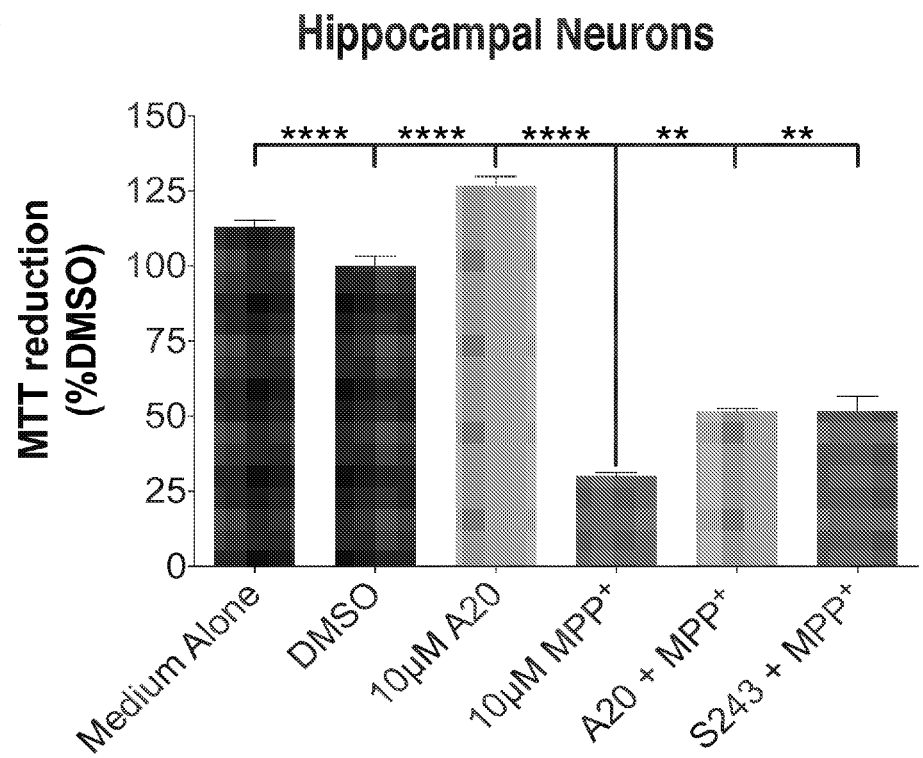
FIGS. 35A-35B. P7C3-S243 and P7C3-A20 protect cultured hippocampal and cortical neurons from MPP$^+$ toxicity.
Figure 35:
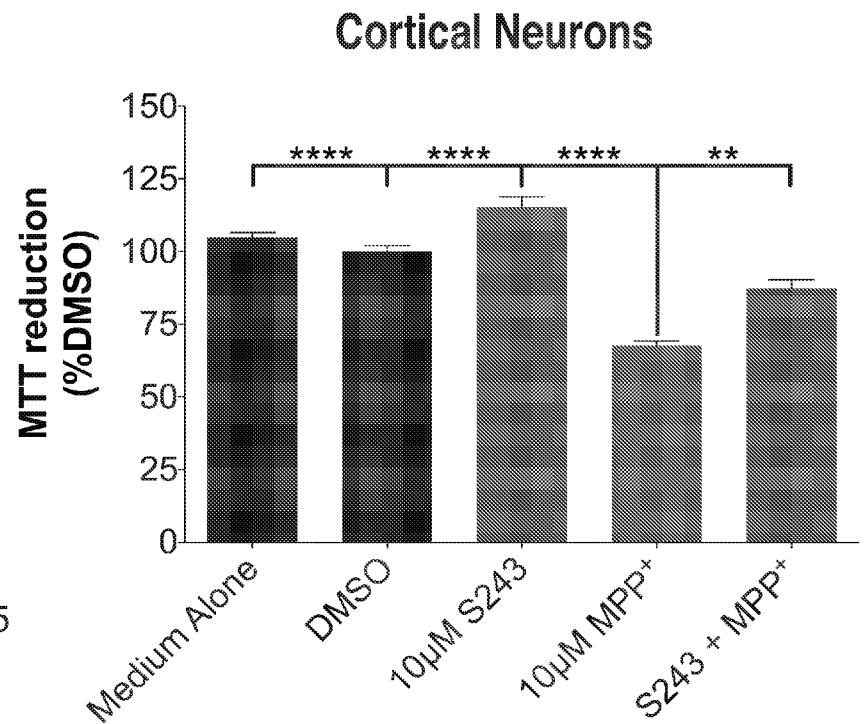
Figure 36:
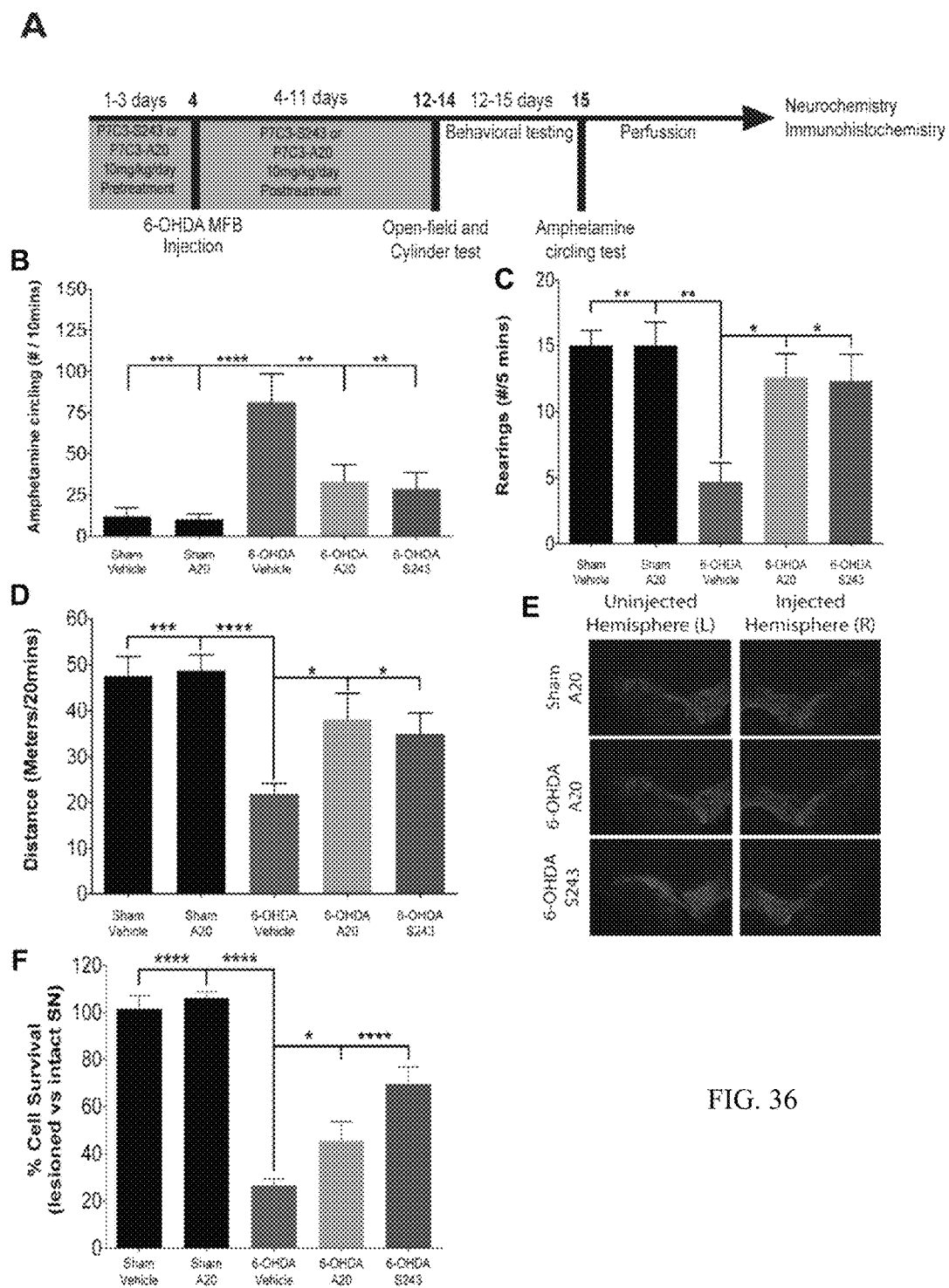
FIGS. 36A-36F. Pretreatment with P7C3-A20 or P7C3-S243 (10 mg/kg/day) protects rats from 6-OHDA toxicity.
Figure 37:
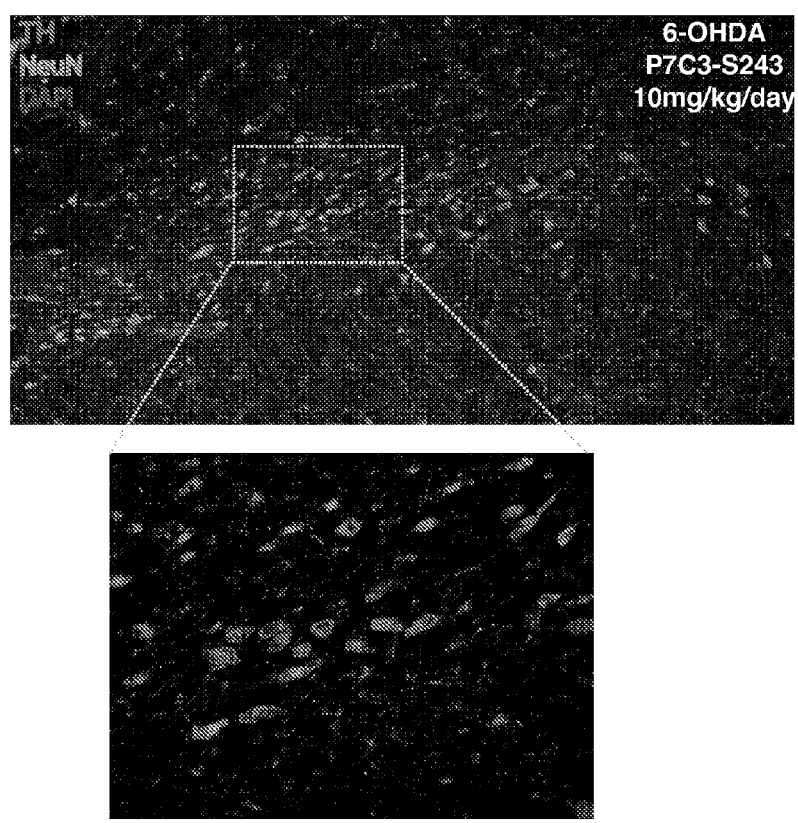
(FIG. 37A) Immunofluorescence of the SNc of a rat injected with 6-OHDA and then treated with P7C3-S243 (10 mg/kg/day) for 7 days shows preservation of co-localized tyrosine hydroxylase (TH) and NeuN (top is low magnification and bottom is high magnification of the indicated region).
(FIG. 37B) Immunofluorescence of the SNc of an animal injected with 6-OHDA and then administered vehicle for 7 days shows loss of both tyrosine hydroxylase (TH) and NeuN labeling (top is low magnification and bottom is high magnification of the indicated region). DAPI was used as a nuclear marker.
Figure 37:
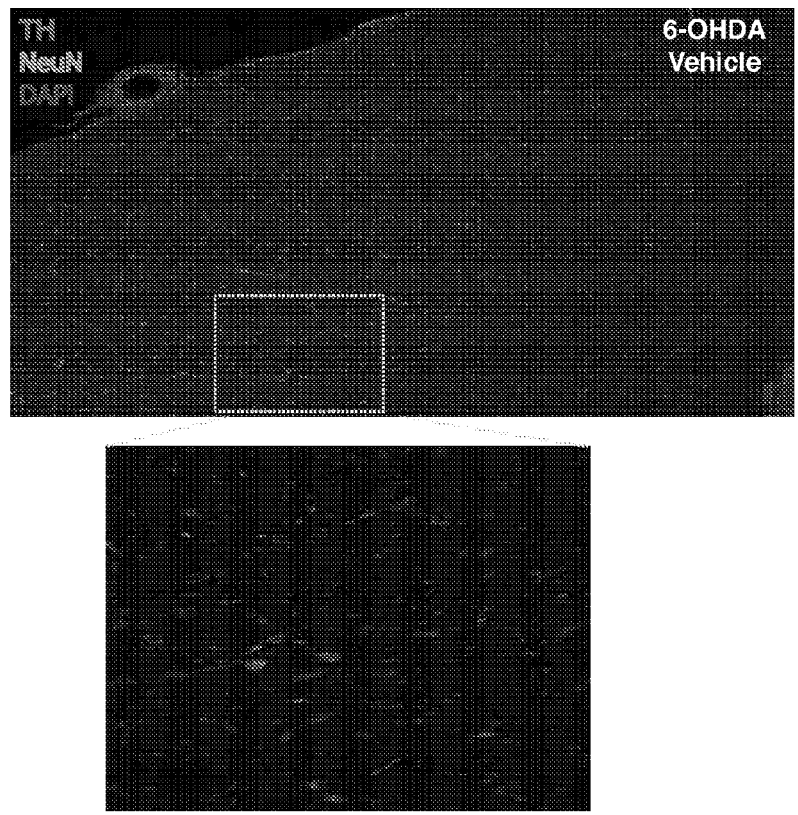

The effect of (−)-P7C3-S243 was tested in a TBI blast injury mice model after an extended period following injury. Surprisingly, the compound was found effective and reverses cognitive decline. Specifically, 10 months after a single blast injury, daily treatment with 3 mg/kg/day of (−)-P7C3-S243 was initiated. After both 4 and 8 weeks of daily treatment, mice showed sustained improvement in cognitive function, as measured by time spent in the escape area (5 cm radius around the escape hole) in the Barnes maze task of hippocampal-dependent learning and memory (FIG. 32). After 8 weeks of treatment, mice were completely withdrawn from treatment with vehicle or compound. The group that had previously received 8 weeks of daily treatment showed sustained improvement in cognition relative to the group that received vehicle. The data indicates that treatment with the P7C3-class of neuroprotective agents might be of therapeutic value for patients suffering from the long term consequences of TBI, who also may have missed the opportunity for acute therapeutic intervention shortly after injury.

Example 6

P7C3-A20 and P7C3-S243 Display Robust Protective Effect in 6-OHDA Parkinson's Disease Model A rat model of Parkinson's disease, incuded by 6-hydroxydopamine (6-OHDA) was used to test various compounds As shown in FIGS. 33A-33D, P7C3-S243 protects cultured hippocampal and cortical neurons from 6-OHDA toxicity. (FIG. 33A) Hippocampal neurons exposed to 6-OHDA showed significant MTT reduction after 24 hrs at 50 µM, 75 µM and 100 µM doses, compared to control neurons treated with DMSO+Ascorbic acid (*$p<0.05$, *$p<0.001$,$p<0.0001$ respectively; one-way ANOVA). 10 µM P7C3-S243 conferred significant protection of hippocampal neurons exposed to 50 µM 6-OHDA ($p<0.005$ using an unpaired t-test). (FIG. 33B) The average number of hippocampal neurons in the 10 µM P7C3-S243 treatment group was not different from the average number of hippocampal neurons treated with medium alone or with DMSO+Ascorbic acid (one-way ANOVA). (FIG. 33C) Cortical neurons exposed to 6-OHDA showed significant MTT reduction after 24 hrs at 50 µM, 75 µM and 100 µM doses, compared to control neurons treated with DMSO+Ascorbic acid (*$p<0.0001$,$p<0.0001$, $p<0.0001$ respectively; one-way ANOVA). (FIG. 33D) 10 µM P7C3-S243 conferred significant protection of cortical neurons exposed to 50 µM and 75 µM 6-OHDA(**$p<0.0001$, *$p<0.05$ respectively, unpaired t-test). The average number of cortical neurons in the 10 µM P7C3-S243 treatment group was not different from the average number of cortical neurons treated with medium alone or with DMSO+Ascorbic acid (one-way ANOVA). Experiments were performed two independent times, with 8-12 replicates of each sample both times.

FIGS. 34A-34H show treatment with P7C3-S243 (10 mg/kg/day) protects rats from 6-OHDA toxicity. (FIG. 34A) Schematic of the experimental design illustrates that rats received a unilateral stereotactic injection of 6-OHDA or saline in the medial forebrain bundle (MFB), followed by daily injection of P7C3-S243 for 7 days. Open field and cylinder tests were performed 8-10 days after 6-OHDA injection, and the amphetamine circling test was conducted on day 11. Rats were transcardially perfused on day 14, and brain tissue was processed for neurochemistry and immunohistochemistry analysis. (FIG. 34B) Graphical illustration of the site of stereotaxic injection in the median forebrain bundle (MFB) shows dopaminergic fibers connecting the striatum and the substantia nigra pars compacta (SNc). (FIG. 34C) Amphetamine-circling test showed a significant increase in ipsilateral (toward the lesion site) rotations of 6-OHDA-exposed animals that received vehicle compared to sham-injured animals that received vehicle ($p<0.005$; one-way ANOVA), and also to 6-OHDA-exposed animals that were treated with P7C3-S243 (*$p<0.001$; one-way ANOVA). (FIG. 34D) Cylinder test showed a significant decrease in the total amount of rearings of 6-OHDA-exposed animals that received vehicle compared to sham-injured animals that received vehicle ($p<0.005$; one-way ANOVA), and also to 6-OHDA-exposed animals that were treated with P7C3-S243 (*$p<0.001$; one-way ANOVA). (FIG. 34E) Open field test showed a significant decrease in the total distance traveled of 6-OHDA-exposed animals that received vehicle compared to sham-injured animals that received vehicle (*$p<0.001$; one-way ANOVA), and also to 6-OHDA-exposed animals that were treated with P7C3-S243 ($p<0.0001$; one-way ANOVA). (FIG. 34F) Representative immunohistochemistry of tyrosine hydroxylase (TH) in the SNc shows that the non-injected side (left) shows no reduction in TH-positive cells in any group, while the injected side (right) shows prominent reduction in TH staining only in rats that were exposed to 6-OHDA and then administered vehicle. Scale bars=250 µm. (FIG. 34G) Quantification of TH-positive cells shows a significant decrease in rats that were exposed to 6-OHDA and then administered vehicle compared to sham-injured rats that received vehicle ($p<0.0001$; one-way ANOVA), and also a significant increase in rats that were exposed to 6-OHDA and then treated with P7C3-S243 compared to the 6-OHDA-Vehicle group (**$p<0.0001$; one-way ANOVA). (FIG. 34H) HPLC analysis of striatal concentration of dopamine, DOPAC, and homovanillic acid showed a significant decrease in rats that were exposed to 6-OHDA and then administered vehicle compared to sham-injured rats that received vehicle, and also a significant increase in rats that were exposed to 6-OHDA and then treated with P7C3-S243 compared to the 6-OHDA-Vehicle group. No difference was found in the concentration of serotonin in all groups (one-way ANOVA). For all experiments in FIG. 34, n=10 per group except for the HPLC analysis, for which n=7.

FIGS. 35A-35B show P7C3-S243 and P7C3-A20 protect cultured hippocampal and cortical neurons from MPP$^+$ toxicity. (FIG. 35A) Hippocampal neurons exposed to 10 µM MPP$^+$ showed significant MTT reduction after 24 hrs, compared to neurons treated with DMSO (**p<0.0001; one-way ANOVA). MPP$^+$-exposed neurons that were also treated with 10 µM P7C3-A20 or 10 µM P7C3-S243 showed significant protection compared to neurons treated with MPP$^+$ alone (p<0.005; one-way ANOVA). (FIG. 35B) Cortical neurons exposed to 10 µM MPP$^+$ showed significant MTT reduction after 24 hrs compared to neurons treated with DMSO (**p<0.0001; one-way ANOVA). MPP$^+$-exposed neurons that were also treated with 10 µM P7C3-S243 showed significant protection compared to neurons treated with MPP$^+$ alone (p<0.005; one-way ANOVA). Experiments were performed 2 independent times with 8-12 replicates of each sample both times.

FIGS. 36A-36F show pretreatment with P7C3-A20 or P7C3-S243 (10 mg/kg/day) protects rats from 6-OHDA toxicity. (FIG. 36A) Schematic of the experimental design illustrates that rats were pretreated for 3 days with either P7C3-A20 or P7C3-S243, and then administered either 6-OHDA or saline by stereotactic injection in the medial forebrain bundle (MFB), followed by 7 more days of treatment with either P7C3-A20 or P7C3-S243. Open field and cylinder tests were performed between days 8-10, and the amphetamine circling test was performed on day 11. Rats were transcardially perfused on day 14, and brain tissue was processed for neurochemistry and immunohistochemistry analysis. (FIG. 36B) Amphetamine-circling test showed a significant increase in ipsilateral (to the lesion site) rotations of 6-OHDA-exposed animals that received vehicle compared to sham-injured animals that received vehicle (*p<0.001; one-way ANOVA), and also to 6-OHDA-exposed animals that were treated with either P7C3-A20 or P7C3-S243 (p<0.005; one-way ANOVA). (FIG. 36C) Cylinder test showed a significant decrease in the total amount of rearings of 6-OHDA-exposed animals that received vehicle compared to sham-injured animals that received vehicle (**p<0.005; one-way ANOVA), and also to 6-OHDA-exposed animals that were treated with either P7C3-A20 or P7C3-S243 (*p<0.05; one-way ANOVA). (FIG. 36D) Open field test showed a significant decrease in the total distance traveled of 6-OHDA-exposed animals that received vehicle compared to sham-injured animals that received vehicle (***p<0.001; one-way ANOVA), and also to 6-OHDA-exposed animals that were treated with either P7C3-A20 or P7C3-S243 (*p<0.05; one-way ANOVA. (FIG. 36E) Representative immunohistochemistry of tyrosine hydroxylase (TH) in the SNc shows that the non-injected side (left) shows no reduction in TH-positive cells in any group, while the injected side (right) shows prominent reduction in TH staining only in rats that were exposed to 6-OHDA and then administered vehicle. Scale bars=250 µm. (FIG. 36F) Quantification of TH-positive cells shows a significant decrease in rats that were exposed to 6-OHDA and then administered vehicle compared to sham-injured rats that received vehicle (****p<0.0001; one-way ANOVA), and also a significant increase in rats that were exposed to 6-OHDA and then treated with either P7C3-A20 or P7C3-S243 group compared to 6-OHDA-Vehicle group (*p<0.05, ****p<0.0001; one-way ANOVA). n=10 per group FIGS. 37A-37B show treatment of 6-OHDA-exposed rats with P7C3-S243 preserves both TH and NeuN staining, illustrating that TH staining corresponds to neuronal survival. (FIG. 37A) Immunofluorescence of the SNc of a rat injected with 6-OHDA and then treated with P7C3-S243 (10 mg/kg/day) for 7 days shows preservation of co-localized tyrosine hydroxylase (TH) and NeuN (top is low magnification and bottom is high magnification of the indicated region). (FIG. 37B) Immunofluorescence of the SNc of an animal injected with 6-OHDA and then administered vehicle for 7 days shows loss of both tyrosine hydroxylase (TH) and NeuN labeling (top is low magnification and bottom is high magnification of the indicated region). DAPI was used as a nuclear marker.

EQUIVALENTS

The present invention provides among other things novel methods and compositions for neurodegenerative diseases. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications, patents and patent applications referenced in this specification are incorporated herein by reference in their entirety for all purposes to the same extent as if each individual publication, patent or patent application were specifically indicated to be so incorporated by reference.

The invention claimed is:

1. A compound having the chemical name of (−)-(S)-N-(3-(3,6-dibromo-9H-carbazol-9-yl-2-fluoropropyl)-6-methoxypyridin-2-amine, or a pharmaceutically acceptable salt thereof.

2. A pharmaceutical composition comprising the compound or salt of claim 1, and a pharmaceutically acceptable carrier.

3. A method for treating a neuropsychiatric or neurodegenerative disease, comprising administering the compound or salt of claim 1 to a patient in need thereof.

4. A method of treating chronic TBI or a long-term symptom associated with TBI, comprising administering an effective amount of the compound or salt of claim 1 to a patient in need thereof.

5. The method of claim 4, wherein the (−)-(S)-N-(3-(3, 6-dibromo-9H-carbazol-9-yl)-2-fluoropropyl)-6-methoxypyridin-2-amine or salt is administered after an extended period following an injury, wherein the extended period is at least one month.

6. The method of claim 4, wherein the (−)-(S)-N-(3-(3, 6-dibromo-9H-carbazol-9-yl)-2-fluoropropyl)-6-methoxypyridin-2-amine or salt is administered for an extended period following an injury, wherein the extended period is at least one hour.

* * * * *